United States Patent
Ding et al.

(10) Patent No.: US 10,683,278 B2
(45) Date of Patent: Jun. 16, 2020

(54) SUBSTITUTED QUINOLONE DERIVATIVES, OR PHARMACEUTICALLY ACCEPTABLE SALTS OR STEREOISOMERS THEREOF, AND PHARMACEUTICAL COMPOSITIONS AND USE THEREOF

(71) Applicants: JINAN UNIVERSITY, Guangdong (CN); SHANGHAI INSTITUTE OF MATERIA MEDICA, CHINESE ACADEMY OF SCIENCES, Pudong Shanghai (CN)

(72) Inventors: Ke Ding, Guangdong (CN); Meiyu Geng, Guangdong (CN); Li Tan, Guangdong (CN); Jian Ding, Guangdong (CN); Zhang Zhang, Guangdong (CN); Jing Ai, Guangdong (CN); Xiaomei Ren, Guangdong (CN); Donglin Gao, Guangdong (CN); Zhengchao Tu, Guangdong (CN); Xiaoyun Lu, Guangdong (CN); Dongmei Zhang, Guangdong (CN)

(73) Assignees: SHANGHAI HAIHE PHARMACEUTICAL CO., LTD., Shanghai (CN); JINAN UNIVERSITY, Guangdong (CN); SHANGHAI INTITUTE OF MATERIA MEDICA, CHINESE ACADEMY OF SCIENCES, Pudong, Shanghai (CN)

( * ) Notice: Subject to any disclaimer, the term of this patent is extended or adjusted under 35 U.S.C. 154(b) by 0 days.

(21) Appl. No.: 15/752,896

(22) PCT Filed: Aug. 18, 2016

(86) PCT No.: PCT/CN2016/095813
§ 371 (c)(1),
(2) Date: Feb. 15, 2018

(87) PCT Pub. No.: WO2017/028797
PCT Pub. Date: Feb. 23, 2017

(65) Prior Publication Data
US 2018/0265496 A1 Sep. 20, 2018

(30) Foreign Application Priority Data
Aug. 18, 2015 (CN) .......................... 2015 1 0509618

(51) Int. Cl.
| | |
|---|---|
| A61K 31/4709 | (2006.01) |
| C07D 215/233 | (2006.01) |
| C07D 401/12 | (2006.01) |
| C07D 471/04 | (2006.01) |
| C07D 471/06 | (2006.01) |
| C07D 487/04 | (2006.01) |
| C07D 491/048 | (2006.01) |
| C07D 498/06 | (2006.01) |
| C07D 513/04 | (2006.01) |
| C07D 519/00 | (2006.01) |

(52) U.S. Cl.
CPC ........ *C07D 401/12* (2013.01); *A61K 31/4709* (2013.01); *C07D 215/233* (2013.01); *C07D 471/04* (2013.01); *C07D 471/06* (2013.01); *C07D 487/04* (2013.01); *C07D 491/048* (2013.01); *C07D 498/06* (2013.01); *C07D 513/04* (2013.01); *C07D 519/00* (2013.01)

(58) Field of Classification Search
CPC combination set(s) only.
See application file for complete search history.

(56) References Cited

FOREIGN PATENT DOCUMENTS

| | | | |
|---|---|---|---|
| CN | 101296928 | | 10/2008 |
| CN | 102652128 | | 8/2012 |
| CN | 103124729 | | 5/2013 |
| CN | 103958497 | | 7/2014 |
| JP | 2011063516 | | 3/2011 |
| JP | 2011063516 | A * | 3/2011 |
| JP | 5525612 | | 6/2014 |
| WO | 2013097280 | | 7/2013 |
| WO | 2014022116 | | 2/2014 |
| WO | 2015012298 | | 1/2015 |
| WO | 2015017607 | | 2/2015 |
| WO | 2015100117 | | 7/2015 |
| WO | 2015164161 | | 10/2015 |

OTHER PUBLICATIONS

Shen et al. Life Sci. 2018, 198, 99-111. (Year: 2018).*
Tan et al. J. Med. Chem. 2016, 59, 6807-6825. (Year: 2016).*
Li, T. et al. "4-Oxo-1, 4-dihydroquinolne-3-carboxamide Derivative as New Axl Kinase Inhibitors", Journal of Medicinal Chemistry, vol. 59, Jul. 5, 2016, pp. 6807-6825.

* cited by examiner

*Primary Examiner* — Amanda L. Aguirre
(74) *Attorney, Agent, or Firm* — JMB Davis Ben-David

(57) ABSTRACT

Provided are a substituted quinolone derivative as shown by formula (I), or a pharmaceutically acceptable salt and a prodrug molecule thereof, and a pharmaceutical composition thereof, as well as the use of same in preparing drugs for the prevention and treatment of a tumor. The quinolone derivative, salt, prodrug molecule, and pharmaceutical composition thereof can be used as a protein kinase inhibitor, which is effective in inhibiting the activity of AXL protein kinase, and is capable of inhibiting the proliferation, migration and invasion of various tumor cells; and can be used in the preparation of anti-tumor drugs, especially drugs for treating hyperproliferative diseases such as a tumor in human beings and other mammals.

11 Claims, 4 Drawing Sheets

SUBSTITUTED QUINOLONE DERIVATIVES, OR PHARMACEUTICALLY ACCEPTABLE SALTS OR STEREOISOMERS THEREOF, AND PHARMACEUTICAL COMPOSITIONS AND USE THEREOF

CROSS-REFERENCE TO RELATED APPLICATIONS

This is the U.S. National Stage of International Application No. PCT/CN2016/095813 filed on Aug. 18, 2016, which was published in Chinese under PCT Article 21(2), which in turn claims the benefit of Chinese Patent Application No. 201510509618.5 filed on Aug. 18, 2015.

TECHNICAL FIELD

The present invention falls within the field of chemical and pharmaceutical technologies, and particularly relates to a substituted quinolone derivative, or a pharmaceutically acceptable salt, a stereoisomer, or prodrug molecule thereof, and a pharmaceutical composition thereof, as well as the use of same in preparing drugs for the prevention and treatment of a tumor. In particularly, the derivative of the present invention, or a salt, a stereoisomer, a prodrug molecule and a pharmaceutical composition thereof can act as a protein kinase inhibitor, which is effective in inhibiting the activity of AXL protein kinase and is capable of inhibiting the proliferation, migration and invasion of various tumor cells.

BACKGROUND ART

AXL is a class of receptor tyrosine kinase and belongs to the TAM receptor tyrosine kinase family which also includes two other members: Mer and Tyro3. TAM was first found in tumor cells, and its overexpression and ectopic expression are closely related to immune regulation, tumor proliferation, growth and migration, etc. AXL was isolated in 1988 from patients with chronic myeloid leukemia and chronic myeloproliferative disorders. AXL is widely expressed in the brain, immune cells, platelets, endothelial cells, skeletal muscle, heart, liver, kidney and other tissues. Vitamin K-dependent protein kinase Gas6 (growth arrest-specific 6) is the most widely studied AXL ligand currently discovered, and the other ligands of the TAM family include Protein S, Tubby, Tulp-1 and Galectin-3. The TAM family share a similar protein structure, which is mainly comprised of three parts, namely, an extracellular domain, a transmembrane region and an intracellular domain, wherein the extracellular domain includes two Igs at the N-terminal immunoglobulin-like region, and two fibronectin III repeat fragments (FNIII). Gas6 binds to the extracellular domain of AXL and then induces the dimerization of AXL, triggering the trans-autophosphorylation of the intracellular domain, and thereby activating intracellular signaling pathways and regulating a series of physiological activities, such as the regulation of cell growth and proliferation through the Src/MAPK/ERK pathway; the stimulation of the expression of anti-apoptotic proteins through the PI3K/AKT pathway; and the regulation of cell migration and proliferation through the PI3K/p38/MAPK pathway. In addition to Gas6-dependent activation, AXL can also be activated in a ligand-independent manner. AXL is involved in the adhesion and immunomodulatory effects of normal cells, and studies have found that the overexpression of AXL occurs in a variety of tumor cells, and Gas6/AXL-regulated signaling pathways are closely related to the occurrence and development of a variety of tumors, such as chronic myelocytic leukemia, breast cancer, prostate cancer, non-small cell lung cancer, pancreatic cancer, melanoma, glioma and renal cell carcinoma. It has been demonstrated that inhibiting the expression of AXL can reduce the proliferation and growth of pancreatic cancer cells, and inhibit the invasion and migration of breast cancer cells. In non-small cell lung cancer, gene-silencing AXL can inhibit tumor growth. Furthermore, the high expression of AXL is also associated with tumor recurrence and tolerance of other anticancer drugs, such as Gliver, Tarceva, and Tyverb. These evidences indicate that AXL is a valid target for tumor targeting therapy.

Bosutinib (SKI606, PF5208763, Bosulif; Pfizer, 2012), Cabozantinib (XL184, Cometriq; Exelixis, 2012), Sunitinib (SU11248, Sutent; Pfizer, 2006) and other marketed drugs, though having AXL activity, are multi-targeted drugs with no specificity. BGB324 (R428; Rigel Pharmaceuticals, BergenBio) is a small molecule inhibitor against AXL with the highest specificity known so far in the market and is being under the first clinical trial, and in December 2014, the FDA awarded BGB324 the title of orphan drug for treating AML. At present, no small molecule inhibitor against AXL kinase has yet been available in the market.

SUMMARY OF THE INVENTION

In order to overcome the above-mentioned disadvantages and shortcomings in the prior art, the primary objective of the present invention is to provide a substituted quinolone derivative, or a pharmaceutically acceptable salt or a stereoisomer thereof.

Another objective of the present invention is to provide a pharmaceutical composition based on the above-mentioned substituted quinolone derivative, or a pharmaceutically acceptable salt or a stereoisomer thereof.

Yet another objective of the present invention is to provide the use of the above-mentioned substituted quinolone derivative, or a pharmaceutically acceptable salt or a stereoisomer thereof.

Still yet another objective of the present invention is to provide the use of the above-mentioned pharmaceutical composition.

The objectives of the present invention are achieved by the following schemes:

A substituted quinolone derivative, or a pharmaceutically acceptable salt or a stereoisomer thereof, which has a structure as shown by formula (I):

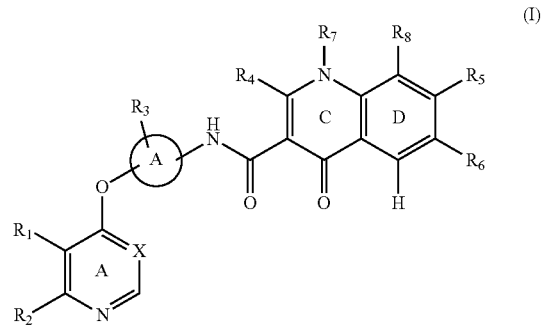

wherein, X is optionally selected from: CH or N;
$R_1$ is optionally selected from: hydrogen or halogen;

$R_2$ is optionally selected from:

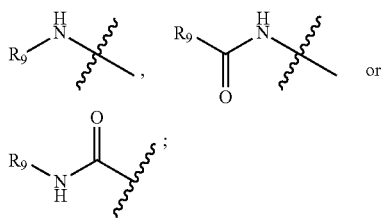

or $R_9$ is optionally selected from: hydrogen, $C_1$-$C_5$ alkyl or $C_3$-$C_6$ cycloalkyl;

or $R_1$, $R_2$ and ring A constitute a fused 5- to 6-membered heterocyclic ring

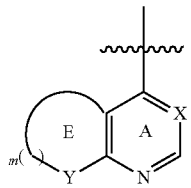

which is substituted or unsubstituted and contains 1-3 N, wherein m=2-3, X is optionally selected from CH or N, and Y is optionally selected from C, N or O;

B is optionally selected from: aryl, heteroaryl, monocyclic or polycyclic alkyl;

$R_3$ is optionally selected from: hydrogen, halogen, trifluoromethyl or $C_1$-$C_3$ alkyl;

$R_4$ is optionally selected from: hydrogen, $C_1$-$C_5$ alkyl, $C_3$-$C_6$ cycloalkyl, $C_1$-$C_3$ alkoxy, substituted or unsubstituted phenyl;

$R_5$ is optionally selected from: hydrogen, —$(CH_2)_r$—$COOR_{22}$, —$(CH_2)_r$—$NR_{23}R_{24}$, -L-heteroaryl or

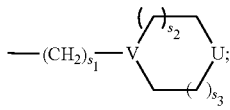

r, $s_1$, $s_2$, and $s_3$ in $R_5$ are each independently selected from 0, 1, 2 or 3;

V is optionally selected from: CH or N;

U is optionally selected from: O, S, $CR_{23}R_{24}$ or $NR_{23}$;

$R_{22}$ is optionally selected from: hydrogen or $C_1$-$C_4$ alkyl;

$R_{23}$ and $R_{24}$ are optionally selected from: H, $C_1$-$C_3$ alkyl, $C_3$-$C_6$ cycloalkyl, —NH($C_1$-$C_3$ alkyl), —N($C_1$-$C_3$ alkyl)($C_1$-$C_3$ alkyl) or —C(=O)($C_1$-$C_3$ alkyl);

L is optionally selected from: $C_1$-$C_3$ alkyl, —$NR_{25}$—, —$NR_{25}CO$—, —$CONR_{25}$—, —O—, —CO—, —SO— or —$SO_2$—; $R_{25}$ is selected from: $C_1$-$C_3$ alkyl;

$R_6$ is optionally selected from: hydrogen, halogen, $C_1$-$C_5$ alkyl, $C_2$-$C_6$ alkenyl, $C_3$-$C_6$ cycloalkyl, $C_4$-$C_6$ cycloalkenyl, $C_1$-$C_5$ alkoxy, trifluoromethyl or trifluoromethoxy;

$R_7$ is optionally selected from: hydrogen, $C_1$-$C_5$ alkyl or $C_3$-$C_6$ cycloalkyl;

$R_8$ is hydrogen;

or $R_7$, $R_8$, ring C and ring D constitute a 5- to 7-membered aliphatic cycloalkane

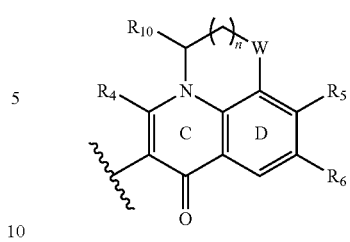

which contains or does not contain a heteroatom;

wherein, n=0-2; W is optionally selected from $CH_2$ or O; and $R_{10}$ is optionally selected from H or $CH_3$.

The substituted quinolone derivative, or a pharmaceutically acceptable salt or a stereoisomer thereof disclosed in the present invention:

preferably, when $R_1$, $R_2$ and ring A constitute a fused 5- to 6-membered substituted heterocyclic ring, the fused 5- to 6-membered substituted heterocyclic ring has preferably one of the following structures:

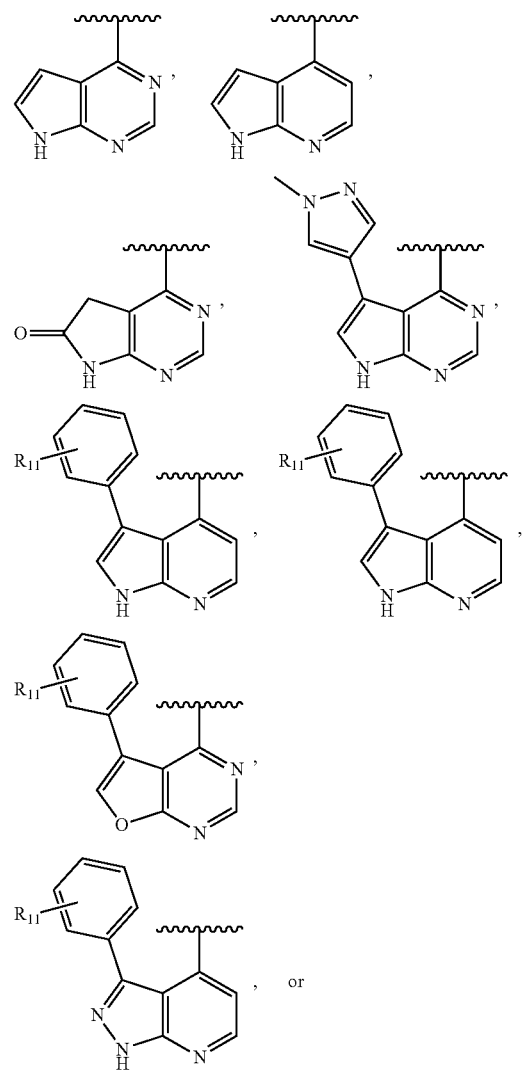

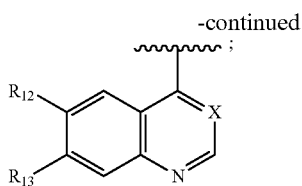

wherein, X is CH₂ or N;

$R_{11}$ is optionally selected from: hydrogen, halogen, methyl, ethyl, propyl, isopropyl, cyclopropyl, methoxy, ethoxy, propoxy or isopropoxy;

$R_{12}$ and $R_{13}$ are the same or different and are optionally selected from: hydrogen, halogen, $-(CR_{15}R_{16})_OR_{14}$, $-O(CR_{15}R_{16})_OR_{14}$, $-(CR_{17}=CR_{18})_PR_{14}$, $O(CR_{17}=CR_{18})_PR_{14}$, $-(C\equiv C)_q-R_{14}$ or $-O-(C\equiv C)_q-R_{14}$;

wherein o, p, and q=0-6, and $R_{14}$, $R_{15}$, $R_{16}$, $R_{17}$, and $R_{18}$ are the same or different and are optionally selected from: —H, —F, —Cl, —Br, —I, —CF₃, —OCF₃, —OH, —COOH, —COOCH₃, —COOC₂H₅, —COOC₃H₇, —COOCH(CH₃)₂, —COOC(CH₃)₃, —(C=O)—NR₁₉R₂₀, —SO_m—NR₁₉R₂₀, —CHR₁₉R₂₀, —OR₁₉ or —NR₁₉R₂₀; m=1-2;

$R_{19}$ and $R_{20}$ are the same or different and are optionally selected from: hydrogen, halogen, or $C_1$-$C_6$ alkyl; or, $R_{19}$ and $R_{20}$ constitute a saturated or an unsaturated 5- to 8-membered heterocyclic group;

or, $R_{12}$ and $R_{13}$ constitute a substituted or an unsubstituted $C_5$-$C_{18}$ aliphatic cycloalkyl which contains 1-4 heteroatoms.

Preferably, the $R_4$ is selected from the following structures: hydrogen, methyl, ethyl, propyl, isopropyl, butyl, isobutyl, pentyl, isopentyl, cyclopropyl, cyclobutyl, cyclopentyl, cyclohexyl, methoxy, ethoxy, propoxy, isopropoxy or

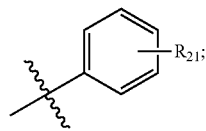

wherein $R_{21}$ is optionally selected from: hydrogen, halogen, $C_1$-$C_5$ alkyl, $C_3$-$C_6$ cycloalkyl or $C_1$-$C_5$ alkyl.

Preferably, the $R_5$ is selected from the following structures: hydrogen,

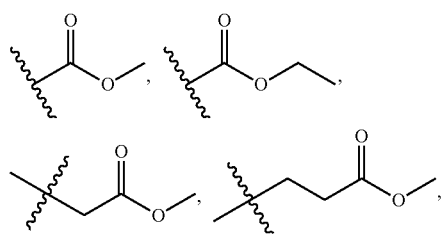

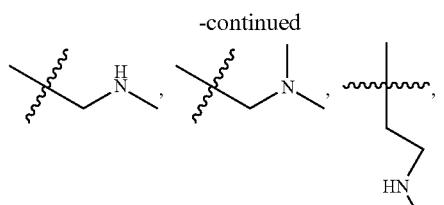

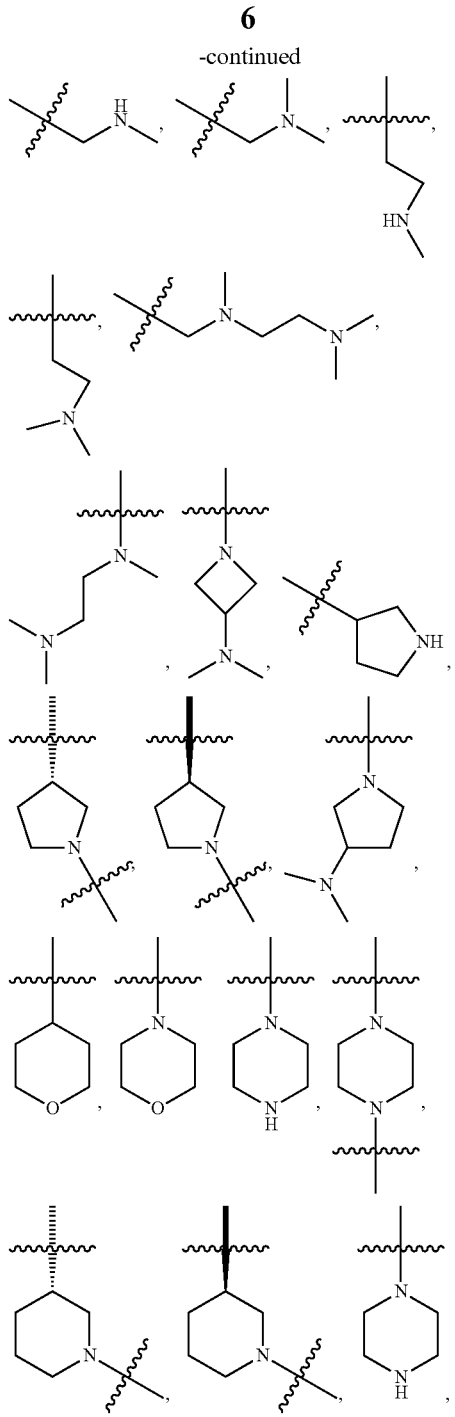

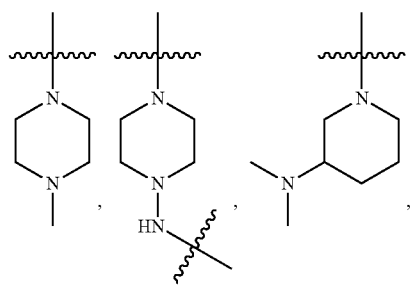

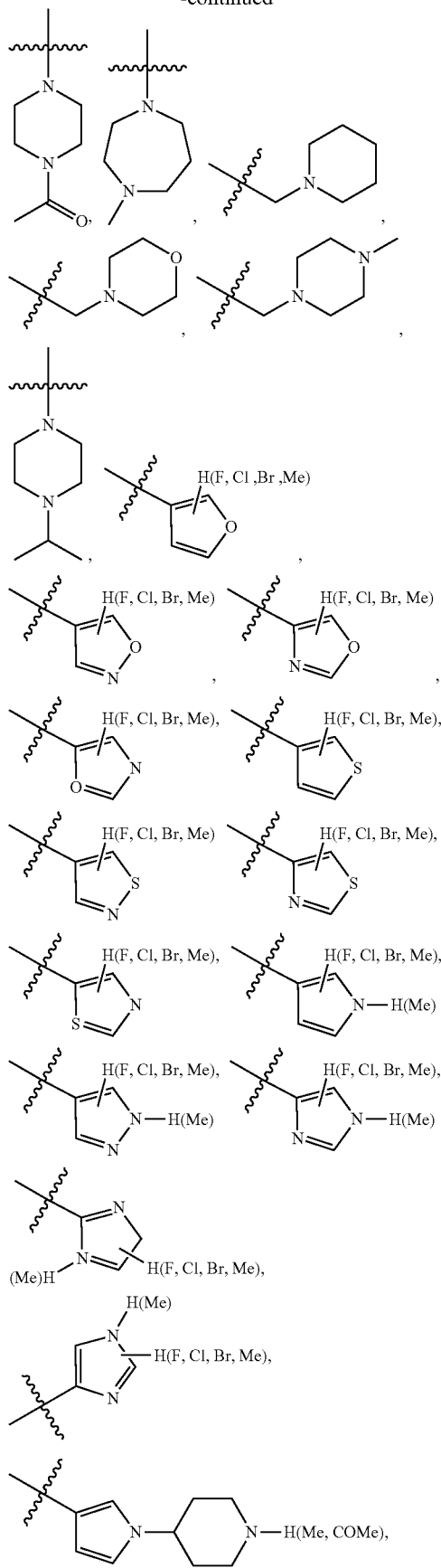
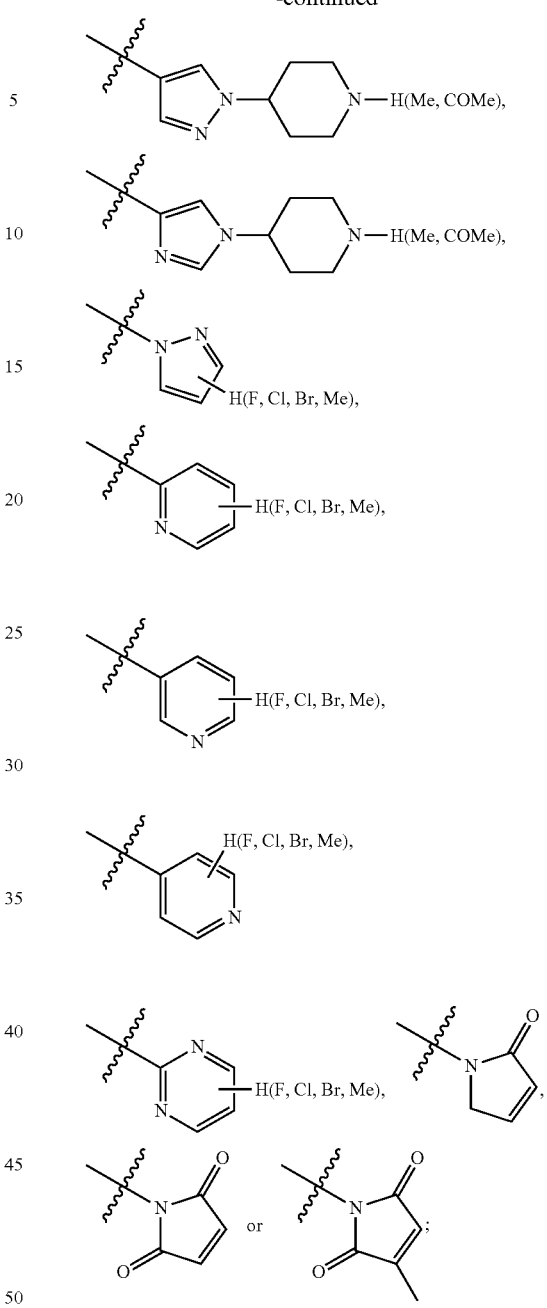

Preferably, the $R_6$ is selected from the following structures: hydrogen, fluorine, chlorine, bromine, methyl, ethyl, propyl, isopropyl, butyl, isobutyl, tert-butyl, pentyl, isopentyl, propenyl, isopropenyl, butenyl, pentenyl, cyclopropyl, cyclobutyl, cyclopentyl, cyclohexyl, cyclobutenyl, cyclopentenyl, cyclohexenyl, methoxy, ethoxy, propoxy, isopropoxy, trifluoromethyl or trifluoromethoxy.

When the $R_8$ is H, $R_7$ is preferably selected from the following structures: hydrogen, methyl, ethyl, propyl, isopropyl, butyl, cyclopropyl, cyclobutyl, cyclopentyl or cyclohexyl.

When the $R_7$, $R_8$, ring C and ring D constitute a fused tricycle, the fused tricycle is preferably one of the following structures:

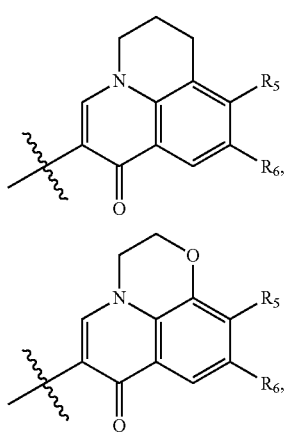
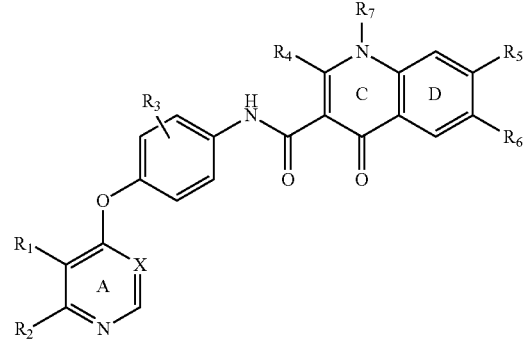
The substituted quinolone derivative, or a pharmaceutically acceptable salt or a stereoisomer thereof disclosed in the present invention, preferably having a structure as shown below:
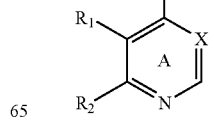
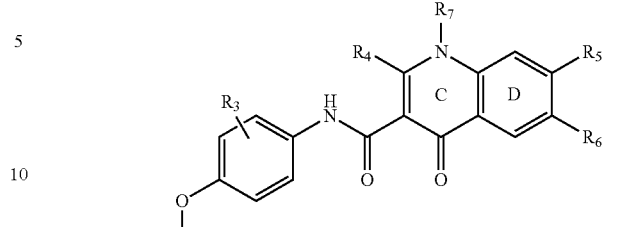
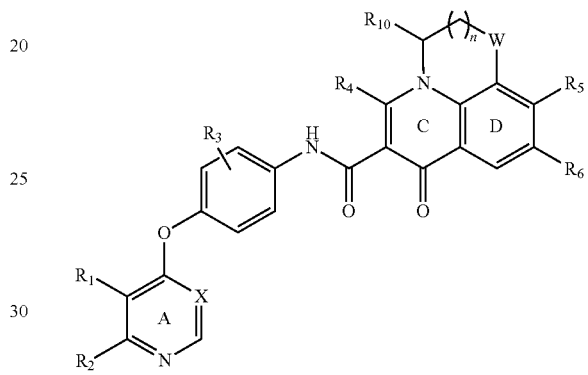
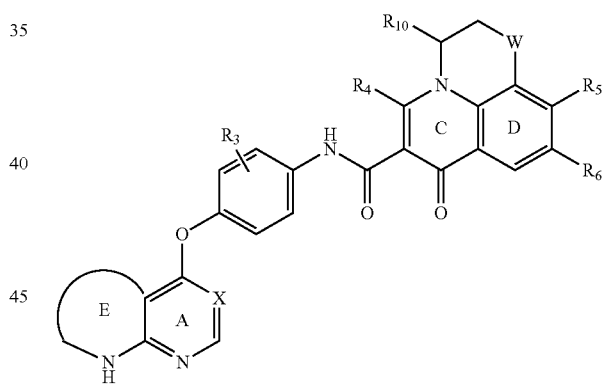
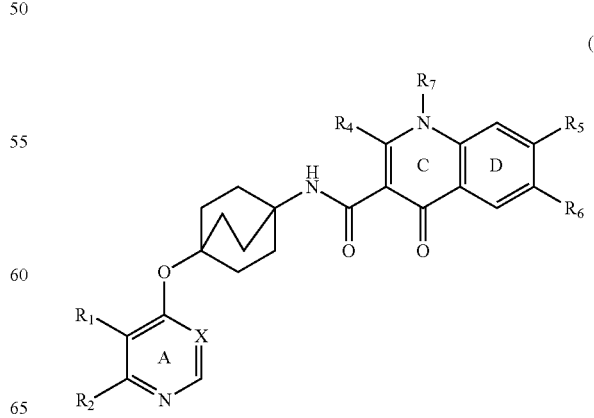
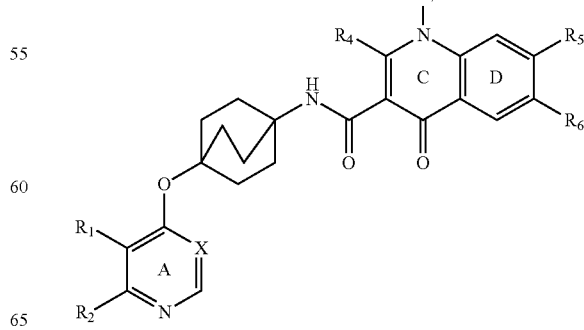

-continued (VII)

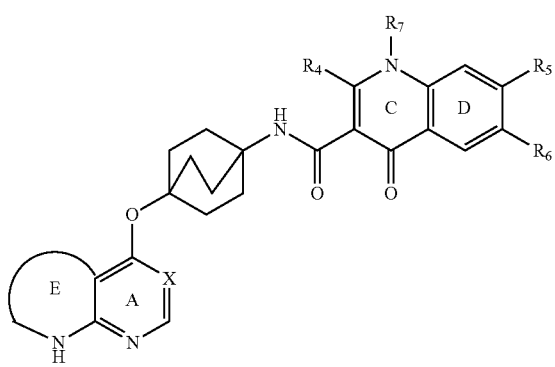

(VIII)

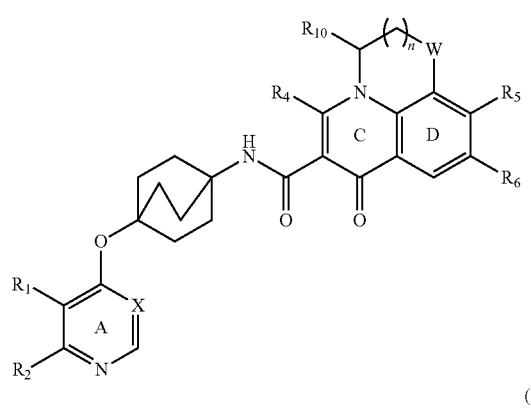

(IX)

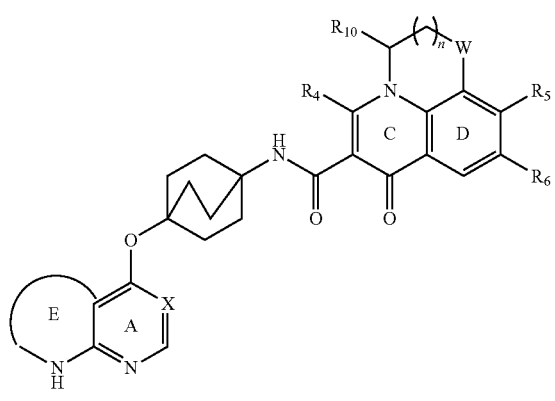

wherein, n=0-2, and W is CH$_2$ or O;
X is optionally selected from: CH or N;
R$_1$ is optionally selected from: hydrogen or halogen;
R$_2$ is optionally selected from:

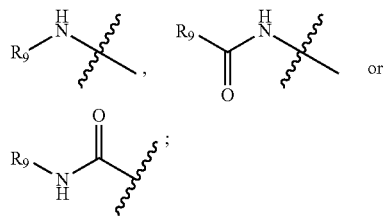

R$_9$ is optionally selected from: hydrogen, C$_1$-C$_5$ alkyl or C$_3$-C$_6$ cycloalkyl;

R$_3$ is optionally selected from: hydrogen, halogen, trifluoromethyl or C$_1$-C$_3$ alkyl;

R$_4$ is optionally selected from: hydrogen, C$_1$-C$_5$ alkyl, C$_3$-C$_6$ cycloalkyl, C$_1$-C$_3$alkoxy, substituted or unsubstituted phenyl;

R$_5$ is optionally selected from: hydrogen, —(CH$_2$)$_r$—COOR$_{22}$, —(CH$_2$)$_r$—NR$_{23}$R$_{24}$, -L-heteroaryl or

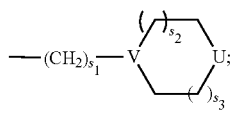

r, s$_1$, s$_2$, and s$_3$ in R$_5$ are each independently selected from 0, 1, 2 or 3;

V is optionally selected from: CH or N;

U is optionally selected from: O, S, CR$_{23}$R$_{24}$ or NR$_{23}$;

R$_{22}$ is optionally selected from: hydrogen or C$_1$-C$_4$ alkyl;

R$_{23}$ and R$_{24}$ are optionally selected from: H, C$_1$-C$_3$ alkyl, C$_3$-C$_6$ cycloalkyl, —NH(C$_1$-C$_3$ alkyl), —N(C$_1$-C$_3$ alkyl)(C$_1$-C$_3$ alkyl) or —C(=O)(C$_1$-C$_3$ alkyl);

L is optionally selected from: C$_1$-C$_3$ alkyl, —NR$_{25}$—, —NR$_{25}$CO—, —CONR$_{25}$—, —O—, —CO—, —SO— or —SO$_2$—; R$_{25}$ is selected from: C$_1$-C$_3$ alkyl;

R$_6$ is optionally selected from: hydrogen, halogen, C$_1$-C$_5$ alkyl, C$_2$-C$_6$ alkenyl, C$_3$-C$_6$ cycloalkyl, C$_4$-C$_6$ cycloalkenyl, C$_1$-C$_5$alkoxy, trifluoromethyl or trifluoromethoxy;

R$_7$ is optionally selected from: hydrogen, C$_1$-C$_5$ alkyl or C$_3$-C$_6$ cycloalkyl;

or R$_7$, ring C and ring D ring constitute a fused tricycle

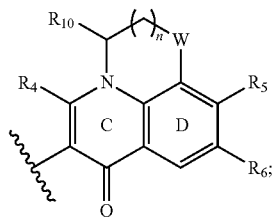

R$_{10}$ is optionally selected from H or CH$_3$.

The fused tricycle is preferably one of the following structures:

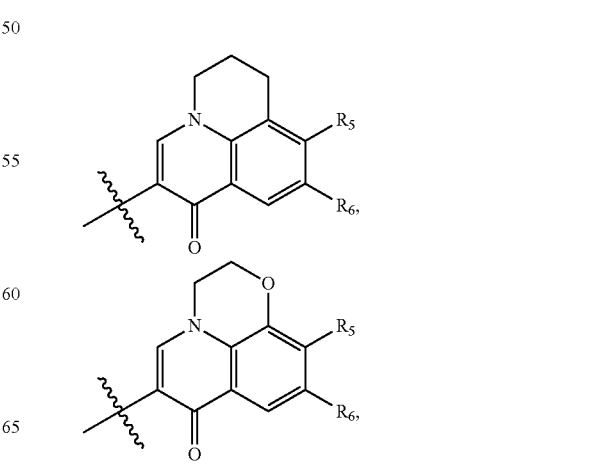

-continued

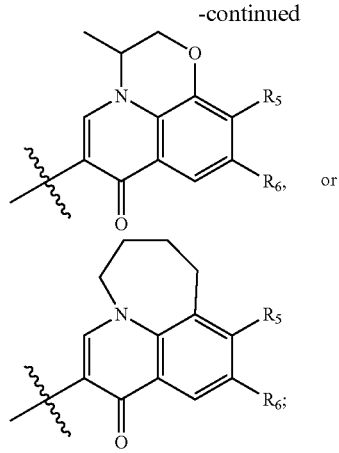

and $R_5$ and $R_6$ have the same definition as above.

The substituted quinolone derivative, or a pharmaceutically acceptable salt or a stereoisomer thereof disclosed in the present invention, having one of the structures as shown by formula (II)-formula (IX), wherein preferably:

$R_4$ is optionally selected from: hydrogen, methyl, ethyl, propyl, isopropyl, butyl, isobutyl, pentyl, isopentyl, cyclopropyl, cyclobutyl, cyclopentyl, cyclohexyl, methoxy, ethoxy, propoxy, isopropoxy or

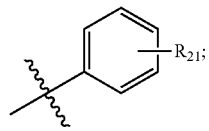

wherein $R_{21}$ is optionally selected from: hydrogen, halogen, $C_1$-$C_5$ alkyl, $C_3$-$C_6$ cycloalkyl or $C_1$-$C_5$ alkyl;

$R_5$ is optionally selected from: hydrogen,

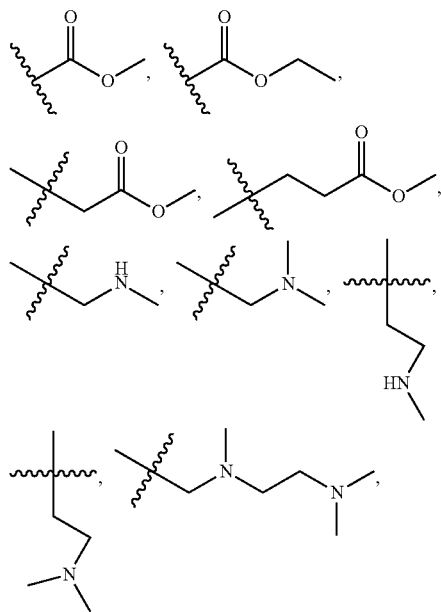

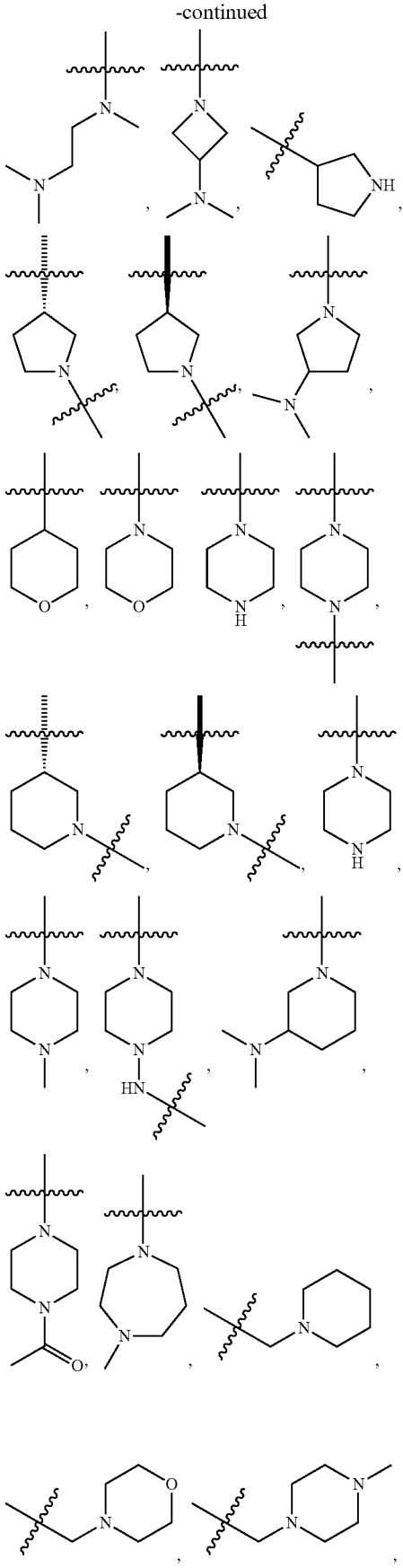

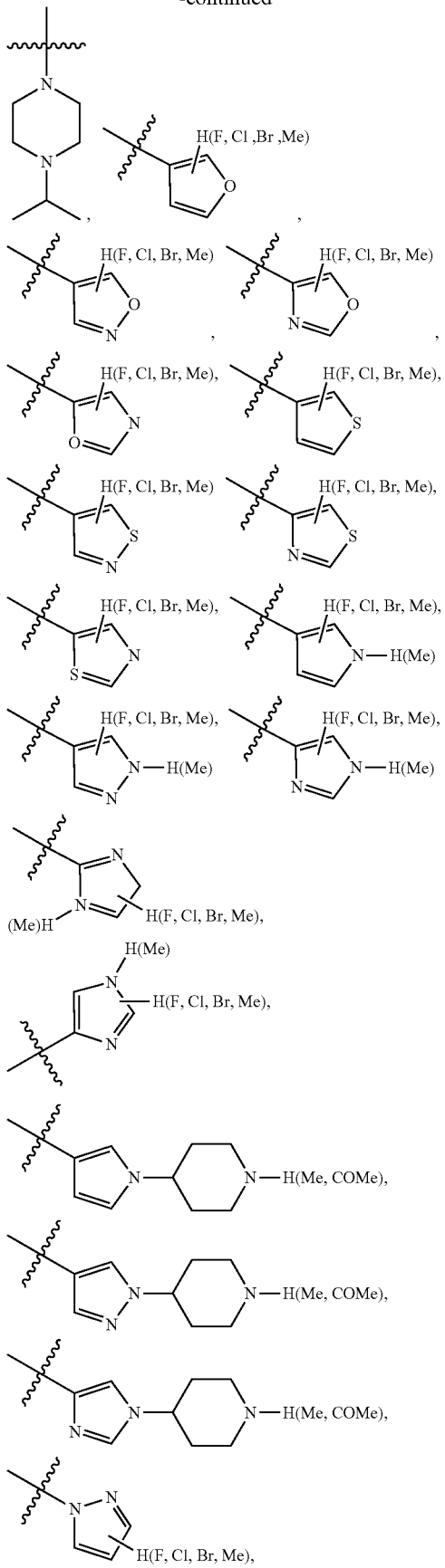

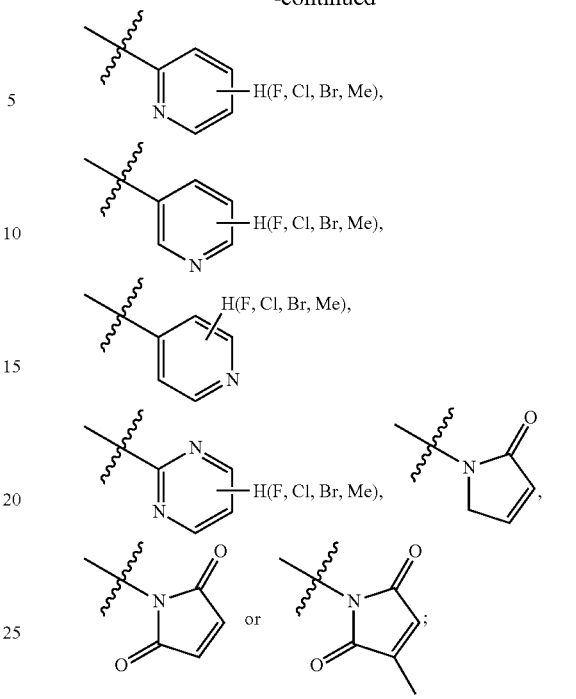

R$_6$ is optionally selected from: hydrogen, fluorine, chlorine, bromine, methyl, ethyl, propyl, isopropyl, butyl, isobutyl, tert-butyl, pentyl, isopentyl, propenyl, isopropenyl, butenyl, pentenyl, cyclopropyl, cyclobutyl, cyclopentyl, cyclohexyl, cyclobutenyl, cyclopentenyl, cyclohexenyl, methoxy, ethoxy, propoxy, isopropoxy, trifluoromethyl or trifluoromethoxy.

The substituted quinolone derivative, or a pharmaceutically acceptable salt or a stereoisomer thereof disclosed in the present invention preferably has the structure of formula (III), formula (V), formula (VII), or formula (IX), i.e., ring E and ring A constitute a fused 5- to 6-membered substituted heterocyclic ring which preferably has a structure as follows:

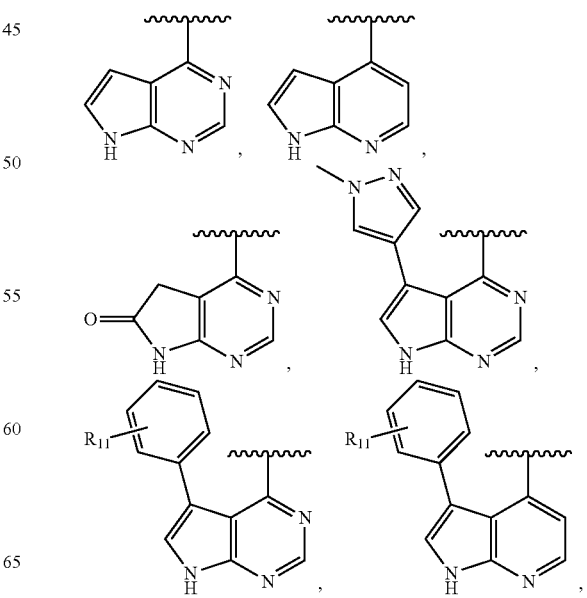

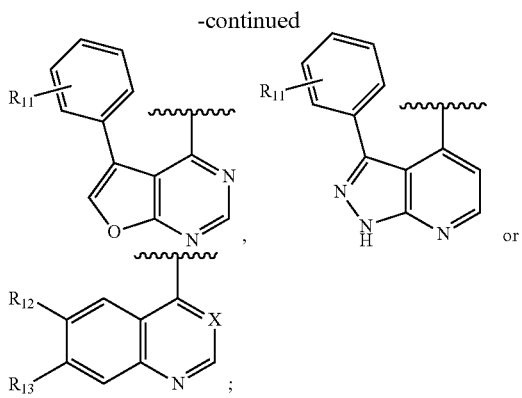

wherein, X is CH or N;

$R_{11}$ is optionally selected from: hydrogen, halogen, methyl, ethyl, propyl, isopropyl, cyclopropyl, methoxy, ethoxy, propoxy or isopropoxy;

$R_{12}$ and $R_{13}$ are the same or different and are optionally selected from: hydrogen, halogen, $-(CR_{15}R_{16})_OR_{14}$, $-O(CR_{15}R_{16})_OR_{14}$, $-(CR_{17}=CR_{18})_PR_{14}$, $-O(CR_{17}=CR_{18})_PR_{14}$, $$-\!\!\!+\!C\!\equiv\!C\!\!\rightarrow_{\!q}\!R_{14} \quad \text{or} \quad -\!\!\!-O\!\!\!+\!C\!\equiv\!C\!\!\rightarrow_{\!q}\!R_{14};$$

wherein o, p and q=0-6; $R_{14}$, $R_{15}$, $R_{16}$, $R_{17}$ and $R_{18}$ are the same or different, and are optionally selected from: —H, —F, —Cl, —Br, —I, —CF$_3$, —OCF$_3$, —OH, —COOH, —COOCH$_3$, —COOC$_2$H$_5$, —COOC$_3$H$_7$, —COOCH(CH$_3$)$_2$, —COOC(CH$_3$)$_3$, —(C=O)—NR$_{19}$R$_{20}$, —SO$_m$—NR$_{19}$R$_{20}$, —CHR$_{19}$R$_{20}$, —OR$_{19}$ or —NR$_{19}$R$_{20}$;

$R_{19}$ and $R_{20}$ are the same or different and are optionally selected from: hydrogen, halogen, or $C_1$-$C_6$ alkyl; or, $R_{19}$ and $R_{20}$ constitute a saturated or an unsaturated 5- to 8-membered heterocyclic group;

or, $R_{12}$ and $R_{13}$ constitute a substituted or an unsubstituted $C_5$-$C_8$ aliphatic cycloalkyl which contains 1-4 heteroatoms.

The substituted quinolone derivative, or a pharmaceutically acceptable salt or a stereoisomer thereof disclosed in the present invention, preferably being one of the following compounds:

N-(3-fluoro-4-(5-phenyl-7H-pyrrolo[2,3-d]pyrimidin-4-yloxy)phenyl)-1,2,6-trimethyl-4-oxo-1,4-dihydroquinoline-3-carboxamide 6-chloro-N-(3-fluoro-4-((3-phenyl-1H-pyrazolo[3,4-b]pyridin-4-yl)oxy)phenyl)-1,2-dimethyl-4-oxo-1,4-dihydroquinoline-3-carboxamide N-(4-((7H-pyrrolo[2,3-d]pyrimidin-4-yl)oxy)-3-fluorophenyl)-6-chloro-1,2-dimethyl-4-oxo-1,4-dihydroquinoline-3-carboxamide 6-chloro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide 7-chloro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide 5-chloro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide N-(3-fluoro-4-(5-phenyl-7H-pyrrolo[2,3-d]pyrimidin-4-yloxy)phenyl)-1,2-dimethyl-4-oxo-7-(trifluoromethyl)-1,4-dihydroquinoline-3-carboxamide 6-fluoro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide N-(4-((1H-pyrrolo[2,3-b]pyridin-4-yl)oxy)-3-fluorophenyl)-6-chloro-1,2-dimethyl-4-oxo-1,4-dihydroquinoline-3-carboxamide N-(3-fluoro-4-((5-phenyl-7H-pyrrolo[2,3-d]pyrimidin-4-yl)oxy)phenyl)-1,2-dimethyl-4-oxo-6-(trifluoromethyl)-1,4-dihydroquinoline-3-carboxamide 6-chloro-N-(3-fluoro-4-((3-phenyl-1H-pyrrolo[2,3-b]pyridin-4-yl)oxy)phenyl)-1,2-dimethyl-4-oxo-1,4-dihydroquinoline-3-carboxamide 6-bromo-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide N-(3-fluoro-4-((5-phenyl-7H-pyrrolo[2,3-d]pyrimidin-4-yl)oxy)phenyl)-1,2-dimethyl-4-oxo-1,4-dihydrobenzo[g]quinoline-3-carboxamide N-(3-fluoro-4-((5-phenyl-7H-pyrrolo[2,3-d]pyrimidin-4-yl)oxy)phenyl)-6-methoxy-1,2-dimethyl-4-oxo-1,4-dihydroquinoline-3-carboxamide N-(3-fluoro-4-((5-phenyl-7H-pyrrolo[2,3-d]pyrimidin-4-yl)oxy)phenyl)-2,6-dimethyl-4-oxo-1,4-dihydroquinoline-3-carboxamide 1-ethyl-N-(3-fluoro-4-(5-phenyl-7H-pyrrolo[2,3-d]pyrimidin-4-yloxy)phenyl)-2,6-dimethyl-4-oxo-1,4-dihydroquinoline-3-carboxamide N-(3-fluoro-4-(5-phenyl-7H-pyrrolo[2,3-d]pyrimidin-4-yloxy)phenyl)-2,6-dimethyl-4-oxo-1-propyl-1,4-dihydroquinoline-3-carboxamide 1-butyl-N-(3-fluoro-4-((5-phenyl-7H-pyrrolo[2,3-d]pyrimidin-4-yl)oxy)phenyl)-2,6-dimethyl-4-oxo-1,4-dihydroquinoline-3-carboxamide 2-ethyl-N-(3-fluoro-4-(5-phenyl-7H-pyrrolo[2,3-d]pyrimidin-4-yloxy)phenyl)-1,6-dimethyl-4-oxo-1,4-dihydroquinoline-3-carboxamide N-(3-fluoro-4-(5-phenyl-7H-pyrrolo[2,3-d]pyrimidin-4-yloxy)phenyl)-1,6-dimethyl-4-oxo-2-phenyl-1,4-dihydroquinoline-3-carboxamide 9-fluoro-N-(3-fluoro-4-((5-phenyl-7H-pyrrolo[2,3-d]pyrimidin-4-yl)oxy)phenyl)-3-methyl-10-(4-methylpiperazin-1-yl)-7-oxo-3,7-dihydro-2H-[1,4]oxazino[2,3,4-ij]quinoline-6-carboxamide 1-cyclopropyl-6-fluoro-N-(3-fluoro-4-((5-phenyl-7H-pyrrolo[2,3-d]pyrimidin-4-yl)oxy)phenyl)-4-oxo-7-(piperazin-1-yl)-1,4-dihydroquinoline-3-carboxamide 9-fluoro-N-(3-fluoro-4-((5-phenyl-7H-pyrrolo[2,3-d]pyrimidin-4-yl)oxy)phenyl)-8-(4-hydroxypiperidin-1-yl)-5-methyl-1-oxo-1,5,6,7-tetrahydropyrido[3,2,1-ij]quinoline-2-carboxamide 6-ethyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide 6-(tert-butyl)-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide N-(3-fluoro-4-((5-phenyl-7H-pyrrolo[2,3-d]pyrimidin-4-yl)oxy)phenyl)-1,2-dimethyl-4-oxo-6-propyl-1,4-dihydroquinoline-3-carboxamide N-(3-fluoro-4-((5-phenyl-7H-pyrrolo[2,3-d]pyrimidin-4-yl)oxy)phenyl)-1,2-dimethyl-4-oxo-6-(trifluoromethoxy)-1,4-dihydroquinoline-3-carboxamide 6-ethyl-1,2-dimethyl-4-oxo-N-(4-((5-phenyl-7H-pyrrolo[2,3-d]pyrimidin-4-yl)oxy)phenyl)-1,4-dihydroquinoline-3-carboxamide 6-ethyl-12-dimethyl-N-(3-methyl-4-(5-phenyl-7H-pyrrolo[2,3-d]pyrimidin-4-yloxy)phenyl)-4-oxo-1,4-dihydroquinoline-3-carboxamide 6-ethyl-N-(2-fluoro-4-(5-phenyl-7H-pyrrolo[2,3-d]pyrimidin-4-yloxy)phenyl)-1,2-dimethyl-4-oxo-1,4-dihydroquinoline-3-carboxamide N-(4-(7H-pyrrolo[2,3-d]pyrimidin-4-yloxy)-3-fluorophenyl)-6-ethyl-1,2-dimethyl-4-oxo-1,4-dihydroquinoline-3-carboxamide 6-ethyl-N-(3-fluoro-4-(3-phenyl-1H-pyrrolo[2,3-b]pyridin-4-yloxy)phenyl)-1,2-dimethyl-4-oxo-1,4-dihydroquinoline-3-carboxamide 6-ethyl-N-(3-fluoro-4-(5-(4-methoxyphenyl)-7H-pyrrolo[2,3-d]pyrimidin-4-yloxy)phenyl)-1,2-dimethyl-4-oxo-1,4-dihydroquinoline-3-carboxamide 6-ethyl-N-(3-fluoro-4-(5-phenyl-7H-pyrrolo[2,3-d]pyrimidin-4-yloxy)phenyl)-1-methyl-4-oxo-1,4-dihydroquinoline-3-carboxamide N-(3-fluoro-4-((5-phenyl-7H-pyrrolo[2,3-d]pyrimidin-4-yl)oxy)phenyl)-9-methyl-1-oxo-1,5,6,7-tetrahydropyrido[3,2,1-ij]quinoline-2-carboxamide N-(4-((6,7-dimethoxyquinazolin-4-yl)oxy)-3-fluorophenyl)-9-methyl-1-oxo-1,5,6,7-tetrahydropyrido[3,2,1-ij]quinoline-2-carboxamide N-(3-fluoro-4-(5-phenyl-7H-pyrrolo[2,3-d]pyrimidin-4-yloxy)phenyl)-1,6-dimethyl-4-oxo-1,4-dihydroquinoline-3-carboxamide N-(3-fluoro-4-(5-phenyl-7H-pyrrolo[2,3-d]pyrimidin-4-yloxy)phenyl)-1,2-dimethyl-4-oxo-6-(prop-1-en-2-yl)-1,4-dihydroquinoline-3-carboxamide 6-cyclopropyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide 6-cyclopentenyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide N-(3-fluoro-4-(5-phenyl-7H-pyrrolo[2,3-d]pyrimidin-4-yloxy)phenyl)-1,2-dimethyl-4-oxo-6-phenyl-1,4-dihydroquinoline-3-carboxamide N-(3-fluoro-4-(5-phenyl-7H-pyrrolo[2,3-d]pyrimidin-4-yloxy)phenyl)-1,2-dimethyl-4-oxo-6-(1-piperidin-4-yl)-1H-pyrazol-4-yl)-1,4-dihydroquinoline-3-carboxamide N-(3-fluoro-4-(5-phenyl-7H-pyrrolo[2,3-d]pyrimidin-4-yloxy)phenyl)-6-isopropyl-1,2-dimethyl-4-oxo-1,4-dihydroquinoline-3-carboxamide 6-cyclopentyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide methyl 3-((3-fluoro-4-(5-phenyl-7H-pyrrolo[2,3-d]pyrimidin-4-yloxy)phenyl)carbamoyl)-1,2-dimethyl-4-oxo-1,4-dihydroquinoline-6-carboxylate N-(3-fluoro-4-(7-methyl-5-phenyl-7H-pyrrolo[2,3-d]pyrimidin-4-yloxy)phenyl)-1,2,6-trimethyl-4-oxo-1,4-dihydroquinoline-3-carboxamide N-(4-(6,7-dimethoxyquinazolin-4-yloxy)-3-fluorophenyl)-6-ethyl-1,2-dimethyl-4-oxo-1,4-dihydroquinoline-3-carboxamide N-(4-((6,7-dimethoxyquinazolin-4-yl)oxy)-3-fluorophenyl)-6-fluoro-1-methyl-7-(4-((5-methyl-2-oxo-1,3-dioxol-4-yl)methyl)piperazin-1-yl)-4-oxo-1,4-dihydro-[1,3]thiazeto[3,2-a]quinoline-3-carboxamide N-(4-((6,7-dimethoxyquinazolin-4-yl)oxy)-3-fluorophenyl)-9-fluoro-8-(4-hydroxypiperidin-1-yl)-5-methyl-1-oxo-1,5,6,7-tetrahydropyrido[3,2,1-ij]quinoline-2-carboxamide (S)—N-(4-((6,7-dimethoxyquinazolin-4-yl)oxy)-3-fluorophenyl)-9-fluoro-3-methyl-10-(4-methylpiperazin-1-yl)-7-oxo-3,7-dihydro-2H-[1,4]oxazino[2,3,4-ij]quinoline-6-carboxamide N-(4-((6,7-dimethoxyquinazolin-4-yl)oxy)-3-fluorophenyl)-9-fluoro-3-methyl-10-(4-methylpiperazin-1-yl)-7-oxo-3,7-dihydro-2H-[1,3,4]oxadiazino[6,5,4-ij]quinoline-6-carboxamide N-(4-(6,7-dimethoxyquinazolin-4-yloxy)-3-fluorophenyl)-6,8-difluoro-1-(2-fluoroethyl)-7-(4-methylpiperazin-1-yl)-4-oxo-1,4-dihydroquinoline-3-carboxamide N-(4-(6,7-dimethoxyquinazolin-4-yloxy)-3-fluorophenyl)-6-fluoro-1-(4-fluorophenyl)-4-oxo-7-(piperazin-1-yl)-1,4-dihydroquinoline-3-carboxamide 5-amino-1-cyclopropyl-N-(4-(6,7-dimethoxyquinazolin-4-yloxy)-3-fluorophenyl)-7-(3,5-dimethylpiperazin-1-yl)-6,8-difluoro-4-oxo-1,4-dihydroquinoline-3-carboxamide 1-cyclopropyl-N-(4-(6,7-dimethoxyquinazolin-4-yloxy)-3-fluorophenyl)-7-(4-ethylpiperazin-1-yl)-6-fluoro-4-oxo-1,4-dihydroquinoline-3-carboxamide 7-(3-aminopyrrolidin-1-yl)-1-(2,4-difluorophenyl)-N-(4-(6,7-dimethoxyquinazolin-4-yloxy)-3-fluorophenyl)-6-fluoro-4-oxo-1,4-dihydro-1,8-naphthyridine-3-carboxamide N-(4-(6,7-dimethoxyquinazolin-4-yloxy)-3-fluorophenyl)-1-ethyl-6-fluoro-4-oxo-7-(piperazin-1-yl)-1,4-dihydro-1,8-naphthyridine-3-carboxamide 1-cyclopropyl-N-(4-(6,7-dimethoxyquinazolin-4-yloxy)-3-fluorophenyl)-6-fluoro-4-oxo-7-(piperazin-1-yl)-1,4-dihydroquinoline-3-carboxamide N-(4-(2-chloropyridin-4-yloxy)-3-fluorophenyl)-6-ethyl-1,2-dimethyl-4-oxo-1,4-dihydroquinoline-3-carboxamide N-(4-(2-benzylpyridin-4-yloxy)-3-fluorophenyl)-6-ethyl-1,2-dimethyl-4-oxo-1,4-dihydroquinoline-3-carboxamide 6-ethyl-N-(3-fluoro-4-(3-phenylfuro[2,3-b]pyridin-4-yloxy)phenyl)-1,2-dimethyl-4-oxo-1,4-dihydroquinoline-3-carboxamide N-(4-(2-carbamoylpyridin-4-yloxy)-3-fluorophenyl)-6-ethyl-1,2-dimethyl-4-oxo-1,4-dihydroquinoline-3-carboxamide N-(4-(2-aminopyridin-4-yloxy)-3-fluorophenyl)-6-ethyl-1,2-dimethyl-4-oxo-1,4-dihydroquinoline-3-carboxamide 6-ethyl-N-(3-fluoro-4-(5-(1-methyl-1H-pyrazol-4-yl)-7H-pyrrolo[2,3-d]pyrimidin-4-yloxy)phenyl)-1,2-dimethyl-4-oxo-1,4-dihydroquinoline-3-carboxamide 2,6-diethyl-N-(3-fluoro-4-(5-phenyl-7H-pyrrolo[2,3-d]pyrimidin-4-yloxy)phenyl)-1-methyl-4-oxo-1,4-dihydroquinoline-3-carboxamide N-(4-(6,7-dimethoxyquinazolin-4-yloxy)-3-fluorophenyl)-2,6-diethyl-1-methyl-4-oxo-1,4-dihydroquinoline-3-carboxamide N-(4-(2-carbamoyl-3-chloropyridin-4-yloxy)-3-fluorophenyl)-6-ethyl-1,2-dimethyl-4-oxo-1,4-dihydroquinoline-3-carboxamide N-(4-((2-amino-3-chloropyridin-4-yl)oxy)-3-fluorophenyl)-6-ethyl-1,2-dimethyl-4-oxo-1,4-dihydroquinoline-3-carboxamide N-(3-fluoro-4-(5-phenyl-7H-pyrrolo[2,3-d]pyrimidin-4-yloxy)phenyl)-2,6-dimethyl-4-oxo-1-phenyl-1,4-dihydroquinoline-3-carboxamide 6-ethyl-N-(3-fluoro-4-(6-methoxy-7-(3-morpholinopropoxy)quinazolin-4-yloxy)phenyl)-1,2-dimethyl-4-oxo-1,4-dihydroquinoline-3-carboxamide N-(4-(7-(2-(dimethylamino)ethoxy)-6-methoxyquinazolin-4-yloxy)-3-fluorophenyl)-6-ethyl-1,2-dimethyl-4-oxo-1,4-dihydroquinoline-3-carboxamide 6-ethyl-N-(3-fluoro-4-(6-methoxy-7-(3-(4-methylpiperazin-1-yl)propoxy)quinazolin-4-yloxy)phenyl)-1,2-dimethyl-4-oxo-1,4-dihydroquinoline-3-carboxamide 6-ethyl-N-(3-fluoro-4-(6-methoxy-7-(2-(pyrrolidin-1-yl)ethoxy)quinazolin-4-yloxy)phenyl)-1,2-dimethyl-4-oxo-1,4-dihydroquinoline-3-carboxamide 6-ethyl-N-(3-fluoro-4-(6-methoxy-7-(3-methoxypropoxy)quinazolin-4-yloxy)phenyl)-1,2-dimethyl-4-oxo-1,4-dihydroquinoline-3-carboxamide N-(4-(7-(3-(dimethylamino)propoxy)-6-methoxyquinazolin-4-yloxy)-3-fluorophenyl)-6-ethyl-1,2-dimethyl-4-oxo-1,4-dihydroquinoline-3-carboxamide N-(4-(6,7-dimethoxyquinazolin-4-yloxy)-3-fluorophenyl)-6-ethyl-1,2-dimethyl-7-(4-methylpiperazin-1-yl)-4-oxo-1,4-dihydroquinoline-3-carboxamide The present invention further provides a pharmaceutical composition for the treatment of a tumor based on the above-mentioned substituted quinolone derivative, or a pharmaceutically acceptable salt or a stereoisomer thereof disclosed in the present invention, wherein the pharmaceutical composition comprises the above-mentioned substituted quinolone derivative, a pharmaceutically acceptable salt and a stereoisomer thereof, or a prodrug molecule thereof, and a pharmaceutically acceptable carrier.

The substituted quinolone derivative, or a pharmaceutically acceptable salt, a prodrug molecule, and a pharmaceutical composition thereof disclosed in the present invention, finds use in preparing drugs for the prevention and treatment of a tumor, especially drugs for treating hematological tumor (such as leukemia), gastrointestinal stromal tumor, histiocytic lymphoma, non-small cell lung cancer, small cell lung cancer, lung adenocarcinoma, lung squamous cell carcinoma, pancreatic cancer, breast cancer, prostate cancer, hepatoma, skin cancer, epithelial cancer, nasopharyngeal cancer and other hyperproliferative diseases.

The substituted quinolone derivative, or a pharmaceutically acceptable salt, a prodrug molecule, and a pharmaceutical composition thereof disclosed in the present invention is effective in inhibiting the action of protein kinases such as AXL, and is capable of inhibiting the proliferation, migration and invasion of various tumor cells, and can be used in the preparation of anti-tumor drugs. As understood by those skilled in the art, the compounds of the present application and pharmaceutically acceptable salts thereof are useful in the preparation of drugs for the treatment of hyperproliferative diseases such as a tumor in humans and other mammals.

DETAILED DESCRIPTION OF EMBODIMENTS

Figure 1:
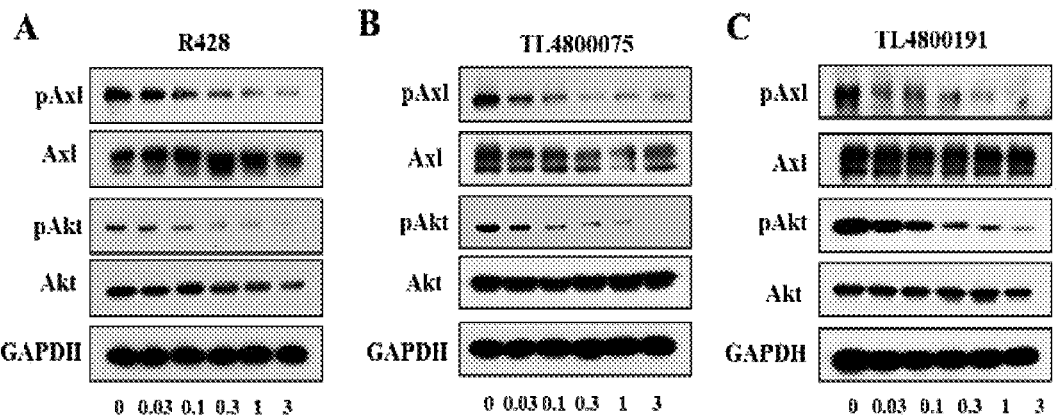
FIG. 1 shows the effect of quinolone derivatives on the AXL kinase phosphorylation of MDA-MB-231 cells.

The present invention will be further described in detail below in conjunction with embodiments and accompanying drawings, but this does not limit the implementation of the present invention.

In the chemicals of the present invention, if any variable (eg, $R_1$, R, etc.) occurs more than once in any component, the definitions of the variable occurred each time are independent to each other. Likewise, combinations of substituents and variables are allowed so long as the combination stabilizes the compound. A line drawn from a substituent into the ring system means that the bond referred to can be linked to any substitutable atom of the ring. If the ring system is polycyclic, it means that such a bond is merely linked to any suitable carbon atom adjacent to the ring. It is to be understood that a person skill in the art would select the substituents and substitution patterns for the compounds of the present invention to provide a compound which is chemically stable and readily synthesized from readily available raw materials by the techniques in the art and methods set forth below. If a substituent per se is substituted with more than one group, it is understood that these groups may be on the same carbon atom or on different carbon atoms as long as the structure is stabilized.

As used herein, the term "alkyl" is intended to include both branched- and straight-chain saturated aliphatic hydrocarbon groups having a specific number of carbon atoms. For example, the definition of "$C_1$-$C_5$" in "$C_1$-$C_5$ alkyl" includes groups having 1, 2, 3, 4 or 5 carbon atoms arranged in a straight or branched chain. For example, the "$C_1$-$C_5$ alkyl" specifically includes methyl, ethyl, n-propyl, isopropyl, n-butyl, tert-butyl, isobutyl and pentyl. The term "cycloalkyl" refers to a monocyclic saturated aliphatic hydrocarbon group having a specific number of carbon atoms. For example, "cycloalkyl" includes cyclopropyl, methyl-cyclopropyl, cyclobutyl, cyclopentyl, cyclohexyl, etc.

The term "heteroaryl" as used herein represents a stable monocyclic carbocycle with up to 5 atoms in the ring or a bicyclic carbocycle with up to 5 atoms in each ring, wherein at least one of the rings is an aromatic ring and contains 1 to 4 heteroatoms selected from O, N, and S. The heteroaryl within the definition includes, but is not limited to: imidazolyl, pyrazolyl, furyl, thienyl, oxazolyl, isoxazolyl, pyrazinyl, pyridinyl, pyrimidinyl, and pyrrolyl. With regard to the definition of the heteroaryl below, the "heteroaryl" is also understood as a N-oxide derivative including any nitrogen-containing heteroaryl. In the case where the heteroaryl substituent is bicyclic and contains one ring that is non-aromatic or contains no heteroatoms, it is understood that each heteroaryl substituent is linked via the aromatic ring or via the heteroatom-containing ring.

The term "heterocycle" or "heterocyclyl" as used herein refers to a 5- to 6-membered aromatic or non-aromatic heterocycle containing 1-4 heteroatoms selected from O, N and S, and includes a bicyclic group. Accordingly, "heterocyclyl" includes the above-mentioned heteroaryl, as well as the dihydrogenated and tetrahydrogenated analogs thereof. Further examples of "heterocyclyl" include, but are not limited to: imidazolyl, thiazolyl, isoxazolyl, oxadiazolyl, oxazolyl, oxetanyl, pyranyl, pyrazinyl, pyrazolyl, pyridazinyl, pyridinyl, pyrimidinyl, pyrrolyl, quinoxalinyl, tetrazolyl, thiadiazolyl, thiazolyl, thiophenyl, and azolyl. The linkage of the heterocycle substituent may be achieved through a carbon atom or through a heteroatom.

As understood by those skilled in the art, "halo" or "halogen" as used herein is intented to include chlorine, fluorine, bromine and iodine.

Unless otherwise defined, alkyl, cycloalkyl, aryl, heteroaryl, and heterocyclyl substituents may be unsubstituted or substituted. For example, $(C_1-C_6)$alkyl can be substituted with one, two or three substituents selected from OH, halogen, nitro, cyano, alkoxy, dialkylamino or heterocyclyl, such as morpholinyl and piperidinyl.

The present invention includes the free form of the compounds of formula I to formula IX, as well as a pharmaceutically acceptable salt and a stereoisomer thereof. Some specific exemplary compounds herein are protonated salts of amine compounds. The term "free form" refers to an amine compound in a non-salt form. The pharmaceutically acceptable salts included therein include not only the exemplary salts of the specific compounds described herein, but also the typical pharmaceutically acceptable salts of the free form of all the compounds of formula I. The free form of the salts specific to the compounds can be separated using techniques known in the art. For example, the free form can be regenerated by treating the salt with a suitable dilute aqueous base such as dilute aqueous NaOH, dilute aqueous potassium carbonate, dilute aqueous ammonia and dilute aqueous sodium bicarbonate. The free form differs somewhat in some physical properties, for example in the solubility in polar solvents from its respective salt form, but for the purposes of the present invention, the acid and base salts are comparable to its respective salt form in other pharmaceutical aspects.

The pharmaceutically acceptable salts of the present invention can be synthesized from the compounds of the present invention that contain a basic or acidic moiety by conventional chemical methods. In general, salts of basic compounds are prepared by ion exchange chromatography or by reaction of a free base and a stoichiometric or excessive amount of desired inorganic or organic acids in a salt form in an appropriate solvent or the combination of multiple solvents. Similarly, salts of acidic compounds are formed by reaction with a suitable inorganic or organic base.

Thus, pharmaceutically acceptable salts of the compounds of the present invention include the conventional non-toxic salts of the compounds of the present invention formed by the reaction of a basic compound of the present invention with an inorganic or organic acid. For example, conventional non-toxic salts include salts obtained from inorganic acids such as hydrochloric acid, hydrobromic acid, sulfuric acid, sulfamic acid, phosphoric acid, and nitric acid, and also included salts prepared from organic acids such as acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, salicylic acid, sulfanilic acid, 2-acetoxymonobenzoic acid, fumaric acid, toluenesulfonic acid, methanesulfonic acid, ethane disulfonic acid, oxalic acid, isethionic acid, and trifluoroacetic acid.

If the compound of the present invention is acidic, suitable "pharmaceutically acceptable salts" refer to salts prepared from pharmaceutically acceptable non-toxic bases, including inorganic bases and organic bases. Salts obtained from inorganic bases include aluminum salts, ammonium salts, calcium salts, copper salts, iron salts, ferrous salts, lithium salts, magnesium salts, manganese salts, manganous salts, potassium salts, sodium salts, zinc salts, etc. In Particular, the salts are preferably ammonium salts, calcium salts, magnesium salts, potassium salts and sodium salts. Salts obtained from pharmaceutically acceptable organic non-toxic bases include salts of primary, secondary, and tertiary amines, and substituted amines include naturally occurring substituted amines, cyclic amines, and basic ion exchange resins such as arginine, betaine, caffeine, choline, N, N'-dibenzylethylenediamine, diethylamine, 2-diethylaminoethanol, 2-dimethylaminoethanol, aminoethanol, ethanolamine, ethylenediamine, N-ethyl morpholine, N-ethyl piperidine, glucosamine, amino-glucose, histidine, hydroxocobalamin, isopropylamine, lysine, methylglucamine, morpholine, piperazine, piperidine, polyamine resins, procaine, purine, theobromine, triethylamine, trimethylamine, tripropylamine, and tromethamine.

The preparations of the pharmaceutically acceptable salts described above and other typical pharmaceutically acceptable salts are described in more detail in Berg et al., "Pharmaceutical Salts," *J. Pharm. Sci.* 1977: 66: 1-19.

Since under physiological conditions, the deprotonated acidic moiety in a compound, for example, a carboxyl, may be anionic, and the charge may then be balanced and counteracted by internal protonated or alkylated basic moieties with cations, such as a tetravalent nitrogen atom, it should be noted that the compounds of the present invention are potentially internal salts or zwitterions.

In addition to the standard methods known in the literature or exemplified in the experimental procedures, the compounds of the present invention can be prepared using the reactions shown in the following schemes. Therefore, the following illustrative schemes are for illustrative purposes and are not limited to the compounds listed or any specific substituents. The number of substituents shown in the schemes does not necessarily conform to the number used in claims, and for clarity, it is shown that a single substituent is linked to the compound in which multiple substituents are allowed under the above definition of formula (I).

Schemes

As shown in Scheme A, the compound of formula (I) can be synthesized by an 8-step reaction using 4-chloropyrrolopyrimidine as the starting material.

Scheme A:

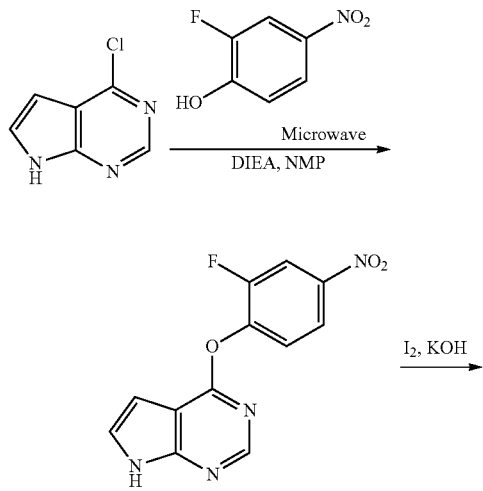

-continued

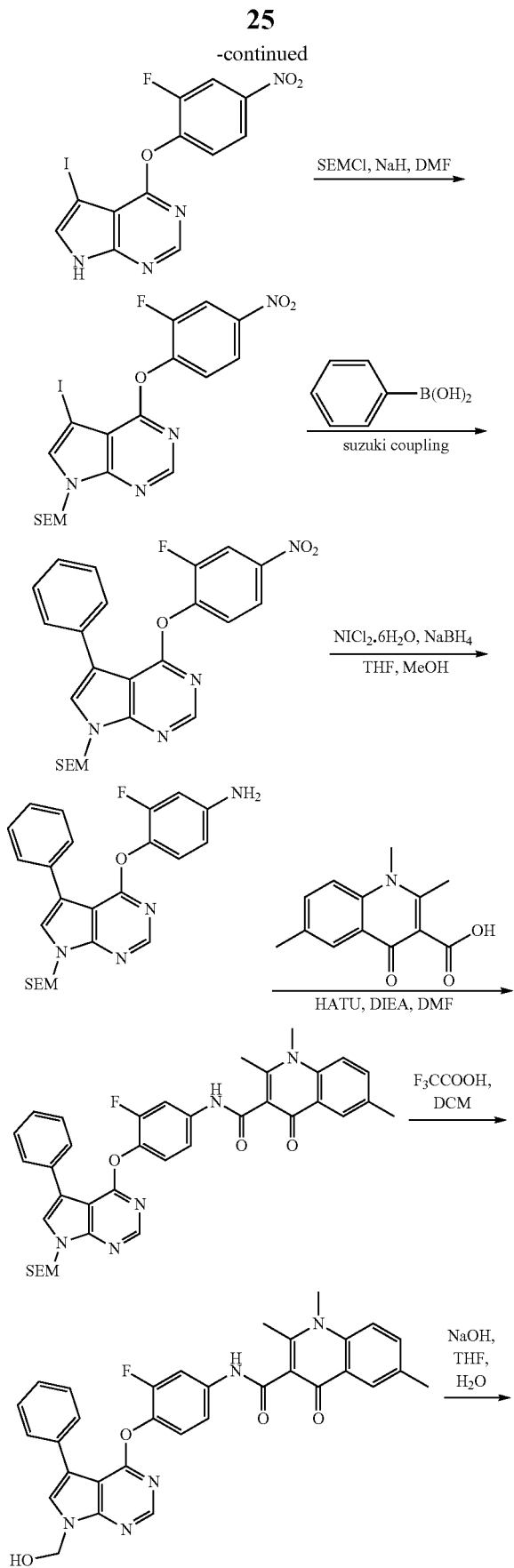

-continued

In one embodiment, the present application provides a method for treating a hyperproliferative disease or condition, such as a tumor, in humans or other mammals, using a compound of formula (I) and a pharmaceutically acceptable salt thereof.

In one embodiment, the compounds designed by the present application and pharmaceutically acceptable salts thereof may be used in the preparation of a drug for the treatment or control of gastrointestinal stromal tumor, histiocytic lymphoma, non-small cell lung cancer, small cell lung cancer, lung adenocarcinoma, lung squamous cell carcinoma, pancreatic cancer, breast cancer, prostate cancer, hepatoma, skin cancer, epithelial cancer, prostate cancer, nasopharyngeal cancer, leukemia and other hyperproliferative diseases.

In one embodiment, the compounds designed by the present application and pharmaceutically acceptable salts thereof can be used in combination with drugs which are currently used or at development phase to enhance clinical effect, such as estrogen receptor modulators, androgen receptor modulators, retinoid receptor modulators, cytotoxins/cytostatics, antiproliferatives, protein transferase inhibitors, HMG-CoA reductase inhibitors, HIV protein kinase inhibitors, reverse transcriptase inhibitors, angiogenesis inhibitors, inhibitors of cell proliferation and survival signaling, drugs that interfere with cell cycle checkpoints and inducers of apoptosis, cytotoxic drugs, tyrosine protein inhibitors, EGFR inhibitors, VEGFR inhibitors, serine/threonine protein inhibitors, Bcr-Abl inhibitors, c-Kit inhibitors, Met inhibitors, Raf inhibitors, MEK inhibitors, MMP inhibitors, topoisomerase inhibitors, histidine sirtuin inhibitors, proteasome inhibitors, CDK inhibitors, Bcl-2 family protein inhibitors, MDM2 family protein inhibitors, IAP family protein inhibitors, STAT family protein inhibitors, PI3K inhibitors, AKT inhibitors, integrin blockers, interferon-α, interleukin-12, COX-2 inhibitors, p53 activators, VEGF antibodies, and EGF antibodies.

The compounds of formula (I) and pharmaceutically acceptable salts or pharmaceutical compositions thereof disclosed in the present application are useful in the preparation of drugs for the prevention and treatment of the following diseases as well as other diseases not listed below:

(1) breast cancers in humans or other mammals, including but not limited to, invasive ductal carcinoma, invasive lobular carcinoma, ductal carcinoma in situ, and lobular carcinoma in situ;

(2) respiratory cancers in humans or other mammals, including but not limited to, small cell and non-small cell lung cancer and bronchial adenoma and pleuropulmonary blastoma;

(3) brain cancers in humans or other mammals, including but not limited to, brain stem and subocular gliomas, cerebellar and cerebral astrocytomas, ependymomas, and neuroectoderm and pineal tumors;

(4) tumors of the male and female reproductive organs in humans or other mammals, wherein the tumors of the male reproductive organs include, but are not limited to, prostate and testicular cancers; the tumors of the female reproductive organs include, but are not limited to, endometrial, cervical, ovarian, vaginal and vulvar cancers, as well as intrauterine tumors;

(5) tumors of the digestive tract in humans or other mammals, including but not limited to, anal, colon, colorectal, esophageal, gastric, pancreatic, rectal, intestinal or salivary gland cancers;

(6) tumors of the urethra in humans or other mammals, including but not limited to, bladder, penile, renal, renal pelvic, ureteral or urethral cancers;

(7) eye cancers in humans or other mammals, including but not limited to, intraocular melanomas and retinocytomas;

(8) liver cancers in humans or other mammals, including but not limited to, hepatocellular carcinomas (hepatocellularcarcinomas with or without fibrolamellar changes), cholangiocarcinomas (intrahepatic cholangiocarcinoma), and mixed hepatocellular cholangiocarcinomas;

(9) skin cancers in humans or other mammals, including but not limited to, squamous cell carcinomas, Kaposi's sarcomas, malignant melanomas, Merck cell skin cancers and non-melanoma cell carcinomas;

(10) head and neck cancers in humans or other mammals, including but not limited to, laryngeal, hypopharyngeal, nasopharyngeal, oropharyngeal, lip and oral cancers;

(11) lymphomas in humans or other mammals, including but not limited to, AIDS-related lymphomas, non-Hodgkin's lymphomas, cutaneous T-cell lymphomas, Hodgkin's lymphomas and central nervous system lymphomas;

(12) sarcomas in humans or other mammals, including but not limited to, soft tissue sarcomas, osteosarcomas, malignant fibrous histiocytomas, lymphosarcomas and rhabdomyosarcomas; and

(13) leukemias in humans or other mammals, including but not limited to, acute myeloid leukemias, acute lymphoblastic leukemias, chronic lymphoblastic leukemias, chronic myeloid leukemias, and hairy cell leukemias.

Mode of Administration and Dose Range

According to standard pharmaceutical techniques, the compounds of the present invention may be administered to a mammal, preferably a human, alone or in combination with a pharmaceutically acceptable receptor, adjuvant or diluent in a pharmaceutical composition. The compounds can be administered orally or subcutaneously, intramuscularly, intraperitoneally, intravenously, rectally and topically, ocularly, pulmonarily, nasally and parenterally.

In one embodiment, the compound of formula (I) is used to prepare a drug for the treatment or control of a patient with cancers, etc., in a dosage range of 0.1-500 mg/day/kg of body weight orally. Suitable modes of administration are single- or multi-dose (such as twice, three times and four times) administrations daily, or by means of sustained-release techniques. For many large mammals, the preferable dose range is 0.1 to 1500 mg/day/kg of body weight, preferably 0.5 to 100 mg/day/kg of body weight. For patients with an average body weight of 70 kg, their daily dose is 1 to 500 mg. For some particularly highly active compounds, adult patients may have daily doses as low as 0.1 mg/day.

Drug Metabolites and Prodrugs

The metabolites of the compounds of the present application and pharmaceutically acceptable salts thereof, as well as prodrugs that can be converted in vivo to the structures of the compounds of the present application and pharmaceutically acceptable salts thereof are also included in the claims of the present application.

Co-Administration

The compounds of formula (I) may be combined with other drugs known to treat or improve a similar condition. When administered in combination, the mode of administration and dose of the original drug remain unchanged while the compound of formula (I) is administered simultaneously or subsequently. When the compound of formula (I) is administered simultaneously with one or more other drugs, it is preferable to use a pharmaceutical composition containing both the one or more known drugs and the compound of formula (I). Co-administration also includes the administration of the compound of formula (I) and one or more other known drugs over an overlapping period of time. When the compound of formula (I) is used in combination with one or more other drugs, the doses of the compound of formula (I) or the known drugs may be lower than administered alone.

The drugs or active ingredients that can be used in combination with the compound of formula (I) include, but are not limited to:

estrogen receptor modulators, androgen receptor modulators, retinoid receptor modulators, cytotoxins/cytostatics, antiproliferatives, protein transferase inhibitors, HMG-CoA reductase inhibitors, HIV protein kinase inhibitors, reverse transcriptase inhibitors, angiogenesis inhibitors, inhibitors of cell proliferation and survival signaling, drugs that interfere with cell cycle checkpoints and inducers of apoptosis, cytotoxic drugs, tyrosine protein inhibitors, EGFR inhibitors, VEGFR inhibitors, serine/threonine protein inhibitors, Bcr-Abl inhibitors, c-Kit inhibitors, Met inhibitors, Raf inhibitors, MEK inhibitors, MMP inhibitors, topoisomerase inhibitors, histidine sirtuin inhibitors, proteasome inhibitors, CDK inhibitors, Bcl-2 family protein inhibitors, MDM2 family protein inhibitors, IAP family protein inhibitors, STAT family protein inhibitors, PI3K inhibitors, AKT inhibitors, integrin blockers, interferon-α, interleukin-12, COX-2 inhibitors, p53, p53 activators, VEGF antibodies, EGF antibodies, etc.

In one embodiment, the drugs or active ingredients that can be used in combination with the compound of formula (I) include, but is not limited to, aldesleukin, alendronic acid, interferon, aqunoin, allopurinol, sodium allopurinol, palonosetron hydrochloride, altretamine, aminoglutethimide, amifostine, amrubicin, amsacrine, arimidex, dolasetron, aranesp, arglabin, arsenic trioxide, aromasin, 5-azacytidine, azathioprine, bacille calmette-guerin or tice bacille calmette-guerin, bestatin, betamethasone acetate, betamethasone sodium phosphate preparations, bexarotene, bleomycin sulfate, bromouridine, bortezomib, busulfan, calcitonin, alemtuzumab injection, capecitabine, carboplatin, casodex, cefesone, celmoleukin, daunorubicin, chlorambucil, cisplatin, cladribine, cladribine, clodronic acids, cyclophosphamide, cytosine arabinoside, dacarbazine, actinomycin D, daunorubicin liposomes, dexamethasone, dexamethasone phosphate, estradiol valerate, denileukin diftitox 2, depo-medrol, deslorelin, dexrazoxane, diethylstilbestrol, diflucan, docetaxel, doxifluridine, doxorubicin, dronabinol, chin-166-chitosan complex, eligard, rasburicase, epirubicin hydrochloride, aprepitant, epirubicin, epoetin alfa, erythropoietin, eptaplatin, levamisole tablets, estradiol preparations, 17-β- estradiol, estramustine sodium phosphate, ethinylestradiol, amifostine, hydroxyphosphates, etopophos, etoposide, fadrozole, tamoxifen preparations, filgrastim, finasteride, filesteride, floxuridine, fluconazole, fludarabine, 5-fluorodeoxyuridine monophosphate, 5-fluorouracil, fluoxymesterone, flutamide, fumistan, 1-β-D-arabinofuranosecytosine-5'-stearyl phosphate, fotemustine, fulvestrant, gamma globulin, gemcitabine, gemtuzumab, imatinib mesylate, carmustine glutinous rice paper capsules, goserelin, granitelon hydrochloride, histrelin, hycamtin, hydrocortisone, erythro-hydroxynonyladenine, hydroxyurea, ibritumomab tiuxetan, idarubicin, ifosfamide, interferon α, interferon-α2, interferon α-2A, interferon α-2B, interferon α-n1, interferon α-n3, interferon β, interferon γ-1a, interleukin-2, intron A, iressa, irinotecan, kytril, lentinan sulfate, letrozole, leucovorin, leuprolide, leuprorelin acetate, levamisole, levofolic acid calcium salts, levothyroxine, levothyroxine preparations, lomustine, lonidamine, dronabinol, mechlorethamine, mecobalamin, medroxyprogesterone acetate, megestrol acetate, melphalan, esterified estrogen, 6-mercaptopurine, mesna, methotrexate, methyl aminolevulinate, miltefosine, minocycline, mitomycin C, mitotane, mitoxantrone, trilostane, doxorubicin citrate liposomes, nedaplatin, pegylated filgrastim, oprelvekin, nilutamide, Tamoxifen, NSC-631570, recombinant human interleukin 1-3, octreotide, ondansetron hydrochloride, dehydro-hydrocortisone oral solution, oxaliplatin, paclitaxel, prednisone sodium phosphate preparations, pegaspargase, pegasys, pentostatin, picibanil preparations, pilocarpine hydrochloride, pirarubicin, plicamycin, porfimer sodium, prednimustine, prednisolone steaglate, prednisone, premarin, procarbadqi, recombinant human erythropoietin, raltitrexed, rebif, rhenium-186 etidronate, rituximab, redoxon-A, romurtide, pilocarpine hydrochloride tablets, octreotide, sargramostim, semustine, sizofiran, sobuzoxane, methylprednisolone sodium, paphos acids, stem cell therapy, streptozocin, strontium chloride-89, Levothyroxine sodium, tamoxifen, tamsulosin, tasunaming, tastolactone, taxotere, teceleukin, temozolomide, teniposide, testosterone propionate, methyltestosterone, thioguanine, thiotepa, thyrotropin, tiludronic acid, topotecan, toremifene, tositumomab, trastuzumab, treosulfan, tretinoin, methotrexate tablets, trimethylmelamine, trimetrexate, triptorelin acetate, triptorelin pamoate, UFT, uridine, valrubicin, vesnarinone, vinblastine, vincristine, vindesine, vinorelbine, virulizin, dexrazoxane, zinostatin stimalamer, ondansetron, paclitaxel protein stable preparations, acolbifene, interferon r-1b, affinitak, aminopterin, arzoxifene, asoprisnil, atamestane, atrasentan, BAY 43-9006, avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implants, holmium-166 DOTMP, ibandronic acid, interferon γ, intron-PEG, ixabepilone, keyhole limpet hemocyanin, L-651582, lanreotide, lasofoxifene, libra, lonafamib, miproxifene, minocolate, MS-209, liposomal MTP-PE, MX-6, nafarelin, nemorubicin, neovastat, nolatrexed, genasense, onco-TCS, osidem, paclitaxel polyglutamate, sodium palatinate, PN-401, QS-21, Quazepam, R-1549, raloxifene, onconase, 13-cis-retinoic acid, satraplatin, seocalcitol, T-138067, tarceva, docosahexaenoic acid paclitaxel, thymosin α1, galazolin, tipifarnib, tirapazamine, TLK-286, toremifene, trans MID-lo7R, valspodar, vapreotide, vatalanib, verteporfin, vinflunine, Z-100 and zoledronic acid, or a combination thereof.

The reagents used in the following embodiments are all commercially available.

Embodiment 1: Preparation of N-(3-fluoro-4-(5-phenyl-7H-pyrrolo[2,3-d]pyrimidin-4-yloxy)phenyl)-1,2,6-trimethyl-4-oxo-1,4-dihydroquinoline-3-carboxamide (named as TL50115)

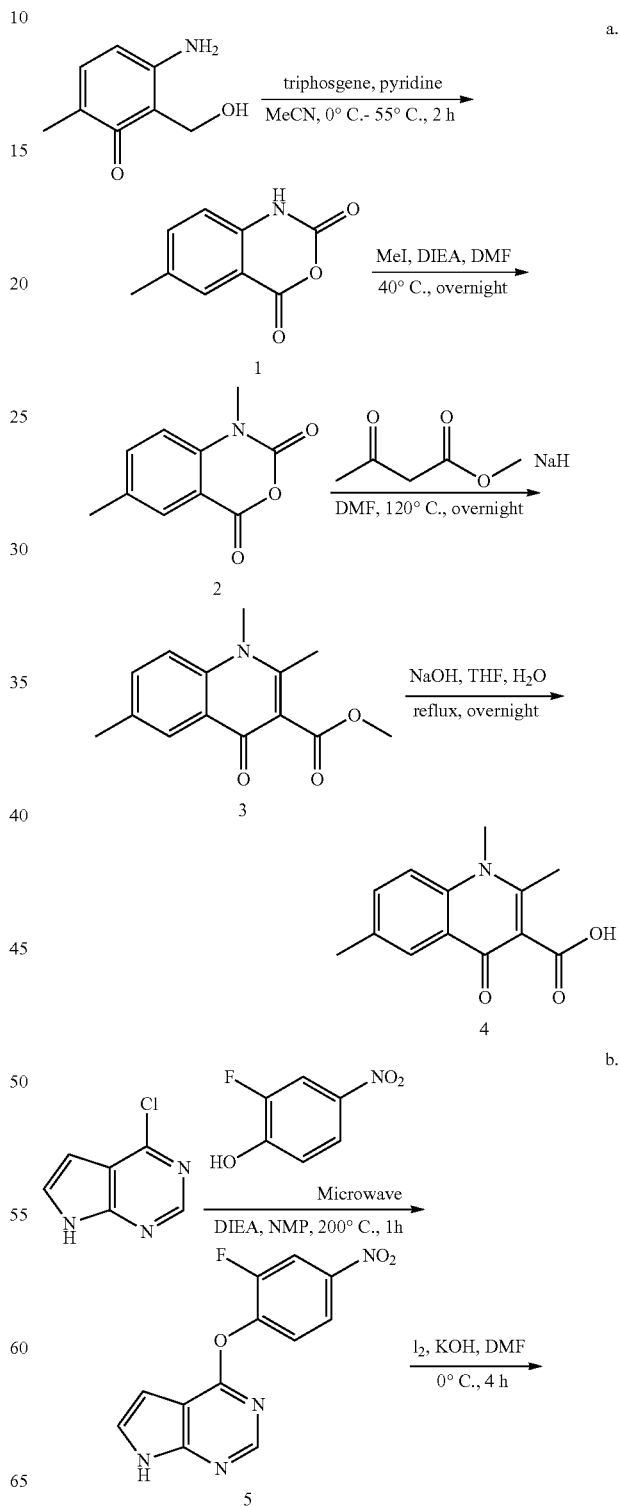

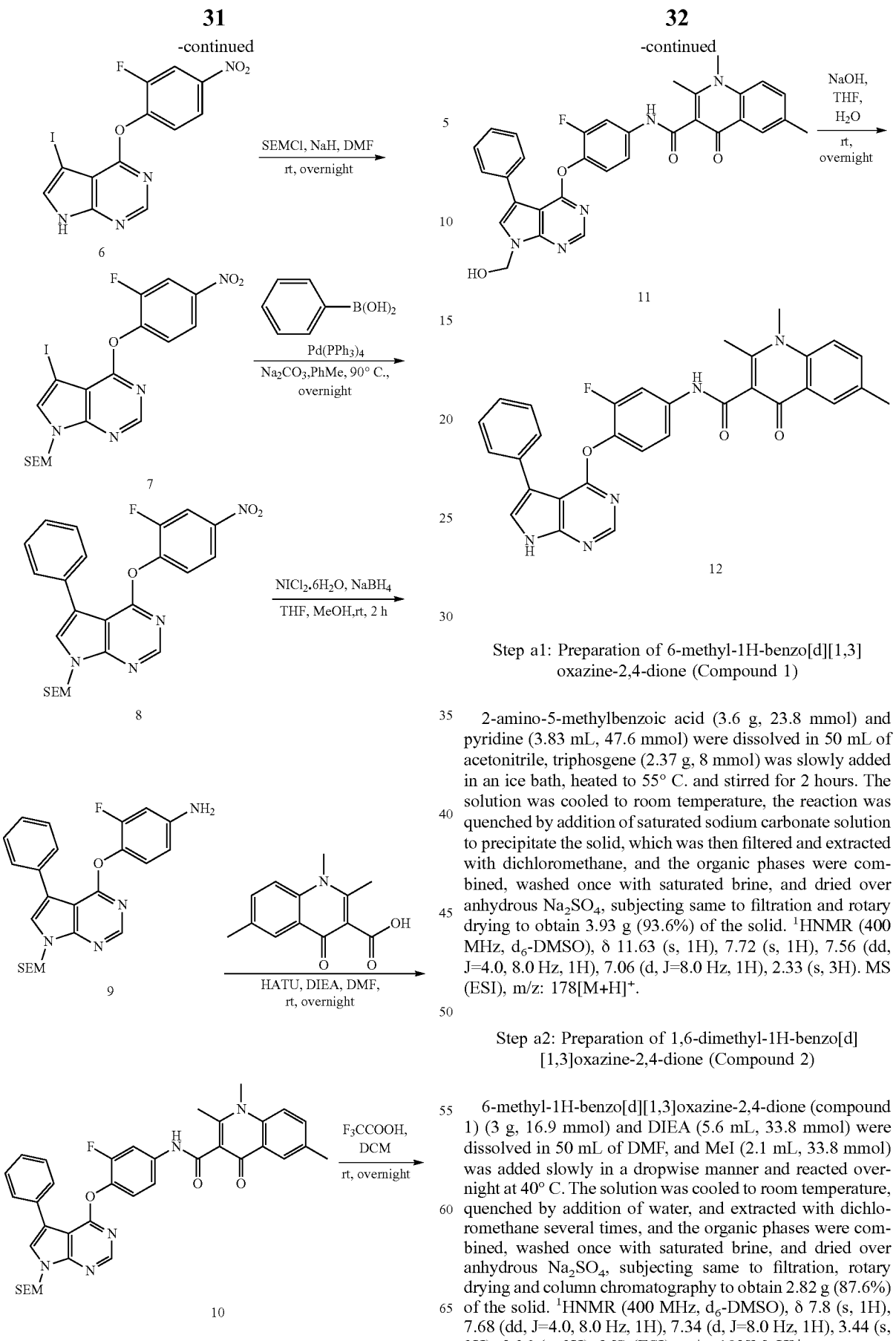

Step a1: Preparation of 6-methyl-1H-benzo[d][1,3]oxazine-2,4-dione (Compound 1)

2-amino-5-methylbenzoic acid (3.6 g, 23.8 mmol) and pyridine (3.83 mL, 47.6 mmol) were dissolved in 50 mL of acetonitrile, triphosgene (2.37 g, 8 mmol) was slowly added in an ice bath, heated to 55° C. and stirred for 2 hours. The solution was cooled to room temperature, the reaction was quenched by addition of saturated sodium carbonate solution to precipitate the solid, which was then filtered and extracted with dichloromethane, and the organic phases were combined, washed once with saturated brine, and dried over anhydrous $Na_2SO_4$, subjecting same to filtration and rotary drying to obtain 3.93 g (93.6%) of the solid. $^1$HNMR (400 MHz, $d_6$-DMSO), δ 11.63 (s, 1H), 7.72 (s, 1H), 7.56 (dd, J=4.0, 8.0 Hz, 1H), 7.06 (d, J=8.0 Hz, 1H), 2.33 (s, 3H). MS (ESI), m/z: 178[M+H]$^+$.

Step a2: Preparation of 1,6-dimethyl-1H-benzo[d][1,3]oxazine-2,4-dione (Compound 2)

6-methyl-1H-benzo[d][1,3]oxazine-2,4-dione (compound 1) (3 g, 16.9 mmol) and DIEA (5.6 mL, 33.8 mmol) were dissolved in 50 mL of DMF, and MeI (2.1 mL, 33.8 mmol) was added slowly in a dropwise manner and reacted overnight at 40° C. The solution was cooled to room temperature, quenched by addition of water, and extracted with dichloromethane several times, and the organic phases were combined, washed once with saturated brine, and dried over anhydrous $Na_2SO_4$, subjecting same to filtration, rotary drying and column chromatography to obtain 2.82 g (87.6%) of the solid. $^1$HNMR (400 MHz, $d_6$-DMSO), δ 7.8 (s, 1H), 7.68 (dd, J=4.0, 8.0 Hz, 1H), 7.34 (d, J=8.0 Hz, 1H), 3.44 (s, 3H), 2.36 (s, 3H). MS (ESI), m/z: 192[M+H]$^+$.

Step a3: Preparation of methyl 1,2,6-trimethyl-4-oxo-1,4-dihydroquinoline-3-carboxylate (Compound 3)

Methyl acetoacetate (1.94 mL, 18 mmol) was dissolved in 50 mL of DMF, and NaH (60%) (720 mg, 18 mmol) was added slowly in an ice bath and reacted at room temperature for 30 min, and 1,6-dimethyl-1H-benzo[d][1,3]oxazine-2,4-dione (compound 2) (2.86 g, 15 mmol) was added with stirring, and reacted overnight at 120° C. The solution was cooled to room temperature, quenched by addition of water, and extracted with dichloromethane several times, and the organic phases were combined, washed once with saturated brine, and dried over anhydrous $Na_2SO_4$, subjecting same to filtration, rotary drying and column chromatography to obtain 3 g (81.7%) of the solid. $^1$HNMR (400 MHz, $d_6$-DMSO), δ 7.95 (s, 1H), 7.74 (d, J=8.0 Hz, 1H), 7.58 (dd, J=4.0, 8.0 Hz, 1H), 3.77 (s, 3H), 3.75 (s, 3H), 2.44 (s, 3H), 2.42 (s, 3H). MS (ESI), m/z: 246[M+H]$^+$.

Step a4: Preparation of 1,2,6-trimethyl-4-oxo-1,4-dihydroquinoline-3-carboxylic acid (Compound 4)

Methyl 1,2,6-trimethyl-4-oxo-1,4-dihydroquinoline-3-carboxylate (compound 3) (3 g, 12.2 mmol) and NaOH (1.95 g, 48.8 mmol) were dissolved in 40 mL of THF and 20 mL of water, and refluxed and reacted overnight. The solution was cooled to room temperature, the majority of the organic solvent was spun to dryness, ice water was added, the pH was adjusted to 7-8 with dilute HCl to precipitate the solid, which was then filtered and drained to obtain 2.6 g (92.8%) of a white solid. $^1$H NMR (400 MHz, $d_6$-DMSO), δ 8.16 (s, 1H), 7.99 (d, J=8.0 Hz, 1H), 7.58 (d, J=8.0 Hz, 1H), 3.96 (s, 3H), 3.11 (s, 3H), 2.49 (s, 3H). MS (ESI), m/z: 232[M+H]$^+$.

Step b1: Preparation of 4-(2-fluoro-4-nitrophenoxy)-7H-pyrrolo[2,3,-d]pyrimidine (Compound 5)

4-Chloropyrrolopyrimidine (7.68 g, 50 mmol), 2-fluoro-4-nitrophenol (11 g, 70 mmol) and DIEA (11.57 mL, 70 mmol) were dissolved in 80 mL of N-methylpyrrolidone and reacted at 200° C. for 1 hour in a microwave reactor. The solution was cooled to room temperature, water was added to precipitate a yellow solid, which was filtered, washed twice with water and extracted with dichloromethane several times, and the organic phases were combined, washed once with saturated brine, and dried over anhydrous $Na_2SO_4$, then subjecting same to filtration and rotary drying to obtain 11.65 g (85%) of a yellow brown solid. $^1$HNMR (400 MHz, $d_6$-DMSO), δ 12.42 (s, 1H), 8.38 (dd, J=2.8, 10.4 Hz, 1H), 8.33 (s, 1H), 8.22 (t, J=1.2 Hz, 1H), 8.20 (t, J=1.2 Hz, 1H), 7.81-7.77 (m, 1H), 7.58 (t, J=2.8 Hz, 1H), 6.68 (dd, J=1.6, 3.6 Hz, 1H). MS (ESI), m/z: 275[M+H]$^+$.

Step b2: Preparation of 4-(2-fluoro-4-nitrophenoxy)-5-iodo-7H-pyrrolo[2,3-d]pyrimidine (Compound 6)

4-(2-fluoro-4-nitrophenoxy)-7H-pyrrolo[2,3,-d]pyrimidine (compound 5) (11 g, 40 mmol) and KOH (6.72 g, 120 mmol) were dissolved in 200 mL of DMF, iodine (15.22 g, 60 mmol) was added in an ice bath and stirred at 0° C. for 4 hours. To the reaction solution was added ice water to precipitate a yellow solid, which was filtered, the solid was washed twice with water and extracted with dichloromethane several times, and the organic phases were combined, washed once with saturated brine, and dried over anhydrous $Na_2SO_4$, then subjecting same to filtration and rotary drying to obtain 14 g (87.5%) of a yellow solid. $^1$HNMR (400 MHz, $d_6$-DMSO), δ 12.74 (s, 1H), 8.38 (dd, J=2.4, 10.0 Hz, 1H), 8.34 (s, 1H), 8.21 (dd, J=1.2, 8.8 Hz, 1H), 7.80 (m, 2H). MS (ESI), m/z: 400[M+H]$^+$.

Step b3: Preparation of 4-(2-fluoro-4-nitrophenoxy)-5-iodo-7((2-trimethylsilyl)ethoxy)methyl)-7H-pyrrolo[2,3-d]pyrimidine (Compound 7)

4-(2-fluoro-4-nitrophenoxy)-5-iodo-7H-pyrrolo[2,3-d]pyrimidine (compound 6) (12 g, 30 mmol) was dissolved in 200 mL of DMF, NaH (1.32 g, 33 mmol) was added to an ice bath and the mixture was stirred for 15 min in the ice bath, 2-(trimethylsilyl)ethoxymethyl chloride (5.84 mL, 33 mmol) was added dropwise to the reaction solution, which was stirred overnight at room temperature. The mixture was quenched with ice water, extracted with dichloromethane three times, washed once with saturated brine, dried over anhydrous $Na_2SO_4$, subjecting same to filtration, rotary drying and column chromatography to give 13.2 g (83%) of a white solid. $^1$H NMR (400 MHz, $d_6$-DMSO) δ 8.43 (s, 1H), 8.39 (dd, J=2.8, 10.4 Hz, 1H), 8.22 (m, 1H), 8.00 (s, 1H), 7.82 (t, J=8.4 Hz, 1H), 5.61 (s, 2H), 3.54 (t, J=8.0 Hz, 2H), 0.84 (t, J=8.0 Hz, 2H), −0.08 (s, 9H). MS (ESI), m/z 531[M+H]$^+$.

Step b4: Preparation of 4-(2-fluoro-4-nitrophenoxy)-5-phenyl-7-((2-(trimethylsilyl)ethoxy)methyl)-7H-pyrrolo[2,3-d]pyrimidine (Compound 8)

4-(2-fluoro-4-nitrophenoxy)-5-phenyl-7-((2-(trimethylsilyl)ethoxy)methyl)-7H-pyrrolo[2,3-d]pyrimidine (compound 7) (12 g, 22.7 mmol), phenylboronic acid (3.32 g, 27.24 mmol), palladium tetrakistriphenylphosphine (1.31 g, 1.14 mmol) and sodium carbonate (7.22 g, 68.1 mmol) were dissolved in 200 mL of toluene and reacted overnight at 90° C. under Ar protection. The solution was cooled to room temperature and filtrated, the filtrate was extracted with dichloromethane several times, and the organic phases were combined, washed once with saturated brine, and dried over anhydrous $Na_2SO_4$, subjecting same to filtration, rotary drying and column chromatography to obtain 8.3 g (76.4%) of a yellow solid. $^1$H NMR (400 MHz, $d_6$-DMSO), δ 8.45 (s, 1H), 8.37 (dd, J=2.8, 10.0 Hz, 1H), 8.21 (m, 1H), 8.01 (s, 1H), 7.86-7.83 (m, 1H), 7.76 (m, 2H), 7.43 (m, 1H), 7.31 (m, 1H), 5.70 (s, 2H), 3.61 (t, J=8.0 Hz, 2H), 0.86 (t, J=8.0 Hz, 2H), −0.08 (s, 9H). MS (ESI), m/z: 481.17[M+H]$^+$.

Step b5: Preparation of 3-fluoro-4-(5-phenyl-7-((2-(trimethylsilyl)ethoxy)methyl)-7H-pyrrolo[2,3-d]pyrimidin-4-yl)oxy)aniline (Compound 9)

4-(2-fluoro-4-nitrophenoxy)-5-phenyl-7-((2-(trimethylsilyl)ethoxy)methyl)-7H-pyrrolo[2,3-d]pyrimidine (compound 8) (8 g, 16.6 mmol) and nickel chloride hexahydrate (394 mg, 1.66 mmol) were dissolved in 90 mL of THF and 30 mL of methanol, and sodium borohydride (3.77 g, 99.6 mmol) was slowly added in an ice bath and stirred at room temperature for 2 hours. The solution was quenched by addition of water and filtered, and extracted with dichloromethane after the organic solvent was spun to dryness, and the organic phases were combined, washed once with saturated brine, and dried over anhydrous $Na_2SO_4$, subjecting same to filtration, rotary drying and column chromatography to obtain 5.32 g (71.2%) of a yellow solid. $^1$H NMR (400

MHz, d$_6$-DMSO), δ 8.39 (s, 1H), 7.89 (s, 1H), 7.74 (m, 2H), 7.41 (t, J=7.6 Hz, 2H), 7.29 (t, J=7.6 Hz, 1H), 7.01 (t, J=8.8 Hz, 1H), 6.47 (dd, J=2.4, 12.8 Hz, 1H), 6.39 (dd, J=2.0, 8.8 Hz, 1H), 5.66 (s, 2H), 3.59 (t, J=8.0 Hz, 2H), 0.85 (t, J=8.0 Hz, 2H), −0.08 (s, 9H). MS (ESI), m/z: 451[M+H]$^+$.

Step b6: Preparation of N-(3-fluoro-4-((5-phenyl-7-((2-trimethylsilyl)ethoxy)methyl)-7H-pyrrolo[2,3-d]pyrimidin-4-yl)oxy)phenyl)-1,2,6-trimethyl-4-oxo-1,4-dihydroquinoline-3-carboxamide (Compound 10)

3-fluoro-4-(5-phenyl-7-((2-(trimethylsilyl)ethoxy)methyl)-7H-pyrrolo[2,3-d]pyrimidin-4-yl)oxy)aniline (compound 9) (450 mg, 1 mmol), 1,2,6-trimethyl-4-oxo-1,4-dihydroquinoline-3-carboxylic acid (compound 4) (277 mg, 1.2 mmol), HATU (570 mg, 1.5 mmol), and DIEA (0.5 mL, 3 mmol) were dissolved in 30 mL of DMF and stirred overnight at room temperature. To the reaction solution was added ice water to precipitate the solid and filtrated, the solid was extracted twice with dichloromethane, and the organic phases were combined, washed once with saturated brine, and dried over anhydrous Na$_2$SO$_4$, subjecting same to filtration, rotary drying and column chromatography to obtain 478 mg (72%) of a white solid. $^1$HNMR (400 MHz, d$_6$-DMSO), δ 11.01 (s, 1H), 8.43 (s, 1H), 8.07 (s, 1H), 7.95 (s, 2H), 7.94-7.90 (dd, J=2.0, 8.8 Hz, 2H), 7.82-7.77 (m, 3H), 7.63 (dd, J=2.0, 8.8 Hz, 1H), 7.48-7.40 (m, 4H), 7.34 (m, 1H), 5.70 (s, 2H), 3.84 (s, 3H), 3.62 (t, J=8.0 Hz, 2H), 2.74 (s, 3H), 2.46 (s, 3H), 0.88 (t, J=8.0 Hz, 2H), −0.06 (s, 9H). MS (ESI), m/z: 664[M+H]$^+$.

Step b7: Preparation of N-(3-fluoro-4-((7-(hydroxylmethyl)-5-phenyl)-7H-pyrrolo[2,3-d]pyrimidin-4-yl)oxy)phenyl)-1,2,6-trimethyl-4-oxo-1,4-dihydroquinoline-3-carboxamide (Compound 11)

N-(3-fluoro-4-((5-phenyl-7-((2-trimethylsilyl)ethoxy)methyl)-7H-pyrrolo[2,3-d]pyrimidin-4-yl)oxy)phenyl)-1,2,6-trimethyl-4-oxo-1,4-dihydroquinoline-3-carboxamide (compound 10)(400 mg, 0.6 mmol) was dissolved in 30 mL of dichloromethane, 3 mL of trifluoroacetic acid was added dropwise, and stirred overnight at room temperature. The majority of the solvent was spun to dryness, the solid was precipitated by addition of water, filtered and washed with dichloromethane and methanol to obtain 300 mg (88.75%) of a white solid. $^1$HNMR (400 MHz, d$_6$-DMSO), δ 11.00 (s, 1H), 8.41 (s, 1H), 8.07 (s, 1H), 7.89 (d, J=12.0 Hz, 2H), 7.85 (s, 1H), 7.81-7.76 (m, 1H), 7.63 (d, J=8 Hz, 1H), 7.47-7.39 (m, 4H), 7.31 (t, J=8.0 Hz, 1H), 5.68 (s, 2H), 3.83 (s, 3H), 2.64 (s, 3H), 2.46 (s, 3H). MS (ESI), m/z: 564[M+H]$^+$.

Step b8: Preparation of N-(3-fluoro-4-((phenyl-7H-pyrrolo[2,3-d]pyrimidin-4-yl)oxy)phenyl)-1,2,6-trimethyl-4-oxo-1,4-dihydroquinoline-3-carboxamide (compound 12, TL50115)

N-(3-fluoro-4-((7-(hydroxylmethyl)-5-phenyl)-7H-pyrrolo[2,3-d]pyrimidin-4-yl)oxy)phenyl)-1,2,6-trimethyl-4-oxo-1,4-dihydroquinoline-3-carboxamide (compound 11) (250 mg, 0.44 mmol) was dissolved in 10 mL of THF and 8 mL of water, NaOH (71 mg, 1.76 mmol) was added and stirred overnight at room temperature. The majority of the solvent was spun to dryness, the precipitated solid was washed with water and methanol, respectively, and filtered to obtain 220 mg (94%) of a white solid. $^1$H NMR (500 MHz, d$_6$-DMSO) δ 12.52 (s, 1H), 11.00 (s, 1H), 8.33 (s, 1H), 8.05 (s, 1H), 7.91 (d, J=13.0 Hz, 1H), 7.79-7.75 (m, 4H), 7.61 (d, J=8.5 Hz, 1H), 7.46 (d, J=8.5 Hz, 1H), 7.41 (m, 3H), 7.27 (t, J=7.0 Hz, 1H), 3.81 (s, 3H), 2.63 (s, 3H), 2.45 (s, 3H). $^{13}$C NMR (125 MHz, d$_6$-DMSO) δ 174.0, 166, 161.7, 154.6, 154.1 (d, J=247.5 Hz, 1C), 152.9, 150.6, 139.5, 138.4 (d, J=9.0 Hz, 1C), 135.1 (d, J=12.8 Hz, 1C), 134.5, 134.4, 133.8, 128.8, 128.6, 126.7, 126.2, 125.5, 124.8, 124.1, 118.6, 117.3, 116.1, 116.0 (d, J=1.9 Hz, 1C), 108.1 (d, J=23.1 Hz, 1C), 102.4, 35.6, 20.8, 19.4. HRMS (ESI) Calcd for [M+H]$^+$=534.1936, found: [M+H]$^+$=534.1934. HPLC analysis: MeOH—H$_2$O (75:25), 4.92 min, 95.33%.

Embodiment 2: Preparation of 6-chloro-N-(3-fluoro-4-((3-phenyl-1H-pyrazolo[3,4-b]pyridin-4-yl)oxy)phenyl)-1,2-dimethyl-4-oxo-1,4-dihydroquinoline-3-carboxamide (named as TL50025)

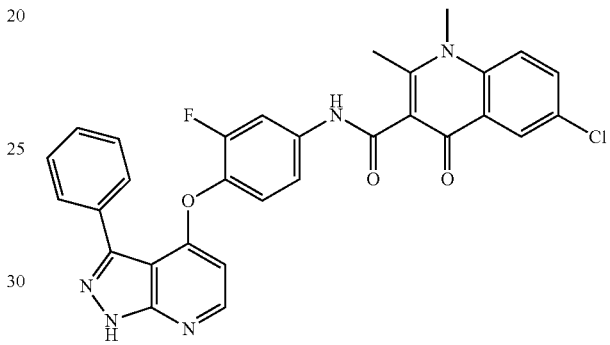

The synthetic method is as shown in Embodiment 1.

HRMS (ESI) Calcd for [M+H]$^+$=554.1390, found: [M+H]$^+$=554.1386.

Embodiment 3: Preparation of N-(4-((7H-pyrrolo[2,3-d]pyrimidin-4-yl)oxy)-3-fluorophenyl)-6-chloro-1,2-dimethyl-4-oxo-1,4-dihydroquinoline-3-carboxamide (named as TL50046)

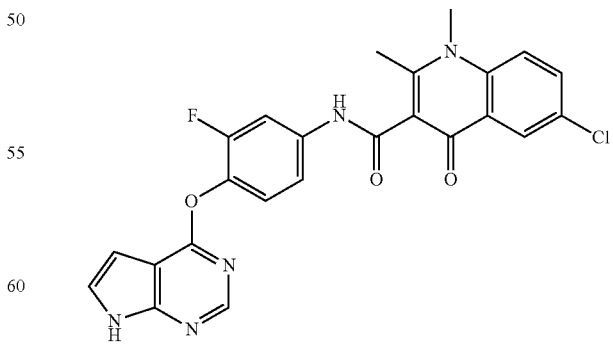

The synthetic method is as shown in Embodiment 1.

MS (ESI) m/z 479[M+H]$^+$. HPLC analysis: MeOH—H$_2$O (85:15), 3.78 min, 98.23%.

Embodiment 4: Preparation of 6-chloro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL50053)

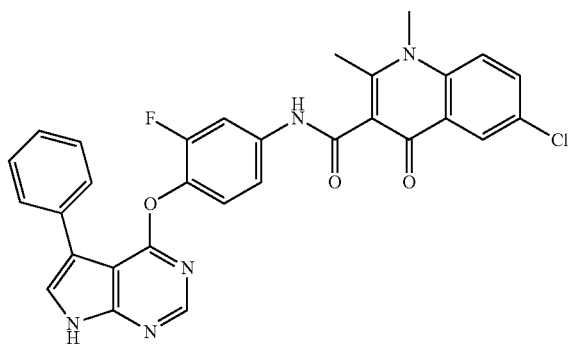

The synthetic method is as shown in Embodiment 1.

$^1$H NMR (500 MHz, d$_6$-DMSO) δ 12.53 (s, 1H), 10.80 (s, 1H), 8.33 (s, 1H), 8.15 (d, J=2.5 Hz, 1H), 7.93-7.89 (m, 2H), 7.81 (dd, J=2.5, 9.0 Hz, 1H), 7.77 (m, 3H), 7.46 (dd, J=1.5, 9.0 Hz, 1H), 7.43-7.39 (m, 3H), 7.27 (t, J=7.5 Hz, 1H), 3.83 (s, 3H), 2.62 (s, 3H).

$^{13}$C NMR (125 MHz, d$_6$-DMSO) δ 172.7, 165.6, 161.7, 154.6, 154.1 (d, J=242.9 Hz, 1C), 152.7, 150.7, 150.5, 140.1, 138.4 (d, J=9.8 Hz, 1C), 135.2 (d, J=13.0 Hz, 1C), 134.6, 132.9, 129.2, 128.9, 128.7, 127.4, 126.8, 125.0, 124.8, 124.2, 120.4, 120.2, 116.0 (d, J=2.5 Hz, 1C), 108.0 (d, J=23.2 Hz, 1C), 102.3, 35.9, 19.5.

HRMS (ESI) for C$_{30}$H$_{21}$ClFN$_5$O$_3$[M+H]$^+$, calcd: 554.1390, found: 554.1386.

HPLC analysis: MeOH—H$_2$O (75:25), 5.18 min, 95.02%

Embodiment 5: Preparation of N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL50054)

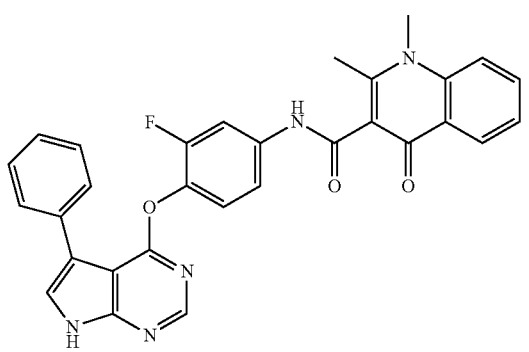 [SMILES: Cc1c(C(=O)Nc2ccc(Oc3ncnc4[nH]cc(-c5ccccc5)c34)c(F)c2)c(=O)c2ccccc2n1C]

The synthetic method is as shown in Embodiment 1.

$^1$H NMR (500 MHz, d$_6$-DMSO) δ 10.91 (s, 1H), 8.32 (s, 1H), 8.25 (dd, J=1.0, 8.0 Hz, 1H), 7.91-7.87 (m, 2H), 7.80 (dd, J=1.5, 7.0 Hz, 1H), 7.76 (d, J=7.5 Hz, 2H), 7.74 (s, 1H), 7.48-7.44 (m, 2H), 7.42-7.38 (m, 3H), 7.26 (t, J=7.0 Hz, 1H), 3.83 (s, 3H), 2.62 (s, 3H).

$^{13}$C NMR (125 MHz, d$_6$-DMSO) δ 174.0, 166.0, 161.7, 154.8, 154.1 (d, J=242.6 Hz, 1C), 152.6, 150.6, 141.4, 138.5 (d, J=9.5 Hz, 1C), 135.1 (d, J=12.8 Hz, 1C), 134.7, 133.2, 128.9, 128.7, 126.7, 126.3, 126.1, 124.9, 124.5, 124.3, 119.7, 117.5, 116.0 (d, J=5.6 Hz, 1C), 108.0 (d, J=23.4 Hz, 1C), 102.3, 35.6, 30.9, 19.6.

HRMS (ESI) for C$_{30}$H$_{22}$FN$_5$O$_3$[M+H]$^+$, calcd: 520.1779, found: 520.1778.

HPLC analysis: MeOH—H$_2$O (80:20), 7.00 min, 99.44% purity.

Embodiment 6: Preparation of 7-chloro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL50080)

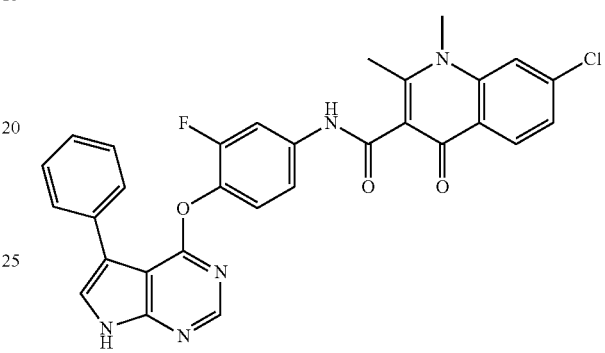

The synthetic method is as shown in Embodiment 1.

$^1$H NMR (500 MHz, d$_6$-DMSO) δ 12.53 (s, 1H), 10.80 (s, 1H), 8.33 (s, 1H), 8.15 (d, J=2.5 Hz, 1H), 7.93-7.89 (m, 2H), 7.81 (dd, J=2.5, 9.0 Hz, 1H), 7.77 (m, 3H), 7.46 (dd, J=1.5, 9.0 Hz, 1H), 7.43-7.39 (m, 3H), 7.27 (t, J=7.5 Hz, 1H), 3.83 (s, 3H), 2.62 (s, 3H).

$^{13}$C NMR (125 MHz, d$_6$-DMSO) δ 172.7, 165.6, 161.7, 154.6, 154.1 (d, J=242.9 Hz, 1C), 152.7, 150.7, 150.5, 140.1, 138.4 (d, J=9.8 Hz, 1C), 135.2 (d, J=13.0 Hz, 1C), 134.6, 132.9, 129.2, 128.9, 128.7, 127.4, 126.8, 125.0, 124.8, 124.2, 120.4, 120.2, 116.0 (d, J=2.5 Hz, 1C), 108.0 (d, J=23.2 Hz, 1C), 102.3, 35.9, 19.5.

HRMS (ESI) for C$_{30}$H$_{21}$ClFN$_5$O$_3$[M+H]$^+$, calcd: 554.1390, found: 554.1386.

HPLC analysis: MeOH—H$_2$O (75:25), 5.18 min, 95.02% purity.

Embodiment 7: Preparation of 5-chloro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL50081)

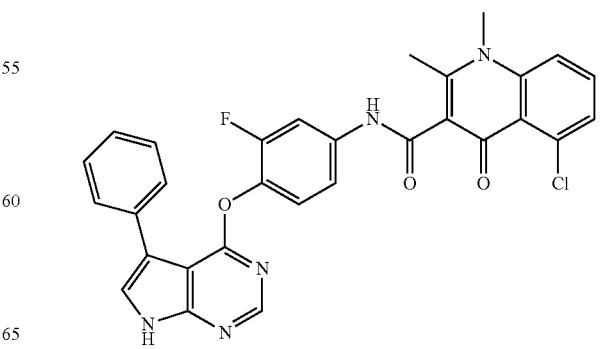

The synthetic method is as shown in Embodiment 1.

$^1$H NMR (500 MHz, d$_6$-DMSO) δ 10.61 (s, 1H), 8.31 (s, 1H), 7.88 (d, J=12.5 Hz, 1H), 7.82 (d, J=9.0 Hz, 1H), 7.78-7.75 (m, 3H), 7.69-7.66 (t, J=8.0 Hz, 1H), 7.46-7.39 (m, 5H), 7.25 (t, J=7.5 Hz, 1H), 3.78 (s, 3H), 2.54 (s, 3H).

$^{13}$C NMR (125 MHz, d$_6$-DMSO) δ 173.3, 165.8, 161.7, 155.1, 154.1 (d, J=242.5 Hz, 1C), 150.4, 150.2, 144.1, 138.4 (d, J=10.4 Hz, 1C), 135.2 (d, J=12.5 Hz, 1C), 134.8, 133.2, 132.5, 128.8, 128.7, 127.1, 126.6, 125.0, 122.7, 122.5, 116.9, 115.9, 107.9 (d, J=23.1 Hz, 1C), 102.4, 36.5, 19.3.

HRMS (ESI) for C$_{30}$H$_{21}$ClFN$_5$O$_3$[M+H]$^+$, calcd: 554.1390, found: 554.1389.

HPLC analysis: MeOH—H$_2$O (85:15), 4.30 min, 97.76% purity.

Melting point: 269.4° C.-271.1° C.

Embodiment 8: Preparation of N-(3-fluoro-4-(5-phenyl-7H-pyrrolo[2,3-d]pyrimidin-4-yloxy)phenyl)-1,2-dimethyl-4-oxo-7-(trifluoromethyl)-1,4-dihydroquinoline-3-carboxamide (named as TL50086)

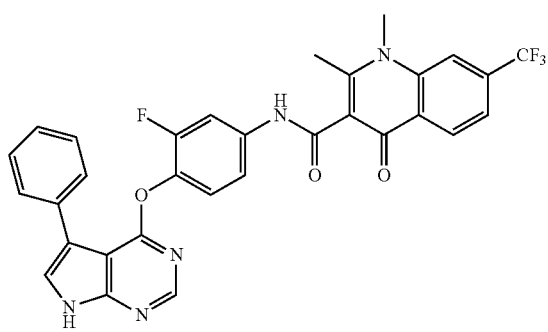 [SMILES: Cc1c(C(=O)Nc2ccc(Oc3ncnc4[nH]cc(-c5ccccc5)c34)c(F)c2)c(=O)c2ccc(C(F)(F)F)cc2n1C]

The synthetic method is as shown in Embodiment 1.
MS (ESI) m/z 588 [M+H]$^+$.

Embodiment 9: Preparation of 6-fluoro-N-(3-fluoro-4-(5-phenyl-7H-pyrrolo[2,3-d]pyrimidin-4-yloxy)phenyl)-1,2-dimethyl-4-oxo-1,4-hydroquinoline-3-carboxamide (named as TL50087)

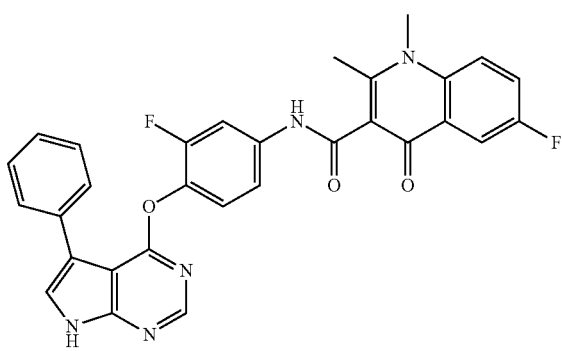 [SMILES: Cc1c(C(=O)Nc2ccc(Oc3ncnc4[nH]cc(-c5ccccc5)c34)c(F)c2)c(=O)c2cc(F)ccc2n1C]

The synthetic method is as shown in Embodiment 1.

$^1$H NMR (500 MHz, d$_6$-DMSO) δ 10.85 (s, 1H), 8.32 (s, 1H), 7.99 (dd, J=4.0, 9.5 Hz, 1H), 7.89 (m, 2H), 7.76 (m, 3H), 7.73-7.69 (m, 1H), 7.45 (m, 1H), 7.40 (m, 3H), 7.26 (m, 1H), 3.86 (s, 3H), 2.63 (s, 3H).

$^{13}$C NMR (125 MHz, d$_6$-DMSO) δ 173.0, 165.8, 161.7, 160.0, 158.1, 154.9, 154.1 (d, J=243.0 Hz, 1C), 152.5, 150.5, 138.4 (d, J=9.9 Hz, 1C), 138.2, 135.2 (d, J=12.8 Hz, 1C), 134.7, 128.9, 128.7, 127.8, 127.7, 126.7, 125.0, 124.8, 121.5, 121.3, 120.8, 120.7, 119.5, 115.9 (d, J=5.8 Hz, 1C), 110.3, 110.1, 108.0 (d, J=23.1 Hz, 1C), 102.3, 36.1, 19.5.

HRMS (ESI) for C$_{30}$H$_{21}$F$_2$N$_5$O$_3$[M+H]$^+$, calcd: 538.1685, found: 538.1680.

HPLC analysis: MeOH—H$_2$O (85:15), 4.56 min, 98.56% purity.

Embodiment 10: Preparation of N-(4-((1H-pyrrolo[2,3-b]pyridin-4-yl)oxy)-3-fluorophenyl)-6-chloro-1,2-dimethyl-4-oxo-1,4-dihydroquinoline-3-carboxamide (named as TL50090)

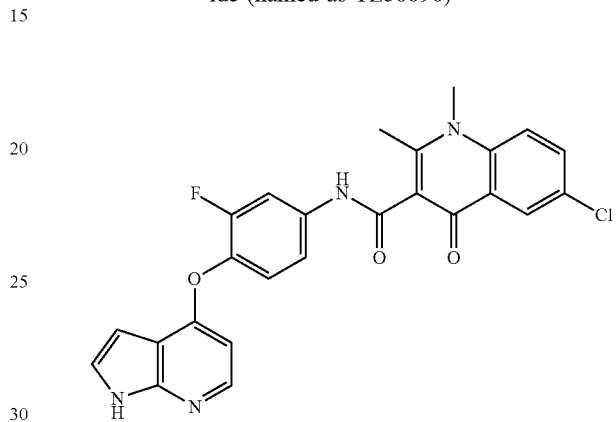

The synthetic method is as shown in Embodiment 1.

$^1$H NMR (500 MHz, d$_6$-DMSO) δ 11.77 (s, 1H), 10.81 (s, 1H), 8.15 (d, J=2.5 Hz, 1H), 8.07 (d, J=5.0 Hz, 1H), 7.98-7.93 (m, 2H), 7.82 (dd, J=2.5, 9.5 Hz, 1H), 7.50 (dd, J=1.0, 8.5 Hz, 1H), 7.40-7.36 (m, 2H), 6.39 (d, J=5.0 Hz, 1H), 6.27 (dd, J=2.0, 3.5 Hz, 1H), 3.84 (s, 3H), 2.62 (s, 3H).

$^{13}$C NMR (125 MHz, d$_6$-DMSO) δ 172.6, 165.7, 157.7, 154.1 (d, J=243.63 Hz, 1C), 138.4 (d, J=9.63 Hz, 1C), 136.8 (d, J=12.25 Hz, 1C), 132.9, 129.2, 127.4, 125.3, 124.8, 124.3, 120.5, 120.3, 116.3 (d, J=2.63 Hz, 1C), 109.8, 108.3 (d, J=23.13 Hz, 1C), 101.1, 97.3, 35.9, 19.6.

MS (ESI) m/z 478 [M+H]$^+$.

HPLC analysis: MeOH—H$_2$O (85:15), 3.78 min, 99.41%.

Embodiment 11: Preparation of N-(3-fluoro-4-((5-phenyl-7H-pyrrolo[2,3-d]pyrimidin-4-yl)oxy)phenyl)-1,2-dimethyl-4-oxo-6-(trifluoromethyl)-1,4-dihydroquinoline-3-carboxamide (named as TL50121)

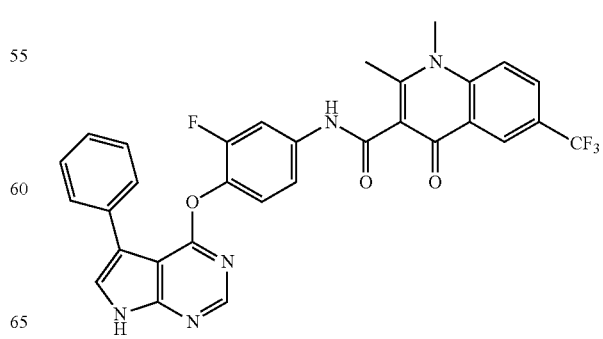

The synthetic method is as shown in Embodiment 1.

¹H NMR (500 MHz, d₆-DMSO) δ 12.54 (s, 1H), 10.74 (s, 1H), 8.50 (s, 1H), 8.33 (s, 1H), 8.11 (s, 2H), 7.89 (d, J=12.5 Hz, 1H), 7.77 (m, 3H), 7.43 (m, 4H), 7.28 (s, 1H), 3.89 (s, 3H), 2.64 (s, 3H). ¹³C NMR (125 MHz, d₆-DMSO) δ 173.0, 165.3, 161.6, 154.5, 154.0 (d, J=243.8 Hz, 1C), 153.0, 150.5, 143.4, 138.2 (d, J=9.9 Hz, 1C), 135.1 (d, J=13.0 Hz, 1C), 134.4, 128.8, 128.6, 126.6, 125.7, 124.9, 124.3 (q, J=33.2 Hz, 1C), 123.3 (q, J=4.4 Hz, 1C), 122.3 (q, J=260.1 Hz, 1C), 115.8 (d, J=5.0 Hz, 1C), 107.9 (d, J=23.7 Hz, 1C), 107.8, 102.1, 35.8, 19.5.

HRMS (ESI) for C₃₁H₂₁F₄N₅O₃[M+H]⁺, calcd: 588.1653, found: 588.1644. HPLC analysis: MeOH—H₂O (75:25), 11.65 min, 95.52% purity.

Embodiment 12: Preparation of 6-chloro-N-(3-fluoro-4-((3-phenyl-1H-pyrrolo[2,3-b]pyridin-4-yl)oxy)phenyl)-1,2-dimethyl-4-oxo-1,4-dihydroquinoline-3-carboxamide (named as TL50128)

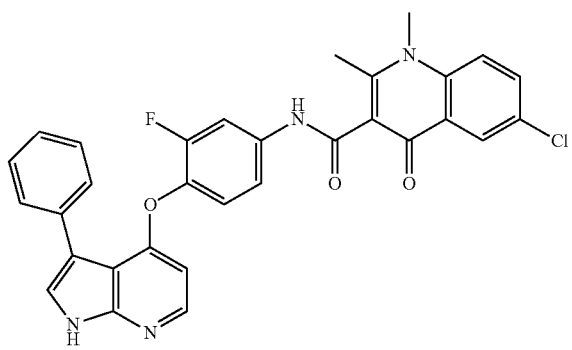 [SMILES: Cc1c(C(=O)Nc2ccc(Oc3ccnc4[nH]cc(-c5ccccc5)c34)c(F)c2)c(=O)c2cc(Cl)ccc2n1C]

The synthetic method is as shown in Embodiment 1.
MS (ESI) m/z 553 [M+H]⁺.

Embodiment 13: Preparation of 6-bromo-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL50133)

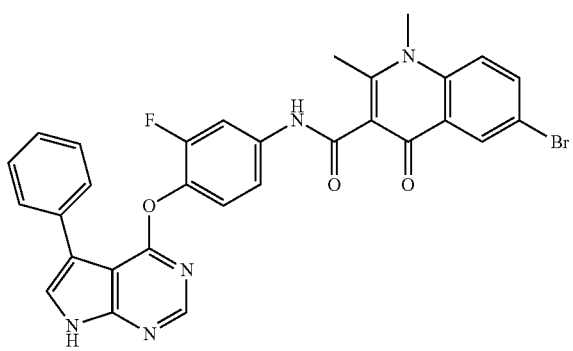 [SMILES: Cc1c(C(=O)Nc2ccc(Oc3ncnc4[nH]cc(-c5ccccc5)c34)c(F)c2)c(=O)c2cc(Br)ccc2n1C]

The synthetic method is as shown in Embodiment 1.

¹H NMR (500 MHz, d₆-DMSO) δ 12.52 (s, 1H), 10.79 (s, 1H), 8.33 (s, 1H), 8.30 (d, J=1.5 Hz, 1H), 7.94-7.86 (m, 3H), 7.77 (t, J=7.5 Hz, 3H), 7.45 (d, J=9.0 Hz, 1H), 7.40 (t, J=8.0 Hz, 3H), 7.28-7.26 (t, J=7.5 Hz, 1H), 3.83 (s, 3H), 2.61 (s, 3H).

¹³C NMR (125 MHz, d₆-DMSO) δ 172.5, 165.6, 161.7, 154.7, 154.1 (d, J=242.8 Hz, 1C), 152.6, 150.7, 140.4, 138.4 (d, J=10.0 Hz, 1C), 135.6, 135.2 (d, J=13.0 Hz, 1C), 134.6, 128.9, 128.7, 128.1, 127.8, 126.8, 126.7, 125.0, 124.3, 120.5, 120.4, 117.2, 116.0, 115.9 (d, J=2.5 Hz, 1C), 108.0 (d, J=23.4 Hz, 1C), 102.3, 35.9, 19.6.

HRMS (ESI) for C₃₀H₂₁BrFN₅O₃[M+H]⁺, calcd: 598.0885, found: 598.0877.

HPLC analysis: MeOH—H₂O (75:25), 5.41 min, 95.02% purity.

Embodiment 14: Preparation of N-(3-fluoro-4-((5-phenyl-7H-pyrrolo[2,3-d]pyrimidin-4-yl)oxy)phenyl)-1,2-dimethyl-4-oxo-1,4-dihydrobenzo[g]quinoline-3-carboxamide (named as TL50198)

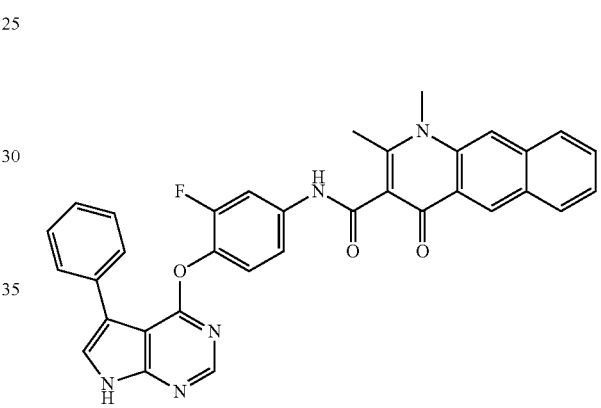

The synthetic method is as shown in Embodiment 1.

¹H NMR (500 MHz, d₆-DMSO) δ 10.91 (s, 1H), 8.91 (s, 1H), 8.40 (s, 1H), 8.34 (s, 1H), 8.2 (d, J=8.0 Hz, 1H), 8.12 (d, J=8.0 Hz, 1H), 7.93 (d, J=12.0 Hz, 1H), 7.79-7.76 (m, 3H), 7.68-7.65 (t, J=7.5 Hz, 1H), 7.55 (d, J=7.5 Hz, 1H), 7.48 (d, J=8.5 Hz, 1H), 7.43-7.40 (m, 3H), 7.27 (t, J=7.5 Hz, 1H), 3.92 (s, 3H), 2.69 (s, 3H).

¹³C NMR (125 MHz, d₆-DMSO) δ 174.9, 166.1, 161.8, 154.6, 154.2, 154.1 (d, J=242.3 Hz, 1C), 150.7, 138.6 (d, J=8.5 Hz, 1C), 135.4, 135.0 (d, J=12.6 Hz, 1C), 134.6, 129.5, 129.4, 128.9, 128.8, 128.7, 128.2, 126.8, 126.7, 126.3, 125.3, 125.0, 124.3, 117.6, 116.0, 115.9 (d, J=2.8 Hz, 1C), 114.5, 107.9 (d, J=22.6 Hz, 1C), 102.3, 35.8, 19.9.

HRMS (ESI) for C₃₄H₂₄FN₅O₃[M+H]⁺, calcd: 570.1936, found: 570.1931.

HPLC analysis: MeOH—H₂O (85:15), 6.37 min, 95.08% purity.

Embodiment 15: Preparation of N-(3-fluoro-4-((5-phenyl-7H-pyrrolo[2,3-d]pyrimidin-4-yl)oxy)phenyl)-6-methoxy-1,2-dimethyl-4-oxo-1,4-dihydroquinoline-3-carboxamide (named as TL4800005)

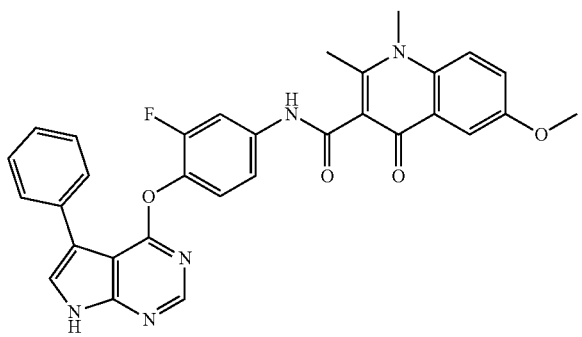

The synthetic method is as shown in Embodiment 1.

¹H NMR (400 MHz, d₆-DMSO) δ 11.10 (s, 1H), 8.30 (s, 1H), 7.92 (dd, J=2.0, 12.8 Hz, 1H), 7.85 (d, J=9.6 Hz, 1H), 7.75-7.78 (m, 3H), 7.67 (d, J=3.2 Hz, 1H), 7.46 (dd, J=1.6, 8.8 Hz, 1H), 7.42-7.38 (m, 4H), 7.25 (m, 1H), 3.87 (s, 3H), 3.83 (s, 3H), 2.65 (s, 3H).

¹³C NMR (125 MHz, d₆-DMSO) δ 173.3, 166.1, 161.6, 156.3, 154.2 (d, J=242.3 Hz, 1C), 151.9, 150.2, 138.4 (d, J=9.4 Hz, 1C), 135.9, 135.1 (d, J=13.6 Hz, 1C), 134.8, 128.7, 128.6, 127.5, 126.4, 125.4, 124.9, 122.6, 119.4, 118.2, 115.9, 115.7, 107.9 (d, J=22.6 Hz, 1C), 105.9, 102.3, 55.9, 35.8, 19.4.

HRMS (ESI) for $C_{31}H_{24}FN_5O_4[M+H]^+$, calcd: 550.1885, found: 550.1881.

HPLC analysis: MeOH—H₂O (85:15), 4.69 min, 95.04% purity.

Embodiment 16: Preparation of N-(3-fluoro-4-((5-phenyl-7H-pyrrolo[2,3-d]pyrimidin-4-yl)oxy)phenyl)-2,6-dimethyl-4-oxo-1,4-dihydroquinoline-3-carboxamide (named as TL4800025)

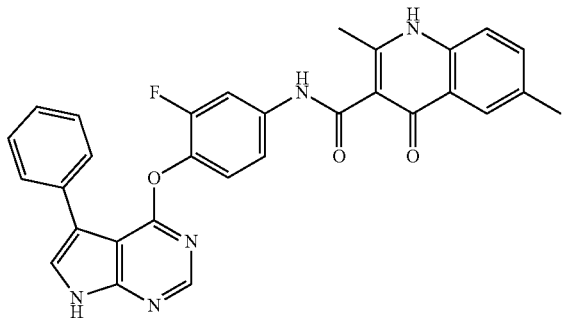 [SMILES: Cc1ccc2[nH]c(C)c(C(=O)Nc3ccc(Oc4ncnc5[nH]cc(-c6ccccc6)c45)c(F)c3)c(=O)c2c1]

The synthetic method is as shown in Embodiment 1.

¹H NMR (500 MHz, d₆-DMSO) δ 12.96 (s, 1H), 12.52 (s, 1H), 8.34 (s, 1H), 8.03 (s, 1H), 7.97 (dd, J₁=2.0, 14.0 Hz, 1H), 7.78 (dd, J₁=1.0, 8.0 Hz, 2H), 7.75 (s, 1H), 7.59-7.54 (m, 2H), 7.43-7.38 (m, 4H), 7.27 (t, J=7.5 Hz, 1H), 2.83 (s, 3H), 2.44 (s 3H).

¹³C NMR (125 MHz, d₆-DMSO) δ 176.6, 165.2, 161.8, 156.2, 154.6, 154.2 (d, J=242.4 Hz, 1C), 150.7, 138.4 (d, J=9.4 Hz, 1C), 136.9, 134.8 (d, J=12.4 Hz, 1C), 134.6, 128.9, 128.7, 126.8, 125.1, 125.0, 124.2, 118.8, 116.2 (d, J=2.6 Hz, 1C), 116.0, 110.7, 108.3 (d, J=23.3 Hz, 1C), 102.3, 22.0, 21.3.

HRMS (ESI) for $C_{30}H_{22}FN_5O_3[M+H]^+$, calcd: 520.1779, found: 520.1784.

HPLC analysis: MeOH—H₂O (85:15), 8.86 min, 98.25% purity.

Embodiment 17: Preparation of 1-ethyl-N-(3-fluoro-4-(5-phenyl-7H-pyrrolo[2,3-d]pyrimidin-4-yloxy)phenyl)-2,6-dimethyl-4-oxo-1,4-dihydroquinoline-3-carboxamide (named as TL4800067)

The synthetic method is as shown in Embodiment 1.

¹H NMR (500 MHz, d₆-DMSO) δ 10.87 (s, 1H), 8.32 (s, 1H), 8.07 (s, 1H), 7.92 (d, J=2.0 Hz, 1H), 7.89-7.76 (m, 4H), 7.62 (dd, J=1.0, 8.5 Hz, 1H), 7.45 (m, 1H), 7.40 (m, 3H), 7.26 (m, 1H), 4.38 (q, J=6.5 Hz, 2H), 2.62 (s, 3H), 2.45 (s, 3H), 1.35 (t, J=6.5 Hz, 3H).

¹³C NMR (125 MHz, d₆-DMSO) δ 173.7, 166.2, 161.7, 154.9, 154.1 (d, J=242.5 Hz, 1C), 150.8, 150.5, 138.5 (d, J=9.6 Hz, 1C), 138.3, 135.1 (d, J=12.6 Hz, 1C), 134.7, 134.6, 133.7, 128.9, 128.7, 126.7, 126.5, 125.7, 125.0, 124.8, 119.9, 117.3, 115.9 (d, J=3.8 Hz, 1C), 107.9 (d, J=23.0 Hz, 1C), 102.3, 42.3, 20.9, 18.6, 14.1.

HRMS (ESI) for $C_{32}H_{26}FN_5O_3 [M+H]^+$, calcd: 548.2092, found: 548.2085.

HPLC analysis: MeOH—H₂O (85:15), 5.32 min, 98.31% purity.

Embodiment 18: Preparation of N-(3-fluoro-4-(5-phenyl-7H-pyrrolo[2,3-d]pyrimidin-4-yloxy)phenyl)-2,6-dimethyl-4-oxo-1-propyl-1,4-dihydroquinoline-3-carboxamide (named as TL4800104)

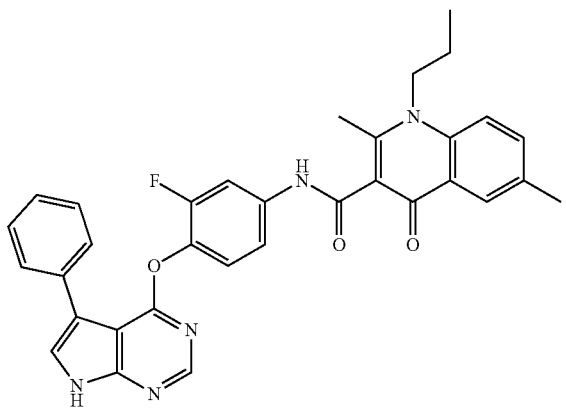 [SMILES: CCCn1c(C)c(C(=O)Nc2ccc(Oc3ncnc4[nH]cc(-c5ccccc5)c34)c(F)c2)c(=O)c2cc(C)ccc21]

The synthetic method is as shown in Embodiment 1.

$^1$H NMR (500 MHz, d$_6$-DMSO) δ 10.85 (s, 1H), 8.29 (s, 1H), 8.06 (s, 1H), 7.91 (d, J=2.0 Hz, 1H), 7.89-7.75 (m, 4H), 7.61 (dd, J=2.0, 9.0 Hz, 1H), 7.45 (m, 1H), 7.44-7.38 (m, 3H), 7.25 (m, 1H), 4.25 (t, J=7.5 Hz, 2H), 2.61 (s, 3H), 2.45 (s, 3H), 1.77-1.73 (m, 2H), 1.02 (t, J=7.5 Hz, 3H).

$^{13}$C NMR (125 MHz, d$_6$-DMSO) δ 173.6, 166.2, 161.7, 155.3, 154.1 (d, J=242.4 Hz, 1C), 150.8, 150.3, 138.5 (d, J=14.3 Hz, 1C), 135.1 (d, J=12.6 Hz, 1C), 134.9, 134.5, 133.7, 128.8, 128.7, 126.5, 126.5, 125.6, 125.3, 125.0, 120.0, 117.5, 115.9 (d, J=2.5 Hz, 1C), 115.8, 107.9 (d, J=22.9 Hz, 1C), 102.3, 48.5, 22.0, 20.9, 18.7, 11.1.

HRMS (ESI) for C$_{33}$H$_{28}$FN$_5$O$_3$[M+H]$^+$, calcd: 562.2249, found: 562.2245.

HPLC analysis: MeOH—H$_2$O (85:15), 6.12 min, 98.11% purity.

Embodiment 19: Preparation of 1-butyl-N-(3-fluoro-4-((5-phenyl-7H-pyrrolo[2,3-d]pyrimidin-4-yl)oxy)phenyl)-2,6-dimethyl-4-oxo-1,4-dihydroquinoline-3-carboxamide (named as TL4800080)

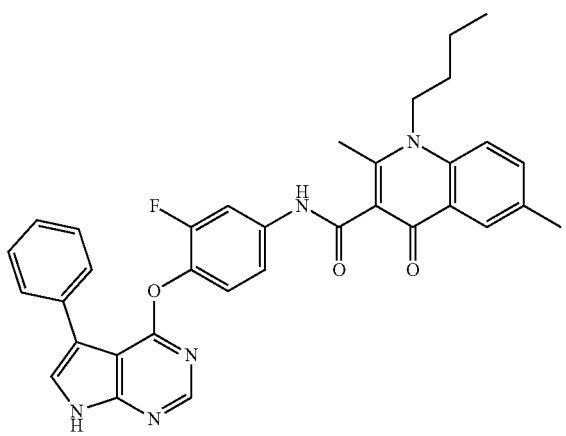 [SMILES: CCCCn1c(C)c(C(=O)Nc2ccc(Oc3ncnc4[nH]cc(-c5ccccc5)c34)c(F)c2)c(=O)c2cc(C)ccc21]

The synthetic method is as shown in Embodiment 1.

$^1$H NMR (500 MHz, d$_6$-DMSO) δ 10.87 (s, 1H), 8.28 (s, 1H), 8.06 (s, 1H), 7.92 (dd, J$_1$=2.0 Hz, J$_2$=13.0 Hz, 1H), 7.78-7.74 (m, 4H), 7.61 (dd, J=1.5, 8.5 Hz, 1H), 7.45 (dd, J=1.0, 9.0 Hz, 1H), 7.41-7.38 (m, 3H), 7.24 (t, J=7.5 Hz, 1H), 4.31-4.27 (t, J=8.0 Hz, 2H), 2.61 (s, 3H), 2.45 (s, 3H), 1.69 (m, 2H), 1.50-1.45 (q, J=7.5 Hz, 2H), 0.97 (t, J=7.5 Hz, 3H).

$^{13}$C NMR (125 MHz, d$_6$-DMSO) δ 173.6, 166.2, 161.6, 155.8, 154.2 (d, J=242.6 Hz, 1C), 150.7, 150.0, 138.5, 138.4 (d, J=10.0 Hz, 1C), 135.3 (d, J=12.9 Hz, 1C), 135.1, 134.5, 133.6, 128.7, 128.6, 126.5, 126.3, 126.1, 125.6, 125.0, 120.0, 117.4, 115.8 (d, J=2.3 Hz, 1C), 115.5, 107.9 (d, J=23.1 Hz, 1C), 102.4, 46.9, 30.7, 26.0, 20.9, 19.7, 18.7, 14.1.

HRMS (ESI) for C$_{34}$H$_{30}$FN$_5$O$_3$[M+H]$^+$, calcd: 576.2405, found: 576.2407.

HPLC analysis: MeOH—H$_2$O (85:15), 7.46 min, 98.19% purity.

Embodiment 20: Preparation of 2-ethyl-N-(3-fluoro-4-(5-phenyl-7H-pyrrolo[2,3-d]pyrimidin-4-yloxy)phenyl)-1,6-dimethyl-4-oxo-1,4-dihydroquinoline-3-carboxamide (named as TL4800139)

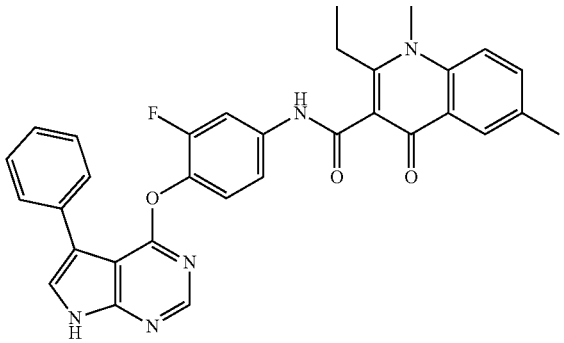 [SMILES: CCc1c(C(=O)Nc2ccc(Oc3ncnc4[nH]cc(-c5ccccc5)c34)c(F)c2)c(=O)c2cc(C)ccc2n1C]

The synthetic method is as shown in Embodiment 1.

$^1$H NMR (500 MHz, d$_6$-DMSO) δ 10.84 (s, 1H), 8.29 (s, 1H), 8.05 (s, 1H), 7.90 (dd, J=2.5, 13.0 Hz, 1H), 7.79-7.76 (m, 3H), 7.74 (s, 1H), 7.62 (dd, J=2.0, 9.0 Hz, 1H), 7.45 (dd, J=2.0, 9.0 Hz, 1H), 7.41-7.37 (m, 3H), 7.24 (t, J=7.0 Hz, 1H), 3.84 (s, 3H), 2.96 (d, J=7.0 Hz, 2H), 2.46 (s, 3H), 1.30 (t, J=7.0 Hz, 3H).

$^{13}$C NMR (125 MHz, d$_6$-DMSO) δ 174.0, 166.2, 161.6, 155.7, 155.5, 154.2 (d, J=242.0 Hz, 1C), 150.1, 139.8, 138.4 (d, J=9.9 Hz, 1C), 135.2 (d, J=13.6 Hz, 1C), 135.0, 134.4, 133.8, 128.8, 128.7, 126.4, 126.3, 125.9, 125.3, 125.0, 119.6, 117.7, 115.9 (d, J=2.5 Hz, 1C), 115.6, 107.9 (d, J=22.5 Hz, 1C), 102.4, 35.3, 25.2, 20.9, 13.7.

HRMS (ESI) for C$_{32}$H$_{26}$FN$_5$O$_3$ [M+H]$^+$, calcd: 548.2092, found: 548.2080.

HPLC analysis: MeOH—H$_2$O (85:15), 5.08 min, 95.14% purity.

Embodiment 21: Preparation of N-(3-fluoro-4-(5-phenyl-7H-pyrrolo[2,3-d]pyrimidin-4-yloxy)phenyl)-1,6-dimethyl-4-oxo-2-phenyl-1,4-dihydroquinoline-3-carboxamide (named as TL4800144)

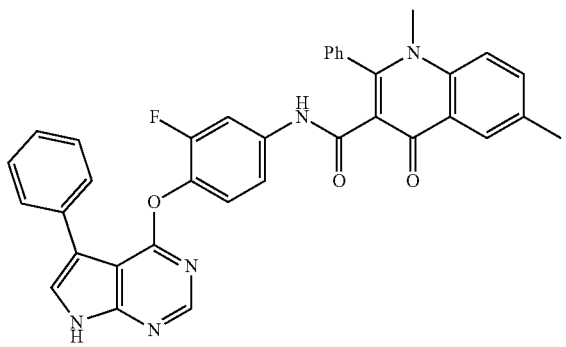 [SMILES: Cc1ccc2c(c1)c(=O)c(C(=O)Nc1ccc(Oc3ncnc4[nH]cc(-c5ccccc5)c34)c(F)c1)c(-c1ccccc1)n2C]

The synthetic method is as shown in Embodiment 1.

$^1$H NMR (500 MHz, d$_6$-DMSO) δ 10.60 (s, 1H), 8.27 (s, 1H), 8.14 (s, 1H), 7.78 (d, J=9.0 Hz, 1H), 7.74 (d, J=8.5 Hz, 3H), 7.71-7.69 (dd, J=2.0, 9.0 Hz, 1H), 7.55-7.50 (m, 6H), 7.39-7.36 (m, 2H), 7.30-7.27 (m, 1H), 7.23 (t, J=7.5 Hz, 1H), 7.19 (dd, J$_1$=1.5, 8.5 Hz, 1H), 3.50 (s, 3H), 2.51 (s, 3H).

$^{13}$C NMR (125 MHz, d$_6$-DMSO) δ 173.8, 164.7, 161.5, 155.6, 154.0 (d, J=242.4 Hz, 1C), 152.6, 150.1, 139.5, 138.1 (d, J=9.8 Hz, 1C), 135.0 (d, J=12.8 Hz, 1C), 134.7, 134.2, 134.1, 130.0, 129.1, 128.9, 128.7, 128.6, 126.7, 126.4, 125.3, 124.8, 120.8, 118.0, 115.6 (d, J=2.5 Hz, 1C), 115.5, 107.6 (d, J=22.9 Hz, 1C), 102.3, 37.6, 21.0.

HRMS (ESI) for C$_{36}$H$_{26}$FN$_5$O$_3$ [M+H]$^+$, calcd: 596.2092, found: 596.2096.

HPLC analysis: MeOH—H$_2$O (85:15), 5.14 min, 98.3% purity.

Embodiment 22: Preparation of 9-fluoro-N-(3-fluoro-4-((5-phenyl-7H-pyrrolo[2,3-d]pyrimidin-4-yl)oxy)phenyl)-3-methyl-10-(4-methylpiperazin-1-yl)-7-oxo-3,7-dihydro-2H-[1,4]oxazino[2,3,4-ij]quinoline-6-carboxamide (named as TL4800088)

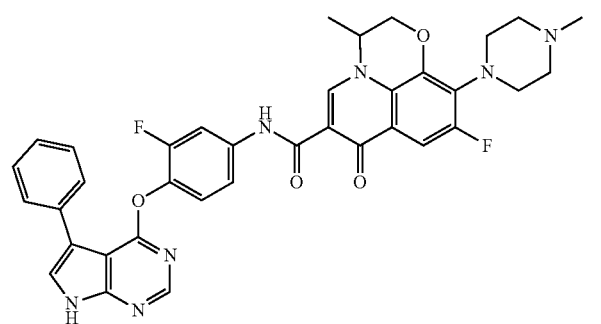 [SMILES: CC1COc2c(N3CCN(C)CC3)c(F)cc3c(=O)c(C(=O)Nc4ccc(Oc5ncnc6[nH]cc(-c7ccccc7)c56)c(F)c4)cn1c23]

The synthetic method is as shown in Embodiment 1.

$^1$H NMR (500 MHz, d$_6$-DMSO) δ 12.56 (s, 1H), 8.93 (s, 1H), 8.31 (s, 1H), 7.98 (d, J=12.0 Hz, 1H), 7.78-7.75 (m, 3H), 7.57 (d, J=12.5 Hz, 1H), 7.42-7.38 (m, 4H), 7.25 (t, J=7.5 Hz, 1H), 4.90 (d, J=6.5 Hz, 1H), 4.56 (d, J=10.5 Hz, 1H), 4.37 (d, J=10.0 Hz, 1H), 3.27 (s, 4H), 2.43 (s, 4H), 2.22 (s, 3H), 1.45 (d, J=6.5 Hz, 3H).

$^{13}$C NMR (125 MHz, d$_6$-DMSO) δ 174.9, 163.3, 161.6, 155.8 (d, J=243.9 Hz, 1C), 155.2, 154.2 (d, J=242.9 Hz, 1C), 150.4, 146.0, 140.7 (d, J=7.1 Hz, 1C), 137.6 (d, J=10.0 Hz, 1C), 135.3 (d, J=12.8 Hz, 1C), 134.8, 131.8 (d, J=14.1 Hz, 1C), 128.8, 128.7, 126.6, 125.2, 124.8, 121.9 (d, J=8.9 Hz, 1C), 116.3, 115.8, 109.8, 108.5 (d, J=22.9 Hz, 1C), 104.0 (d, J=23.8 Hz, 1C), 102.3, 68.6, 55.8, 54.8, 50.6, 50.6, 46.5, 18.3.

HRMS (ESI) for C$_{36}$H$_{31}$F$_2$N$_7$O$_4$[M+H]$^+$, calcd: 664.2478, found: 664.2467.

HPLC analysis: MeOH—H$_2$O (85:15), 16.90 min, 96.01% purity.

Embodiment 23: Preparation of 1-cyclopropyl-6-fluoro-N-(3-fluoro-4-((5-phenyl-7H-pyrrolo[2,3-d]pyrimidin-4-yl)oxy)phenyl)-4-oxo-7-(piperazin-1-yl)-1,4-dihydroquinoline-3-carboxamide (named as TL4800095)

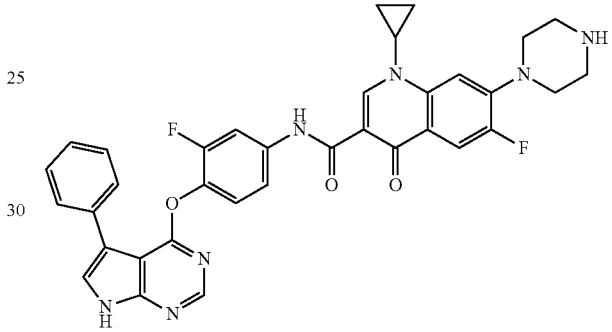

The synthetic method is as shown in Embodiment 1.
MS (ESI) m/z 634[M+H]$^+$.

Embodiment 24: Preparation of 9-fluoro-N-(3-fluoro-4-((5-phenyl-7H-pyrrolo[2,3-d]pyrimidin-4-yl)oxy)phenyl)-8-(4-hydroxypiperidin-1-yl)-5-methyl-1-oxo-1,5,6,7-tetrahydropyrido[3,2,1-ij]quinoline-2-carboxamide (named as GDL5000076)

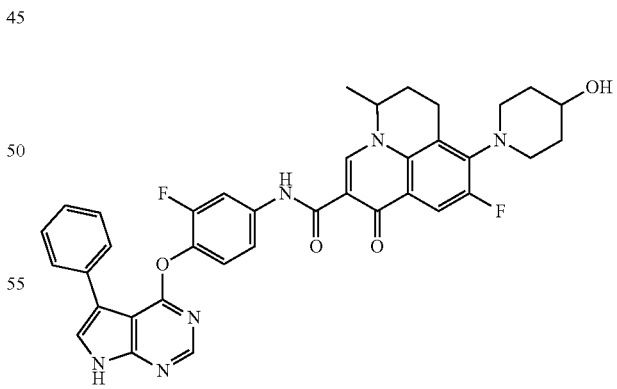

The synthetic method is as shown in Embodiment 1.

$^1$H NMR (500 MHz, d$_6$-DMSO) δ 12.61 (s, 1H), 8.95 (s, 1H), 8.30 (s, 1H), 7.98 (d, J=12.5 Hz, 1H), 7.88 (d, J=12.5 Hz, 1H), 7.78-7.74 (m, 3H), 7.43-7.38 (m, 4H), 7.24 (t, J=7.0 Hz, 1H), 4.86 (s, 1H), 3.68 (s, 1H), 3.20 (m, 4H), 2.92 (m, 3H), 2.13-2.06 (m, 2H), 1.85 (m, 2H), 1.62 (d, J=8.5 Hz, 2H), 1.52 (s, 1H), 1.43 (d, J=6.0 Hz, 3H).

13C NMR (125 MHz, d6-DMSO) δ 175.1, 163.3, 161.5, 157.5 (d, J=247.9 Hz, 1C), 155.5, 154.3 (d, J=243.0 Hz, 1C), 150.2, 147.4, 142.4, 137.6 (d, J=9.9 Hz, 1C), 135.4 (d, J=12.9 Hz, 1C), 135.0, 133.6, 128.8, 128.7, 126.4, 125.8, 125.2, 124.2, 116.3, 115.7, 109.8 (d, J=22.8 Hz, 1C), 109.6, 108.5 (d, J=22.9 Hz, 1C), 102.4, 57.1, 25.6, 20.1, 19.0.

HRMS (ESI) for $C_{37}H_{32}F_2N_6O_4[M+H]^+$, calcd: 663.2526, found: 663.2520.

HPLC analysis: MeOH—H2O (85:15), 11.93 min, 99.22% purity.

Embodiment 25: Preparation of 6-ethyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL4800075)

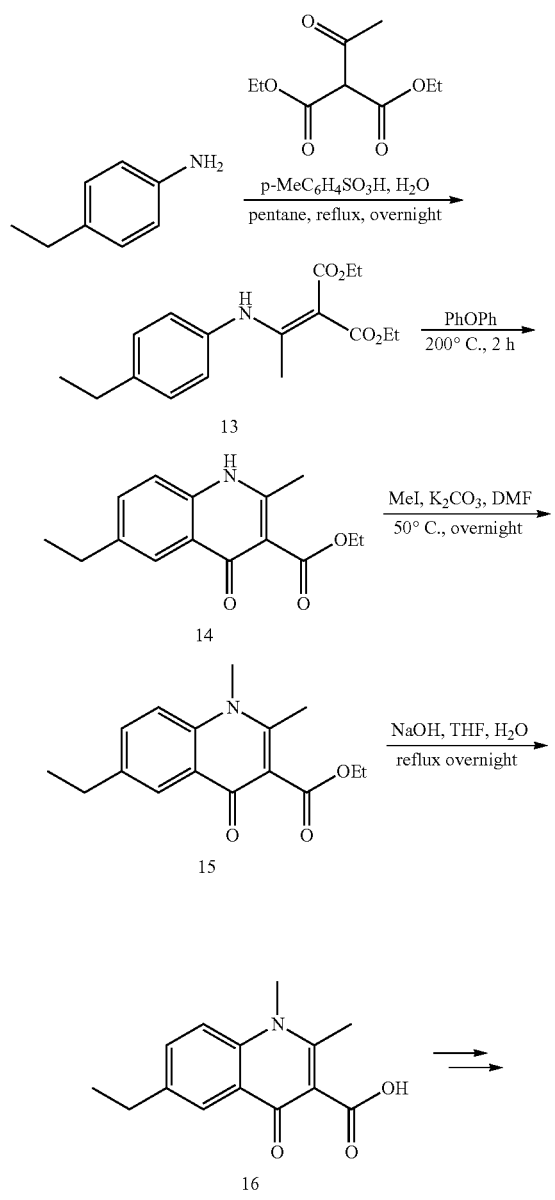

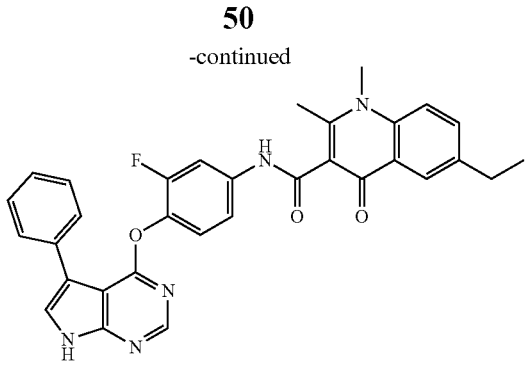

Step c1: 2-(1-((4-ethylphenyl)amino)ethylidene) diethyl malonate (Compound 13)

P-ethylaniline (2.42 g, 20 mmol) and diethyl acetymalonate (2.02 g, 10 mmol) were dissolved in 50 mL of n-pentane, a catalytic amount of p-toluenesulfonic acid (20 mg) was added and the reaction was refluxed overnight. The solution was cooled to room temperature, a small amount of saturated NaHCO3 was added, extracted twice with EA, and the organic phases were combined, washed once with saturated brine, and dried over anhydrous Na2SO4, subjecting same to filtration, rotary drying and column chromatography to obtain 2.68 g (87.8%) of the solid. 1HNMR (400 MHz, d6-DMSO), δ 10.98 (s, 1H), 7.23 (d, J=8.0 Hz, 2H), 7.14 (d, J=8.0 Hz, 2H), 4.10 (m, 4H), 2.63-2.58 (q, J=8.0 Hz, 2H), 2.00 (s, 3H), 1.21-1.16 (m, 9H). MS (ESI), m/z: 306[M+H]+.

Step c2: ethyl 6-ethyl-2-methyl-4-oxo-1,4-dihydroquinoline-3-carboxylate (Compound 14)

2-(1-((4-ethylphenyl)amino)ethylidene)diethyl malonate (compound 13) (2.5 g, 8.2 mmol) was dissolved in 25 mL of diphenyl ether, heated to 200° C. with stirring and reacted for 2 hours. The solution was cooled to room temperature to precipitate the solid, which was filtered and washed with PE, and drained to obtain 2 g (94.3%) of a white solid. 1H NMR (400 MHz, d6-DMSO), δ 11.78 (s, 1H), 7.86 (s, 1H), 7.53 (d, J=8.0 Hz, 1H), 7.45 (d, J=8.0 Hz, 1H), 4.23 (q, J=8.0 Hz, 2H), 2.73-2.68 (q, J=8.0 Hz, 2H), 2.37 (s, 3H), 1.26 (t, J=8.0 Hz, 3H), 1.21 (t, J=8.0 Hz, 3H). MS (ESI), m/z: 260[M+H]+.

Step c3: ethyl 6-ethyl-1,2-dimethyl-4-oxo-1,4-dihydroquinoline-3-carboxylate (Compound 15)

Ethyl 6-ethyl-2-methyl-4-oxo-1,4-dihydroquinoline-3-carboxylate (compound 14) (2 g, 7.7 mmol) and K2CO3 (3.18 g, 23.1 mmol) were dissolved in 50 mL of DMF, and MeI (0.72 mL, 11.55 mmol) was added with stirring, and reacted at 50° C. overnight. The solution was cooled to room temperature, quenched by addition of water to precipitate the solid, and washed with water several times, and the solid was extracted several times with DCM, the organic phases were combined, subjecting same to rotary drying and column chromatography to obtain 1.52 g (72.4%) of a white solid. 1HNMR (400 MHz, CDCl3), δ 8.23 (s, 1H), 7.46 (d, J=8.0 Hz, 1H), 7.37 (d, J=8.0 Hz, 1H), 4.40 (q, J=8.0 Hz, 2H), 3.719 (s, 3H), 2.76-2.71 (q, J=8.0 Hz, 2H), 2.48 (s, 3H), 1.38 (t, J=8.0 Hz, 3H), 1.26 (t, J=8.0 Hz, 3H). MS (ESI), m/z: 274[M+H]+.

Step c4: 6-ethyl-1,2-dimethyl-4-oxo-1,4-dihydroquinoline-3-carboxylic acid (Compound 16)

Ethyl 6-ethyl-1,2-dimethyl-4-oxo-1,4-dihydroquinoline-3-carboxylate (compound 15) (1.5 g, 5.5 mmol) and NaOH (880 mg, 22 mmol) were dissolved in 30 mL of ethanol and 15 mL of water, and the reaction was refluxed overnight. The solution was cooled to room temperature, the majority of the organic solvent was spun to dryness, water was added, the pH was adjusted to 7-8 with dilute HCl in an ice bath to precipitate the solid, which was then filtered and drained to obtain 1.25 g (93.3%) of a white solid. $^1$HNMR (400 MHz, $d_6$-DMSO), δ 8.11 (s, 1H), 7.88 (d, J=8.0 Hz, 1H), 7.69 (d, J=8.0 Hz, 1H), 3.87 (s, 3H), 2.87 (s, 3H), 2.80-2.74 (q, J=8.0 Hz, 2H), 2.48 (s, 3H), 1.24 (t, J=8.0 Hz, 3H). MS (ESI), m/z: 246[M+H]$^+$.

Step c5: 6-ethyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (compound 17, TL4800075)

The synthetic route of intermediates 16 and 17 are as shown in Embodiment 1b.
$^1$H NMR (500 MHz, $d_6$-DMSO) δ 11.02 (s, 1H), 8.33 (s, 1H), 8.09 (s, 1H), 7.93 (d, J=1.5 Hz, 1H), 7.91-7.76 (m, 4H), 7.65 (m, 1H), 7.46 (d, J=9.5 Hz, 1H), 7.41 (m, 3H), 7.26 (m, 1H), 3.82 (s, 3H), 2.75 (q, J=7.5 Hz, 2H), 2.65 (s, 3H), 1.24 (t, J=7.5 Hz, 3H).
$^{13}$C NMR (125 MHz, $d_6$-DMSO) δ 174.0, 166.1, 161.7, 154.8, 154.1 (d, J=242.6 Hz, 1C), 152.4, 150.5, 139.9, 139.6, 138.5 (d, J=9.8 Hz, 1C), 135.0 (d, J=13.1 Hz, 1C), 133.3, 128.8, 128.6, 126.6, 126.2, 124.9, 124.6, 124.1, 119.0, 117.5, 115.9, 107.9 (d, J=23.8 Hz, 1C), 102.3, 35.6, 27.9, 19.4, 15.9.
HRMS (ESI) for $C_{32}H_{26}FN_5O_3$ [M+H]$^+$, calcd: 548.2092, found: 548.2089.
HPLC analysis: MeOH—H$_2$O (85:15), 5.61 min, 97.34% purity.

Embodiment 26: Preparation of 6-(tert-butyl)-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL4800062)

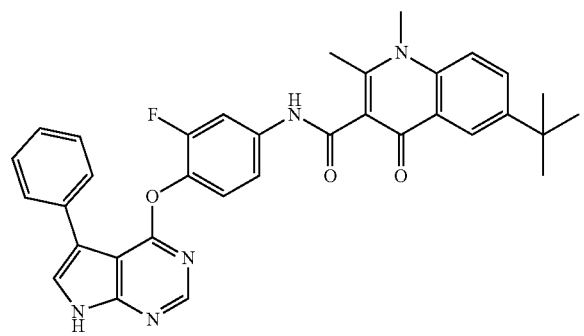 [SMILES: Cc1c(C(=O)Nc2ccc(Oc3ncnc4[nH]cc(-c5ccccc5)c34)c(F)c2)c(=O)c2cc(C(C)(C)C)ccc2n1C]

The synthetic method is as shown in Embodiment 25.
$^1$H NMR (500 MHz, $d_6$-DMSO) δ 11.03 (s, 1H), 8.32 (s, 1H), 8.25 (d, J=2.0 Hz, 1H), 7.92-7.87 (m, 2H), 7.83 (m, 1H), 7.78 (d, J=7.5 Hz, 2H), 7.75 (s, 1H), 7.45 (dd, J=2.0, 8.5 Hz, 1H), 7.42-7.38 (m, 3H), 7.26 (t, J=7.5 Hz, 1H), 3.84 (s, 3H), 2.66 (s, 3H), 1.36 (s, 9H).
$^{13}$C NMR (125 MHz, $d_6$-DMSO) δ 174.2, 166.1, 161.7, 154.8, 154.1 (d, J=242.6 Hz, 1C), 152.7, 150.6, 146.8, 139.4, 138.5 (d, J=9.8 Hz, 1C), 135.0 (d, J=13.0 Hz, 1C), 134.7, 131.1, 128.9, 128.7, 126.7, 125.8, 125.0, 124.6, 121.5, 118.9, 117.5, 115.9, 108.0 (d, J=23.4 Hz, 1C), 102.3, 35.6, 34.8, 31.5, 19.5.
HRMS (ESI) for $C_{34}H_{30}FN_5O_3$[M+H]$^+$, calcd: 576.2405, found: 576.2411.
HPLC analysis: MeOH—H$_2$O (85:15), 7.12 min, 97.03% purity.

Embodiment 27: Preparation of N-(3-fluoro-4-((5-phenyl-7H-pyrrolo[2,3-d]pyrimidin-4-yl)oxy)phenyl)-1,2-dimethyl-4-oxo-6-propyl-1,4-dihydroquinoline-3-carboxamide (named as TL4800116)

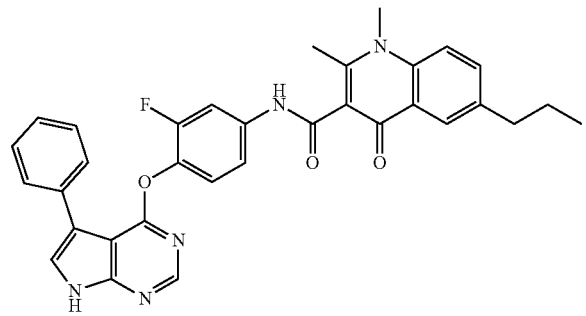 [SMILES: CCCc1ccc2c(c1)c(=O)c(C(=O)Nc1ccc(Oc3ncnc4[nH]cc(-c5ccccc5)c34)c(F)c1)c(C)n2C]

The synthetic method is as shown in Embodiment 25.
$^1$H NMR (500 MHz, $d_6$-DMSO) δ 11.00 (s, 1H), 8.30 (s, 1H), 8.06 (d, J=2.0 Hz, 1H), 7.91 (dd, J=2.0, 12.5 Hz, 1H), 7.81-7.77 (m, 3H), 7.74 (s, 1H), 7.64 (dd, J=2.0, 9.0 Hz, 1H), 7.45 (dd, J=1.5, 9.0 Hz, 1H), 7.41-7.38 (m, 3H), 7.25 (m, 1H), 3.83 (s, 3H), 2.71 (t, J=7.2 Hz, 2H), 2.64 (s, 3H), 1.69-1.61 (q, J=7.1 Hz, 2H), 0.89 (t, J=7.0 Hz, 3H).
$^{13}$C NMR (125 MHz, $d_6$-DMSO) δ 174.0, 166.1, 161.6, 155.4, 154.2 (d, J=242.8 Hz, 1C), 152.4, 150.3, 139.7, 138.5 (d, J=9.8 Hz, 1C), 138.3, 135.2 (d, J=12.8 Hz, 1C), 134.9, 133.8, 128.8, 128.7, 126.5, 126.2, 125.5, 125.0, 119.1, 117.5, 115.9 (d, J=2.6 Hz, 1C), 115.7, 108.0 (d, 23.1 Hz, 1C), 102.4, 36.9, 35.7, 24.4, 19.5, 13.9.
HRMS (ESI) for $C_{33}H_{28}FN_5O_3$[M+H]$^+$, calcd: 562.2249, found: 562.2249.
HPLC analysis: MeOH—H$_2$O (85:15), 6.60 min, 95.83% purity.

Embodiment 28: Preparation of N-(3-fluoro-4-((5-phenyl-7H-pyrrolo[2,3-d]pyrimidin-4-yl)oxy)phenyl)-1,2-dimethyl-4-oxo-6-(trifluoromethoxy)-1,4-dihydroquinoline-3-carboxamide (named as TL4800117)

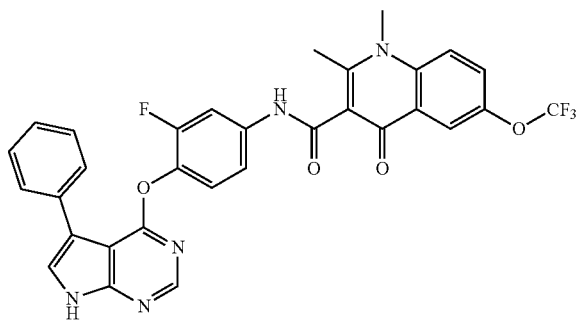 [SMILES: Cc1c(C(=O)Nc2ccc(Oc3ncnc4[nH]cc(-c5ccccc5)c34)c(F)c2)c(=O)c2cc(OC(F)(F)F)ccc2n1C]

The synthetic method is as shown in Embodiment 25.

$^1$H NMR (500 MHz, $d_6$-DMSO) δ 12.53 (s, 1H), 10.76 (s, 1H), 8.33 (s, 1H), 8.09 (m, 2H), 7.89 (d, J=12.5 Hz, 1H), 7.82-7.76 (m, 4H), 7.46-7.40 (m, 4H), 7.27 (m, 1H), 3.87 (s, 3H), 2.63 (s, 3H).

$^{13}$C NMR (125 MHz, $d_6$-DMSO) δ 172.9, 165.6, 161.7, 154.6, 154.1 (d, J=242.8 Hz, 1C), 152.8, 150.7, 144.9, 140.1, 138.4 (d, J=9.8 Hz, 1C), 135.2 (d, J=12.5 Hz, 1C), 134.6, 128.9, 128.7, 126.8, 126.2, 125.0, 124.3, 121.7, 120.7, 120.3, 119.6, 116.8, 116.0, 115.9, 108.0 (d, J=23.4 Hz, 1C), 102.3, 36.0, 19.6.

HRMS (ESI) for $C_{31}H_{21}F_4N_5O_4[M+H]^+$, calcd: 604.1602, found: 604.1597.

HPLC analysis: MeOH—$H_2O$ (85:15), 5.31 min, 97.59% purity.

Embodiment 29: Preparation of 6-ethyl-1,2-dimethyl-4-oxo-N-(4-((5-phenyl-7H-pyrrolo[2,3-d]pyrimidin-4-yl)oxy)phenyl)-1,4-dihydroquinoline-3-carboxamide (named as TL4830014)

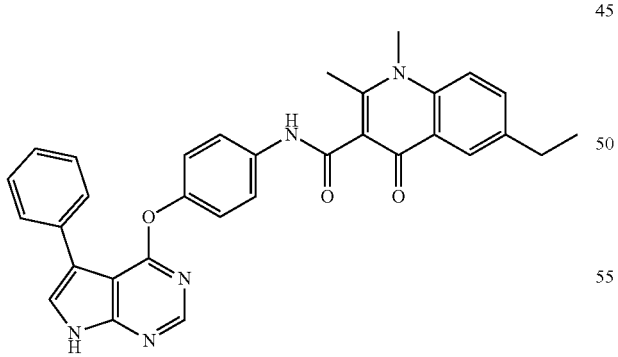

The synthetic method is as shown in Embodiment 25.

$^1$H NMR (500 MHz, $d_6$-DMSO) δ 10.81 (s, 1H), 8.29 (s, 1H), 8.09 (s, 1H), 7.81 (d, J=9.0 Hz, 1H), 7.78-7.75 (m, 4H), 7.70 (s, 1H), 7.65 (dd, J=1.5, 8.5 Hz, 1H), 7.38 (m, 2H), 7.26-7.21 (m, 3H), 3.83 (s, 3H), 2.79-2.74 (q, J=7.5 Hz, 2H), 2.64 (s, 3H), 1.24 (t, J=7.5 Hz, 3H).

$^{13}$C NMR (125 MHz, $d_6$-DMSO) δ 174.9, 174.0, 165.8, 162.5, 152.2, 150.4, 148.5, 139.9, 139.7, 137.0, 135.1, 133.3, 128.9, 128.6, 126.4, 126.3, 124.2, 122.6, 120.9, 119.5, 117.5, 115.8, 103.0, 35.6, 27.9, 19.5, 16.0.

HRMS (ESI) for $C_{32}H_{27}N_5O_3[M+H]^+$, calcd: 530.2187, found: 530.2182.

HPLC analysis: MeOH—$H_2O$ (85:15), 5.25 min, 97.83% purity.

Embodiment 30: Preparation of 6-ethyl-12-dimethyl-N-(3-methyl-4-(5-phenyl-7H-pyrrolo[2,3-d]pyrimidin-4-yloxy)phenyl)-4-oxo-1,4-dihydroquinoline-3-carboxamide (named as TL4830016)

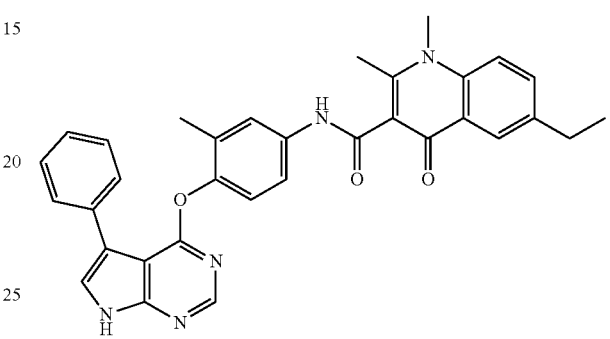

The synthetic method is as shown in Embodiment 25.

$^1$H NMR (500 MHz, $d_6$-DMSO) δ 10.79 (s, 1H), 8.28 (s, 1H), 8.09 (s, 1H), 7.80 (m, 3H), 7.71-7.65 (m, 3H), 7.53 (d, J=7.5 Hz, 1H), 7.40 (t, J=7.5 Hz, 2H), 7.26 (t, J=7.5 Hz, 1H), 7.11 (d, J=8.5 Hz, 1H), 3.83 (s, 3H), 2.76 (q, J=7.5 Hz, 2H), 2.65 (s, 3H), 2.09 (s, 3H), 1.24 (t, J=7.5 Hz, 3H).

$^{13}$C NMR (125 MHz, $d_6$-DMSO) δ 174.0, 165.7, 162.2, 154.7, 152.3, 150.7, 147.0, 139.9, 139.7, 137.2, 134.8, 133.3, 130.7, 128.9, 128.6, 126.6, 126.3, 124.2, 123.0, 122.2, 119.3, 118.6, 117.5, 116.1, 102.6, 35.6, 27.9, 19.5, 16.9, 15.9.

HRMS (ESI) for $C_{33}H_{29}N_5O_3[M+H]^+$, calcd: 544.2343, found: 544.2348.

HPLC analysis: MeOH—$H_2O$ (85:15), 5.74 min, 96.04% purity.

Embodiment 31: Preparation of 6-ethyl-N-(2-fluoro-4-(5-phenyl-7H-pyrrolo[2,3-d]pyrimidin-4-yloxy)phenyl)-1,2-dimethyl-4-oxo-1,4-dihydroquinoline-3-carboxamide (named as GDL5000091)

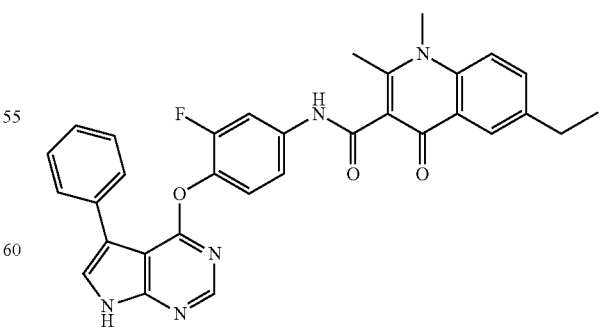

The synthetic method is as shown in Embodiment 25.

$^1$H NMR (400 MHz, $d_6$-DMSO) δ 12.13 (s, 1H), 8.29 (s, 1H), 8.24 (t, J=8.8 Hz, 1H), 8.17 (s, 1H), 7.88 (d, J=8.8 Hz,

1H), 7.76 (d, J=7.6 Hz, 2H), 7.71-7.69 (m, 2H), 7.40-7.34 (m, 3H), 7.22 (t, J=8.0 Hz, 1H), 7.10 (d, J=7.2 Hz, 1H), 3.90 (s, 3H), 2.91 (s, 3H), 2.79 (q, J=7.6 Hz, 2H), 1.26 (t, J=7.6 Hz, 3H).

$^{13}$C NMR (125 MHz, d$_6$-DMSO) δ 175.6, 165.9, 162.4, 157.4, 156.2, 153.9 (d, J=244.0 Hz, 1C), 150.5, 149.3 (d, J=10.5 Hz, 1C), 141.1, 139.7, 135.6, 134.1, 129.3, 129.0, 126.7, 126.5, 126.4, 125.0 (d, J=11.1 Hz, 1C), 124.8, 124.1, 118.7, 118.2, 116.0, 115.2, 110.9 (d, J=22.3 Hz, 1C), 103.5, 36.6, 28.4, 20.3, 16.3.

HRMS (ESI) for C$_{32}$H$_{26}$FN$_5$O$_3$[M+H]$^+$, calcd: 548.2092, found: 548.2098.

HPLC analysis: MeOH—H$_2$O (85:15), 7.37 min, 95.08% purity.

Melting point: 241.1° C.-243.7° C.

Embodiment 32: Preparation of N-(4-((7H-pyrrolo[2,3-d]pyrimidin-4-yl)oxy)-3-trifluorophenyl)-6-1,2-dimethyl-4-oxo-1,4-dihydroquinoline-3-carboxamide (named as TL4800147)

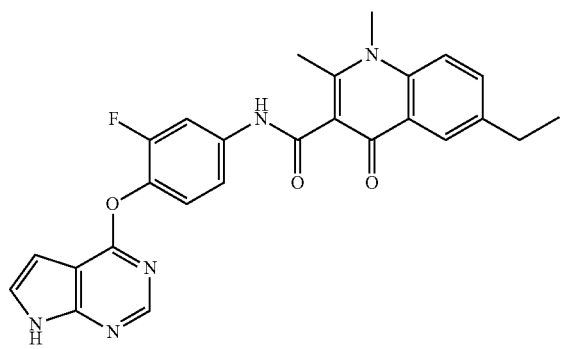 [SMILES: CCc1ccc2c(c1)c(=O)c(C(=O)Nc1ccc(Oc3ncnc4[nH]ccc34)c(F)c1)c(C)n2C]

The synthetic method is as shown in Embodiment 25.

$^1$H NMR (500 MHz, d$_6$-DMSO) δ 12.28 (s, 1H), 10.98 (s, 1H), 8.30 (d, J=2.0 Hz, 1H), 7.92 (dd, J=2.0, 12.5 Hz, 1H), 7.81 (d, J=9.0 Hz, 1H), 7.66 (dd, J=2.0, 9.0 Hz, 1H), 7.51 (m, 1H), 7.87 (dd, J=2.0, 9.0 Hz, 1H), 7.39 (m, 1H), 6.59 (m, 1H), 3.83 (s, 3H), 2.79-2.75 (q, J=7.5 Hz, 2H), 2.64 (s, 3H), 1.24 (t, J=7.5 Hz, 3H).

$^{13}$C NMR (125 MHz, d$_6$-DMSO) δ 174.0, 166.2, 161.5, 154.2 (d, J=242.9 Hz, 1C), 154.1, 152.3, 150.5, 140.0, 138.6 (d, J=9.9 Hz, 1C), 135.1 (d, J=12.9 Hz, 1C), 133.4, 126.3, 126.0, 124.9, 124.2, 119.2, 117.6, 115.9 (d, J=2.6 Hz, 1C), 108.0 (d, J=23.2 Hz, 1C), 104.5, 98.3, 35.7, 27.9, 19.5, 16.0.

HRMS (ESI) for C$_{26}$H$_{22}$FN$_5$O$_3$ [M+H]$^+$, calcd: 472.1779, found: 472.1776.

HPLC analysis: MeOH—H$_2$O (85:15), 3.99 min, 96.56% purity.

Embodiment 33: Preparation of 6-ethyl-N-(3-fluorophenyl-1H-pyrrolo[2,3-d]pyridin-4-yl)oxy)phenyl)-1,2-dimethyl-4-oxo-1,4-dihydroquinoline-3-carboxamide (named as TL4800172)

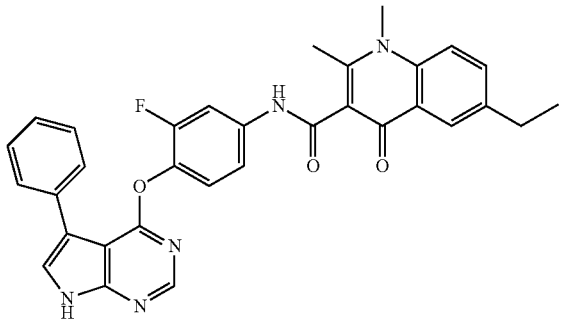 [SMILES: CCc1ccc2c(c1)c(=O)c(C(=O)Nc1ccc(Oc3ncnc4[nH]cc(-c5ccccc5)c34)c(F)c1)c(C)n2C]

The synthetic method is as shown in Embodiment 25.

$^1$H NMR (500 MHz, d$_6$-DMSO) δ 12.03 (s, 1H), 11.02 (s, 1H), 8.08 (m, 2H), 7.98-7.95 (d, J=13.0 Hz, 2H), 7.81 (d, J=8.5 Hz, 1H), 7.70 (d, J=7.5 Hz, 2H), 7.66 (d, J=8.5 Hz, 1H), 7.60 (s, 1H), 7.47 (d, J=9.0 Hz, 1H), 7.54 (m, 3H), 7.21 (t, J=7 Hz, 1H), 6.31 (d, J=5.0 Hz, 1H), 3.83 (s, 3H), 2.79-2.74 (q, J=7.5 Hz, 2H), 2.64 (s, 3H), 1.24 (t, J=7.5 Hz, 3H).

$^{13}$C NMR (125 MHz, d$_6$-DMSO) δ 174.0, 166.2, 158.8, 153.9 (d, J=243.8 Hz, 1C), 152.4, 152.0, 145.1, 140.0, 139.7, 138.5 (d, J=9.4 Hz, 1C), 136.1 (d, J=11.9 Hz, 1C), 135.8, 133.4, 129.1, 128.4, 126.3, 126.2, 124.2, 119.1, 117.6, 116.4 (d, J=2.6 Hz, 1C), 115.6, 108.5 (d, J=22.0 Hz, 1C), 107.6, 101.1, 35.7, 27.9, 19.5, 16.0.

HRMS (ESI) for C$_{33}$H$_{27}$FN$_4$O$_3$ [M+H]$^+$, calcd: 547.214, found: 547.2145.

HPLC analysis: MeOH—H$_2$O (85:15), 6.31 min, 95.08% purity.

Embodiment 34: Preparation of 6-ethyl-N-(3-fluoro-4-(5-(4-methoxyphenyl)-7H-pyrrolo[2,3-d]pyrimidin-4-yloxy)phenyl)-1,2-dimethyl-4-oxo-1,4-dihydroquinoline-3-carboxamide (named as GDL5000037)

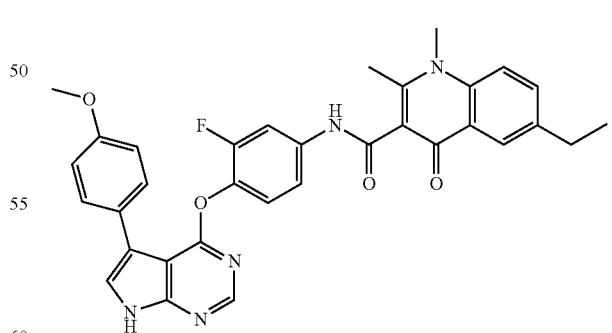

The synthetic method is as shown in Embodiment 25.

$^1$H NMR (400 MHz, d$_6$-DMSO) δ 10.99 (s, 1H), 8.28 (s, 1H), 8.09 (s, 1H), 7.90 (dd, J=2.0, 15.0 Hz, 1H), 7.81 (d, J=8.0 Hz, 1H), 7.70-7.64 (m, 4H), 7.46-7.36 (m, 2H), 6.97 (d, J=8 Hz, 2H), 3.84 (s, 3H), 3.78 (s, 3H), 2.76 (q, J=7.5 Hz, 2H), 2.65 (s, 3H), 1.24 (t, J=7.5 Hz, 3H).

$^{13}$C NMR (125 MHz, d$_6$-DMSO) δ 174.4, 166.6, 162.1, 158.9, 155.6 (d, J=244.0 Hz, 1C), 155.4, 152.8, 150.71, 140.4, 140.1, 138.9 (d, J=9.8 Hz, 1C), 135.6 (d, J=13.2 Hz, 1C), 133.8, 130.4, 127.6, 126.7, 125.41, 124.6, 119.5, 118.0, 116.4 (d, J=1.3 Hz, 1C), 116.0, 114.7, 108.4 (J=233 Hz, 1C), 102.8, 56.0, 36.1, 28.4, 19.9, 16.4.

HRMS (ESI) for C$_{33}$H$_{28}$FN$_5$O$_4$[M+H]$^+$, calcd: 578.2198, found: 578.2190.

HPLC analysis: MeOH—H$_2$O (85:15), 5.22 min, 96.31%.

Embodiment 35: Preparation of 6-ethyl-N-(3-fluoro-4-(5-phenyl-7H-pyrrolo[2,3-d]pyrimidin-4-yloxy)phenyl)-1-methyl-4-oxo-1,4-dihydroquinoline-3-carboxamide (TL4800178)

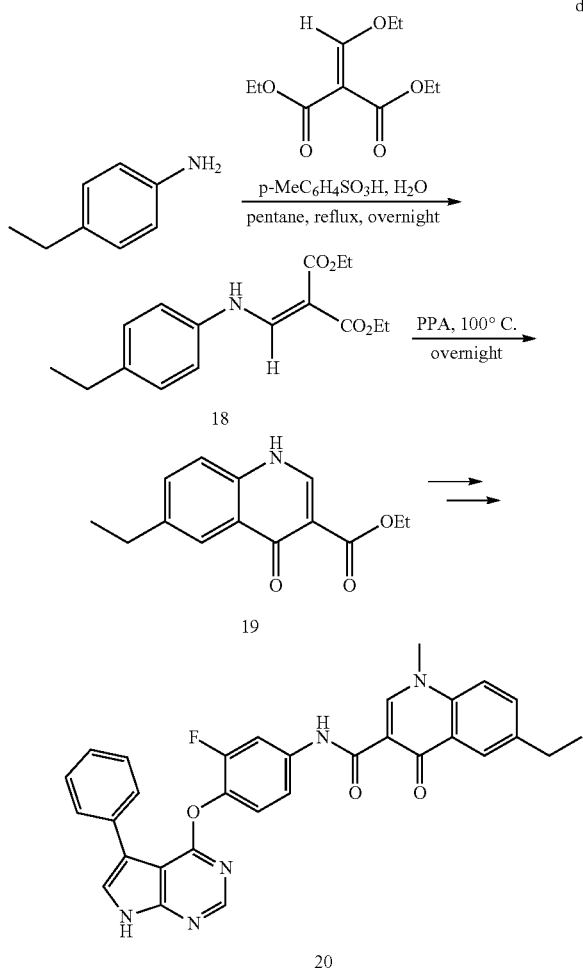

Step d1: 2-(((4-ethylphenyl)amino)methylene)diethyl malonate (Compound 18)

P-ethylaniline (3.21 g, 30 mmol), diethyl ethoxymethylenemalonate (3.24 g, 15 mmol) and a catalytic amount of p-toluenesulfonic acid were dissolved in n-pentane, and the reaction was refluxed overnight. The solution was cooled to room temperature, a small amount of saturated NaHCO$_3$ was added, extracted twice with EA, and the organic phases were combined, washed once with saturated brine, and dried over anhydrous Na$_2$SO$_4$, subjecting same to filtration, rotary drying and column chromatography to obtain 3.98 g (96%) of the solid. $^1$H NMR (400 MHz, CDCl$_3$), δ 10.98 (d, J=12.0 Hz, 1H), 8.50 (d, J=12.0 Hz, 1H), 7.18 (d, J=8.0 Hz, 2H), 7.05 (d, J=8.0 Hz, 2H), 4.32-4.28 (q, J=4.0 Hz, 2H), 4.26-4.21 (q, J=4.0 Hz, 2H), 2.65-2.60 (q, J=4.0 Hz, 3H), 1.37 (t, J=4.0 Hz, 3H), 1.32 (t, J=4.0 Hz, 3H), 1.21 (t, J=4.0 Hz, 3H). MS (ESI), m/z: 292[M+H]$^+$.

Step d2: ethyl 6-ethyl-4-oxo-1,4-dihydroquinoline-3-carboxylate (Compound 19)

2-(((4-ethylphenyl)amino)methylene)diethyl malonate (compound 18) (3.5 g, 12 mmol) was dissolved in polyphosphoric acid, and heated to 100° C. and reacted overnight. The solution was cooled to room temperature, water was added with stirring to precipitate the solid and filtered, the solid was washed three times with PE and dissolved in EA, subjecting same to rotary drying and column chromatography to obtain 2.65 g (90%) of the solid.

Step d3: 6-ethyl-N-(3-fluoro-4-(5-phenyl-7H-pyrrolo[2,3-d]pyrimidin-4-yloxy)phenyl)-1-methyl-4-oxo-1,4-dihydroquinoline-3-carboxamide (compound 20, TL4800178)

The other synthetic steps are as shown in the synthetic methods of compounds 15-17 in Embodiment 25.

$^1$H NMR (500 MHz, d$_6$-DMSO) δ 12.70 (s, 1H), 8.99 (s, 1H), 8.29 (s, 1H), 8.24 (s, 1H), 7.98 (d, J=12.0 Hz, 1H), 7.81-7.75 (m, 5H), 7.43-7.40 (m, 4H), 7.24 (s, 1H), 4.07 (s, 3H), 2.81 (d, J=6.5 Hz, 2H), 1.27 (t, J=6.5 Hz, 3H).

$^{13}$C NMR (125 MHz, d$_6$-DMSO) δ 176.1, 163.5, 161.5, 150.1, 149.4, 142.0, 138.8, 135.0, 134.1, 128.8, 128.7, 127.2, 126.4, 125.2, 124.5, 118.3, 116.2, 115.6, 110.2, 108.5, 102.4, 41.9, 28.2, 15.9.

HRMS (ESI) Calcd for [M+H]$^+$=534.1936, found: [M+H]$^+$=534.1932.

HPLC analysis: MeOH—H$_2$O (85:15), 11.54 min, 97.15%.

Embodiment 36: Preparation of N-(3-fluoro-4-((5-phenyl-7H-pyrrolo[2,3-d]pyrimidin-4-yl)oxy)phenyl)-9-methyl-1-oxo-1,5,6,7-tetrahydropyrido[3,2,1-ij]quinoline-2-carboxamide (named as TL4800160)

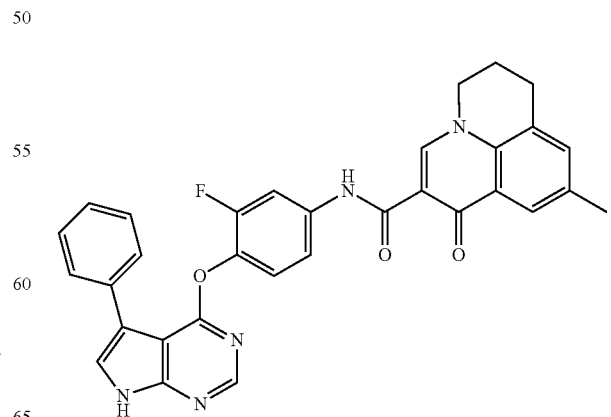

The synthetic method is as shown in Embodiment 35.

$^1$H NMR (500 MHz, $d_6$-DMSO) δ 12.75 (s, 1H), 8.86 (s, 1H), 8.28 (s, 1H), 8.01 (s, 1H), 8.00-7.97 (m, 1H), 7.77 (d, J=7.5 Hz, 2H), 7.74 (s, 1H), 7.49 (s, 1H), 7.44-7.38 (m, 4H), 7.24 (t, J=7.5 Hz, 1H), 4.42 (t, J=5.0 Hz, 2H), 3.03 (t, J=6.0 Hz, 2H), 2.45 (s, 3H), 2.14 (t, J=5.0 Hz, 2H).

$^{13}$C NMR (125 MHz, $d_6$-DMSO) δ 176.0, 163.6, 161.5, 155.8, 154.3 (d, J=243.0 Hz, 1C), 150.0, 147.4, 137.7 (d, J=9.9 Hz, 1C), 135.3 (d, J=12.9 Hz, 1C), 135.2, 135.1, 135.1, 134.2, 129.0, 128.7, 128.67, 127.2, 126.3, 125.2, 123.6, 116.2, 115.6, 109.8, 108.4 (d, J=23.1 Hz, 1C), 102.4, 52.9, 26.5, 21.2, 21.2.

HRMS (ESI) for $C_{32}H_{24}FN_5O_3[M+H]^+$, calcd: 546.1936, found: 546.1932.

HPLC analysis: MeOH—$H_2O$ (85:15), 12.28 min, 97.3% purity.

Embodiment 37: Preparation of N-(4-((6,7-dimethoxyquinazolin-4-yl)oxy)-3-fluorophenyl)-9-methyl-1-oxo-1,5,6,7-tetrahydropyrido[3,2,1-ij]quinoline-2-carboxamide (TL4830032)

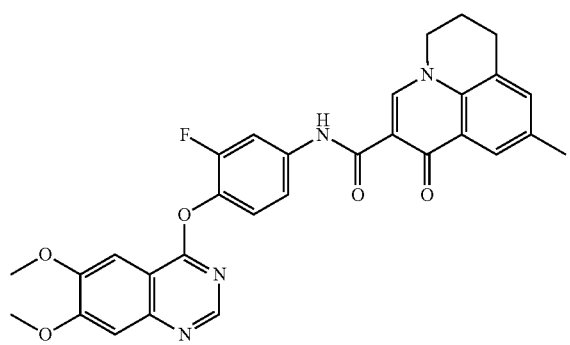

The synthetic method is as shown in Embodiment 35.

$^1$H NMR (500 MHz, CDCl$_3$) δ 12.64 (s, 1H), 8.73 (s, 1H), 8.63 (d, J=1.5 Hz, 1H), 8.17 (s, 1H), 8.01 (d, J=12.5 Hz, 1H), 7.59 (s, 1H), 7.47 (d, J=2.1 Hz, 1H), 7.36 (s, 1H), 7.33 (s, 1H), 7.28 (m, 1H), 4.29 (s, 2H), 4.08 (s, 3H), 4.07 (s, 3H), 3.08 (s, 2H), 2.49 (s, 3H), 2.28 (s, 2H).

$^{13}$C NMR (125 MHz, CDCl$_3$) δ 176.7, 164.9, 163.5, 156.0, 154.3 (d, J=246.0 Hz, 1C), 152.9, 150.3, 149.5, 146.1, 137.9 (d, J=9.9 Hz, 1C), 135.5, 135.3 (d, J=13.1 Hz, 1C), 134.8, 133.9, 127.5, 127.1, 124.5, 123.8, 116.1 (d, J=3.0 Hz, 1C), 110.8, 110.3, 109.2 (d, J=23.1 Hz, 1C), 106.9, 101.1, 56.4, 53.2, 26.7, 21.4, 21.16.

HRMS (ESI) for $C_{30}H_{25}FN_4O_5[M+H]^+$, calcd: 658.2472, found: 658.2753.

HPLC analysis: MeOH—$H_2O$ (85:15), 10.41 min, 97.42% purity.

Embodiment 38: Preparation of N-(3-fluoro-4-(5-phenyl-7H-pyrrolo[2,3-d]pyrimidin-4-yloxy)phenyl)-1,6-dimethyl-4-oxo-1,4-dihydroquinoline-3-carboxamide (named as TL4800167)

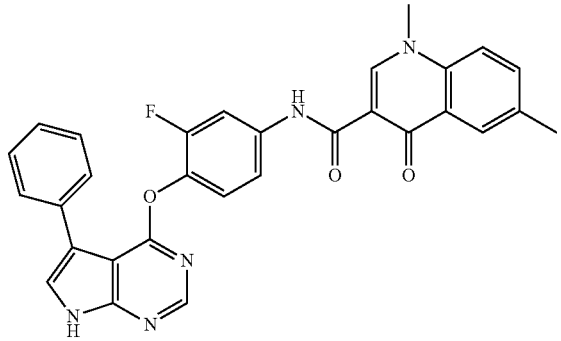 [SMILES: Cc1ccc2c(c1)c(=O)c(C(=O)Nc1ccc(Oc3ncnc4[nH]cc(-c5ccccc5)c34)c(F)c1)cn2C]

The synthetic method is as shown in Embodiment 35.

$^1$H NMR (500 MHz, $d_6$-DMSO) δ 12.67 (s, 1H), 8.97 (s, 1H), 8.30 (s, 1H), 8.20 (s, 1H), 7.99-7.97 (d, J=12.5 Hz, 1H), 7.80-7.74 (m, 5H), 7.42-7.38 (m, 4H), 7.25 (m, 1H), 4.06 (s, 3H), 2.49 (s, 3H).

$^{13}$C NMR (125 MHz, $d_6$-DMSO) δ 176.0, 163.5, 161.6, 155.3, 154.3 (d, J=242.5 Hz, 1C), 150.3, 149.4, 138.6, 137.7 (d, J=9.6 Hz, 1C), 135.8, 135.3 (d, J=12.9 Hz, 1C), 135.1, 134.9, 128.8, 128.7, 127.1, 126.5, 125.8, 125.2, 118.2, 116.3 (d, J=2.9 Hz, 1C), 115.8, 110.2, 108.5 (d, J=23.3 Hz, 1C), 102.4, 41.9, 21.1.

HRMS (ESI) for $C_{31}H_{24}FN_5O_3[M+H]^+$, calcd: 534.1936, found: 534.19324.

HPLC analysis: MeOH—$H_2O$ (85:15), 3.78 min, 97.54% purity.

Embodiment 39: Preparation of N-(3-fluoro-4-(5-phenyl-7H-pyrrolo[2,3-d]pyrimidin-4-yloxy)phenyl)-1,2-dimethyl-4-oxo-6-(prop-1-en-2-yl)-1,4-dihydroquinoline-3-carboxamide (named as T50167)

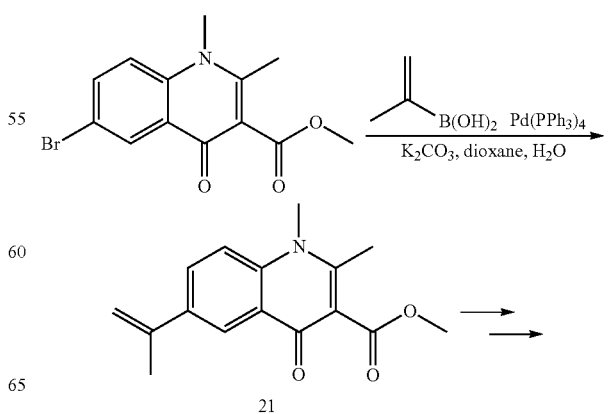

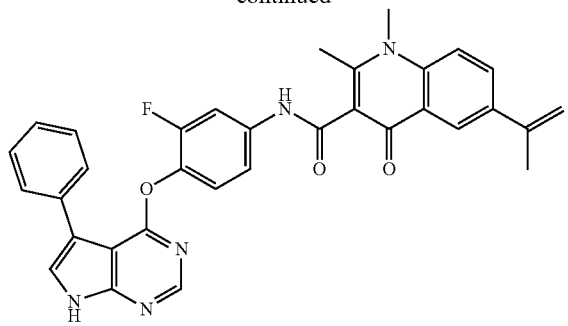

22

Step e1: methyl 1,2-dimethyl-4-oxo-6-(prop-1-en-2-yl)-1,4-dihydroquinoline-3-carboxylate (Compound 21)

Methyl 6-bromo-1,2-dimethyl-4-oxo-1,4-dihydroquinoline-3-carboxylate (1.5 g, 4.85 mmol), 2-propyleneboronic acid (1.22 g, 7.28 mmol), Pd(PPh$_3$)$_4$ (280 mg, 0.24 mmol), and K$_2$CO$_3$ (1.34 g, 9.7 mmol) were dissolved in 30 mL of dioxane and 5 mL of water, and reacted overnight at 90° C. under the protection of argon. The solution was cooled to room temperature and filtered, the majority of the organic solvent was spun to dryness, extracted twice with EA, and the organic phases were combined, washed once with saturated brine, and dried over anhydrous Na$_2$SO$_4$, subjecting same to filtration, rotary drying and column chromatography to obtain 1.23 g (93.8%) of the solid. $^1$HNMR (500 MHz, d$_6$-DMSO), δ 8.18 (s, 1H), 8.96 (d, J=10.0 Hz, 1H), 7.80 (d, J=10.0 Hz, 1H), 5.58 (m, 1H), 5.21 (s, 1H), 3.78 (s, 3H), 3.77 (s, 3H), 2.45 (s, 3H), 2.17 (s, 3H). MS (ESI), m/z: 272[M+H]$^+$.

Step e2: N-(3-fluoro-4-(5-phenyl-7H-pyrrolo[2,3-d]pyrimidin-4-yloxy)phenyl)-1,2-dimethyl-4-oxo-6-(prop-1-en-2-yl)-1,4-dihydroquinoline-3-carboxamide (compound 22, TL50167)

The other synthetic steps are as shown in Embodiment 25.
$^1$H NMR (500 MHz, d$_6$-DMSO) δ 10.93 (s, 1H), 8.29 (m, 2H), 8.01 (d, J=9.0 Hz, 1H), 7.92-7.86 (m, 2H), 7.78-7.74 (m, 3H), 7.45 (d, J=9.0 Hz, 1H), 7.41-7.38 (t, J=8.0 Hz, 3H), 7.25 (t, J=7.5 Hz, 1H), 5.61 (s, 1H), 5.23 (s, 1H), 3.85 (s, 3H), 2.64 (s, 3H), 2.20 (s, 3H).

$^{13}$C NMR (125 MHz, d$_6$-DMSO) δ 174.0, 166.0, 161.8, 154.6, 154.1 (d, J=242.3 Hz, 1C), 152.5, 150.7, 141.6, 140.7, 138.5 (d, J=9.6 Hz, 1C), 135.9, 135.1 (d, J=12.8 Hz, 1C), 134.6, 130.2, 128.9, 128.7, 126.8, 126.0, 125.0, 124.3, 122.1, 119.7, 117.7, 116.0, 113.9, 108.0 (d, J=21.9 Hz, 1C), 102.3, 35.7, 21.8, 19.5.

HRMS (ESI) for C$_{33}$H$_{26}$FN$_5$O$_3$ [M+H]$^+$, calcd: 560.2092, found: 560.2081.

HPLC analysis: MeOH—H$_2$O (90:10), 8.13 min, 97.79% purity.

Embodiment 40: Preparation of 6-cyclopropyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL50148)

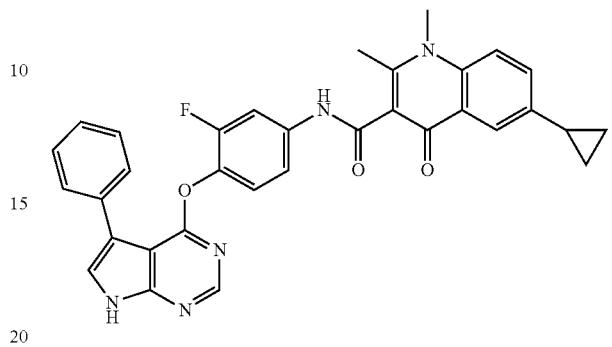

The synthetic method is as shown in Embodiment 39.
$^1$H NMR (500 MHz, d$_6$-DMSO) δ 11.02 (s, 1H), 8.29 (s, 1H), 7.95 (d, J=2.0 Hz, 1H), 7.90 (dd, J=2.0, 12.5 Hz, 1H), 7.79-7.77 (m, 3H), 7.73 (s, 1H), 7.51 (dd, J=2.0, 8.5 Hz, 1H), 7.45 (dd, J=2.0, 9.5 Hz, 1H), 7.41-7.37 (m, 3H), 7.24 (t, J=7.0 Hz, 1H), 3.82 (s, 3H), 2.64 (s, 3H), 2.14-2.09 (m, 1H), 1.04 (m, 2H), 0.76 (m, 2H).

$^{13}$C NMR (125 MHz, d$_6$-DMSO) δ 173.8, 166.1, 161.6, 154.2 (d, J=242.8 Hz, 1C), 152.4, 150.1, 140.1, 139.4, 138.4 (d, J=9.9 Hz, 1C), 135.2 (d, J=13.1 Hz, 1C), 135.0, 130.9, 128.8, 128.7, 126.4, 126.3, 125.0, 121.8, 119.0, 117.6, 115.9, 115.6, 108.0 (d, J=23.4 Hz, 1C), 102.4, 35.7, 19.5, 15.0, 10.2.

HRMS (ESI) for C$_{33}$H$_{26}$FN$_5$O$_3$ [M+H]$^+$, calcd: 560.2092, found: 560.2081.

HPLC analysis: MeOH—H$_2$O (75:25), 5.63 min, 95.14% purity.

Embodiment 41: Preparation of 6-cyclopentenyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL50160)

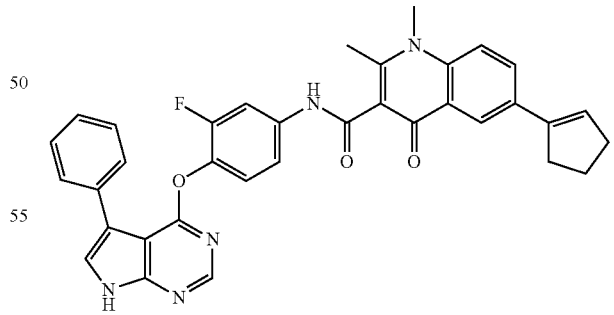

The synthetic method is as shown in Embodiment 39.
$^1$H NMR (500 MHz, d$_6$-DMSO) δ 12.52 (s, 1H), 10.98 (s, 1H), 8.33 (s, 1H), 8.16 (s, 1H), 7.99 (d, J=8.0 Hz, 1H), 7.91 (d, J=12.0 Hz, 1H), 7.83 (d, J=9.0 Hz, 1H), 7.77 (m, 3H), 7.46 (d, J=9.0 Hz, 1H), 7.41 (m, 3H), 7.27 (t, J=7.0 Hz, 1H), 6.87 (s, 1H), 6.44 (s, 1H), 3.84 (s, 3H), 2.75 (m, 2H), 2.64 (s, 3H), 2.53 (m, 2H), 2.01 (m, 2H).

$^{13}$C NMR (125 MHz, d$_6$-DMSO) δ 174.0, 166.0, 161.8, 154.6, 154.1 (d, J=243.0 Hz, 1C), 152.4, 151.9, 150.7, 141.2, 140.3, 139.6, 138.5 (d, J=10.0 Hz, 1C), 135.1 (d, J=12.6 Hz, 1C), 134.6, 132.1, 130.7, 128.9, 128.7, 127.5, 127.8, 126.8, 126.2, 125.4, 124.9, 124.2, 122.0, 119.5, 117.7, 116.0 (d, J=2.1 Hz, 1C), 108.0 (d, J=23.3 Hz, 1C), 102.3, 67.5, 35.7, 34.8, 33.6, 33.2, 30.9, 25.6, 23.3, 21.5, 19.5.

HPLC analysis: MeOH—H$_2$O (85:15), 6.78 min, 95.15% purity.

Embodiment 43: Preparation of N-(3-fluoro-4-(5-phenyl-7H-pyrrolo[2,3-d]pyrimidin-4-yloxy)phenyl)-1,2-dimethyl-4-oxo-6-(1-piperidin-4-yl)-1H-pyrazol-4-yl)-1,4-dihydroquinoline-3-carboxamide (named as TL50180)

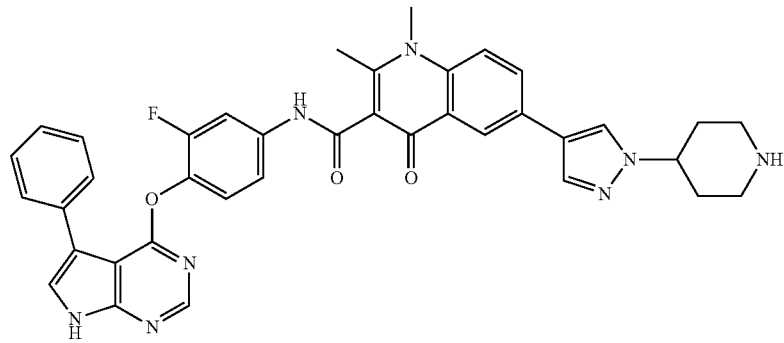

HRMS (ESI) for C$_{35}$H$_{28}$FN$_5$O$_3$[M+H]$^+$, calcd: 586.2249, found: 586.2243.

HPLC analysis: MeOH—H$_2$O (85:15), 11.32 min, 97.72% purity.

The synthetic method is as shown in Embodiment 39. MS (ESI) m/z 669 [M+H]$^+$.

Embodiment 42: Preparation of N-(3-fluoro-4-(5-phenyl-7H-pyrrolo[2,3-d]pyrimidin-4-yloxy)phenyl)-1,2-dimethyl-4-oxo-6-phenyl-1,4-dihydroquinoline-3-carboxamide (named as TL50163)

Embodiment 44: Preparation of N-(3-fluoro-4-(5-phenyl-7H-pyrrolo[2,3-d]pyrimidin-4-yloxy)phenyl)-6-isopropyl-1,2-dimethyl-4-oxo-1,4-dihydroquinoline-3-carboxamide (named as TL50172)

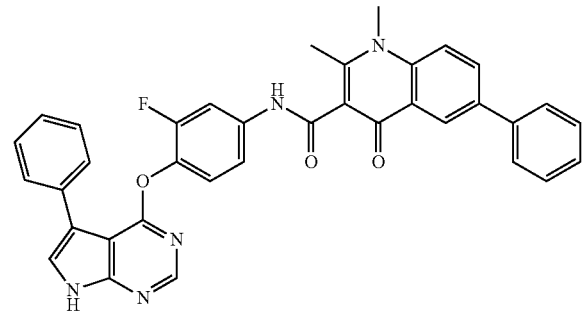 [SMILES: Cc1c(C(=O)Nc2ccc(Oc3ncnc4[nH]cc(-c5ccccc5)c34)c(F)c2)c(=O)c2cc(-c3ccccc3)ccc2n1C]

The synthetic method is as shown in Embodiment 39.

$^1$H NMR (500 MHz, d$_6$-DMSO) δ 10.94 (s, 1H), 8.51 (d, J=2.0 Hz, 1H), 8.31 (s, 1H), 8.13 (dd, J=2.5, 9.0 Hz, 1H), 7.99 (d, J=9.0 Hz, 1H), 7.91 (dd, J=2.0, 13.0 Hz, 1H), 7.78 (m, 4H), 7.75 (s, 1H), 7.52 (t, J=7.5 Hz, 2H), 7.47 (dd, J$_1$=2.0, 9.0 Hz, 1H), 7.43-7.39 (m, 4H), 7.26 (t, J=7.5 Hz, 1H), 3.88 (s, 3H), 2.65 (s, 3H).

$^{13}$C NMR (125 MHz, d$_6$-DMSO) δ 174.0, 166.0, 161.7, 155.2, 154.2 (d, J=242.9 Hz, 1C), 152.5, 150.4, 140.8, 139.2, 138.4 (d, J=9.8 Hz, 1C), 135.9, 135.2 (d, J=12.9 Hz, 1C), 134.8, 131.5, 129.7, 128.8, 128.7, 128.3, 127.1, 126.6, 125.0, 123.3, 119.9, 118.4, 116.0 (d, J=2.9 Hz, 1C), 115.8, 108.0 (d, J=23.0 Hz, 1C), 102.4.35.8, 19.5.

HRMS (ESI) for C$_{36}$H$_{26}$FN$_5$O$_3$ [M+H]$^+$, calcd: 596.2092, found: 596.2089.

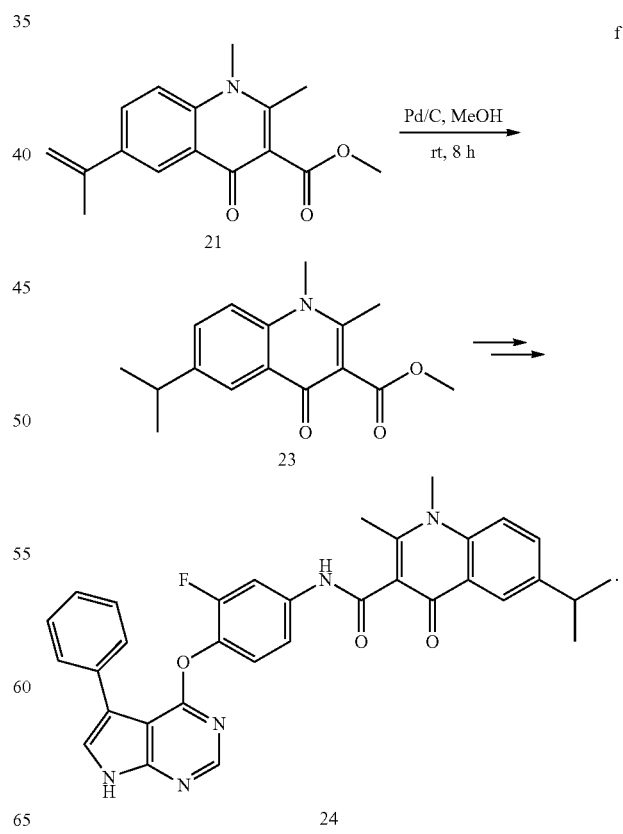

Step f1: ethyl 6-isopropyl-1,2-dimethyl-4-oxo-1,4-dihydroquinoline-3-carboxylate (Compound 23)

Methyl 1,2-dimethyl-4-oxo-6-(prop-1-en-2-yl)-1,4-dihydroquinoline-3-carboxylate (compound 21) (542 mg, 2 mmol) was dissolved in MeOH, 55 mg of Pd/C catalyst was added, and reacted at room temperature for 8 hours under the protection of hydrogen pressure. The solution was filtered, subjecting the filtrate to rotary drying and column chromatography to obtain 440 mg (80.59%) of the solid. $^1$HNMR (400 MHz, d$_6$-DMSO), δ 7.99 (s, 1H), 7.77 (d, J=8.0 Hz, 1H), 7.67 (d, J=8.0 Hz, 1H), 3.77 (s, 3H), 3.76 (s, 3H), 3.08-3.01 (m, 1H), 2.44 (s, 3H), 1.26 (s, 3H), 1.24 (s, 3H). MS (ESI), m/z: 274[M+H]$^+$.

Step f2: N-(3-fluoro-4-(5-phenyl-7H-pyrrolo[2,3-d]pyrimidin-4-yloxy)phenyl)-6-isopropyl-1,2-dimethyl-4-oxo-1,4-dihydroquinoline-3-carboxamide (compound 24, TL50172)

The other synthetic steps are as shown in Embodiment 25.
$^1$H NMR (500 MHz, d$_6$-DMSO) δ 11.02 (s, 1H), 8.31 (s, 1H), 8.12 (s, 1H), 7.90 (d, J=12.5 Hz, 1H), 7.84-7.72 (m, 5H), 7.46-7.27 (m, 4H), 7.27 (d, J=6.5 Hz, 1H), 3.84 (s, 3H), 3.07 (m, 1H), 2.66 (s, 3H), 1.27 (m, 6H).

$^{13}$C NMR (125 MHz, d$_6$-DMSO) δ 174.1, 166.1, 161.7, 154.2 (d, J=246.0 Hz, 1C), 152.5, 150.4, 144.5, 139.8, 138.5 (d, J=9.1 Hz, 1C), 135.1 (d, J=12.6 Hz, 1C), 134.8, 132.1, 128.8, 128.7, 126.6, 126.2, 125.1, 125.0, 122.6, 119.0, 117.6, 115.9, 115.8, 108.0 (d, J=23.3 Hz, 1C), 102.4, 35.7, 33.2, 24.2, 19.5.

HRMS (ESI) for C$_{33}$H$_{28}$FN$_5$O$_3$[M+H]$^+$, calcd: 562.2249, found: 562.2253.

HPLC analysis: MeOH—H$_2$O (85:15), 6.28 min, 98.65% purity.

Embodiment 45: Preparation of 6-cyclopentyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (named as TL50161)

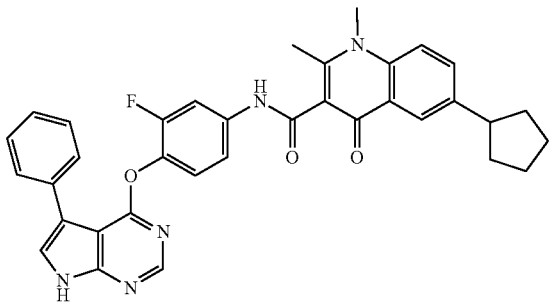 [SMILES: Cc1c(C(=O)Nc2ccc(Oc3ncnc4[nH]cc(-c5ccccc5)c34)c(F)c2)c(=O)c2cc(C3CCCC3)ccc2n1C]

The synthetic method is as shown in Embodiment 44.
$^1$H NMR (500 MHz, d$_6$-DMSO) δ 11.03 (s, 1H), 8.33 (d, J=2.0 Hz, 1H), 8.12 (d, J=1.5 Hz, 1H), 7.91 (dd, J=2.0, 12.5 Hz, 1H), 7.82-7.75 (m, 4H), 7.69 (dd, J=2.0, 9.0 Hz, 1H), 7.45 (dd, J=1.5, 9.0 Hz, 1H), 7.42-7.38 (m, 3H), 7.27 (m, 1H), 3.83 (s, 3H), 3.15 (m, 1H), 2.65 (s, 3H), 2.10-2.06 (m, 2H), 1.82-1.78 (m, 2H), 1.71-1.68 (m, 2H), 1.62-1.56 (m, 2H).

$^{13}$C NMR (125 MHz, d$_6$-DMSO) δ 174.0, 166.1, 161.7, 154.7, 154.1 (d, J=242.5 Hz, 1C), 152.6, 150.6, 142.2, 139.7, 138.5 (d, J=9.9 Hz, 1C), 135.0 (d, J=12.8 Hz, 1C), 134.6, 132.6, 128.9, 128.8, 128.7, 126.7, 126.1, 125.4 124.9, 124.4, 123.3, 118.9, 117.5, 116.0, 115.9 (d, J=2.8 Hz, 1C), 108.0 (d, J=23.0 Hz, 1C), 102.3, 45.0, 35.7, 34.6, 30.9, 25.5, 19.5.

HRMS (ESI) for C$_{35}$H$_{30}$FN$_5$O$_3$[M+H]$^+$, calcd: 588.2405, found: 588.2394.

HPLC analysis: MeOH—H$_2$O (85:15), 8.40 min, 96.84% purity.

Embodiment 46: Preparation of methyl 3-((3-fluoro-4-(5-phenyl-7H-pyrrolo[2,3-d]pyrimidin-4-yloxy)phenyl)carbamoyl)-1,2-dimethyl-4-oxo-1,4-dihydroquinoline-6-carboxylate (named as TL4800019)

g.

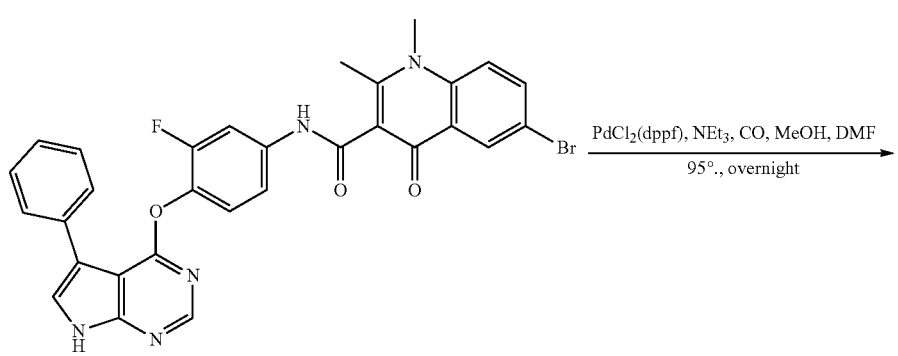

-continued

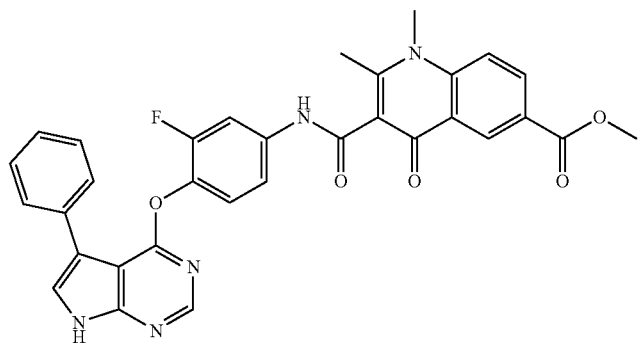

25

Step g1: methyl 3-((3-fluoro-4-(5-phenyl-7H-pyrrolo[2,3-d]pyrimidin-4-yloxy)phenyl)carbamoyl)-1,2-dimethyl-4-oxo-1,4-dihydroquinoline-6-carboxylate (compound 25, TL4800019)

6-Bromo-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide (200 mg, 0.33 mmol), PdCl$_2$(dppf), and triethylamine were dissolved in methanol and a catalytic amount of DMF, and reacted at 95° C. overnight under CO pressure. The solution was cooled to room temperature and filtered, the majority of the organic solvent was spun to dryness, extracted twice with DCM, and the organic phases were combined, washed once with saturated brine, and dried over anhydrous Na$_2$SO$_4$, subjecting same to filtration, rotary drying and column chromatography to obtain 120 mg (63.16%) of the solid.

$^1$H NMR (500 MHz, d$_6$-DMSO) δ 12.52 (s, 1H), 10.76 (s, 1H), 8.82 (d, J=2.0 Hz, 1H), 8.33 (s, 1H), 8.25 (dd, J=2.0, 9.0 Hz, 1H), 8.00 (d, J=9.0 Hz, 1H), 7.91-7.88 (dd, J=2.0, 12.5 Hz, 1H), 7.77 (m, 3H), 7.46 (dd, J=1.0, 9.0 Hz, 1H), 7.41 (m, 3H), 7.28 (t, J=7.0 Hz, 1H), 3.92 (s, 3H), 3.86 (s, 3H), 2.62 (s, 3H).

$^{13}$C NMR (125 MHz, d$_6$-DMSO) δ 173.7, 166.0, 165.5, 161.7, 154.6, 154.1 (d, J=242.8 Hz, 1C), 152.8, 150.7, 144.2, 138.3 (d, J=10.0 Hz, 1C), 135.2 (d, J=12.8 Hz, 1C), 134.7, 132.7, 128.9, 128.7, 128.1, 126.8, 125.8, 125.0, 124.9, 124.3, 121.4, 118.3, 116.0, 115.9 (d, J=2.5 Hz, 1C), 108.0 (d, J=23.0 Hz, 1C), 102.3, 52.8, 35.9, 19.6.

HRMS (ESI) for C$_{32}$H$_{24}$FN$_5$O$_5$[M+H]$^+$, calcd: 578.1834, found: 578.1833.

HPLC analysis: MeOH—H$_2$O (85:15), 4.26 min, 96.31% purity.

Embodiment 47: Preparation of N-(3-fluoro-4-(7-methyl-5-phenyl-7H-pyrrolo[2,3-d]pyrimidin-4-yloxy)phenyl)-1,2,6-trimethyl-4-oxo-1,4-dihydroquinoline-3-carboxamide (named as TL50134)

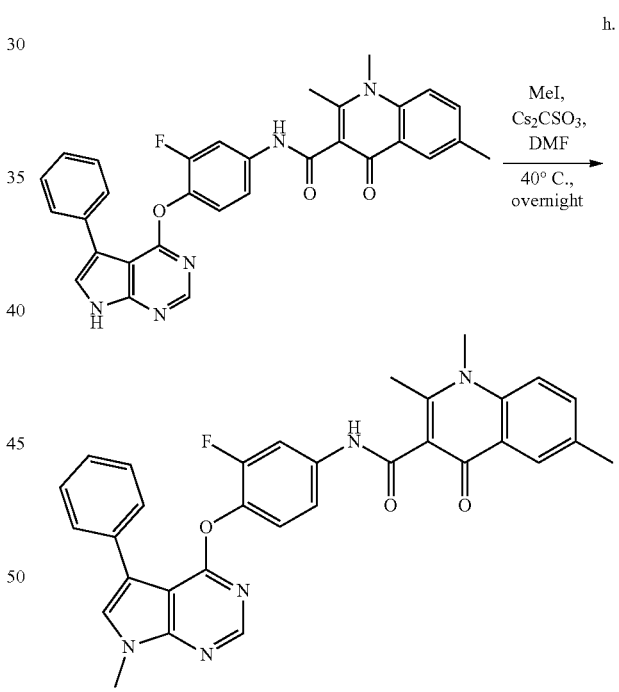

Step h1: N-(3-fluoro-4-(7-methyl-5-phenyl-7H-pyrrolo[2,3-d]pyrimidin-4-yloxy)phenyl)-1,2,6-trimethyl-4-oxo-1,4-dihydroquinoline-3-carboxamide (compound 26, TL50134)

N-(3-fluoro-4-(5-phenyl-7H-pyrrolo[2,3-d]pyrimidin-4-yloxy)phenyl)-1,2,6-trimethyl-4-oxo-1,4-dihydroquinoline-3-carboxamide (100 mg, 0.18 mmol) and cesium carbonate (122 mg, 0.36 mmol) were dissolved in 20 mL of DMF, MeI (22 μL, 0.36 mmol) was added and reacted overnight at 40° C. The solution was cooled to room temperature, quenched by addition of water, extracted twice with DCM, and the organic phases were combined, washed once with saturated brine, and dried over anhydrous $Na_2SO_4$, subjecting same to filtration, rotary drying and column chromatography to obtain 80 mg (81.63%) of the solid.

$^1$H NMR (500 MHz, $d_6$-DMSO) δ 11.00 (s, 1H), 8.38 (s, 1H), 8.06 (s, 1H), 7.90 (dd, J=2.0, 13.0 Hz, 1H), 7.82-7.75 (m, 4H), 7.62 (dd, J=2.0, 8.5 Hz, 1H), 7.47-7.38 (m, 4H), 7.28 (t, J=7.5 Hz, 1H), 3.89 (s, 3H), 3.82 (s, 3H), 2.63 (s, 3H), 2.45 (s, 3H).

$^{13}$C NMR (125 MHz, $d_6$-DMSO) δ 173.9, 166.1, 161.8, 154.1 (d, J=242.8 Hz, 1C), 153.1, 152.3, 150.6, 139.5, 138.6 (d, J=10.5 Hz, 1C), 135.0 (d, J=12.6 Hz, 1C), 134.4, 134.2, 133.8, 128.8, 128.8, 128.3, 126.9, 126.2, 125.5, 124.9, 119.2, 117.4, 115.9 (d, J=2.4 Hz, 1C), 115.3, 108.0 (d, J=23.0 Hz, 1C), 102.4, 35.6, 31.8, 20.9, 19.5.

HRMS (ESI) Calcd for $[M+H]^+$=548.2092, found: $[M+H]^+$=548.2087.

HPLC analysis: MeOH—$H_2O$ (85:15), 5.86 min, 97.75%.

Embodiment 48: Preparation of N-(4-(6,7-dimethoxyquinazolin-4-yloxy)-3-fluorophenyl)-6-ethyl-1,2-dimethyl-4-oxo-1,4-dihydroquinoline-3-carboxamide (named as TL4800191)

i.

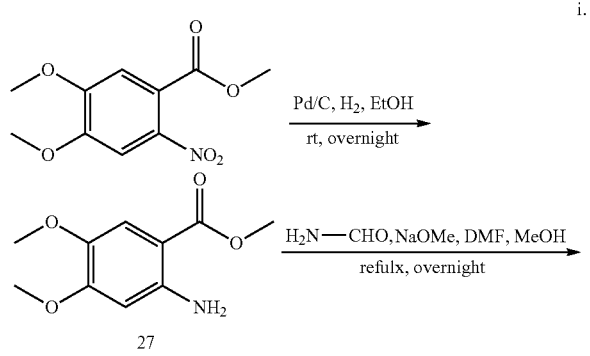

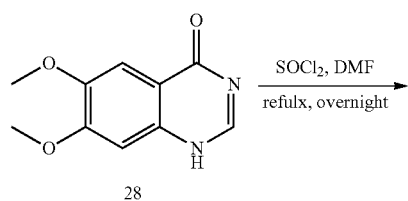

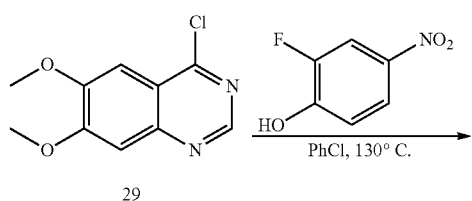

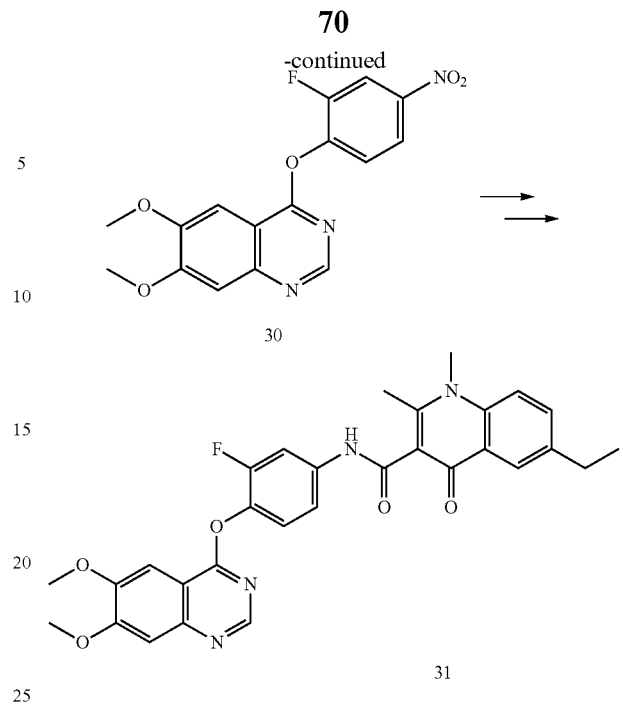

Step j1: methyl 2-amino-4,5-dimethoxy benzoate (Compound 27)

4,5-Dimethoxy-2-nitromethyl benzoate (10 g, 41 mmol) and 1 g of Pd/C were dissolved in 200 mL of ethanol, and reacted under hydrogen pressure at room temperature overnight. The solution was filtered, subjecting the organic phases to rotary drying and column chromatography to obtain 7.3 g (84.88%) of the solid. $^1$HNMR (500 MHz, $d_6$-DMSO), δ 7.33 (s, 1H), 7.31 (s, 1H), 5.62 (s, 2H), 3.90 (s, 3H), 3.89 (s, 3H), 3.87 (s, 3H). MS (ESI), m/z: 212[M+H]$^+$.

Step j2: 6,7-dimethoxyquinazoline-4(1)-one (Compound 28)

methyl 2-amino-4,5-dimethoxy benzoate (compound 27) (7 g, 33 mmol) was dissolved in 100 mL of DMF and 50 mL of methanol, and to the mixture was added formamide (10.5 mL, 264 mmol) and sodium methoxide (10.69 g, 198 mmol), and the reaction was refluxed overnight. The mixture was cooled to room temperature, quenched by addition of water, neutralized with dilute hydrochloric acid, filtered, washed with water and ether, and drained to obtain 6.08 g (89.44%) of the solid. $^1$HNMR (500 MHz, $d_6$-DMSO), δ 12.05 (s, 1H), 7.98 (s, 1H), 7.44 (s, 1H), 7.13 (s, 1H), 3.90 (s, 3H), 3.87 (s, 3H). MS (ESI), m/z: 207[M+H]$^+$.

Step j3: 4-chloro-6,7-dimethoxyquinazoline (Compound 29)

6,7-dimethoxyquinazoline-4(1H)-one (compound 28) (6 g, 29 mmol) was dissolved in 100 mL of thionyl chloride and 10 mL of DMF, and the reaction was refluxed overnight. The solution was cooled to room temperature, the majority of the solvent was spun to dryness, then slowly poured into ice water to precipitate the solid, filtered, washed with water and ether, and drained to obtain 5.34 g (82.15%) of the solid.

¹HNMR (500 MHz, d₆-DMSO), δ 8.88 (s, 1H), 7.46 (s, 1H), 7.40 (s, 1H), 4.02 (s, 3H), 4.00 (s, 3H). MS (ESI), m/z: 226[M+H]⁺.

Step j4: 4-(2-fluoro-4-nitrophenoxy)-6,7-dimethoxy-quinazoline (Compound 30)

4-chloro-6,7-dimethoxyquinazoline (compound 29) (5 g, 22.3 mmol) and 2-fluoro-4-nitrophenol (4.2 g, 26.7 mmol) were dissolved in 100 mL of chlorobenzene, and reacted overnight at 130° C. The solution was cooled to room temperature and filtered, and the solid was stirred in NaOH solution for 1 hour and filtered again to obtain 5.22 g (67.8%) of the solid. ¹HNMR (500 MHz, d₆-DMSO), δ 8.59 (s, 1H), 8.42 (dd, J=5.0, 10.0 Hz, 1H), 8.25 (dd, J=5.0, 10.0 Hz, 1H), 7.85 (t, J=10.0 Hz, 1H), 7.60 (s, 1H), 7.50 (s, 1H), 4.01 (s, 3H), 4.00 (s, 3H). MS (ESI), m/z: 346[M+H]⁺.

Step j5: N-(4-(6,7-dimethoxyquinazolin-4-yloxy)-3-fluorophenyl)-6-ethyl-1,2-dimethyl-4-oxo-1,4-dihydroquinoline-3-carboxamide (compound 31, TL4800191)

The other synthetic steps are as shown in Embodiment 25.

¹H NMR (500 MHz, CDCl₃) δ 12.69 (s, 1H), 8.64 (s, 1H), 8.34 (s, 1H), 7.99 (dd, J=2.0, 12.5 Hz, 1H), 7.60 (m, 2H), 7.53 (d, J=8.5 Hz, 1H), 7.45 (d, J=8.5 Hz, 1H), 7.36 (s, 1H), 7.29-7.26 (m, 1H), 4.09 (s, 3H), 4.07 (s, 3H), 3.91 (s, 3H), 3.08 (s, 3H), 2.84-2.80 (q, J=7.5 Hz, 2H), 1.35-1.32 (t, J=7.5 Hz, 3H).

¹³C NMR (125 MHz, CDCl₃) δ 176.6, 165.0, 164.9, 158.2, 156.0, 154.3 (d, J=245.6 Hz, 1C), 152.9, 150.3, 149.4, 141.5, 138.7, 138.3 (d, J=9.6 Hz, 1C), 135.12 (d, J=12.9 Hz, 1C), 133.6, 126.4, 125.4, 125.3, 123.7, 123.7, 116.2 (d, J=2.8 Hz, 1C), 115.8, 113.6, 110.3, 109.4 (d, J=22.9 Hz, 1C), 106.8, 101.1, 56.4, 35.7, 28.3, 20.4, 15.3.

HRMS (ESI) Calcd for [M+H]⁺=543.2038, found: [M+H]⁺=543.2035.

HPLC analysis: MeOH—H₂O (85:15), 5.03 min, 99.75%.

Embodiment 49: Preparation of N-(4-((6,7-dimethoxyquinazolin-4-yl)oxy)-3-fluorophenyl)-6-fluoro-1-methyl-7-(4-((5-methyl-2-oxo-1,3-dioxol-4-yl)methyl)piperazin-1-yl)-4-oxo-1,4-dihydro-[1,3]thiazeto[3,2-a]quinoline-3-carboxamide (named as GDL5000082)

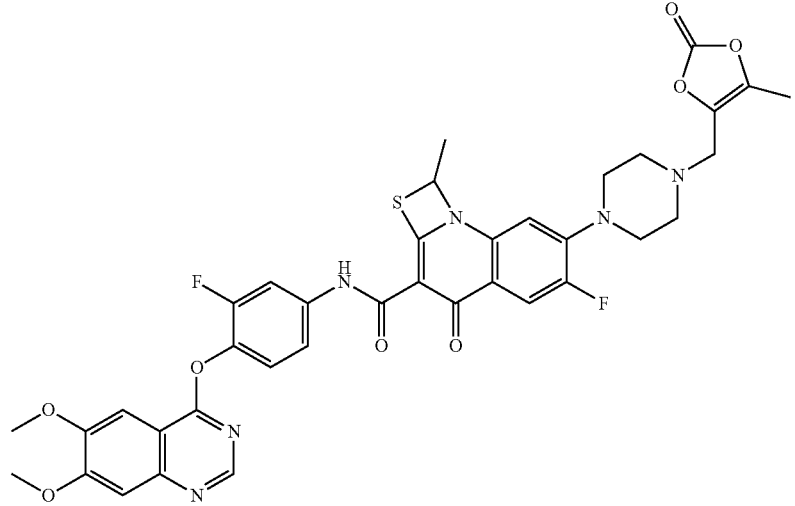

The synthetic method is as shown in Embodiment 48.

¹H NMR (500 MHz, d₆-DMSO) δ 12.08 (s, 1H), 8.56 (s, 1H), 7.93 (d, J=13.0 Hz, 1H), 7.80 (d, J=13.5 Hz, 1H), 7.56 (s, 1H), 7.46-7.40 (m, 3H), 6.86 (d, J=7.0 Hz, 1H), 6.33 (q, J=6.0 Hz, 1H), 4.00 (s, 3H), 3.98 (s, 3H), 3.46 (s, 2H), 3.27 (s, 4H), 2.63 (s, 4H), 2.13-2.10 (m, 6H).

¹³C NMR (125 MHz, d₆-DMSO) δ 173.8, 164.5, 163.8, 163.6, 156.4, 154.1 (d, J=243.5 Hz, 1C), 152.9, 152.6, 152.2 (d, J=243.9 Hz, 1C), 150.8, 149.4, 144.9 (d, J=10.4 Hz, 1C), 138.9, 137.7 (d, J=9.6 Hz, 1C), 135.8, 135.1 (d, J=12.8 Hz, 1C), 134.9, 125.0, 119.8 (d, J=6.5 Hz, 1C), 116.1, 112.9 (d, J=23.3 Hz, 1C), 109.6, 108.3 (d, J=23.0 Hz, 1C), 107.3, 104.3, 102.8, 101.0, 72.2, 56.7, 56.5, 52.0, 49.9, 49.6, 21.0, 9.2.

HRMS (ESI) for C₃₇H₃₂F₂N₆O₈S [M+H]⁺, calcd: 759.2042, found: 759.2046.

HPLC analysis: MeOH—H₂O (85:15), 9.48 min, 95.23% purity.-

Embodiment 50: Preparation of N-(4-((6,7-dimethoxyquinazolin-4-yl)oxy)-3-fluorophenyl)-9-fluoro-8-(4-hydroxypiperidin-1-yl)-5-methyl-1-oxo-1,5,6,7-tetrahydropyrido[3,2,1-ij]quinoline-2-carboxamide (named as TL4830031)

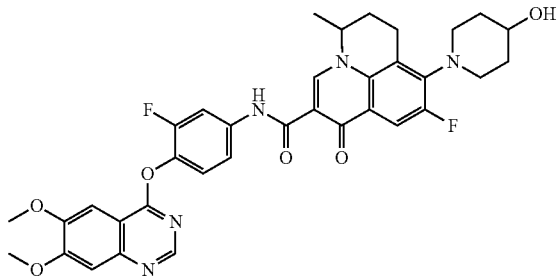 [SMILES: COc1cc2ncnc(Oc3ccc(NC(=O)c4cn5c6c(c(N7CCC(O)CC7)c(F)cc6c4=O)CCC5C)cc3F)c2cc1OC]

The synthetic method is as shown in Embodiment 48.

¹H NMR (500 MHz, d₆-DMSO) δ 12.66 (s, 1H), 8.95 (s, 1H), 8.57 (s, 1H), 8.02 (d, J=12.0 Hz, 1H), 7.89 (d, J=12.5 Hz, 1H), 7.58 (s, 1H), 7.48 (s, 2H), 7.41 (s, 1H), 4.87 (s, 1H), 4.75 (s, 1H), 3.99 (s, 6H), 3.68 (s, 1H), 3.20 (m, 3H), 2.93 (m, 2H), 2.14-2.06 (m, 2H), 1.86 (m, 2H), 1.63-1.51 (m, 2H), 1.43 (d, J=5.0 Hz, 3H).

¹³C NMR (125 MHz, d₆-DMSO) δ 175.04, 164.47, 163.30, 157.47 (d, J=249.3 Hz, 1C), 156.41, 154.04 (d, J=244.9 Hz, 1C), 152.51, 150.74, 149.41, 147.12, 142.33 (d, J=13.7 Hz, 1C), 138.01 (d, J=9.4 Hz, 1C), 135.06 (d, J=12.9 Hz, 1C), 133.57, 126.65, 124.92, 124.16, 116.22, 109.79, 109.60, 109.56, 108.37 (d, J=23.2 Hz, 1C), 107.21, 101.03, 57.09, 56.60, 56.46, 49.08, 35.86, 35.50, 25.58, 20.05, 18.94.

HRMS (ESI) for $C_{35}H_{33}F_2N_5O_6[M+H]^+$, calcd: 658.2472, found: 658.2753.

HPLC analysis: MeOH—H₂O (85:15), 10.63 min, 99.51% purity.

Embodiment 51: Preparation of (S)—N-(4-((6,7-dimethoxyquinazolin-4-yl)oxy)-3-fluorophenyl)-9-fluoro-3-methyl-10-(4-methylpiperazin-1-yl)-7-oxo-3,7-dihydro-2H-[1,4]oxazino[2,3,4-ij]quinoline-6-carboxamide (named as GDL5000111)

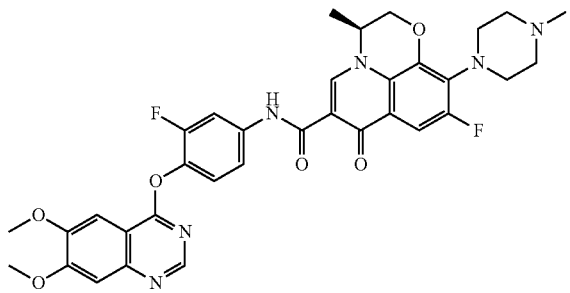

The synthetic method is as shown in Embodiment 48.

¹H NMR (500 MHz, d₆-DMSO) δ 12.59 (s, 1H), 8.95 (s, 1H), 8.57 (s, 1H), 8.01 (m, 1H), 7.58 (m, 2H), 7.46 (m, 2H), 7.40 (s, 1H), 4.92 (m, 1H), 4.57 (d, J=10.5 Hz, 1H), 4.38 (d, J=9.5 Hz, 1H), 4.00 (s, 3H), 3.99 (s, 3H), 3.33 (m, 4H), 2.63 (s, 4H), 2.37 (s, 3H), 1.47 (d, J=7.0 Hz, 3H).

¹³C NMR (125 MHz, d₆-DMSO) δ 174.8, 164.5, 163.3, 156.4, 155.8 (d, J=244.0 Hz, 1C), 154.09 (d, J=243.5 Hz, 1C), 152.6, 150.8, 149.5, 146.0, 140.8 (d, J=7.1 Hz, 1C), 138.0 (d, J=10.1 Hz, 1C), 135.1 (d, J=12.9 Hz, 1C), 131.4 (d, J=14.8 Hz, 1C), 125.1, 124.8, 122.1 (d, J=8.6 Hz, 1C), 116.4, 109.8, 109.6, 108.5 (d, J=21.1 Hz, 1C), 107.3, 104.0 (d, J=23.3 Hz, 1C), 101.0, 68.6, 56.7, 56.5, 55.4, 54.9, 50.0, 45.8, 18.4.

HRMS (ESI) for $C_{34}H_{32}F_2N_6O_6[M+H]+$, calcd: 659.2424, found: 659.2425.

HPLC analysis: MeOH—H₂O (85:15), 15.81 min, 98.54% purity.

Embodiment 52: Preparation of N-(4-((6,7-dimethoxyquinazolin-4-yl)oxy)-3-fluorophenyl)-9-fluoro-3-methyl-10-(4-methylpiperazin-1-yl)-7-oxo-2,3-dihydro-7H-[1,3,4] oxadiazino[6,5,4-ij]quinoline-6-carboxamide (named as TL4830039)

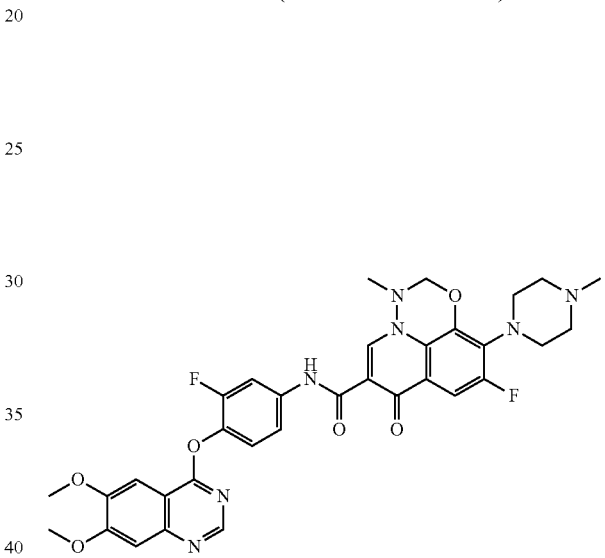

The synthetic method is as shown in Embodiment 48.

¹H NMR (500 MHz, d₆-DMSO) 12.47 (s, 1H), 8.73 (s, 1H), 8.56 (s, 1H), 7.99 (m, 1H), 7.57 (t, J=6.0 Hz, 2H), 7.45 (m, 2H), 7.41 (s, 1H), 5.32 (s, 2H), 4.00 (s, 3H), 3.99 (s, 3H), 3.33 (m, 4H), 3.03 (s, 3H), 2.45 (s, 4H), 2.24 (s, 3H).

¹³C NMR (125 MHz, d₆-DMSO) δ 174.5, 164.5, 162.8, 156.4, 155.7 (d, J=244.5 Hz, 1C), 154.08 (d, J=243.5 Hz, 1C), 152.6, 150.8, 149.5, 144.7, 138.7 (d, J=7.4 Hz, 1C), 137.9 (d, J=10.0 Hz, 1C), 135.2 (d, J=12.8 Hz, 1C), 131.5 (d, J=14.1 Hz, 1C), 125.1, 123.9, 121.5 (d, J=8.1 Hz, 1C), 116.4, 109.6, 109.5, 108.5 (d, J=22.8 Hz, 1C), 107.3, 104.5 (d, J=23.4 Hz, 1C), 101.0, 82.6, 56.7, 56.5, 55.7, 50.5, 46.5, 43.2.

HRMS (ESI) for $C_{33}H_{31}F_2N_7O_6[M+H]^+$, calcd: 660.2377, found: 660.2373.

HPLC analysis: MeOH—H₂O (85:15), 15.48 min, 99.89% purity.

Embodiment 53: Preparation of N-(4-(6,7-dimethoxyquinazolin-4-yloxy)-3-fluorophenyl)-6,8-difluoro-1-(2-fluoroethyl)-7-(4-methylpiperazin-1-yl)-4-oxo-1,4-dihydroquinoline-3-carboxamide (named as TL4830040)

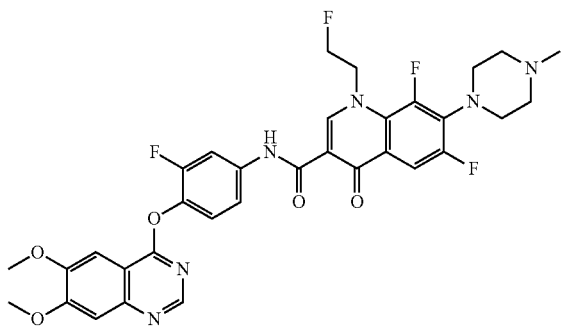

The synthetic method is as shown in Embodiment 48.

$^1$H NMR (500 MHz, d$_6$-DMSO) δ 12.35 (s, 1H), 8.84 (s, 1H), 8.57 (s, 1H), 8.00 (d, J=12.5 Hz, 1H), 7.88 (d, J=12.0 Hz, 1H), 7.57 (s, 1H), 7.48 (s, 2H), 7.41 (s, 1H), 4.95 (s, 2H), 4.88 (m, 2H), 4.00 (s, 3H), 3.99 (s, 3H), 3.33 (s, 4H), 2.45 (s, 4H), 2.23 (s, 3H).

$^{13}$C NMR (125 MHz, CDCl$_3$) δ 174.6, 164.8, 162.4, 156.0, 155.0 (d, J=249.0 Hz, 1C), 154.3 (d, J=246.3 Hz, 1C), 152.9, 150.9, 150.3, 149.5, 145.9 (dd, J=6.4, 244.4 Hz, 1C), 137.5 (d, J=9.5 Hz, 1C), 135.5 (d, J=13.0 Hz, 1C), 133.8 (t, J=13.8 Hz, 1C), 126.6 (d, J=52 Hz, 1C), 123.9, 122.9 (d, J=7.9 Hz, 1C), 116.1 (d, J=2.8 Hz, 1C), 111.0, 110.3, 109.3 (d, J=23.1 Hz, 1C), 108.8 (d, J=22.9 Hz, 1C), 106.9, 101.1, 81.3 (dd, J=5.4, 172.3 Hz, 1C), 58.3 (dd, J=14.9, 20.4 Hz, 1C), 56.4, 56.4, 55.5, 50.9 (t, J=4.0 Hz, 2C), 46.3.

HRMS (ESI) for C$_{33}$H$_{30}$F$_4$N$_6$O$_5$[M+H]$^+$, calcd: 667.2287, found: 667.2290.

HPLC analysis: MeOH—H$_2$O (85:15), 14.66 min, 99.56% purity.

Embodiment 54: Preparation of N-(4-(6,7-dimethoxyquinazolin-4-yloxy)-3-fluorophenyl)-6-fluoro-1-(4-fluorophenyl)-4-oxo-7-(piperazin-1-yl)-1,4-dihydroquinoline-3-carboxamide (named as TL4830042)

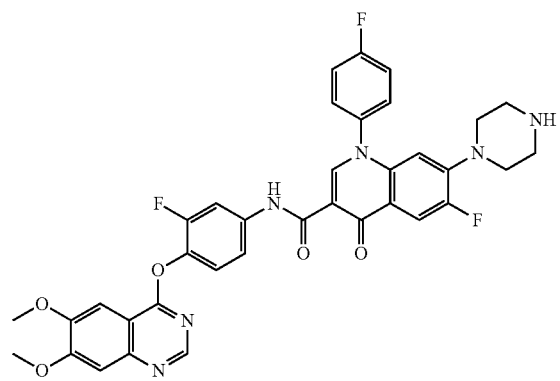 [SMILES: COc1cc2ncnc(Oc3ccc(NC(=O)c4cn(-c5ccc(F)cc5)c5cc(N6CCNCC6)c(F)cc5c4=O)cc3F)c2cc1OC]

The synthetic method is as shown in Embodiment 48.

$^1$H NMR (500 MHz, d$_6$-DMSO) δ 12.51 (s, 1H), 8.61 (s, 1H), 8.54 (s, 1H), 7.96 (m, 1H), 7.92 (d, J=13.0 Hz, 1H), 7.81 (m, 2H), 7.55 (m, 3H), 7.45 (m, 2H), 7.39 (s, 1H), 3.98 (s, 3H), 3.97 (s, 3H), 2.91 (s, 4H), 2.77 (s, 4H).

$^{13}$C NMR (125 MHz, d$_6$-DMSO) δ 180.0, 169.3, 167.7, 167.7 (d, J=246.1 Hz, 1C), 161.2, 158.8 (d, J=243.5 Hz, 1C), 158.0 (d, J=247.0 Hz, 1C), 157.3 (d, J=24.4 Hz, 1C), 155.5, 154.2, 152.9 (d, J=23.1 Hz, 1C), 150.4 (d, J=10.4 Hz, 1C), 143.8, 142.6 (d, J=9.8 Hz, 1C), 141.9, 140.0 (d, J=12.9 Hz, 1C), 135.1, 129.8, 125.1 (d, J=7.3 Hz, 1C), 122.6 (d, J=23.4 Hz, 1C), 121.2, 116.6, 115.2, 114.4, 113.3, 112.0, 111.2, 105.8 (d, J=12.6 Hz, 1C), 61.4, 61.3, 55.7, 50.5.

HRMS (ESI) for C$_{36}$H$_{29}$F$_3$N$_6$O$_5$[M+H]$^+$, calcd: 683.2224, found: 683.2226.

HPLC analysis: MeOH—H2O (85:15), 13.93 min, 95.12% purity.

Embodiment 55: Preparation of 5-amino-1-cyclopropyl-N-(4-(6,7-dimethoxyquinazolin-4-yloxy)-3-fluorophenyl)-7-(3,5-dimethylpiperazin-1-yl)-6,8-difluoro-4-oxo-1,4-dihydroquinoline-3-carboxamide (named as TL4830044)

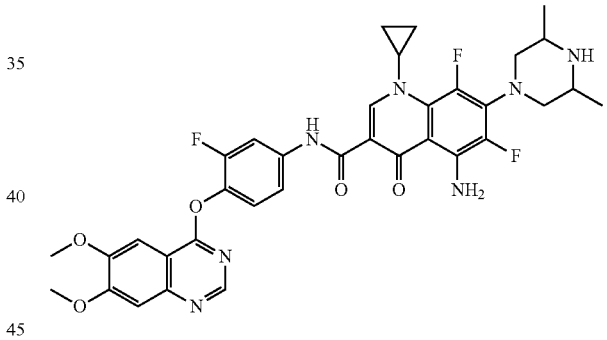

The synthetic method is as shown in Embodiment 48.

$^1$H NMR (500 MHz, d$_6$-DMSO) δ 12.19 (s, 1H), 8.58 (s, 1H), 8.53 (s, 1H), 7.96 (d, J=12.5 Hz, 1H), 7.55 (s, 1H), 7.44-7.37 (i, 5H), 3.98 (s, 3H), 3.97 (s, 3H), 3.34 (d, J=12.0 Hz, 2H), 3.10 (s, 2H), 2.92 (t, J=11.5 Hz, 2H), 1.90 (s, 2H), 1.13-1.07 (i, 10H).

$^{13}$C NMR (125 MHz, d$_6$-DMSO) δ 178.9, 172.7, 164.5, 162.8, 156.4, 154.0 (d, J=243.3 Hz, 1C), 152.6, 150.7, 149.7, 149.4, 139.8 (d, J=230.5 Hz, 1C), 137.9 (d, J=9.8 Hz, 1C), 136.9 (d, J=13.3 Hz, 1C), 135.1 (d, J=13.1 Hz, 1C), 133.2, 128.4, 125.0, 116.5, 109.6, 109.2, 108.5 (d, J=23.5 Hz, 1C), 107.3, 107.2, 101.0, 56.7, 56.5, 56.1, 21.6, 17.9, 9.0, 9.0.

HRMS(ESI) for C$_{35}$H$_{34}$F$_3$N$_7$O$_5$[M+H]$^+$, calcd: 690.2646, found: 690.2622.

HPLC analysis: MeOH—H$_2$O (85:15), 10.22 min, 95.56% purity.

Embodiment 56: Preparation of 1-cyclopropyl-N-(4-(6,7-dimethoxyquinazolin-4-yloxy)-3-fluorophenyl)-7-(4-ethylpiperazin-1-yl)-6-fluoro-4-oxo-1,4-dihydroquinoline-3-carboxamide (named as GDL5000093)

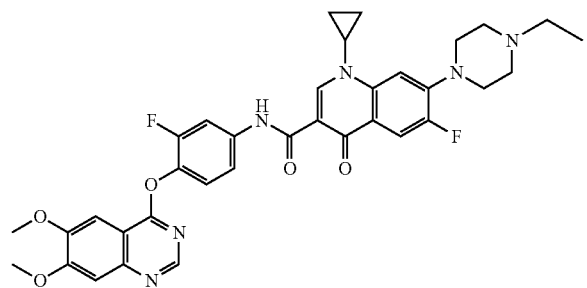 [SMILES: CCN1CCN(c2cc3c(cc2F)c(=O)c(C(=O)Nc2ccc(Oc4ncnc5cc(OC)c(OC)cc45)c(F)c2)cn3C2CC2)CC1]

The synthetic method is as shown in Embodiment 48.

¹H NMR (500 MHz, CDCl₃) δ 12.50 (s, 1H), 8.89 (s, 1H), 8.63 (s, 1H), 8.06 (d, J=13.5 Hz, 1H), 8.00 (dd, J=2.5, 12.5 Hz, 1H), 7.58 (s, 1H), 7.46 (dd, J=0.5, 8.5 Hz, 1H), 7.36 (d, J=7.0 Hz, 1H), 7.33 (s, 1H) 7.28 (m, 1H), 4.08 (s, 3H), 4.06 (s, 3H), 3.52 (m, 1H), 3.35 (t, J=4.5 Hz, 4H), 2.69 (s, 4H), 2.52 (q, J=7.0 Hz, 2H), 1.36 (t, J=6.5 Hz, 2H), 1.21 (m, 2H), 1.15 (t, J=7.0 Hz, 3H).

¹³C NMR (125 MHz, CDCl₃) δ 175.6, 164.9, 163.2, 155.9, 154.3 (d, J=246.1 Hz, 1C), 153.6 (d, J=248.6 Hz, 1C), 152.9, 150.3, 149.5, 147.0, 145.3 (d, J=10.4 Hz, 1C), 138.6, 137.8 (d, J=9.9 Hz, 1C), 135.3 (d, J=13.0 Hz, 1C), 123.8, 121.5 (d, J=7.3 Hz, 1C), 116.1 (d, J=2.6 Hz, 1C), 112.7 (d, J=23.1 Hz, 1C), 111.0, 110.3, 109.3 (d, J=23.3 Hz, 1C), 106.9, 104.7, 101.1, 56.4, 56.4, 52.5, 52.3, 50.0, 50.0, 35.0, 12.0, 8.2.

HRMS (ESI) for C₃₅H₃₄F₂N₆O₅[M+H]⁺, calcd: 657.2632, found: 657.2625.

HPLC analysis: MeOH—H₂O (85:15), 20.53 min, 98.36% purity.

Embodiment 57: Preparation of 7-(3-aminopyrrolidin-1-yl)-1-(2,4-difluorophenyl)-N-(4-(6,7-dimethoxyquinazolin-4-yloxy)-3-fluorophenyl)-6-fluoro-4-oxo-1,4-dihydro-1,8-naphthyridine-3-carboxamide (named as GDL5000101)

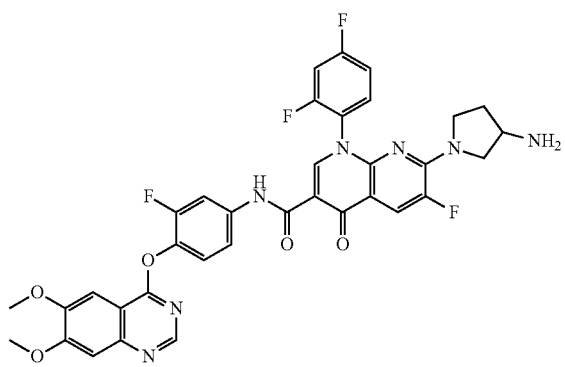 [SMILES: COc1cc2ncnc(Oc3ccc(NC(=O)c4cn(-c5ccc(F)cc5F)c5nc(N6CCC(N)C6)c(F)cc5c4=O)cc3F)c2cc1OC]

The synthetic method is as shown in Embodiment 48.

¹HNMR (500 MHz, d₆-DMSO) δ 12.52 (s, 1H), 8.75 (s, 1H), 8.57 (s, 1H), 8.06 (d, J=13.0 Hz, 1H), 7.98 (d, J=12.5 Hz, 1H), 7.85 (m, 1H), 7.59 (m, 2H), 7.47 (d, J=12.5 Hz, 2H), 7.36 (t, J=8.0 Hz, 1H), 4.62 (s, 2H), 4.00 (s, 3H), 3.99 (s, 3H), 3.62 (m, 5H), 2.02 (s, 1H), 1.76 (s, 1H).

¹³C NMR (125 MHz, CDCl₃) δ 176.0 (d, J=1.6 Hz, 1C), 164.8, 163.0 (dd, J=10.9, 251.1 Hz, 1C), 157.8 (dd, J=12.4, 253.9 Hz, 1C), 156.0, 154.2 (d, J=246.1 Hz, 1C), 152.8, 150.3, 149.4, 148.9 (d, J=12.6 Hz, 1C), 146.4 (d, J=256.3 Hz, 1C), 146.2, 146.0, 137.6 (d, J=9.6 Hz, 1C), 135.4 (d, J=13.3 Hz, 1C), 130.0 (d, J=10.1 Hz, 1C), 124.7 (dd, J=4.3, 13.3 Hz, 1C), 123.8, 118.5 (d, J=20.6 Hz, 1C), 116.1 (d, J=2.6 Hz, 1C), 112.7, 112.4 (d, J=2.5 Hz, 1C), 112.0 (dd, J=3.4, 22.5 Hz, 1C), 110.2, 109.2 (d, J=23.0 Hz, 1C), 106.8, 104.9 (t, J=23.5 Hz, 1C), 101.0, 56.6, 56.6, 56.4, 56.4, 46.9, 30.3.

HRMS (ESI) for C₃₅H₂₇F₄N₇O₅ [M+H]⁺, calcd: 702.2083, found: 702.2074.

HPLC analysis: MeOH—H₂O (85:15), 12.42 min, 99.81% purity.

Embodiment 58: Preparation of N-(4-((6,7-dimethoxyquinazolin-4-yl)oxy)-3-fluorophenyl)-1-ethyl-6-fluoro-4-oxo-7-(piperazin-1-yl)-1,4-dihydro-1,8-naphthyridine-3-carboxamide (named as GDL5000102)

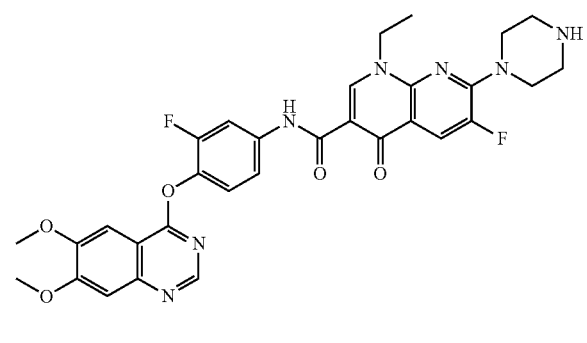 [SMILES: CCn1cc(C(=O)Nc2ccc(Oc3ncnc4cc(OC)c(OC)cc34)c(F)c2)c(=O)c2cc(F)c(N3CCNCC3)nc21]

The synthetic method is as shown in Embodiment 48.

¹H NMR (500 MHz, CDCl₃) δ 12.51 (s, 1H), 8.79 (s, 1H), 8.63 (s, 1H), 8.13 (d, J=13.5 Hz, 1H), 7.80 (dd, J=2.0, 12.0 Hz, 1H), 7.58 (s, 1H), 7.46 (d, J=8.5 Hz, 1H), 7.28 (m, 1H), 4.41 (q, J=7.0 Hz, 2H), 4.08 (s, 3H), 4.06 (s, 3H), 3.82 (t, J=4.5 Hz, 4H), 3.04 (t, J=4.5 Hz, 4H), 1.51 (t, J=7.0 Hz, 3H).

¹³C NMR (125 MHz, CDCl₃) δ 175.7, 164.9, 163.1, 156.0, 154.3 (d, J=245.9 Hz, 1C), 152.9, 150.4 (d, J=9.0 Hz, 1C), 150.3, 149.5, 147.4 (d, J=247.0 Hz, 1C), 146.0, 144.7, 137.8 (d, J=9.6 Hz, 1C), 135.3 (d, J=13.1 Hz, 1C), 123.8, 120.7 (d, J=21.9 Hz, 1C), 116.1 (d, J=2.9 Hz, 1C), 115.1 (d, J=3.0 Hz, 1C), 112.2, 110.3, 109.3 (d, J=23.3 Hz, 1C), 106.9, 101.1, 56.4, 56.4, 48.4, 48.3, 47.4, 46.1, 15.0.

HRMS (ESI) for C₃₁H₂₉F₂N₇O₅[M+H]⁺, calcd: 618.2271, found: 618.2264.

HPLC analysis: MeOH—H₂O (85:15), 16.99 min, 96.81% purity.

Embodiment 59: Preparation of 1-cyclopropyl-N-(4-(6,7-dimethoxyquinazolin-4-yloxy)-3-fluorophenyl)-6-fluoro-4-oxo-7-(piperazin-1-yl)-1,4-dihydroquinoline-3-carboxamide (named as GDL5000110)

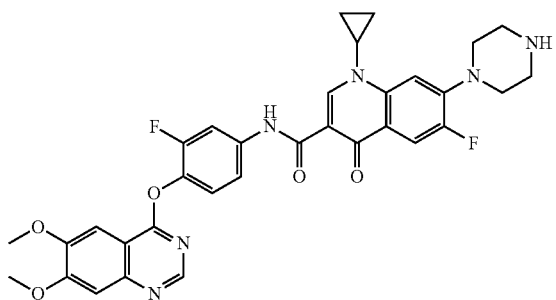 [SMILES: COc1cc2ncnc(Oc3ccc(NC(=O)c4cn(C5CC5)c5cc(N6CCNCC6)c(F)cc5c4=O)cc3F)c2cc1OC]

The synthetic method is as shown in Embodiment 48.

$^1$H NMR (500 MHz, CDCl$_3$) δ 12.50 (s, 1H), 8.89 (s, 1H), 8.62 (s, 1H), 8.05 (d, J=13.5 Hz, 1H), 8.00 (dd, J=2.0, 12.5 Hz, 1H), 7.58 (s, 1H), 7.46 (d, J=9.0 Hz, 1H), 7.34 (m, 2H), 7.27 (m, 1H), 4.07 (s, 3H), 4.06 (s, 3H), 3.52 (m, 1H), 3.28 (t, J=4.5 Hz, 4H), 3.10 (t, J=4.5 Hz, 4H), 1.37 (q, J=6.5 Hz, 2H), 1.22 (m, 2H).

$^{13}$C NMR (125 MHz, CDCl$_3$) δ 175.6, 164.9, 163.2, 156.0, 154.3 (d, J=246.3 Hz, 1C), 153.7 (d, J=248.5 Hz, 1C), 152.9, 150.3, 149.4, 147.0, 145.7 (d, J=10.1 Hz, 1C), 138.6, 137.8 (d, J=9.8 Hz, 1C), 135.3 (d, J=12.6 Hz, 1C), 123.8, 121.4 (d, J=7.3 Hz, 1C), 116.1 (d, J=3.0 Hz, 1C), 112.7 (d, J=23.3 Hz, 1C), 111.0, 110.3, 109.3 (d, J=23.0 Hz, 1C), 106.8, 104.7 (d, J=2.8 Hz, 1C), 101.1, 56.4, 56.4, 51.2, 51.1, 46.0, 35.0, 8.2.

HRMS (ESI) for C$_{33}$H$_{30}$F$_2$N$_6$O$_5$[M+H]$^+$, calcd: 629.2319, found: 629.2306.

HPLC analysis: MeOH—H$_2$O (85:15), 17.78 min, 97.22% purity.

Embodiment 60: Preparation of N-(4-(2-chloropyridin-4-yloxy)-3-fluorophenyl)-6-ethyl-1,2-dimethyl-4-oxo-1,4-dihydroquinoline-3-carboxamide (named as TL4800199)

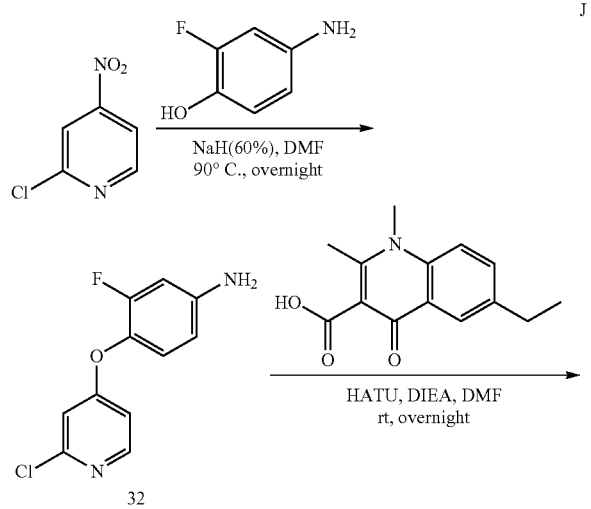

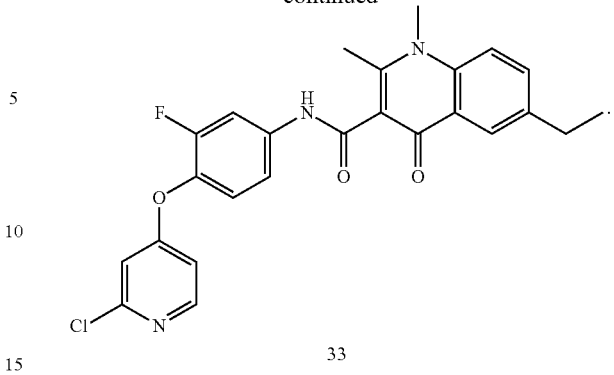

Step J1: 4-((2-chloropyridin-4-yl)oxy-3-fluoroaniline (Compound 32)

4-amino-2-fluorophenol (4.3 g, 32 mmol, 1.1 eq) was dissolved in 100 mL of DMF, added NaH (60%, 32 mmol, 1.1 eq) at room temperature and reacted for 10 min, and 2-chloro-4-nitropyridine (5 g, 31 mmol, 1.0 eq) was added with stirring, and heated to 90° C. and reacted overnight. The solution was cooled to room temperature, quenched with saturated NaCl, extracted with DCM/H$_2$O several times, and the organic phases were combined, subjecting same to column chromatography to obtain 5.5 g (75%) of the product.

Step J2: N-(4-(2-chloropyridin-4-yloxy)-3-fluorophenyl)-6-ethyl-1,2-dimethyl-4-oxo-1,4-dihydroquinoline-3-carboxamide (compound 33, TL4800199)

The other synthetic steps are as shown in Embodiment 25.

$^1$H NMR (500 MHz, d$_6$-DMSO) δ 11.06 (s, 1H), 8.31 (d, J=6.0 Hz, 1H), 8.06 (d, J=2.0 Hz, 1H), 8.00 (dd, J=2.0, 13.0 Hz, 1H), 7.79 (d, J=9.0 Hz, 1H), 7.65 (dd, J=2.0, 9.0 Hz, 1H), 7.52 (dd, J=1.0, 9.0 Hz, 1H), 7.39 (t, J=9.0 Hz, 1H), 7.09 (d, J=2.0 Hz, 1H), 7.00 (dd, J=2.0, J$_1$=6.0 Hz, 1H), 3.81 (s, 3H), 2.78-2.74 (q, J=7.5 Hz, 2H), 2.63 (s, 3H), 1.24 (t, J=7.5 Hz, 3H).

$^{13}$C NMR (125 MHz, d$_6$-DMSO) δ 174.2, 166.3, 166.1, 153.7 (d, J=244.1 Hz, 1C), 153.1, 152.1, 151.8, 140.1, 139.6, 139.2 (d, J=9.8 Hz, 1C), 135.2 (d, J=12.3 Hz, 1C), 133.3, 126.3, 124.2, 124.0, 118.3, 117.5, 116.6, 111.4, 111.2, 108.6 (d, J=22.8 Hz, 1C), 35.7, 27.9, 19.4, 15.7.

HRMS (ESI) for C$_{25}$H$_{21}$ClFN$_3$O$_3$[M+H]$^+$, calcd: 466.1328, found: 466.1325.

HPLC analysis: MeOH—H$_2$O (85:15), 5.44 min, 98.91% purity.

Embodiment 61: Preparation of N-(4-(2-benzylpyridin-4-yloxy)-3-fluorophenyl)-6-ethyl-1,2-dimethyl-4-oxo-1,4-dihydroquinoline-3-carboxamide (named as TL4800200)

Embodiment 62: Preparation of 6-ethyl-N-(3-fluoro-4-(3-phenylfuro[2,3-b]pyridin-4-yloxy)phenyl)-1,2-dimethyl-4-oxo-1,4-dihydroquinoline-3-carboxamide (named as GDL5000039)

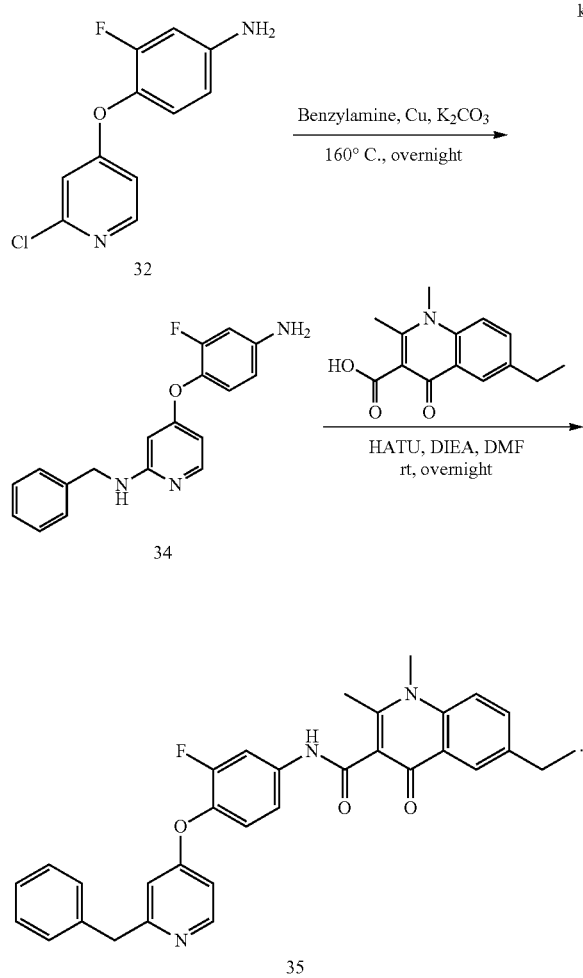

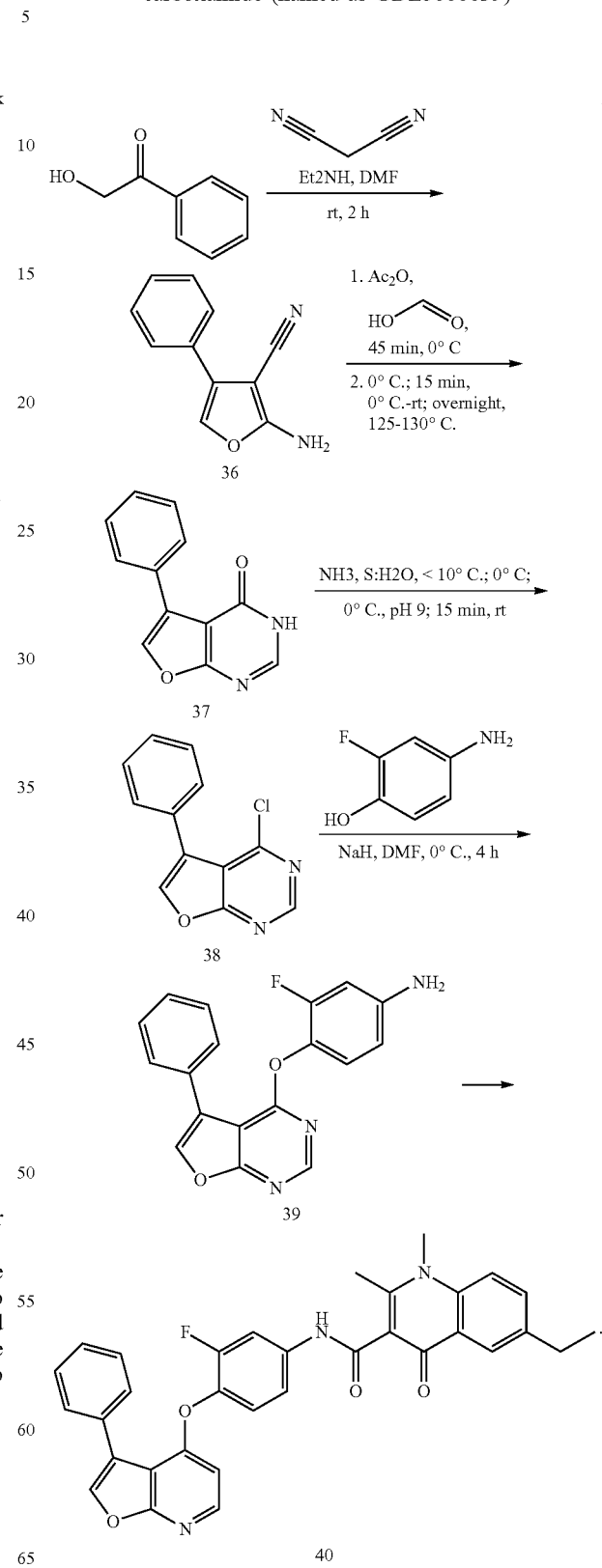

Step k1: 4-(4-amino-2-fluorophenoxy)-N-benzylpyridine-2-amino (Compound 34)

Compound 33 (1.5 g, 6 mmol, 1.0 eq), copper powder (384 mg, 6 mmol, 1.0 eq) and K₂CO₃ (834 mg, 6 mmol, 1 eq) were added into 30 mL of benzylamine, sealed in a tube and reacted overnight at 160° C. The solution was cooled to room temperature, quenched with saturated NaCl, extracted with DCM/H₂O several times, and the organic phases were combined, subjecting same to column chromatography to obtain the product (900 mg, 50%).

Step k2: N-(4-(2-benzylpyridin-4-yloxy)-3-fluorophenyl)-6-ethyl-1,2-dimethyl-4-oxo-1,4-dihydroquinoline-3-carboxamide (compound 35, TL4800200)

The other synthetic steps are as shown in Embodiment 25.
HPLC analysis: MeOH—H₂O (85:15), 6.08 min, 96.21%.

Step 11: 2-amino-4-phenylfuran-3-carbonitrile (Compound 36)

Hydroxyacetophenone (5 g, 1 eq) and malononitrile (2.426 g, 1 eq) were dissolved in 12 mL of DMF, 1.9 mL of diethylamine was added dropwise at room temperature, the mixture was stirred for 2 h, then 100 mL of water was added at 0° C., stirred at 10° C. for 30 min, filtered, washed twice with water, and dried in vacuum to obtain 5.8 g of products. $^1$H NMR (400 MHz, t/g-DMSO) δ7.61 (m, 2H), 7.46 (s, 2H), 7.42 (m, 2H), 7.39 (s, 1H), 7.33 (m, 1H).

Step 12: 5-phenylfuran[2,3-d]pyrimidine-4(3H)-one (Compound 37)

Under Ar protection, 37 mL of HCOOH was added slowly in a dropwise manner to 76 mL of Ac$_2$O at 0° C., stirred for 45 min, 5.8 g (compound 36) was added in portions, and after 15 min, the reaction solution turned from black into dark blue, and the mixture was warmed to room temperature, stirred for 15 min and then refluxed overnight at 125° C. The reaction solution was subjected to rotary drying and column chromatography (DCM:MeOH=50:1) to obtain 1.65 g of products. $^1$H NMR (400 MHz, d$_6$-DMSO) δ 12.68 (s, 1H), 8.23 (s, 1H), 8.16 (s, 1H), 7.97 (d, 2H), 7.42 (m, 2H), 7.33 (m, 1H).

Step 13: 4-chloro-5-phenylfuran[2,3-d]pyrimidine (Compound 38)

1.65 g of compound 37 was taken and placed in a 25 mL eggplant-shaped flask, 9 mL of POCl$_3$ was added in an ice bath, and refluxed at 115° C. for 90 min, and the reaction solution was slowly poured into ice water and quenched, stirred for 15 min, extracted three times by addition of EA, subjecting same to rotary drying and column chromatography (PE:EA=10:1) to obtain 1.35 g of a white solid. $^1$H NMR (400 MHz, d$_6$-DMSO) δ8.90 (s, 1H), 8.47 (s, 1H), 7.61 (m, 2H), 7.50 (m, 3H).

Step 14: 3-fluoro-4-((5-phenylfuran[2,3-d]pyrimidin-4-yl)oxy)aniline (Compound 39)

Under Ar protection, 563 mg of 4-amino-2-fluorophenol was dissolved in 20 mL of DMF at 0° C., 300 mg of NaH was added in portions, stirred for 30 min, 600 mg (compound 38) was dissolved in 10 mL of DMF, and then added dropwise into the reaction system and reacted at 0° C. for 4 h. The solution was quenched by addition of saturated NH$_4$Cl solution, extracted with EA three times, subjecting same to rotary drying and column chromatography to obtain 628 g (75%) of products. $^1$H NMR (400 MHz, d$_6$-DMSO) δ8.55 (s, 1H), 8.46 (s, 1H), 7.80 (m, 2H), 7.48 (m, 2H), 7.40 (t, J=7.2 Hz, 1H), 7.06 (t, J=4.8 Hz, 1H), 6.49 (dd, J=13.2, 2.4 Hz, 1H), 6.40 (dd, J=8.8, 2.4 Hz, 1H), 5.39 (s, 2H).

Step 15: 6-ethyl-N-((3-fluoro-4-((-phenylfluoro[2,3-d]pyrimidin-4-yl)oxy)phenyl)-1,2-dimethyl-4-oxo-1,4-dihydroquinoline-3-carboxamide (compound 40, GDL5000039)

The other synthetic steps are as shown in Embodiment 25.
$^1$H NMR (400 MHz, d$_6$-DMSO) δ11.04 (s, 1H), 8.58 (s, 1H), 8.51 (s, 1H), 8.09 (s, 1H), 7.94 (d, J=13.2 Hz, 1H), 7.83 (m, 3H), 7.66 (dd, J=1.6, 8.8 Hz, 1H), 7.52-7.48 (m, 4H), 7.41 (t, J=7.2 Hz, 1H), 3.84 (s, 3H), 2.80-0.74 (q, J=7.6 Hz, 2H), 2.65 (s, 3H), 1.24 (t, J=7.6 Hz, 3H).

$^{13}$C NMR (125 MHz, d$_6$-DMSO) δ 174.0, 169.2, 166.2, 163.2, 153.9 (d, J=243.8 Hz, 1C), 153.4, 152.5, 142.3, 140.0, 139.7, 139.0 (d, J=10.0 Hz, 1C), 134.5 (d, J=12.5 Hz, 1C), 133.4, 130.2, 129.1, 128.9, 128.6, 126.3, 124.7, 124.1, 120.8, 119.0, 117.6, 116.0, 108.0 (d, J=22.5 Hz, 1C), 103.3, 35.7, 27.3, 19.49, 15.9.

HRMS (ESI) for C$_{32}$H$_{25}$FN$_4$O$_4$[M+H]$^+$, calcd: 549.1933, found: 549.1936.

HPLC analysis: MeOH—H$_2$O (85:15), 6.91 min, 97.17% purity.

Embodiment 63: Preparation of N-(4-(2-carbamoylpyridin-4-yloxy)-3-fluorophenyl)-6-ethyl-1,2-dimethyl-4-oxo-1,4-dihydroquinoline-3-carboxamide (named as GDL5000045)

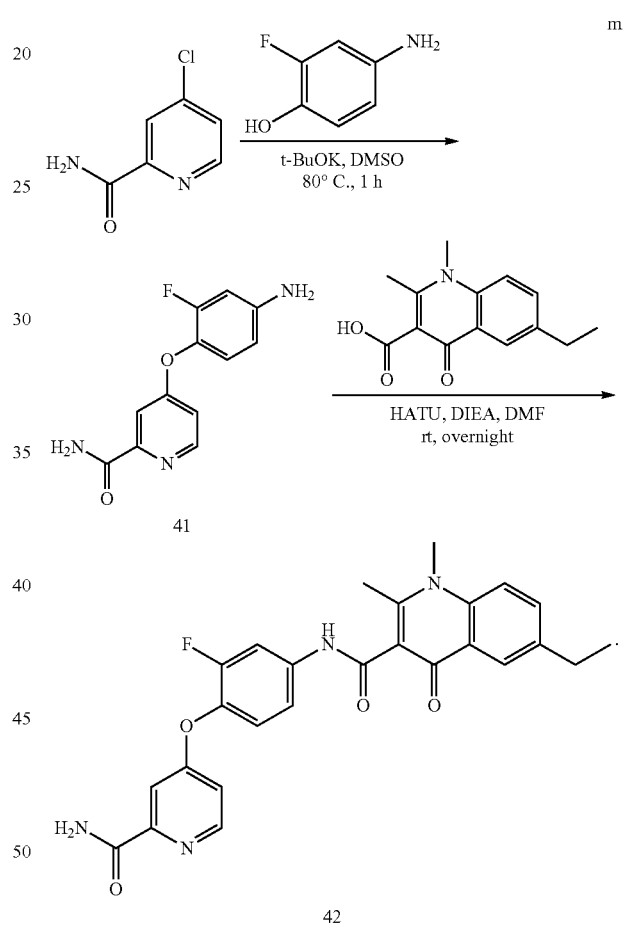

Step m1: 4-((4-amino-2-fluorophenoxy)pyridine amide (Compound 41)

Under Ar protection, 4-amino-2-fluorophenol (2.43 g, 19 mmol, 1.5 eq) was dissolved in 25 mL of DMSO, t-BuOK (2.3 g, 21 mmol, 1.6 eq) was added and reacted for 15 min at room temperature, and 4-chloropyridine-2-carboxamide (2 g, 13 mmol, 1.0 eq) was added with stirring, heated to 80° C. and reacted for 1 h. The solution was cooled to room temperature, 25 mL of 1 M NaOH solution and 25 mL of water were added, stirred for 5 h, filtered, washed with water and dried to obtain 2.7 g (85%) of products. $^1$H NMR (400

MHz, d$_6$-DMSO) δ8.49 (d, J=5.6 Hz, 1H), 8.09 (s, 1H), 7.68 (s, 1H), 7.35 (d, J=2.4 Hz, 1H), 7.14 (q, J=2.8 Hz, 1H), 7.02 (t, J=8.8 Hz, 1H), 6.53 (dd, J=13.2, 2.4 Hz, 1H), 6.53 (dd, J=13.2, 2.4 Hz, 1H), 6.44 (dd, J=8.4, 1.6 Hz, 1H), 5.50 (s, 2H).

Step m2: N-(4-(2-carbamoylpyridin-4-yloxy)-3-fluorophenyl)-6-ethyl-1,2-dimethyl-4-oxo-1,4-dihydroquinoline-3-carboxamide (compound 42, GDL5000045)

The other synthetic steps are as shown in Embodiment 25.
$^1$H NMR (400 MHz, d$_6$-DMSO) δ11.06 (s, 1H), 8.54 (d, J=5.6 Hz, 1H), 8.12 (s, 1H), 8.08 (s, 1H), 8.00 (d, J=13.2 Hz, 1H), 7.82 (d, J=8.8 Hz, 1H), 7.72 (s, 1H), 7.67 (d, J=8.0 Hz, 1H), 7.53 (d, J=8.8 Hz, 1H), 7.41 (m, 2H), 7.22 (m, 1H), 3.84 (s, 3H), 2.80-2.74 (q, J=7.6 Hz, 2H), 2.64 (s, 3H), 1.24 (t, J=7.6 Hz, 3H).
$^{13}$C NMR (125 MHz, d$_6$-DMSO) δ174.0, 166.3, 165.8, 165.7, 153.9 (d, J=243.8 Hz, 1C), 153.3, 152.4, 151.1, 140.0, 139.6, 139.2 (d, J=10.0 Hz, 1C), 135.2 (d, J=12.5 Hz, 1C), 133.4, 126.2, 124.4, 124.1, 119.0, 117.6, 116.6, 113.9, 108.7, 108.4 (d, J=22.5 Hz, 1C), 35.7, 27.9, 19.5, 15.9.
HRMS (ESI) for C$_{26}$H$_{23}$FN$_4$O$_4$ [M+H]$^+$, calcd: 475.1776, found: 475.1772.
HPLC analysis: MeOH—H$_2$O (75:25), 4.92 min, 98.23% purity.

Embodiment 64: Preparation of N-(4-(2-aminopyridin-4-yloxy)-3-fluorophenyl)-6-ethyl-1,2-dimethyl-4-oxo-1,4-dihydroquinoline-3-carboxamide (named as GDL5000050)

Step n1: N-(4-(2-aminopyridin-4-yloxy)-3-fluorophenyl)-6-ethyl-1,2-dimethyl-4-oxo-1,4-dihydroquinoline-3-carboxamide (compound 43, GDL5000050)

N-(4-((2-aminopyridine-4-yl)oxy)-3-fluorophenyl)-6-ethyl-1,2-dimethyl-4-oxo-1,4-dihydroquinoline-3-carboxamide (106 mg, 0.22 mmol, 1.0 eq) was dissolved in 2 mL of DMF, H$_2$O (11 mg, 0.60 mmol, 2.6 eq) and pyridine (70 mg, 0.88 mmol, 3.9 eq), and [bis(trifluoroacetoxy)iodo]benzene (135 mg, 0.31 mmol, 1.4 eq) was added, stirred at room temperature for 4 h, 50 mL of water was added and stirred for 30 min, filtered, and the filter residue was subjected to column chromatography to obtain the product.

$^1$H NMR (400 MHz, d$_6$-DMSO) δ10.94 (s, 1H), 8.08 (s, 1H), 7.95 (d, J=13.2 Hz, 1H), 7.81 (m, 2H), 7.67 (m, 1H), 7.48 (d, J=8.8 Hz, 1H), 7.30 (t, J=8.8 Hz, 1H), 6.19 (dd, J=2.0, 5.6 Hz, 1H), 5.95 (s, 2H), 5.80 (s, 1H), 3.83 (s, 3H), 2.79-2.74 (q, J=7.6 Hz, 2H), 2.62 (s, 3H), 1.24 (t, J=7.6 Hz, 3H).
$^{13}$C NMR (125 MHz, d$_6$-DMSO) δ 174.4, 166.6, 166.2, 154.5 (d, J=243.6 Hz, 1C), 152.6, 150.3, 140.4, 140.1, 139.0 (d, J=9.8 Hz, 1C), 136.3 (d, J=12.1 Hz, 1C), 133.8, 126.7, 124.9, 124.6, 119.7, 118.0, 116.7, 108.7 (d, J=23.1 Hz, 1C), 102.1, 93.3, 28.4, 19.9, 16.4.
HRMS (ESI) for C$_{25}$H$_{23}$FN$_4$O$_3$[M+H]$^+$, calcd: 447.1827, found: 447.1822.
HPLC analysis: MeOH—H$_2$O (75:25), 4.92 min, 95.41% purity.

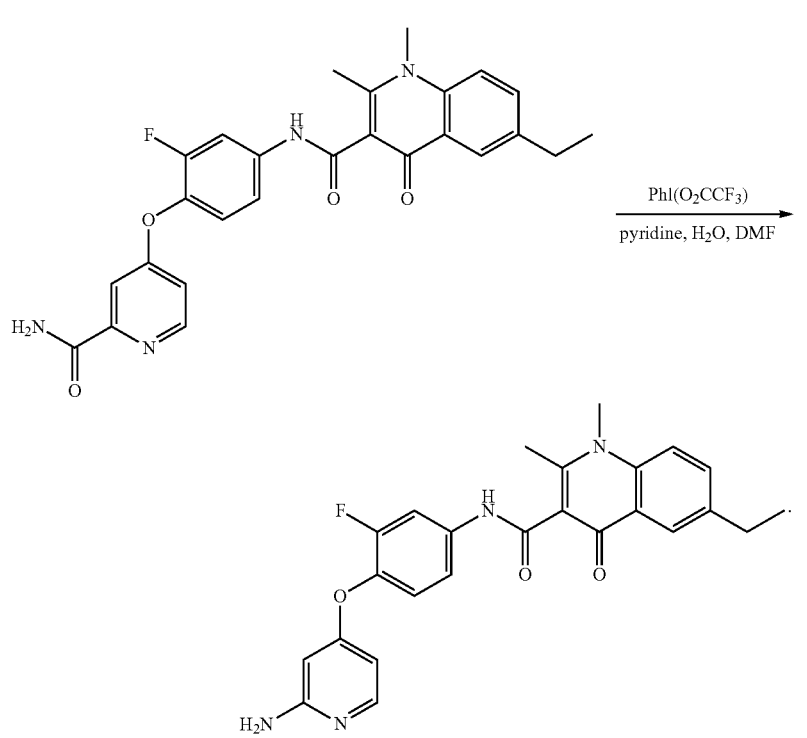

43

Embodiment 65: Preparation of 6-ethyl-N-(3-fluoro-4-(5-(1-methyl-1H-pyrazol-4-yl)-7H-pyrrolo[2,3-d]pyrimidin-4-yloxy)phenyl)-1,2-dimethyl-4-oxo-1,4-dihydroquinoline-3-carboxamide (named as GDL5000038)

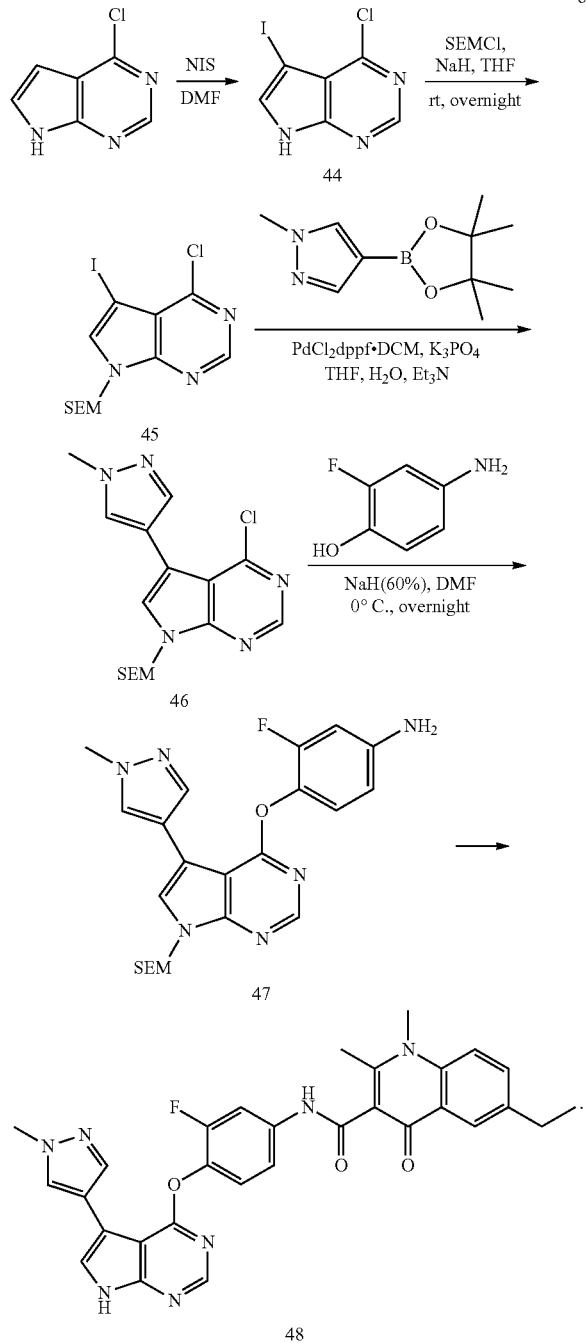

Step o1: 4-chloro-5-iodo-7H-pyrrolo[2,3,-d]pyrimidine (Compound 44)

4-chloro-7H-pyrrolo[2,3-d]pyrimidine (8.0 g, 52.32 mmol, 1.0 eq) was dissolved in DMF (40 mL), NIS (15.7 g, 57.55 mmol, 1.1 eq) was added at 0° C., stirred overnight at room temperature, 200 mL of saturated $Na_2S_2O_3$ solution was added, filtered, washed with water three times, and dried in vacuum to obtain 14.6 g (100%) of products. $^1$H NMR (400 MHz, $d_6$-DMSO): δ12.94 (s, 1H), 8.59 (s, 1H), 7.93 (d, J=2.4 Hz, 1H).

Step o2: 4-chloro-5-iodo-7-((2-(trimethylsilyl)ethoxy)methyl)-7H-pyrrolo[2,3-d]pyrimidine (Compound 45)

NaH (60%, 160 mg, 4 mmol, 1.10 eq) was added to anhydrous THF (20 mL), 4-chloro-5-iodo-7H-pyrrolo[2,3-d]pyrimidine (1.00 g, 3.6 mmol, 1.00 eq) was added dropwise after dissolving in THF (10 mL), and reacted for 15 min, cooled down to 0° C., and SEMCl (0.7 mL, 3.8 mmol, 1.05 eq) was added slowly in a dropwise manner, and stirred overnight. The reaction was quenched with saturated $NH_4Cl$ solution, extracted with EtOAc three times, the organic phases were combined, subjecting same to column chromotography to obtain 1.1 g (75%) of products. $^1$H NMR (400 MHz, $d_6$-DMSO): δ 8.69 (s, 1H), 8.13 (s, 1H), 5.60 (s, 2H), 3.52 (t, J=8.0 Hz, 2H); 0.82 (t, J=8.0 Hz, 2H); −0.09 (s, 9H).

Step o3: 4-chloro-5-(1-methyl-1H-pyrazole-4-yl)-7-((2-(trimethylsilyl)ethoxy)methyl)-7H-pyrrolo[2,3-d]pyrimidine (Compound 46)

4-chloro-5-iodo-7-((2-(trimethylsilyl)ethoxy)methyl)-7H-pyrrolo[2,3-d]pyrimidine (200 mg, 0.5 mmol, 1.0 eq), 1-methyl-4-(4,4,5,5-tetramethyl-1,3,2-dioxapentaborane-2-yl)-1H-pyrazol (124 mg, 0.6 mmol, 1.2 eq), $K_3PO_4$ (126 mg, 0.6 mmol, 1.2 eq), PdCl$_2$dppfDCM (40 mg, 0.05 mmol, 0.1 eq), $H_2O$ (0.64 mL) and $Et_3N$ (0.4 mL) were added to THF (6.4 mL), refluxed for 18 h, cooled down to room temperature, and exacted with ethyl acetate, subjecting same to column chromatography to obtain 85 mg (48%) of products. $^1$H NMR (400 MHz, $d_6$-DMSO): δ 8.68 (s, 1H), 7.94 (s, 1H), 7.88 (s, 1H), 7.64 (s, 1H), 5.66 (s, 2H), 3.90 (s, 3H), 3.56 (t, J=8.0 Hz, 2H); 0.85 (t, J=8.0 Hz, 2H); −0.09 (s, 9H).

Step o4: 3-fluoro-4-((5-(1-methyl-1H-pyrazole-4-yl)-7-((2-(trimethylsilyl)ethoxy)methyl)-7H-pyrrolo[2,3-d]pyrimidine-4-yl)oxy) aniline (Compound 47)

Under Ar protection, 4-amino-2-fluorophenol (430 mg, 3.4 mmol, 1.7 eq) was dissolved in 20 mL of DMF, NaH (230 mg, 5.8 mmol, 2.9 eq) was added and reacted at 0° C. for 15 min, and 4-chloro-5-(1-methyl-1H-pyrazole-4-yl)-7-((2-(trimethylsilyl)ethoxy)methyl)-7H-pyrrolo[2,3-d]pyrimidine (720 mg, 2.0 mmol, 1.0 eq) was added with stirring, and stirred overnight. The reaction was quenched with saturated $NH_4Cl$ solution, and extracted with EtOAc three times, subjecting same to column chromatography to obtain 580 mg (64%) of products. $^1$H NMR (400 MHz, $d_6$-DMSO): δ 8.34 (s, 1H), 7.99 (s, 1H), 7.82 (m, 2H), 7.07 (t, J=7.2 Hz, 1H), 6.49 (dd, J=10.4, 2.0 Hz, 1H), 6.42 (dd, J=6.8, 2.0 Hz, 1H), 5.61 (s, 2H), 5.36 (s, 2H), 3.85 (s, 3H), 3.55 (t, J=6.4 Hz, 2H); 0.85 (t, J=6.4 Hz, 2H); −0.08 (s, 9H).

Step o5: 6-ethyl-N-(3-fluoro-4-(5-(1-methyl-1H-pyrazol-4-yl)-7H-pyrrolo[2,3-d]pyrimidin-4-yloxy)phenyl)-1,2-dimethyl-4-oxo-1,4-dihydroquinoline-3-carboxamide (compound 48, GDL5000038)

The other synthetic steps are as shown in Embodiment 25.
$^1$H NMR (400 MHz, d$_6$-DMSO) δ 12.30 (s, 1H), 11.00 (s, 1H), 8.28 (s, 1H), 8.09 (s, 1H), 8.00 (s, 1H), 7.90 (m, 1H), 7.83 (m, 2H), 7.66 (m, 2H), 7.49-7.42 (m, 2H), 3.85 (s, 3H), 3.84 (s, 3H), 2.78 (q, J=7.5 Hz, 2H), 2.65 (s, 3H), 1.2 (t, J=7.5 Hz, 3H).
$^{13}$C NMR (125 MHz, d$_6$-DMSO) δ 174.4, 166.6, 162.1, 154.7 (d, J=242.5 Hz, 1C), 154.5, 152.8, 151.0, 140.4, 140.1, 139.0 (d, J=10.0 Hz, 1C), 138.4, 135.4 (d, J=12.5 Hz, 1C), 133.8, 129.4, 126.7, 125.4, 124.6, 122.5, 119.5, 118.0, 116.4 (d, J=1.3 Hz, 1C), 115.6, 108.4 (d, J=22.5 Hz, 1C), 107.4, 102.6, 40.0, 39.5, 36.1, 28.2, 19.9, 16.4.
HRMS (ESI) for $C_{30}H_{26}FN_7O_3$ [M+H]$^+$, calcd: 552.2154, found: 552.2156.
HPLC analysis: MeOH—H$_2$O (75:25), 5.34 min, 99.20% purity.

Embodiment 66: Preparation of 2,6-diethyl-N-(3-fluoro-4-(5-phenyl-7H-pyrrolo[2,3-d]pyrimidin-4-yloxy)phenyl)-1-methyl-4-oxo-1,4-dihydroquinoline-3-carboxamide (named as TL4830005)

dissolved in 50 mL of DMF, NaH (190 mg, 4.8 mmol, 1.5 eq) was added in an ice bath, and MeI (900 mg, 6.63 mmol, 2 eq) was added with stirring and reacted overnight at 80° C. The solution was cooled to room temperature, water was added to precipitate the solid and filtered, the solid was extracted with DCM/H$_2$O several times, and the organic phases were combined, subjecting same to rotary drying and column chromatography to obtain 440 mg (51%) of products. $^1$H NMR (500 MHz, d$_6$-DMSO) δ 7.96 (d, J=2.0 Hz, 1H), 7.77 (d, J=8.5 Hz, 1H), 7.64 (dd, J=2.0, 8.5 Hz, 1H), 3.79 (s, 3H), 3.78 (s 3H), 2.77-2.50 (m, 4H), 1.24-1.20 (m, 6H).

Step p2: 2,6-diethyl-N-(3-fluoro-4-(5-phenyl-7H-pyrrolo[2,3-d]pyrimidin-4-yloxy)phenyl)-1-methyl-4-oxo-1,4-dihydroquinoline-3-carboxamide (compound 50, TL4830005)

The other synthetic steps are as shown in Embodiment 25.
HPLC analysis: MeOH—H$_2$O (85:15), 5.75 min, 98.06%.

Embodiment 67: Preparation of N-(4-(6,7-dimethoxyquinazolin-4-yloxy)-3-fluorophenyl)-2,6-diethyl-1-methyl-4-oxo-1,4-dihydroquinoline-3-carboxamide (named as TL4830074)

The synthetic steps are as shown in Embodiment 66.

p

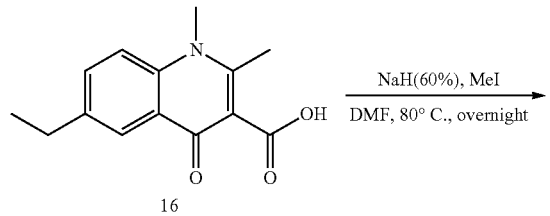

16

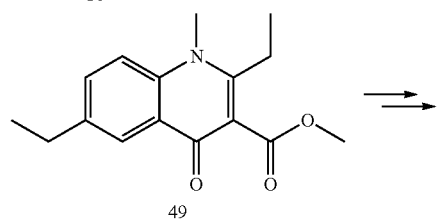

49

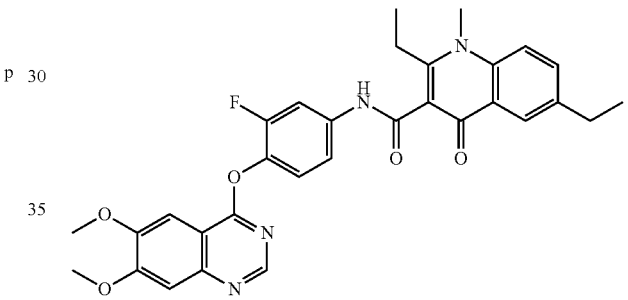

Embodiment 68: Preparation of N-(4-(2-carbamoyl-3-chloropyridin-4-yloxy)-3-fluorophenyl)-6-ethyl-1,2-dimethyl-4-oxo-1,4-dihydroquinoline-3-carboxamide (named as GDL5000056)

q

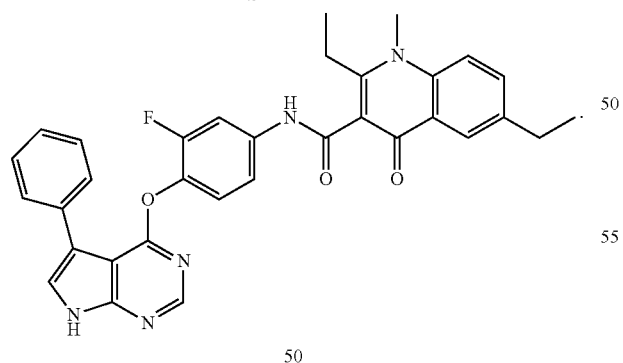

50

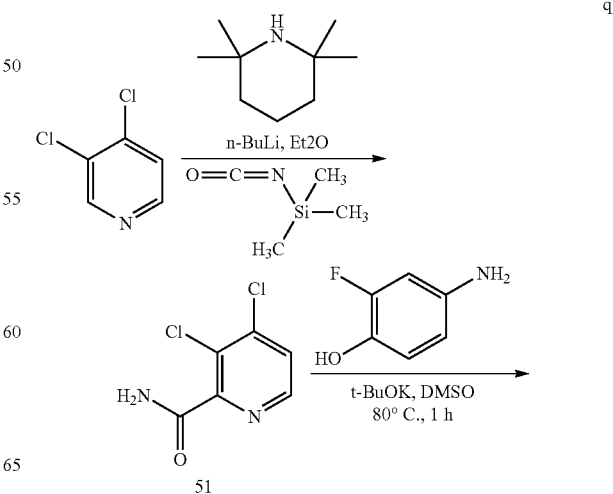

51

Step p1: methyl 2,6-diethyl-1-methyl-4-oxo-1,4-dihydroquinoline-3-carboxylate (Compound 49)

6-Ethyl-1,2-dimethyl-4-oxo-1,4-dihydroquinoline-3-carboxylic acid (compound 16) (780 mg, 3.18 mmol) was

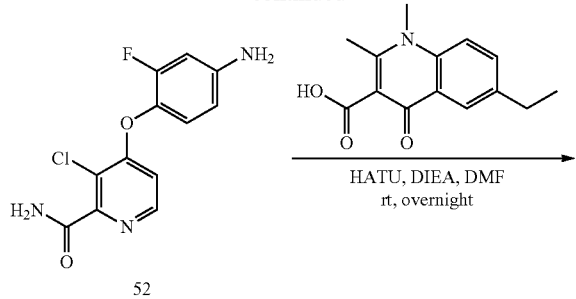

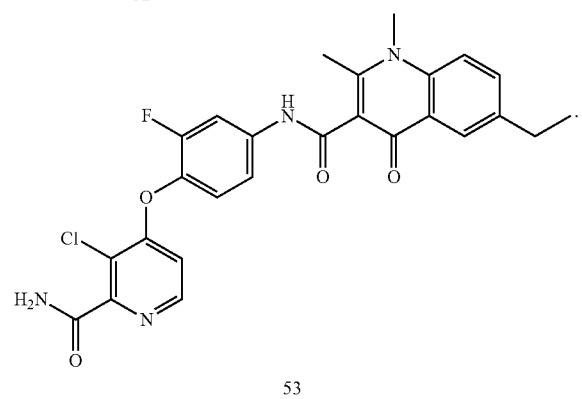

Step q1: 3,4-dichloro-2-pyridinecarboxamide (Compound 51)

At −78° C., n-BuLi (2.4 M, 19.5 mL, 31 mol, 1.15 eq) was added slowly in a dropwise manner into a solution of 2,2,6,6-tetramethylpiperidine (4.4 g, 31 mmol, 1.15 eq) in ether (50 mL), reacted for 2 h, a solution of 3,4-dichloropyridine (4 g, 27 mol, 1.0 eq) in ether (5 mL) was then added into the reaction solution, reacted at −78° C. for another 2 h, and trimethylsilyl isocyanate (95% pure, 5.6 mL, 40 mol, 1.5 eq) was added dropwise to the reaction system, warmed slowly to room temperature, and reacted for 2 h. The reaction was quenched by addition of acetic acid (5.4 g, 90 mmol) and water (27 mL), the mixture was stirred overnight, filtered and washed with a little ether to obtain 2.51 g (49%) of products. $^1$H NMR (400 MHz, d$_6$-DMSO) δ 8.48 (d, J=5.2 Hz, 1H), 8.07 (s, 1H), 7.82 (m, 2H).

Step q2: 4-((4-amino-2-fluorophenoxy)-3-chloropyridine amide (Compound 52)

Under Ar protection, 4-amino-2-fluorophenol (0.93 g, 7.3 mmol, 1.4 eq) was dissolved in 10 mL of DMF, t-BuOK (0.88 g, 7.8 mmol, 1.6 eq) was added and reacted for 30 min at room temperature, and 3,4-dichloro-2-pyridinecarboxamide (1 g, 5.2 mmol, 1.0 eq) was added with stirring, heated to 50° C. and reacted for 3 h. The mixture was cooled to room temperature, saturated NaHCO$_3$ solution was added, and exacted with ethyl acetate, subjecting same to column chromatography to obtain 440 mg (30%) of products. $^1$H NMR (400 MHz, d$_6$-DMSO) δ8.30 (d, J=5.6 Hz, 1H), 8.01 (s, 1H), 7.71 (s, 1H), 7.03 (t, J=8.8 Hz, 1H), 6.72 (d, J=5.2 Hz, 1H), 6.54 (dd, J=13.6, 2.4 Hz, 1H), 6.45 (m, 1H), 5.53 (s, 2H).

Step q3: N-(4-(2-carbamoyl-3-chloropyridin-4-yloxy)-3-fluorophenyl)-6-ethyl-1,2-dimethyl-4-oxo-1,4-dihydroquinoline-3-carboxamide (compound 53, GDL5000056)

The other synthetic steps are as shown in Embodiment 25.
$^1$HNMR (400 MHz, d$_6$-DMSO) δ 11.05 (s, 1H), 8.33 (d, J=5.6 Hz, 1H), 8.08-8.00 (m, 3H), 7.83 (d, J=8.8 Hz, 1H), 7.74 (s, 1H), 7.67 (m, 1H), 7.53 (d, J=8.8 Hz, 1H), 7.42 (t, J=8.8 Hz, 1H), 6.87 (d, J=5.2 Hz, 1H), 3.84 (s, 3H), 2.80-2.74 (q, J=7.2 Hz, 2H), 2.64 (s, 3H), 1.25 (t, J=7.2 Hz, 3H).
$^{13}$C NMR (125 MHz, d$_6$-DMSO) δ 174.4, 167.4, 166.7, 161.0, 155.1, 153.9 (d, J=244.3 Hz, 1C), 152.8, 149.6, 140.5, 140.1, 139.8 (d, J=9.5 Hz, 1C), 135.6 (d, J=12.4 Hz, 1C), 133.8, 126.7, 124.6, 124.5, 119.5, 118.0, 117.3, 117.0, 111.6, 108.9 (d, J=22.8 Hz, 1C), 36.1, 28.4, 19.9, 16.4.
HRMS (ESI) for C$_{26}$H$_{22}$ClFN$_4$O$_4$ [M+H]$^+$, calcd: 509.1386, found: 509.1380.
HPLC analysis: MeOH—H$_2$O (70:30), 6.43 min, 99.81% purity.

Embodiment 69: Preparation of N-(4-((2-amino-3-chloropyridin-4-yl)oxy)-3-fluorophenyl)-6-ethyl-1,2-dimethyl-4-oxo-1,4-dihydroquinoline-3-carboxamide (named as GDL5000059)

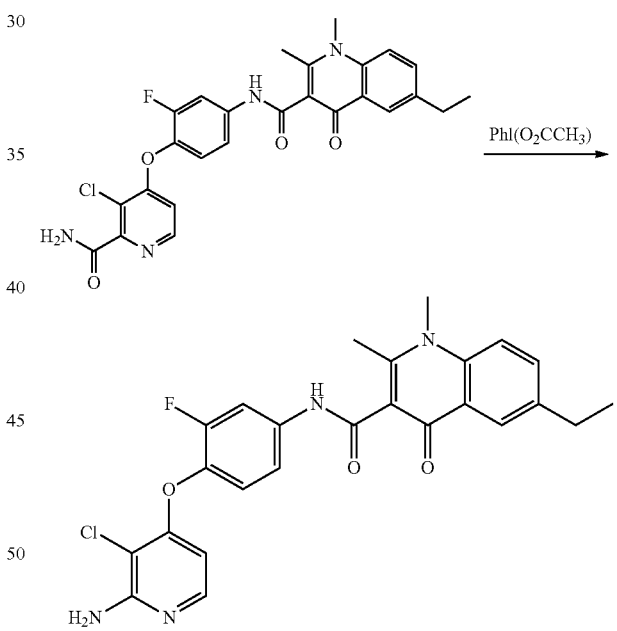

At 0° C., N-(4-(2-carbamoyl-3-chloropyridin-4-yloxy)-3-fluorophenyl)-6-ethyl-1,2-dimethyl-4-oxo-1,4-dihydroquinoline-3-carboxamide (100 mg, 0.19 mmol, 1.0 eq), 2 mL of ethyl acetate, 2 mL of acetonitrile, 1 mL of H$_2$O, and PhI(OCCH$_3$)$_2$(80 mg, 0.25 mmol, 1.3 eq) were stirred overnight, subjecting same to column chromatography to obtain 50 mg of products.
$^1$H NMR (400 MHz, d$_6$-DMSO) δ 10.99 (s, 1H), 8.08 (s, 1H), 7.98-7.94 (dd, J$_1$=2.4 Hz, 4=13.6 Hz, 1H), 7.82 (d, J=8.8 Hz, 1H), 7.75 (d, J=5.6 Hz, 1H), 7.68-7.65 (dd, J=2.0, 8.8 Hz, 1H), 7.48 (d, J=9.6 Hz, 1H), 7.42 (t, J=8.8 Hz, 1H), 6.40 (s, 2H), 5.95 (d, J=5.6 Hz, 1H), 3.83 (s, 3H), 2.80-2.74 (q, J=72 Hz, 2H), 2.63 (s, 3H), 1.25 (t, J=7.2 Hz, 3H).

$^{13}$C NMR (125 MHz, d$_6$-DMSO) δ 174.4, 166.6, 160.7, 158.3, 154.1 (d, J=243.8 Hz, 1C), 152.8, 148.1, 140.4, 140.1 139.2 (d, J=9.9 Hz, 1C), 136.4 (d, J=12.1 Hz, 1C), 133.8, 126.6, 124.5, 124.3, 119.5, 118.0, 116.7, 108.7 (d, J=22.8 Hz, 1C), 101.1, 101.0, 36.1, 28.3, 19.9, 16.3.

HRMS (ESI) for C$_{25}$H$_{22}$ClFN$_4$O$_3$[M+H]$^+$, calcd: 481.1437, found: 481.1435.

HPLC analysis: MeOH-HaO (80:20), 5.43 min, 99.59% purity.

Embodiment 70: Preparation of N-(3-fluoro-4-((5-phenyl-7H-pyrrolo[2,3-d]pyrimidine-4-yl)oxy)phenyl)-2,6-dimethyl-4-oxo-1-phenyl-1,4-hydroquinoline-3-carboxamide (named as GDL5000083)

Step r1: 2-chloro-5-methyl benzoyl chloride (Compound 54)

At 0° C., oxalyl chloride (2.6 mL, 30.5 mmol, 5.2 eq) was added slowly in a dropwise manner into a solution of 2-chloro-5-methyl-benzoic acid (1 g, 5.9 mmol, 1.0 eq) in CH$_2$Cl$_2$ (15 mL), a drop of DMF was added, and stirred overnight at room temperature, subjecting same to rotary drying.

Step r2: methyl (E)-3-(phenylamino) butenoate (Compound 55)

Methyl acetoacetate (5 g, 43 mmol, 1.0 eq) was added to aniline (4 g, 43 mmol, 1.0 eq), followed by acetic acid (260

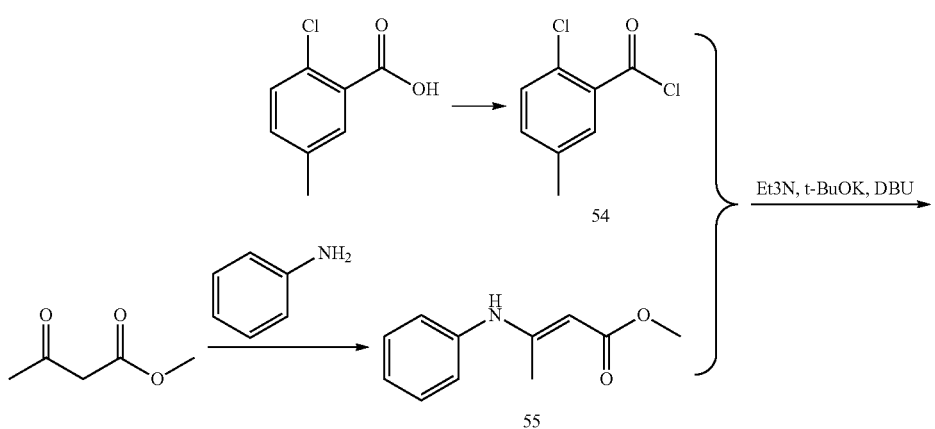

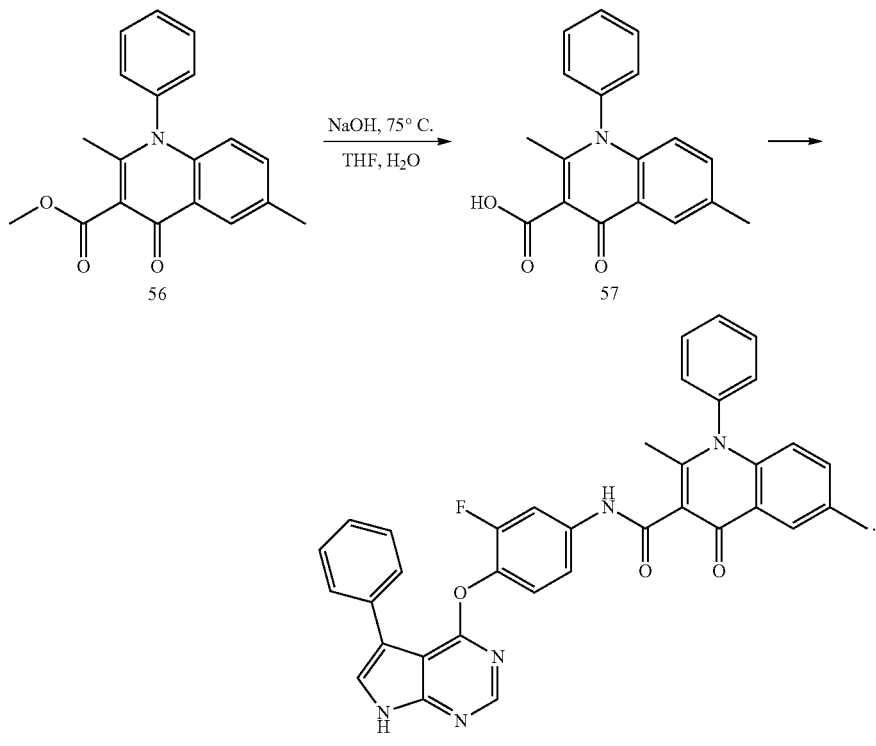

mg, 4.3 mmol, 0.1 eq), and heated to 90° C. overnight. The solution was subjected to column chromatography to obtain 5.1 g (62%) of products. $^1$H NMR (400 MHz, CDCl$_3$) δ 10.35 (s, 1H), 7.32 (t, J=7.6 Hz, 2H), 7.16 (t, J=7.6 Hz, 1H), 7.09 (d, J=7.6 Hz, 2H), 4.70 (s, 1H), 3.69 (s, 3H), 2.00 (s, 3H).

Step r3: methyl 2,6-dimethyl-4-oxo-1-phenyl-1,4-dihydroquinoline-3-carboxylate (Compound 56)

At 0° C., under Ar protection, 2-chloro-5-methyl-benzoyl chloride (1.1 g, 5.8 mmol, 1.0 eq) was dissolved in anhydrous dioxane (4 mL), 3-phenylamino-but-2-enoic acid methyl ester (1.1 g, 5.8 mmol, 1.0 eq) and Et$_3$N (587 mg, 5.8 mmol, 1.0 eq) were added slowly in a dropwise manner, stirred at room temperature for 30 min, then warmed to 65° C., stirred for 1 h, cooled to room temperature, t-BuOK (1.3 g, 11.6 mmol, 2.0 eq) and DBU (1.8 g, 11.6 mmol, 2.0 eq) were further added at 0° C., heated to reflux for 6 h, cooled to room temperature, quenched by addition of water, and extracted with ethyl acetate, subjecting same to column chromatography to obtain 100 mg (6%) of products. $^1$H NMR (400 MHz, d$_6$-DMSO) δ 7.99 (s, 1H), 7.65-7.72 (m, 3H), 7.51 (m, 2H), 7.40 (dd, J=8.8, 2.0 Hz, 1H), 6.53 (d, J=8.8 Hz, 1H), 3.79 (s, 3H), 2.39 (s, 3H), 2.00 (s, 3H).

Step r4: 2,6-dimethyl-4-oxo-1-phenyl-1,4-dihydroquinoline-3-carboxylic acid (Compound 57)

2,6-dimethyl-4-oxo-1-phenyl-1,4-dihydro-quinoline-3-carboxylic acid methyl ester (200 mg, 0.65 mmol, 1.0 eq) was dissolved in 5 mL of THF and 5 mL of H$_2$O, 1 g of NaOH was added, and heated to reflux for 72 h. The solution was allowed to cool, the THF was spun to dryness and 1 M HCl was added to adjust the solution to acidity, a white solid was precipitated, filtered, and washed to obtain 180 mg (95%) of products. $^1$H NMR (400 MHz, d$_6$-DMSO) δ 8.21 (s, 1H), 7.76-7.69 (m, 3H), 7.56 (m, 3H), 6.63 (d, J=8.8 Hz, 1H), 2.62 (s, 3H), 2.46 (s, 3H). MS (ESI), m/z 294 [M+H]$^+$.

Step r5: N-(3-fluoro-4-(5-phenyl-7H-pyrrolo[2,3-d]pyrimidin-4-yloxy)phenyl)-2,6-dimethyl-4-oxo-1-phenyl-1,4-dihydroquinoline-3-carboxamide (compound 58, GDL5000083)

The other synthetic steps are as shown in Embodiment 1.
$^1$H NMR (500 MHz, d$_6$-DMSO) δ 11.25 (s, 1H), 8.29 (s, 1H), 8.11 (s, 1H), 7.90-7.93 (dd, J=2.0, 12.5 Hz, 1H), 7.78-7.68 (m, 6H), 7.47 (m, 3H), 7.38-7.44 (m, 4H), 7.25 (t, J=7.5 Hz, 1H), 6.57 (d, J=9.0 Hz, 1H), 2.42 (s, 3H), 2.22 (s, 3H).
$^{13}$C NMR (125 MHz, d$_6$-DMSO) δ 175.0, 165.9, 162.0, 156.0, 154.6 (d, J=242.8 Hz, 1C), 152.2, 150.6, 140.7, 139.4, 138.7 (d, J=9.6 Hz, 1C), 135.7 (d, J=12.8 Hz, 1C), 135.4, 134.7, 134.6, 131.6, 130.8, 129.8, 129.2, 129.1, 126.8, 126.1, 125.9, 125.6, 125.4, 118.9, 118.8, 116.4, 116.0, 108.5 (d, J=23.5 Hz, 1H), 102.8, 21.3, 20.8.
HRMS (ESI) for C$_{36}$H$_{26}$FN$_5$O$_3$ [M+H]$^+$, calcd: 596.2092, found: 596.2098.
HPLC analysis: MeOH—H$_2$O (85:15), 8.93 min, 97.96% purity.

Embodiment 71: Preparation of 6-ethyl-N-(3-fluoro-4-((6-methoxy-7-(3-morpholinopropoxy) quinazolin-4-yl)oxy)phenyl)-1,2-dimethyl-4-oxo-1,4-dihydroquinoline-3-carboxamide (named as GDL5000123)

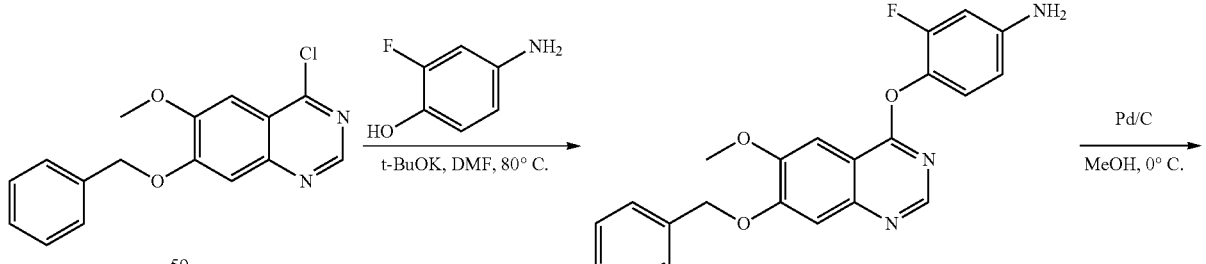

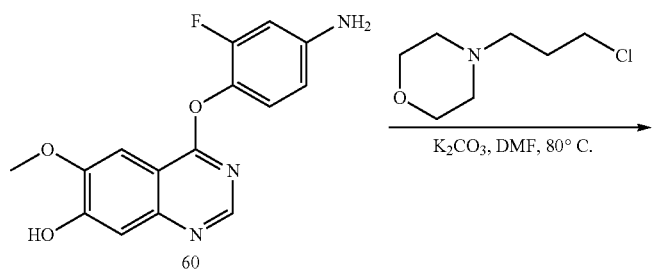

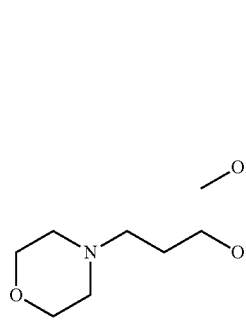
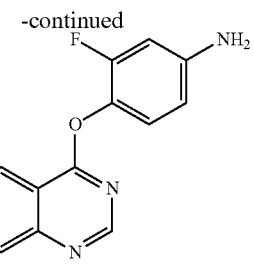

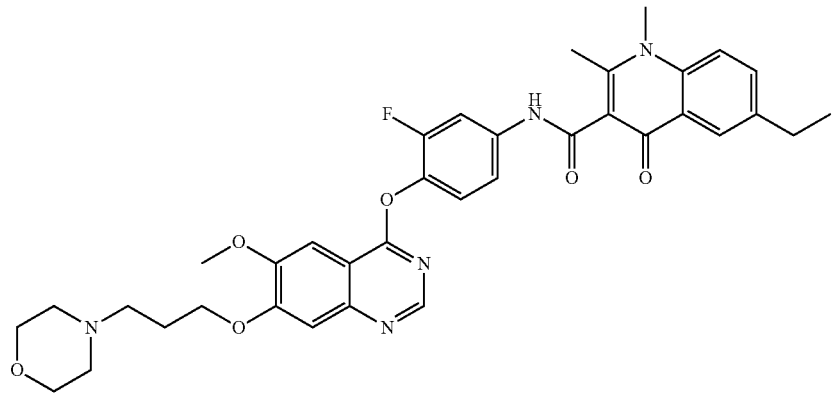

Step s1: 4-((7-benzyloxy)-6-methoxyquinazolin-4-yl)oxy)-3-fluoroaniline (Compound 59)

To the reaction flask were added 7-benzyloxy-4-chloro-6-methoxyquinazoline (4.5 g, 15 mmol), 4-amino-2-fluorophenol (2.3 g, 18 mmol), potassium tert-butoxide (2.4 g, 21 mmol), and DMF (250 mL), heated to 80° C. and reacted for 2 hours, the reaction was then stopped, and the solvent was removed under reduced pressure, subjecting same to drying and column chromatography to obtain 3.6 g (62%) of 4-((7-benzyloxy)-6-methoxyquinazolin-4-yl)oxy)-3-fluoroaniline. $^1$H NMR (400 MHz, d$_6$-DMSO) δ 8.53 (s, 1H), 7.55 (s, 1H), 7.52 (m, 2H), 7.49 (s, 1H), 7.44 (t, J=7.2 Hz, 2H), 7.37 (t, J=7.2 Hz, 1H), 7.04 (t, J=8.8 Hz, 1H), 6.50 (dd, J=2.4, 13.2 Hz, 1H), 6.42 (dd, J=2.4, 8.8 Hz, 1H), 5.39 (s, 2H), 5.35 (s, 2H), 3.97 (s, 3H). MS (ESI), m/z: 391 [M+H]$^+$.

Step s2: 4-(4-amino-2-fluorophenoxy)-6-methoxyquinazolin-7-ol (Compound 60)

4-((7-Benzyloxy)-6-methoxyquinazolin-4-yl)oxy)-3-fluoroaniline (compound 59, 5.2 g, 13.3 mmol), Pd/C (0.4 g), and methanol (250 mL) were reacted overnight at 0° C. under the action of hydrogen, and Pd/C was removed by filtration, subjecting the filtrate to concentration and column chromotography to obtain 2.4 g (60%) of 4-(4-amino-2-fluorophenoxy)-6-methoxyquinazolin-7-ol. $^1$H NMR (400 MHz, d$_6$-DMSO) δ 10.72 (s, 1H), 8.45 (s, 1H), 7.52 (s, 1H), 7.22 (d, J=3.2 Hz, 1H), 7.02 (t, J=8.8 Hz, 1H), 6.49 (dd, J=2.4, 12.8 Hz, 1H), 6.41 (dd, J=2.0, 8.8 Hz, 1H), 5.37 (s, 2H), 3.97 (s, 3H). MS (ESI), m/z: 301 [M+H]$^+$.

Step s3: Preparation of 3-fluoro-4-((6-methoxy-7-(3-morpholinopropoxy)quinazolin-4-yl)oxy)aniline (Compound 61)

4-(4-amino-2-fluorophenoxy)-6-methoxyquinazolin-7-ol (compound 60, 400 mg, 1.3 mmol), 4-(3-chloropropyl) morpholin (3-5a) (640 mg, 3.9 mmol) and potassium carbonate (540 mg, 3.9 mmol) were added into DMF (50 mL), heated to 80° C. and reacted for two hours, extracted three times with ethyl acetate, and the organic phases were combined, then washed with saturated saline, subjecting the organic phases to rotary drying and column chromatography to obtain 380 mg (67%) of 3-fluoro-4-((6-methoxy-7-(3-morpholinopropoxy) quinazolin-4-yl)oxy)aniline. $^1$H NMR (400 MHz, CDCl$_3$) δ 8.60 (s, 1H), 7.53 (s, 1H), 7.31 (s, 1H), 7.05 (t, J=8.8 Hz, 1H), 6.49 (dd, J=2.4, 12.0 Hz, 1H), 6.41 (dd, J=2.4, 8.8 Hz, 1H), 4.26 (t, J=6.4 Hz, 2H), 4.02 (s, 3H), 3.71 (t, J=4.4 Hz, 4H), 2.56 (t, J=7.2 Hz, 2H), 2.47 (s, 4H), 2.11 (m, 2H). MS (ESI), m/z: 428 [M+H]$^+$.

Step s4: Preparation of 6-ethyl-N-(3-fluoro-4-((6-methoxy-7-(3-morpholinopropoxy)quinazolin-4-yl)oxy)phenyl)-1,2-dimethyl-4-oxo-1,4-dihydroquinoline-3-carboxamide (compound 62, GDL5000123)

The other synthetic steps are as shown in Embodiment 25.
$^1$H NMR (500 MHz, d$_6$-DMSO) δ 11.01 (s, 1H), 8.56 (s, 1H), 8.08 (d, J=1.5 Hz, 1H), 7.97-7.94 (dd, J=2.0, 13.0 Hz, 1H), 7.81 (d, J=9.0 Hz, 1H), 7.67-7.65 (dd, J=2.0, 8.5 Hz, 1H), 7.58 (s, 1H), 7.50 (m, 1H), 7.44 (t, J=9.0 Hz, 1H), 7.40 (s, 1H), 4.26 (t, J=6.0 Hz, 2H), 3.99 (s, 3H), 3.83 (s, 3H), 3.60 (s, 4H), 2.77 (q, J=7.5 Hz, 2H), 2.65 (s, 3H), 2.50 (m, 2H), 2.41 (s, 4H), 1.99 (t, J=6.5 Hz, 2H), 1.25 (t, J=7.5 Hz, 2H).
$^{13}$C NMR (125 MHz, d$_6$-DMSO) δ 174.4, 166.6, 165.0, 156.2, 154.4 (d, J=243.0 Hz, 1C), 153.0, 152.7, 151.3, 149.8, 140.4, 140.1, 139.3 (d, J=9.8 Hz, 1C), 135.3 (d, J=12.9 Hz, 1C), 133.8, 126.7, 125.2, 124.6, 119.6, 118.0, 116.4, 109.9, 108.4, 108.2, 101.6, 68.0, 67.1, 57.0, 55.6, 54.2, 36.1, 28.4, 26.4, 19.9, 16.4.

HRMS (ESI) for $C_{36}H_{38}FN_5O_6[M+H]^+$, calcd: 656.2879, found: 656.2882.

HPLC analysis: MeOH—H$_2$O (85:15), 7.87 min, 98.65% purity.

Embodiment 72: Preparation of N-(4-(7-(2-(dimethylamino)ethoxy)-6-methoxyquinazolin-4-yloxy)-3-fluorophenyl)-6-ethyl-1,2-dimethyl-4-oxo-1,4-dihydroquinoline-3-carboxamide (named as GDL5000128)

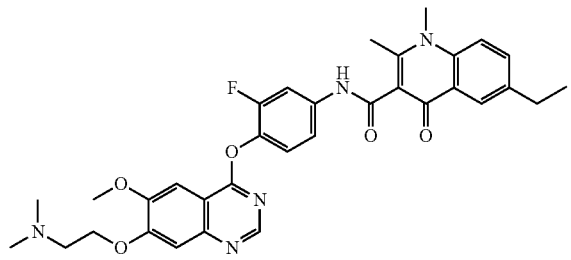 [SMILES: CCc1ccc2c(c1)c(=O)c(C(=O)Nc1ccc(Oc3ncnc4cc(OCCN(C)C)c(OC)cc34)c(F)c1)c(C)n2C]

The synthetic steps are as shown in Embodiment 71.

$^1$H NMR (500 MHz, d$_6$-DMSO) δ 11.07 (s, 1H), 8.61 (s, 1H), 8.12 (s, 1H), 7.99 (d, J=13.0 Hz, 1H), 7.84 (d, J=8.5 Hz, 1H), 7.69 (d, J=8.5 Hz, 1H), 7.64 (s, 1H), 7.54 (d, J=9.0 Hz, 1H), 7.51-7.45 (m, 2H), 4.42 (t, J=5.0 Hz, 2H), 4.04 (s, 3H), 3.87 (s, 3H), 3.05 (s, 2H), 2.80 (q, J=7.5 Hz, 2H), 2.69 (s, 3H), 2.53 (s, 2H), 1.28 (t, J=7.5 Hz, 3H).

$^{13}$C NMR (125 MHz, d$_6$-DMSO) δ 174.4, 166.6, 165.0, 155.7, 154.4 (d, J=243.1 Hz, 1C), 153.0, 152.8, 151.2, 149.7, 140.4, 140.1, 139.3 (d, J=10.0 Hz, 1C), 135.25 (d, J=12.9 Hz, 1C), 133.8, 126.7, 125.2, 124.5, 119.5, 118.0, 116.4, 110.2, 108.6, 108.4 (d, J=23.0 Hz, 1C), 101.7, 67.1, 57.6, 57.1, 45.8, 36.1, 28.3, 19.9, 16.4.

HRMS (ESI) for $C_{33}H_{34}FN_5O_5[M+H]^+$, calcd: 600.2617, found: 600.2621.

HPLC analysis: MeOH—H$_2$O (85:15), 7.17 min, 98.97% purity.

Embodiment 73: Preparation of 6-ethyl-N-(3-fluoro-4-(6-methoxy-7-(3-(4-methylpiperazin-1-yl)propoxy)quinazolin-4-yloxy)phenyl)-1,2-dimethyl-4-oxo-1,4-dihydroquinoline-3-carboxamide (named as GDL5000138)

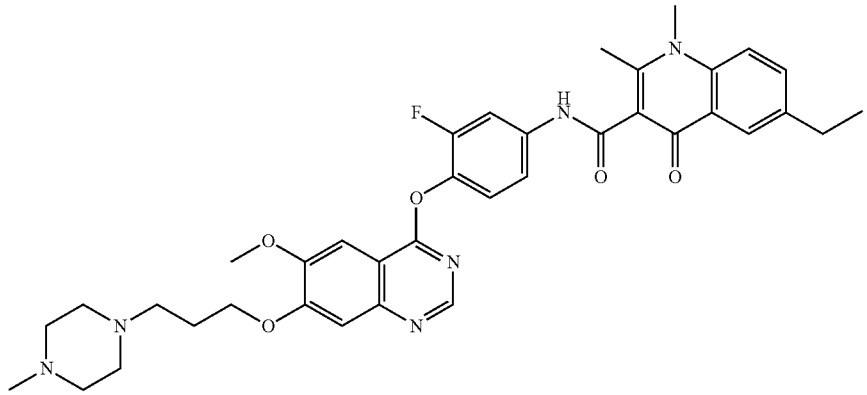 [SMILES: CCc1ccc2c(c1)c(=O)c(C(=O)Nc1ccc(Oc3ncnc4cc(OCCCN5CCN(C)CC5)c(OC)cc34)c(F)c1)c(C)n2C]

The synthetic steps are as shown in Embodiment 71.

$^1$H NMR (500 MHz, d$_6$-DMSO) δ 11.00 (s, 1H), 8.56 (s, 1H), 8.08 (s, 1H), 7.96 (m, 1H), 7.82 (d, J=8.5 Hz, 1H), 7.66 (dd, J=2.0, 8.5 Hz, 1H), 7.58 (s, 1H), 7.50 (d, J=9.0 Hz, 1H), 7.44 (t, J=9.0 Hz, 1H), 7.39 (s, 1H), 4.24 (t, J=6.5 Hz, 2H), 3.99 (s, 3H), 3.83 (s, 3H), 2.77 (q, J=7.5 Hz, 2H), 2.64 (s, 3H), 2.50-2.33 (m, 8H), 2.15 (s, 3H), 1.97 (t, J=6.5 Hz, 2H), 1.24 (t, J=7.5 Hz, 3H).

$^{13}$C NMR (125 MHz, d$_6$-DMSO) δ 174.4, 166.6, 165.0, 156.2, 154.4 (d, J=243.0 Hz, 1C), 153.0, 152.7, 151.3, 149.9, 140.4, 140.1, 139.3 (d, J=10.3 Hz, 1C), 135.3 (d, J=12.6 Hz, 1C), 133.8, 126.7, 125.3, 124.6, 119.6, 118.0, 116.4, 109.9, 108.4, 108.2, 101.6, 68.1, 57.0, 55.7, 55.2, 53.6, 46.7, 36.1, 28.4, 26.9, 19.9, 16.4.

HRMS (ESI) for $C_{37}H_{41}FN_6O_5[M+H]^+$, calcd: 669.3195, found: 669.3182.

HPLC analysis: MeOH—H$_2$O (85:15), 15.65 min, 99.55% purity.

Embodiment 74: Preparation of 6-ethyl-N-(3-fluoro-4-((6-methoxy-7-(2-(pyrrolidin-1-yl)ethoxy)quinazolin-4-yl)oxy)phenyl)-1,2-dimethyl-4-oxo-1,4-dihydroquinoline-3-carboxamide (named as TL4830058)

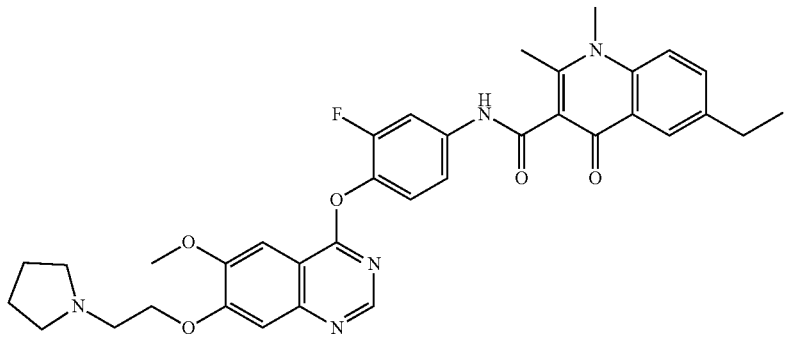 [SMILES: CCc1ccc2c(c1)c(=O)c(C(=O)Nc1ccc(Oc3ncnc4cc(OCCN5CCCC5)c(OC)cc34)c(F)c1)c(C)n2C]

The synthetic steps are as shown in Embodiment 71.

$^1$H NMR (500 MHz, d$_6$-DMSO) δ 10.99 (s, 1H), 8.56 (s, 1H), 8.09 (s, 1H), 7.96 (d, J=13.0 Hz, 1H), 7.83 (d, J=8.5 Hz, 1H), 7.67 (d, J=9.0 Hz, 1H), 7.59 (s, 1H), 7.50 (d, J=9.0 Hz, 1H), 7.44 (m, 2H), 4.30 (t, J=5.0 Hz, 2H), 3.99 (s, 3H), 3.84 (s, 3H), 2.89 (t, J=5.5 Hz, 2H), 2.77 (q, J=7.5 Hz, 2H), 2.64 (s, 3H), 2.56 (s, 4H), 1.70 (s, 4H), 1.24 (t, J=7.5 Hz, 3H).

$^{13}$C NMR (125 MHz, d$_6$-DMSO) δ 173.9, 166.2, 164.6, 155.7, 154.0 (d, J=242.8 Hz, 1C), 152.6, 152.2, 150.8, 149.4, 140.0, 139.7, 138.9 (d, J=19.4 Hz, 1C), 134.9 (d, J=12.6 Hz, 1C), 133.4, 126.3, 124.8, 124.2, 119.3, 117.6, 116.0, 109.6, 107.9 (d, J=23.1 Hz, 1C), 107.9, 101.1, 68.5, 56.6, 54.5, 54.4, 35.7, 27.9, 23.7, 19.5, 16.0.

HRMS (ESI) for C$_{35}$H$_{36}$FN$_5$O$_5$[M+H]$^+$, calcd: 626.2773, found: 626.2777.

HPLC analysis: MeOH—H$_2$O (85:15), 15.28 min, 98.83% purity.

Embodiment 75: Preparation of 6-ethyl-N-(3-fluoro-4-((6-methoxy-7-(3-methoxypropoxy)quinazolin-4-yl)oxy)phenyl)-1,2-dimethyl-4-oxo-1,4-dihydroquinoline-3-carboxamide (named as TL4830073)

The synthetic steps are as shown in Embodiment 71.

$^1$H NMR (500 MHz, CDCl$_3$) δ 12.70 (s, 1H), 8.62 (s, 1H), 8.35 (s, 1H), 8.01-7.98 (dd, J=2.0, 12.0 Hz, 1H), 7.62-7.60 (dd, J=2.0, 9.0 Hz, 1H), 7.56 (m, 2H), 7.45 (d, J=8.5 Hz, 1H), 7.34 (s, 1H), 7.27 (t, J=9.0 Hz, 1H), 4.31 (t, J=6.5 Hz, 2H), 4.06 (s, 3H), 3.92 (s, 3H), 3.62 (t, J=6.0 Hz, 2H), 3.38 (s, 3H), 3.09 (s, 3H), 2.82 (q, J=7.5 Hz, 2H), 2.21 (m, 2H), 1.33 (t, J=7.5 Hz, 2H).

$^{13}$C NMR (125 MHz, CDCl$_3$) 165.0, 164.9, 158.3, 155.4, 154.3 (d, J=245.5 Hz, 1C), 152.8, 150.5, 149.4, 141.5, 138.7, 138.2 (d, J=9.6 Hz, 1C), 135.2 (d, J=12.9 Hz, 1C), 133.6, 126.4, 125.4, 123.7, 116.3, 116.3, 115.8, 113.6, 110.2, 109.4 (d, J=24.4 Hz, 1C), 107.6, 101.2, 69.1, 66.3, 58.8, 56.4, 35.8, 29.2, 28.3, 20.4, 15.4.

HRMS (ESI) for C$_{33}$H$_{33}$FN$_4$O$_6$[M+H]$^+$, calcd: 601.2457, found: 601.24553.

HPLC analysis: MeOH—H$_2$O (85:15), 7.64 min, 98.54% purity.

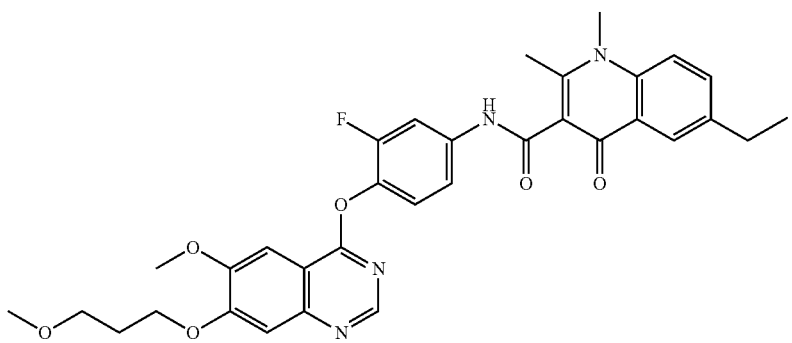 [SMILES: CCc1ccc2c(c1)c(=O)c(C(=O)Nc1ccc(Oc3ncnc4cc(OCCCOC)c(OC)cc34)c(F)c1)c(C)n2C]

Embodiment 76: Preparation of N-(4-(7-(3-(dimethylamino)propoxy)-6-methoxyquinazolin-4-yloxy)-3-fluorophenyl)-6-ethyl-1,2-dimethyl-4-oxo-1,4-dihydroquinoline-3-carboxamide (named as TL4830076)

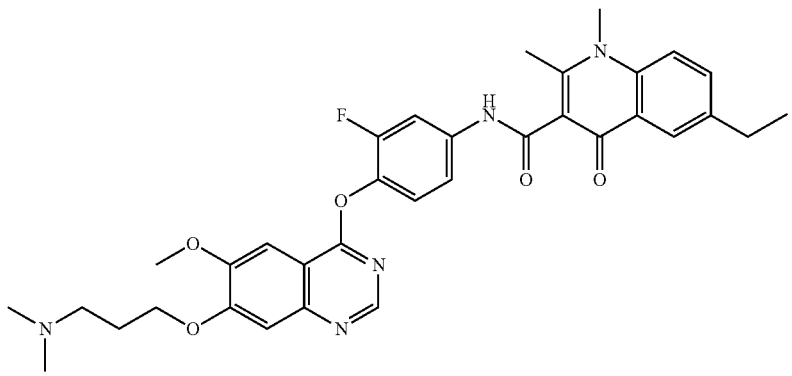 [SMILES: CCc1ccc2c(c1)c(=O)c(C(=O)Nc1ccc(Oc3ncnc4cc(OCCCN(C)C)c(OC)cc34)c(F)c1)c(C)n2C]

The synthetic steps are as shown in Embodiment 71.

$^1$H NMR (500 MHz, CDCl$_3$) δ 12.68 (s, 1H), 8.61 (s, 1H), 8.32 (s, 1H), 7.97 (d, J=12.5 Hz, 1H), 7.57 (m, 2H), 7.51 (m, 1H), 7.44 (d, J=8.5 Hz, 1H), 7.33 (s, 1H), 7.26 (m, 1H), 4.26 (t, J=6.5 Hz, 2H), 4.05 (s, 3H), 3.88 (m, 3H), 3.05 (m, 3H), 2.80 (q, J=7.5 Hz, 2H), 2.50 (t, J=7.5 Hz, 2H), 2.27 (s, 6H), 2.11 (t, J=7.0 Hz, 2H), 1.32 (t, J=7.5 Hz, 3H).

$^{13}$C NMR (125 MHz, CDCl$_3$) δ 176.6, 165.0, 164.9, 158.2, 155.4, 154.3 (d, J=245.8 Hz, 1C), 152.8, 150.5, 149.4, 141.4, 138.6, 138.2 (d, J=9.8 Hz, 1C), 135.2 (d, J=13.3 Hz, 1C), 133.6, 126.3, 125.3, 123.7, 116.2, 115.8, 113.6, 110.2, 109.4 (d, J=22.9 Hz, 1C), 107.6, 101.2, 67.7, 56.3, 56.2, 45.5, 35.7, 28.3, 27.1, 20.3, 15.3.

HRMS (ESI) for C$_{34}$H$_{36}$FN$_5$O$_5$[M+H]$^+$, calcd: 614.2778, found: 601.2769.

HPLC analysis: MeOH—H$_2$O (85:15), 14.10 min, 97.25% purity.

Embodiment 77: Preparation of N-(4-(6,7-dimethoxyquinazolin-4-yloxy)-3-fluorophenyl)-6-ethyl-1,2-dimethyl-7-(4-methylpiperazin-1-yl)-4-oxo-1,4-dihydroquinoline-3-carboxamide (named as TL4830071)

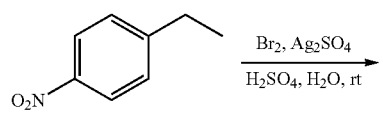

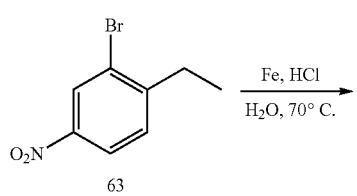

-continued

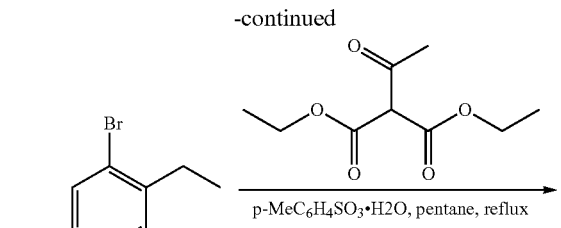

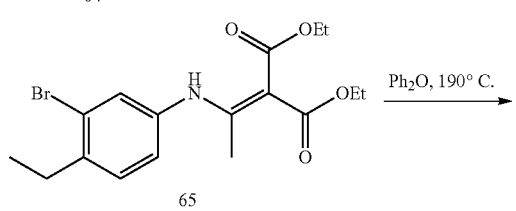

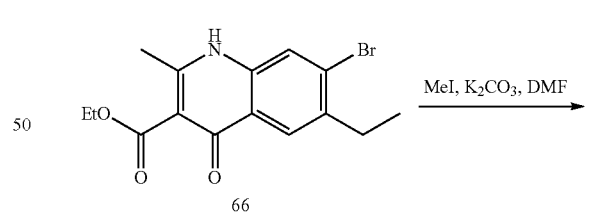

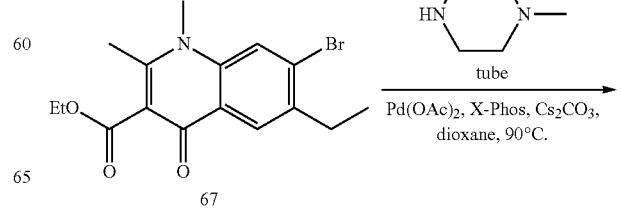

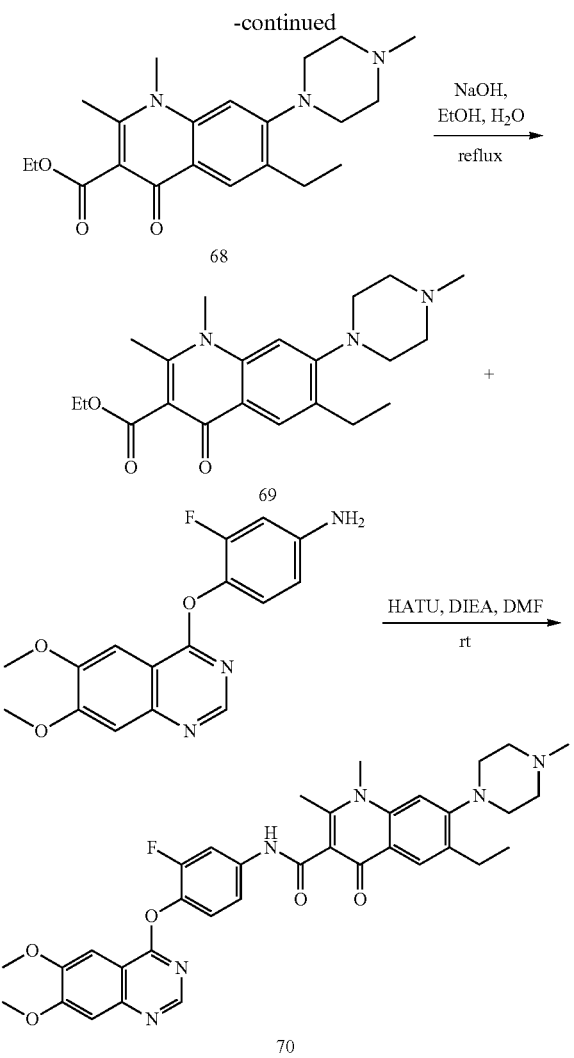

Step t1: 2-bromo-1-ethyl-4-nitrobenzene (Compound 63)

To the reaction flask were added p-nitroethylbenzene (16 g, 106 mmol), silver sulfate (33 g, 106 mmol), concentrated sulfuric acid (95 mL), and water (12 mL), and liquid bromine (5.4 mL, 106 mmol) was added slowly in a dropwise manner into the above mixture, reacting same for 4 hours at room temperature. The reaction solution was poured into sodium sulfite solution, filtered with gauze, and the filtrate was extracted twice with dichloromethane, subjecting same to column chromatography to obtain 15 g (68%) of products. $^1$H NMR (400 MHz, CDCl$_3$) δ 8.40 (d, J=2.4 Hz, 1H), 8.10 (dd, J=2.4, 8.4 Hz, 1H), 7.39 (d, J=8.4 Hz, 1H), 2.88-2.83 (q, J=7.6 Hz, 2H), 1.27 (t, J=7.6 Hz, 3H). MS (ESI), m/z: 229 [M+H]$^+$.

Step t2: 3-bromo-4-ethylaniline (Compound 64)

2-bromo-1-ethyl-4-nitrobenzene (compound 63, 15 g, 66 mmol) was added into a mixed solution of ethanol (75 mL) and water (75 mL), 5 mL of hydrochloric acid and iron powder (14 g, 264 mmol) were then slowly added, and the reaction was refluxed overnight. The solution was cooled to room temperature, filtered, subjecting the solvent to rotary drying and column chromatography to obtain 9 g (69%) of products. MS (ESI), m/z: 200 [M+H]$^+$ Step t3: 2-(1-((3-bromo-4-ethylphenyl)amino)ethylidene diethyl malonate (Compound 65)

P-3-bromo-4-ethylaniline (compound 64, 9 g, 45 mmol) and diethyl acetylmalonate (9.1 g, 45 mmol) were dissolved in 150 mL of n-pentane, a catalytic amount of p-toluenesulfonic acid (40 mg) was added and the reaction was refluxed overnight. The solution was cooled to room temperature, a small amount of saturated NaHCO$_3$ was added, extracted twice with EA, and the organic phases were combined, washed once with saturated brine, and dried over anhydrous Na$_2$SO$_4$, subjecting same to filtration, rotary drying and column chromatography to obtain 14.5 g (85%) of the solid. $^1$H NMR (400 MHz, CDCl$_3$), δ 11.14 (s, 1H), 7.29 (d, J=2.0 Hz, 1H), 7.19 (d, J=8.0 Hz, 1H), 6.98 (dd, J=2, 8 Hz, 1H), 4.27-4.16 (m, 4H), 2.76-2.71 (q, J=7.6 Hz, 2H), 2.07 (s, 3H), 1.33-1.26 (m, 6H), 1.21 (t, J=7.6 Hz, 3H). MS (ESI), m/z: 385[M+H]+.

Step t4: ethyl 7-bromo-6-ethyl-2-methyl-4-oxo-1,4-dihydroquinoline-3-carboxylate (Compound 66)

2-(1-((3-bromo-4-ethylphenyl)amino)ethylidene diethyl malonate (compound 65, 14 g, 37 mmol) was dissolved in 75 mL of diphenyl ether, heated to 200° C. with stirring and reacted for 2 hours. The solution was cooled to room temperature to precipitate the solid, which was filtered and washed with PE, subjecting same to column chromatography to obtain 5.6 g (45%) of products. $^1$HNMR (400 MHz, CDCl$_3$), δ 11.84 (s, 1H), 7.95 (s, 1H), 7.75 (s, 1H), 4.23 (q, J=8.0 Hz, 2H), 2.81-2.75 (q, J=8.0 Hz, 2H), 2.37 (s, 3H), 1.26 (t, J=8.0 Hz, 3H), 1.21 (t, J=8.0 Hz, 3H). MS (ESI), m/z: 338[M+H]$^+$.

Step t5: ethyl 7-bromo-6-ethyl-1,2-dimethyl-4-oxo-1,4-dihydroquinoline-3-carboxylate (Compound 67)

Ethyl 7-bromo-6-ethyl-2-methyl-4-oxo-1,4-dihydroquinoline-3-carboxylate (compound 66, 5.6 g, 17 mmol) and K$_2$CO$_3$ (7 g, 51 mmol) were dissolved in 75 mL of DMF, and MeI (1.6 mL, 25.5 mmol) was added with stirring, and reacted at 50° C. overnight. The solution was cooled to room temperature, quenched by addition of water to precipitate the solid, and washed with water several times, and the solid was extracted several times with DCM, the organic phases were combined, subjecting same to rotary drying and column chromatography to obtain 4.5 g (75%) of a white solid. $^1$HNMR (400 MHz, d$_6$-DMSO), δ 8.09 (s, 1H), 8.04 (s, 1H), 4.25 (q, J=7.2 Hz, 2H), 3.74 (s, 3H), 2.80 (q, J=7.2 Hz, 2H), 2.44 (s, 3H), 1.27 (t, J=7.2 Hz, 3H), 1.22 (t, J=7.2 Hz, 3H). MS (ESI), m/z: 352[M+H]$^+$.

Step t6: ethyl 6-ethyl-1,2-dimethyl-7-(-4-methylpiperazin-1-yl)-4-oxo-1,4-dihydroquinoline-3-carboxylate (Compound 68)

To the sealed tube were added ethyl 7-bromo-6-ethyl-1,2-dimethyl-4-oxo-1,4-dihydroquinoline-3-carboxylate (compound 67, 4 g, 11 mmol), N-methylpiperazine (2.4 mL, 22 mmol), Pd(OAc)$_2$ (123 mg, 0.55 mmol), X-Phos (367 mg, 0.77 mmol), CS$_2$CO$_3$ (7.2 g, 22 mmol), and dioxane (60 mL), and reacted at 90° C. overnight after argon replacement. The solution was cooled to room temperature, filtered, washed twice with water, extracted with DCM several times, and the organic phases were combined, subjecting same to rotary drying and column chromatography to obtain 780 mg (19%) of products. MS (ESI), m/z: 372 [M+H]$^+$.

Step t7: 6-ethyl-1,2-dimethyl-7-(-4-methylpiperazin-1-yl)-4-oxo-1,4-dihydroquinoline-3-carboxylic acid (Compound 69)

To ethyl 6-ethyl-1,2-dimethyl-7-(-4-methylpiperazin-1-yl)-4-oxo-1,4-dihydroquinoline-3-carboxylate (compound 68, 780 mg, 2 mmol) in the mixed solution of ethanol (15 mL) and water (10 mL) was added sodium hydroxide (240 mg, 6 mmol), and the reaction was refluxed overnight. The mixture was cooled to room temperature, and the solvent was subjected to rotary drying, then directly used in the next reaction.

Step t8: N-(4-(6,7-dimethoxyquinazolin-4-yloxy)-3-fluorophenyl)-6-ethyl-1,2-dimethyl-7-(4-methylpiperazin-1-yl)-4-oxo-1,4-dihydroquinoline-3-carboxamide (compound 70, TL4830071)

The other synthetic steps are as shown in Embodiment 48.
$^1$H NMR (500 MHz, d$_6$-DMSO) δ 11.19 (s, 1H), 8.57 (s, 1H), 8.08 (s, 1H), 7.95 (d, J=13.0 Hz, 1H), 7.59 (s, 1H), 7.49 (d, J=9 Hz, 1H), 7.44 (t, J=9.0 Hz, 1H), 7.42 (s, 1H), 7.21 (s, 1H), 4.00 (s, 3H), 3.99 (s, 3H), 3.03 (s, 4H), 2.74 (q, J=7.5 Hz, 2H), 2.66 (s, 3H), 2.53 (s, 4H), 2.27 (s, 3H), 1.27 (t, J=7.5 Hz, 3H). $^{13}$C NMR (125 MHz, d$_6$-DMSO) δ 173.7, 166.2, 164.6, 156.4, 156.1, 154.4 (d, J=243.0 Hz, 1C), 152.7, 152.6, 151.8, 149.5, 140.6, 138.9 (d, J=11.1 Hz, 1C), 135.1, 134.8 (d, J=12.8 Hz, 1C), 125.8, 124.8, 121.7, 118.3, 116.0, 109.6, 108.1, 107.9, 107.3, 106.5, 101.1, 56.7, 56.6, 55.5, 52.1, 46.3, 35.6, 23.1, 19.6, 14.9. HPLC analysis: MeOH—H$_2$O (85:15), 10.76 min, 97.64% purity.

Embodiment 78: IC$_{50}$ Test of Quinolone Derivatives on AXL and FLT3 Kinases

Kinase activity detection: The activity of compounds on kinases was detected by a secondary reaction which used the Z'-LYTE™ technique (a detection using fluorescence, enzyme coupling, and based on differences in susceptibility of phosphorylated and non-phosphorylated polypeptides to proteolytic cleavage), followed the fluorescence resonance energy transfer (FRET) principle, and used Z'-LYTE™ FRET peptide substrates (Invitrogen, Z'-LYTE™ KINASE ASSAY KIT—TYR 2 PEPTIDE, PV3191). AXL kinase (invitrogen, PV4803) was diluted stepwise, FRET peptide was then added, followed by ATP, then by compounds at different concentrations, reacted for 1 h, site-specific proteases were then added to recognize and cleave non-phosphorylated FRET peptides, reacted for 1 h, and absorptions at 445 nm and 520 nm were detected using excitation wavelength of 400 nm. The results showed that the inhibition rate was positively correlated to the drug concentration, the relation curve between the kinase activity and concentration was established, the IC$_{50}$ value was calculated, and the results are as shown in Table 1.

$$\text{Emission Ratio} = \frac{\text{Coumarin Emission (445 nm)}}{\text{Fluorescein Emission (520 nm)}} \% \text{ Phosphorylation} =$$

$$1 - \frac{(\text{Emission Ratio} \times F100\%) - C100\%}{(C0\% - C100\%) + [\text{Emission Ratio} \times (F100\% - F0\%)]}$$

In the competitive experiment of quinolone derivatives with ATP, some compounds (such as TL4800075, TL4800172, TL4830005, TL4800191, TL4800144, TL4800116, TL4830073, TL4830074, GDL5000037, GDL5000038, GDL5000123, GDL5000128 and GDL5000138) showed strong inhibitory activity on AXL kinase. During the modification of the R$_5$ substituent in the general formula (I), it is found that when R$_5$ is a hydrophobic substituent, it shows better activity and shows the best activity when it is ethyl; when the R$_6$ substituent is methyl, it shows better activity under which greater modification of the substituent is tolerated; and when the R$_4$ substituent is a hydrophobic group, it shows better activity under which greater modification of the substituent is tolerated likewise.

TABLE 1

Compound numbers and activity results of corresponding kinases.

| Compds | AXL IC$_{50}$ (μM) | Compds | AXL IC$_{50}$ (μM) | Compds | AXL IC$_{50}$ (μM) |
|---|---|---|---|---|---|
| TL50115 | 0.102 | TL4800116 | 0.061 | TL4830040 | 0.224 |
| TL50025 | 0.569 | TL4800117 | 0.075 | TL4830042 | 0.038 |
| TL50046 | >10 | TL4830014 | 0.105 | TL4830044 | 0.503 |
| TL50053 | 1.889 | TL4830016 | 1.122 | GDL5000093 | 0.277 |
| TL50054 | >10 | GDL5000091 | 0.042 | GDL5000101 | 0.081 |
| TL50080 | >10 | TL4800147 | 0.157 | GDL5000102 | 0.064 |
| TL50081 | >10 | TL4800172 | 0.0298 | GDL5000110 | 0.020 |
| TL50086 | >10 | GDL5000037 | 0.016 | TL4800199 | >10 |
| TL50087 | >10 | TL4800178 | 0.056 | TL4800200 | >10 |
| TL50090 | 2.629 | TL4800160 | 0.129 | GDL5000039 | 0.192 |
| TL50121 | 0.153 | TL4830032 | 0.0265 | GDL5000045 | 4.377 |
| TL50128 | 0.211 | TL4800167 | 0.152 | GDL5000050 | 0.888 |
| TL50133 | 3.118 | TL50167 | 0.324 | GDL5000038 | 0.034 |
| TL50198 | >10 | TL50148 | 0.227 | TL4830005 | 0.023 |
| TL4800005 | 0.099 | TL50160 | 4.53 | TL4830074 | 0.009 |
| TL4800025 | 0.557 | TL50163 | >10 | GDL5000056 | >10 |
| TL4800067 | 0.146 | TL50180 | >10 | GDL5000059 | 0.072 |
| TL4800104 | 0.533 | TL50172 | 0.026 | GDL5000083 | 0.618 |
| TL4800080 | 0.476 | TL50161 | 0.195 | GDL5000123 | 0.008 |
| TL4800139 | 0.078 | TL4800019 | >10 | GDL5000128 | 0.006 |
| TL4800144 | 0.078 | TL50134 | >10 | GDL5000138 | 0.003 |
| TL4800088 | 0.429 | TL4800191 | 0.004 | TL4830058 | 0.008 |

TABLE 1-continued

Compound numbers and activity results of corresponding kinases.

| Compds | AXL IC$_{50}$ (μM) | Compds | AXL IC$_{50}$ (μM) | Compds | AXL IC$_{50}$ (μM) |
|---|---|---|---|---|---|
| TL4800095 | 0.110 | GDL5000082 | 0.720 | TL4830073 | 0.005 |
| GDL5000076 | 0.627 | TL4830031 | 0.028 | TL4830076 | 0.0011 |
| TL4800075 | 0.006 | GDL5000111 | 1.084 | TL4830071 | 0.0148 |
| TL4800062 | 0.042 | TL4830039 | 0.058 | | |

Embodiment 79: Test on Inhibition Rate of Quinolone Derivatives on FLT3 Kinase

Conventional enzyme-linked immunosorbent assay (ELISA) method is used, and the specific steps are as follows Compound Preparation:

12,000 g of compounds were centrifuged for 5 min, DMSO was added to make a $10^{-2}$M stock solution, vortexed uniformly and sonicated for 10 min for standby application, and stored at −40° C. The compounds were diluted from the stock solution with DMSO to 100 times the concentration to be tested (concentration of DMSO in the system being 1%) during the test.

Test Method:

1. The enzyme reaction substrate Poly (Glu, Tyr) 4:1 was diluted to 20 μg/mL with potassium-free PBS (10 mM sodium phosphate buffer, 150 mM NaCl, pH 7.2-7.4), the ELISA plate was coated with same in 125 μL/well, and reacted at 37° C. for 12-16 hours, the liquid in wells was discarded, the plate was washed three times, for 5 minutes each time, with T-PBS (potassium-free PBS with 0.1% Tween-20, 200 μL/well), and the ELISA plate was dried in an oven at 37° C. for 1-2 hours.

2. To each well were added 49 μL of ATP solution diluted with reaction buffer (50 mM HEPES pH 7.4, 50 mM MgCl$_2$, 0.5 mM MnCl$_2$, 0.2 mM Na$_3$VO$_4$, 1 mM DTT), 1 μL of compounds to be tested, and 50 μL FLT-3 kinase domain recombinant protein diluted with reaction buffer to initiate the reaction (two ATP-free control wells are required for each experiment). Subject to a shaker (100 rpm) at 37° C. and reacted for 1 hour. The liquid in wells was discarded, and the plate was washed three times with T-PBS.

3. Antibody PY99 diluent (the antibody was diluted in 1:500 with T-PBS which contains 5 mg/mL BSA) was added in 100 μL/well, subjected same to a shaker at 37° C. and reacted for 0.5 hour. The liquid in wells was discarded, and the plate was washed three times with T-PBS.

4. Horseradish peroxidase labeled goat anti-mouse secondary antibody diluent (the antibody was diluted in 1:2000 with T-PBS which contains 5 mg/ml BSA) was added in 100 μL/well, subjected same to a shaker at 37° C. and reacted for 0.5 hour. The liquid in wells was discarded, and the plate was washed three times with T-PBS.

5. 2 mg/ml of OPD developing solution (diluted with 0.1 M citric acid-sodium citrate buffer which contains 0.03% H$_2$O$_2$ (pH=5.4)) was added in 100 μL/well, and reacted at 25° C. in the dark for 1-10 minutes.

6. 2 M H$_2$SO$_4$ was added in 50 μL/well to stop the reaction, and the reading from the wavelength-adjustable microwell plate ELIASA VERSAmax was performed with a wavelength of 490 nm.

7. Result analysis $$\text{Inhibition rate \%} = \left(1 - \frac{\text{the }OD\text{ value of the compound} - \text{the }OD\text{ value of the ATP-free control well}}{\text{the }OD\text{ value of the negative control} - \text{the }OD\text{ value of the ATP-free control well}}\right) \times 100\%$$

Experimental Results:

1. The enzyme activity inhibition rates of this batch of compounds against FLT-3 are as shown in Table 2, and most of the compounds show strong inhibitory effect on enzyme activity of FLT-3.

2. The enzyme activity inhibitory activity of positive compounds against FLT-3 is similar to that reported in the literature.

TABLE 2

Enzyme activity inhibition rate of compounds against receptor tyrosine kinase FLT-3 (%)

| Compound (nM) | 1000 | 100 | 10 |
|---|---|---|---|
| | | Inhibition rate (%) | |
| TL4830005 | 71.4 | 50.1 | 55.7 |
| | 59.9 | 53.3 | 49.8 |
| TL4830016 | 70.1 | 66.1 | 66.5 |
| | 67.1 | 58.3 | 50.2 |
| TL4830031 | 79.5 | 71.4 | 56.8 |
| | 76.4 | 65.8 | 57.9 |
| TL4830032 | 72.0 | 69.8 | 63.8 |
| | 68.5 | 56.6 | 62.8 |
| TL4830039 | 87.6 | 66.4 | 44.7 |
| | 80.9 | 57.4 | 49.8 |
| TL4830058 | 95.2 | 74.0 | 54.7 |
| | 92.3 | 75.8 | 49.4 |
| TL4830042 | 92.3 | 53.8 | 52.3 |
| | 87.0 | 44.5 | 40.0 |
| TL4800062 | 84.0 | 69.5 | 40.5 |
| | 79.1 | 65.8 | 44.9 |
| TL4800075 | 86.6 | 76.3 | 48.7 |
| | 80.7 | 70.4 | 41.9 |
| TL4800117 | 83.8 | 76.3 | 59.5 |
| | 74.1 | 70.2 | 61.5 |
| TL4800172 | 85.5 | 74.9 | 63.7 |
| | 72.0 | 67.8 | 55.0 |
| TL4800191 | 84.7 | 86.4 | 70.7 |
| | 83.2 | 77.1 | 67.0 |
| GDL5000037 | 100.5 | 74.3 | 65.3 |
| | 91.6 | 66.5 | 59.8 |
| GDL5000038 | 98.2 | 80.7 | 58.3 |
| | 95.9 | 73.0 | 55.0 |
| GDL5000059 | 88.7 | 67.8 | 55.9 |
| | 82.3 | 63.8 | 52.7 |
| TL50087 | 84.0 | 47.4 | 46.1 |
| | 67.2 | 45.8 | 41.8 |
| GDL5000091 | 81.8 | 47.1 | 46.9 |
| | 67.6 | 53.6 | 50.0 |
| GDL5000110 | 83.5 | 50.3 | 48.5 |

TABLE 2-continued

Enzyme activity inhibition rate of compounds against receptor tyrosine kinase FLT-3 (%)

| Compound (nM) | 1000 | 100 | 10 |
|---|---|---|---|
| | | Inhibition rate (%) | |
| | 81.2 | 51.8 | 49.2 |
| TL50121 | 84.4 | 66.7 | 58.2 |
| | 77.6 | 63.3 | 61.6 |
| GDL5000123 | 103.8 | 89.3 | 75.4 |
| | 97.4 | 83.8 | 74.8 |
| GDL5000128 | 87.9 | 75.4 | 59.1 |
| | 87.9 | 79.5 | 71.7 |
| GDL5000138 | 98.0 | 81.5 | 67.7 |
| | 98.1 | 83.0 | 66.4 |
| TL50172 | 81.8 | 62.6 | 59.4 |
| | 84.6 | 72.9 | 54.2 |

Embodiment 80: Inhibitory Effect of Quinolone Derivatives Against the Proliferation of Molm-13 and MV4-11 Cells Compound Preparation:

12000 g of compounds were centrifuged for 5 min, DMSO was added to make a $10^{-2}$M stock solution, vortexed uniformly and sonicated for 10 min for standby application, and stored at −40° C. The compounds were diluted from the stock solution with saline to 10 times the concentration to be tested (concentration of DMSO in the system being no more than 0.5%) during the test.

Test Method:

The inhibitory effect of the compounds on the proliferation of MV4-11 cells was detected using a CCK-8 cell counting kit (Dojindo). The specific steps are as follows: the MV4-11 cells in logarithmic growth phase were seeded into a 96-well culture plate at a suitable density in 90 μL/well, cultured overnight, compounds at different concentrations were then added and acted on cells for 72 hr, and the solvent control group (negative control) was set up. The effect of the compounds on cell proliferation was detected using a CCK-8 cell counting kit (Dojindo) after the compounds had acted on the cells for 72 h. 10 μL of CCK-8 reagent was added to each well, same was placed in an incubator at 37° C. for 2-4 hours, and the reading from the full-wavelength microwell plate ELIASA SpectraMax 190 was performed with a wavelength of 450 nm.

The inhibition rate (%) of the compounds on tumor cell growth was calculated using the following formula:

Inhibition rate (%)=(the OD of the control well−the OD of the administration well)/the OD of the control well×100%

$IC_{50}$ value was calculated using a software included with ELIASA by the four-parameter regression.

Experimental Results:

The effects of this batch of compounds on the proliferation of MV4-11 cells are shown in the following table, wherein some of the compounds have a strong inhibitory effect on the proliferation of MV4-11 cells; positive compound activity is similar to that reported in the literature (results as shown in Table 3).

TABLE 3

$IC_{50}$ values (nM) for the inhibition of the compounds on the proliferation of Molm-13 and MV4-11 cell strains

| | $IC_{50}$ (nM) | |
|---|---|---|
| Compound | Molm-13 | MV4-11 |
| TL4830031 | 238.7 ± 21.9 | >500 |
| TL4830073 | 38.6 ± 18.0 | 72.7 ± 16.2.2 |
| TL4830074 | >300 | >500 |
| GDL5000123 | 3.5 ± 3.2 | 51.7 ± 17.6 |
| GDL5000128 | 50.2 ± 9.9 | 57.3 ± 10.4 |
| GDL5000138 | 3.9 ± 2.9 | <2 |
| TL4800191 | 101.6 ± 10.9 | 193.6 ± 103.8 |
| AC220 | 19.5 ± 2.7 | <2 |

$IC_{50}$ for the inhibition of the compounds on each stain of cells was derived from two independent repeated tests, and the results are shown as the mean±standard deviation.

Embodiment 81

Effect of quinolone derivatives on AXL kinase phosphorylation of MDA-MB-231 and 4T1 cells A conventional Western Blot was used, which includes four steps: sample preparation; electrophoretic separation; membrane transfer of proteins; and immunological hybridization and developing (protein detection).

Sample Preparation

1. MDA-MB-231 cells were seeded into a 6-well plate at an appropriate density, cultured for 24 hours until the cell confluency reached about 80%, drug-containing medium at corresponding concentration was added respectively, and co-cultured for 2-24 hours.

2. The medium was discarded at a predetermined time point, the well plate was washed twice with precooled PBS at 4° C. and the residual liquid was washed away.

3. 1×SDS sample buffer (CST recommended, 6-well plate, 300 μL) was added, scraping all the cells in the dish with a cell scraper, and transferring same to a 1.5 mL of EP tube (operated on ice).

4. The cell lysate was sonicated for 10-15 seconds to cut off DNA, so as to reduce sample viscosity.

5. Boil the sample for 5 min.

6. 12000 g of samples were centrifuged at 4° C. for 5 min, and the supernatant was taken and stored at −20° C. or −80° C. for western blot analysis.

Detection of Protein Samples

1. Electrophoretic separation: 15-20 μL of 8%-12% SDS-PAGE polyacrylamide gel was loaded, with 90 v electrophoresis for the upper gel, and 120 v electrophoresis for the lower gel.

2. Assembly and transferring of the sandwich: submerging the polyacrylamide gel in transfer buffer and equilibrated for 10 min. According to the size of polyacrylamide gel, PVDF membrane (Mili pore) and 6 pieces of filter paper were cut out and placed in transfer buffer and equilibrated for 10 min. The PVDF membrane needs to be immersed in methanol for 3-5 seconds. Placed in such sequence as sponge→3 layers of filter paper→gel→membrane→3 layers of filter paper→sponge. Ensure there are no bubbles.

3. Membrane transferring: the transfer tank was placed in an ice bath, and the sandwich was added. Ensure the gel facing the negative electrode, and the PVDF facing the positive electrode. 1× membrane transferring buffer was added and placed under the constant pressure, subjecting same to membrane transferring at 110 V for 0.5 to 2 h depending on the molecular weight of the protein to be tested.

4. Blocking: the PVDF membrane was removed after the membrane transferring, blocked with blocking solution (1×TBS, containing 0.5% Tween-20 and 5% skim milk powder), and shaked slowly for 2 h on a horizontal shaker.

5. Incubation of the primary antibody: after blocking, diluting the primary antibody (antibody AXL, phosphor-AXL, AKT, phosphor-AKT, GAPDH, etc.) at 1: 200-1:1000. The PVDF membrane and the antibody were incubated overnight in a wet box at 4° C. to allow sufficient binding of the antibody to the protein of interest.

6. Incubation of the secondary antibody: removing the PVDF membrane and washing the membrane with 1×TBST 4 times, for 5 min each time. Preparing 5% skim milk powder solution with 1×TBST solution, and diluting the horseradish peroxidase (HRP, sigma) labeled secondary antibody by 1000 times, and putting the PVDF membrane into a wet box for incubation for 2 hours at room temperature. Washed with 1×TBST 4 times, for 10 min each time.

7. Development: strips on the PVDF membrane were chemiluminescent by following the instructions using the ECL Western Blotting Detection Kit (Thermo Scientific, USA). X-ray films were developed and fixed by enhancing chemiluminescence (Thermo), and finally rinsed with tap water, and dried for storage. Scan the films and record the results.

As can be seen from FIG. 1, among the quinolone compounds, TL4800075 and TL4800191 can significantly inhibit the phosphorylation of AXL and its downstream signaling protein AKT of MDA-MB-231 cells.

Figure 2:
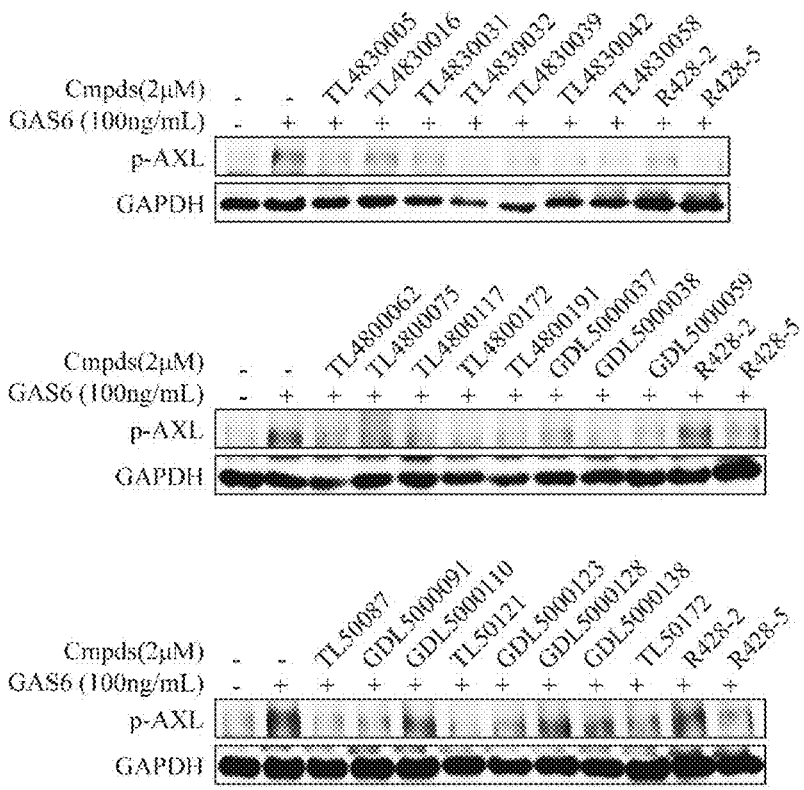
FIG. 2 shows the effect of quinolone derivatives on the AXL kinase phosphorylation of A549 cells.

As can be seen from FIG. 2, most quinolone compounds can significantly inhibit GAS6-induced AXL phosphorylation level in A549 cells.

Embodiment 82

Effects of quinolone derivatives on TGF-β1-induced EMT transformation, and the invasion and migration of MDA-MB-231 cells.

Immunofluorescence experiments were used to determine the effect of the compounds on EMT marker proteins.

Immunofluorescence Microscopy Assay

MDA-MB-231 cells were seeded onto a glass slide preplaced in a 6-well plate, and then treated with compounds to be tested at different concentrations (0.04, 0.2, 1.5 μM) with or without TGF-β1 (10 ng/ml) for 96 hours. At room temperature, the cells were fixed with a 4% formaldehyde solution for 15 minutes, treated with 0.5% Triton X-100 for 10 minutes, and blocked with PBS solution containing 3% goat serum albumin for one hour, and then incubated with antibodies against E-cadherin and N-cadherin (1:1000; Abeam, ab10983) for 1.5 hours at room temperature. The cells were then washed with PBST and co-incubated with Alexa Fluor 555 labeled rabbit secondary antibody (4413; CST, USA) or Alexa Fluor 488 labeled murine secondary antibody (4408; CST, USA) for one hour at room temperature in the dark. Cell nuclei were stained with ProLong Gold antifade reagent (P36931; Invitrogen, USA) for 5 minutes, glass slides were covered with pieces of glass, and samples were observed using a laser scanning confocal microscope (Zeiss 710; Germany).

Figure 3:
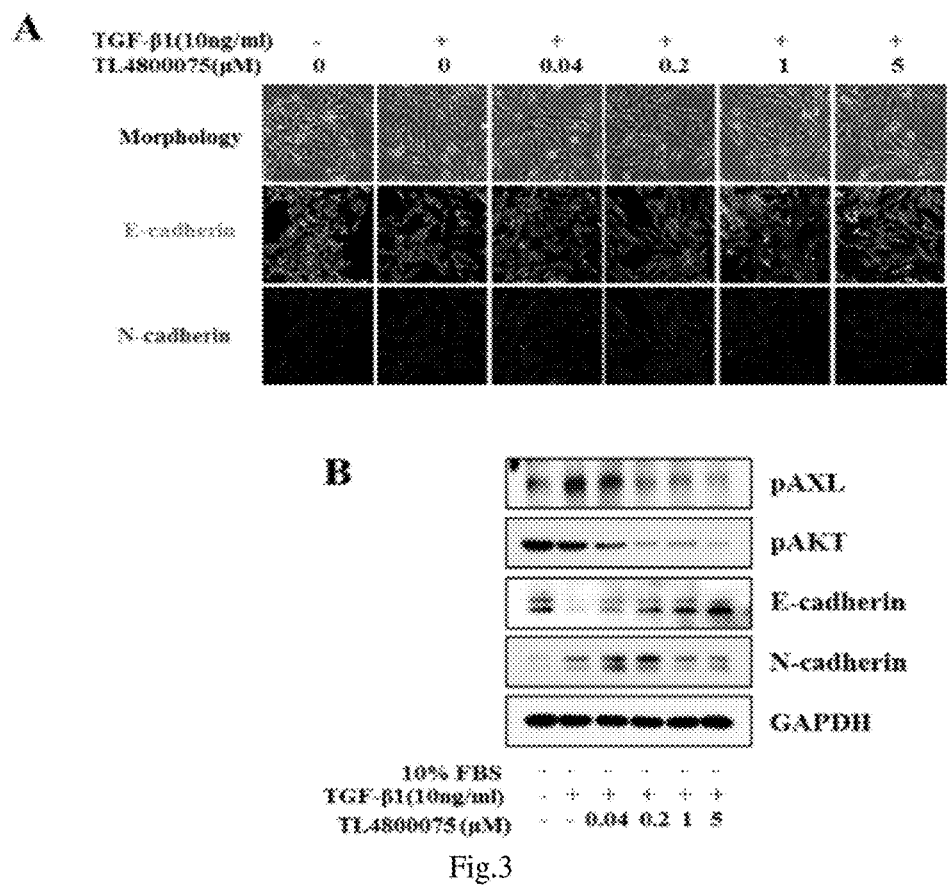
FIG. 3 shows the effect of quinolone derivatives on the cell morphology and protein expression during the EMT of MDA-MB-231 cells induced by TGF-β1.
Figure 4:
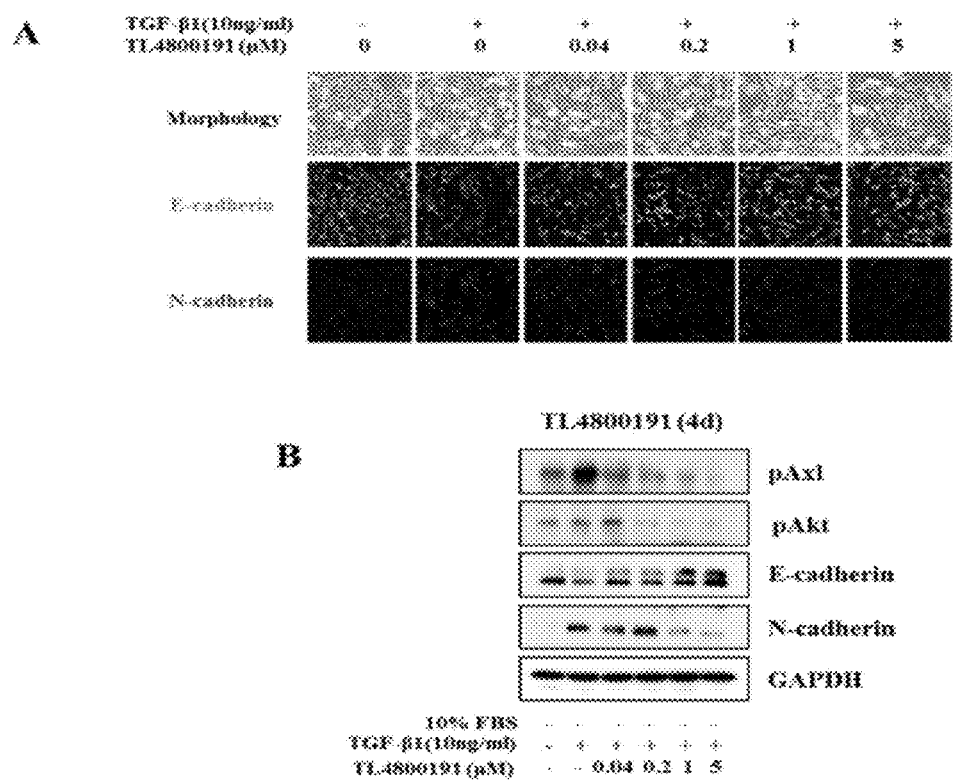
FIG. 4 shows the effect of quinolone derivatives on the cell morphology and protein expression during the EMT of MDA-MB-231 cells induced by TGF-β1.

The experimental results showed that compounds TL4800075 and TL4800191 could inhibit the phosphorylation level of AXL in a dose-dependent manner, and significantly upregulate the expression of E-cadherin and meanwhile down-regulate the expression of N-cadherin (see FIGS. 3 and 4).

Compounds were tested for their effects on EMT using routine transwell and wound-healing experiments.

Wound-Healing Assay

MDA-MB-231 breast cancer cells were inoculated into a 6-well plate in $5 \times 10^5$ cells/well, and when the cells occupied 100% of the medium, the medium was removed, and a scratch of a constant width was drawn in the middle of the monolayer cell with a 200-μL pipette tip. The cells were washed three times with phosphate buffered saline (PBS) to remove cell debris, followed by addition of 2% FBS with or without TGF-β1 (10 ng/mL) and substances to be tested at different concentrations, and cultured in RPMI-1640 for 24 hours. At the time points of 0 and 24 hour, three scratch areas were selected, and examined and photographed using a phase contrast inverted fluorescence microscopy (CKX41; Olympus) and Image-ProPlus image capture software. The degree of scratch closure was calculated using Adobe Photoshop 7.0.1 software (Adobe Systems Inc., San Jose, Calif.). The final result is determined by averaging three results.

Experiments on Inhibition of Cell Invasion and Migration

Migration and invasion studies were performed using Transwell chambers (353097, 353504; Corning Costar) or Magrigel Invasion chambers (354480; Corning Costar) in small chambers according to the manufacturer's instructions. Specific steps are as follows:

1. Cells were trypsinized and centrifuged, then resuspended and counted, and resuspended with serum-free medium, diluted to $5 \times 10^4$ to $5 \times 10^5$ cells/mL; AXL inhibitor solution at different concentrations were prepared with the cell suspension, and added into the upper chamber, and 800 μL of a medium containing 10% FBS was added into the lower chamber.

2. After 4 hours, the media in the upper and lower chambers were removed, fixed with methanol for 30 min, and the adherent cells in the upper chamber were carefully removed with a cotton swab, and washed with PBS 2 times.

3. Stain with 0.2% crystal violet for 30 min.

4. Wash with clear water to remove redundant dye.

5. Take pictures under a microscope.

6. Count by using Photoshop, obtaining the statistics of the mean and standard deviation of each group using Excell, and obtaining the statistics of differences between groups using SPSS1.0.

Figure 5:
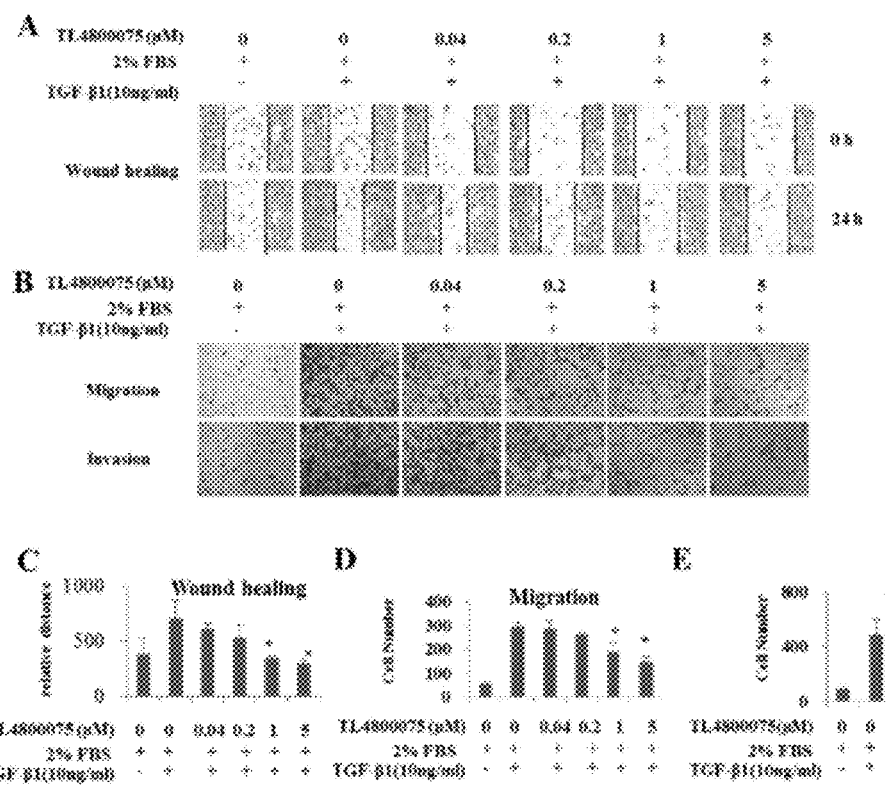
FIG. 5 shows the effect of quinolone derivatives on the migration and invasion of MDA-MB-231 cells
Figure 6:
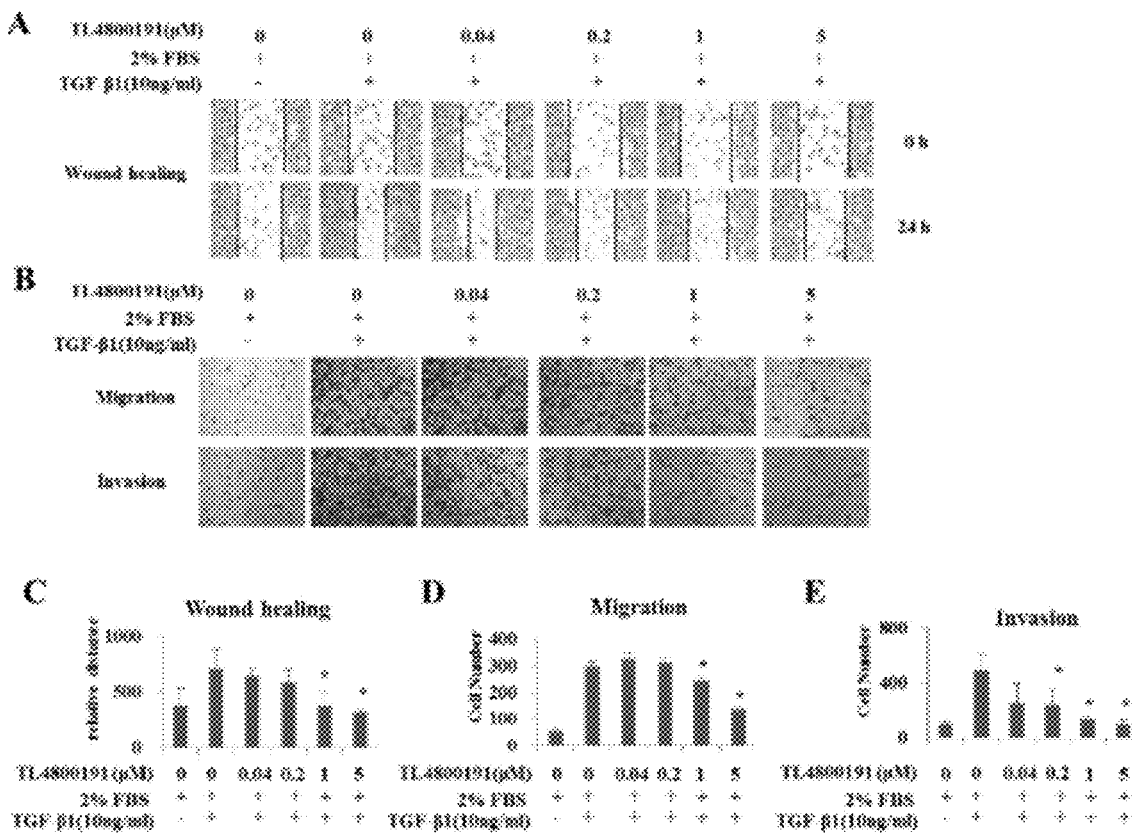
FIG. 6 shows the effect of quinolone derivatives on the migration and invasion of MDA-MB-231 cells

The experimental results show that compounds TL4800075 and TL4800191 can inhibit the invasion and migration of breast cancer MDA-MB-231 cells induced by TGF-β1 in a dose-dependent manner (see FIGS. 5 and 6).

Embodiment 83: Inhibition of Quinolone Derivatives on Migration of In Vivo Xenograft BALB/c mice were selected and 4T1 cells ($0.5 \times 10^6$/mouse) were inoculated subcutaneously on their right sides. Twenty-four days after inoculation, the mice were randomly divided into treatment and control groups (10 in each group). The mice in each group were orally administered for 21 days, and the drug dose in the treatment group was 30 mg/kg and 90 mg/kg of compound 2-lin per day, respectively. The mice were measured for body weight and tumor volume every two days. After the mice reached the end of administration, the liver tissues of mice were excised and collected, fixed with 10% formaldehyde solution, embedded in paraffin, sectioned, and stained with eosin. Microscopic examination of micrometastases in at least three fields of view was performed and the number of liver micrometastases was calculated.

The tumor volume is calculated by the formula of $TV=W^2$ (L/2), wherein L is the length and W is the width.

Figure 7:
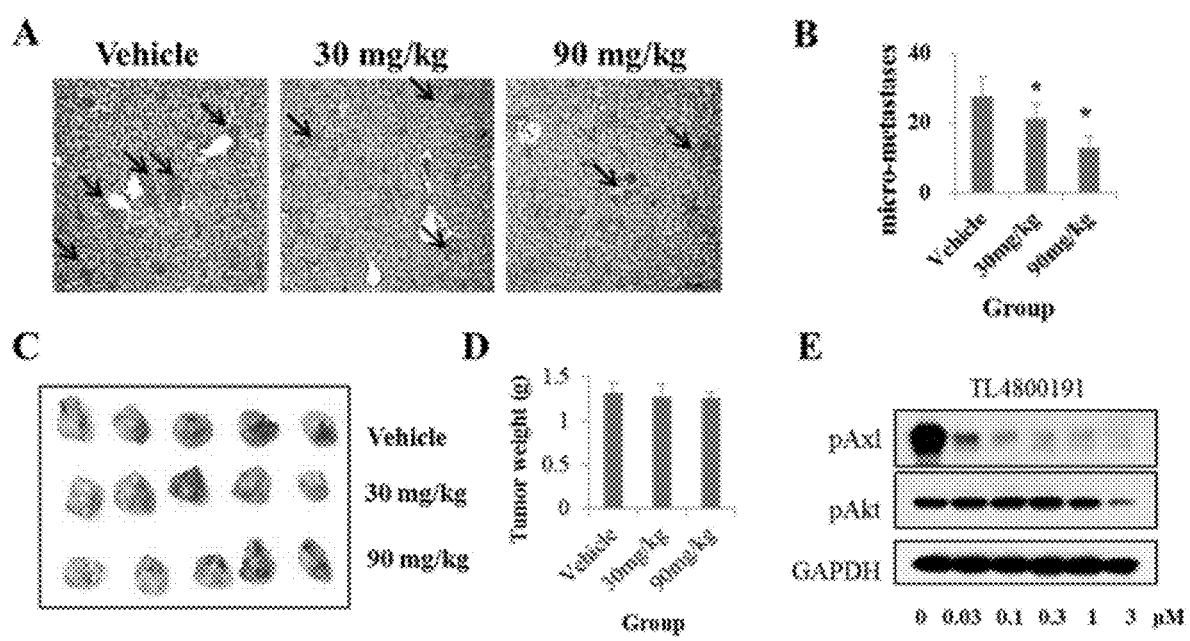
FIG. 7 shows the effect of quinolone derivatives on the in vivo metastasis of 4T1 xenografts

The results show that compound TL4800191 has no obvious inhibitory effect on the growth of in situ tumor, however it can inhibit the number and size of liver metastasis in a dose-dependent manner. (See FIG. 7)

Embodiment 84: In Vivo Pharmacokinetic Experiments of Quinolone Derivatives

Pharmacokinetic and bioavailability experiments of rats. SD rats were administered orally (25 mg/kg) and intravenously (2.5 to 5 mg/kg) at a single dose. Animal blood samples were taken at appropriate time points after administration, heparin was added as anticoagulant, and same were centrifuged at 8000 rpm/min for 6 minutes, the supernatant was then taken and stored at −20° C. for HPLC-MS analysis. The proteins in blood samples were precipitated with acetonitrile at 12000 rpm for 10 min, and the supernatant was used for HPCL-MS analysis. Data were fit using DAS2.0 to obtain compartmental model and non-compartmental model parameters, respectively. The oral bioavailability of each compound was calculated according to AUC data. The results are as shown in the table below, wherein hydrochlorides of TL4900191, GDL5000123, GDL5000128, GDL5000138, and TL4830058, etc. all have an appropriate pharmacokinetic parameter, which can meet the needs of in vivo efficacy test.

TABLE 4

Pharmacokinetic data for some compounds

| NO. | Mode of administration | Dose (mg/kg) | $T_{1/2}$ (h) | Cmax (μg/L) | AUC(0-t) (μg/L * h) | AUC(0-∞) (μg/L * h) | CL (L/h/kg) | F (%) |
|---|---|---|---|---|---|---|---|---|
| TL4800075 | iv | 2.5 | 0.87 | 2910.13 | 3024.64 | 3029.64 | 0.83 | 1.23 |
|  | Po | 25 | 3.72 | 121.74 | 371.03 | 505.71 | NA |  |
| TL4800191 | iv | 5 | 25.2 | 1168 | 30457 | 42325 | 0.1 | 14.9 |
|  | Po | 25 | 10.2 | 1967 | 31308 | 31505 | 0.9 |  |
| TL4830031 | iv | 5 | 4.26 | 4358.24 | 20277.98 | 20680.55 | 0.12 | 12.05 |
|  | o | 25 | 5.68 | 2386.87 | 24440.68 | 25944.71 | NA |  |
| TL4830039 | iv | 5 | 12.71 | 1137.38 | 9600.80 | 12978.37 | 0.39 | 7.92 |
|  | Po | 25 | 35.46 | 218.87 | 3802.63 | 12206.41 | NA |  |
| TL4830042 | iv | 5 | 15.82 | 884.60 | 9775.35 | 15179.04 | 0.35 | 0.20 |
|  | Po | 25 | 14.53 | 7.15 | 98.90 | 151.18 | NA |  |
| TL4830058 | iv | 5 | 4.05 | 13269.06 | 28353.79 | 28670.25 | 0.18 | 27.99 |
|  | Po | 25 | 11.01 | 4093.09 | 39685.03 | 50253.45 | NA |  |
| GDL5000123 | iv | 5 | 6.7 | 6478.87 | 43835.35 | 47682.25 | 0.11 | 23.50 |
|  | Po | 25 | 26.72 | 3076.52 | 51512.38 | 117957.52 | NA |  |
| GDL5000128 | iv | 5 | 5.82 | 16792.61 | 11312.50 | 11609.50 | 0.45 | 44.32 |
|  | Po | 25 | 4.59 | 4628.77 | 25067.22 | 25556.89 | NA |  |
| GDL5000138 | iv | 5 | 5.72 | 3557.00 | 8216.53 | 8526.42 | 0.59 | 27.50 |
|  | Po | 25 | 34.80 | 656.13 | 11296.44 | 31299.15 | NA |  |

The above-mentioned embodiments are preferred implementations of the present invention. However, the implementations of the present invention are not limited to the above-mentioned embodiments, and any other changes, modifications, substitutions, combinations and simplifications made without departing from the spirit and principle of the present invention should all be equivalent replacement methods and should all be included in the scope of protection of the present invention.

The invention claimed is:

1. A substituted quinolone derivative, or a pharmaceutically acceptable salt or a stereoisomer thereof, having a structure as shown by formula (I):

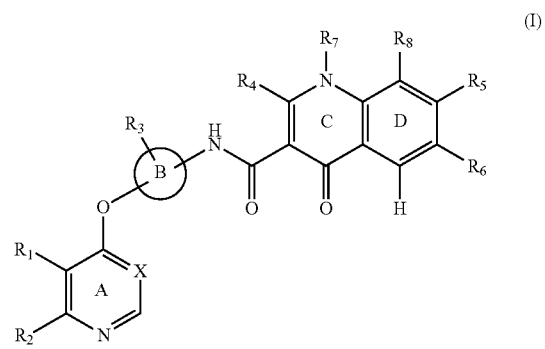

wherein, X is N;

$R_1$ is optionally selected from: hydrogen or halogen;

$R_2$ is optionally selected from:

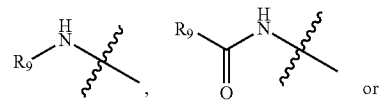

-continued

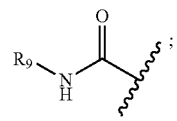

$R_9$ is optionally selected from: hydrogen, $C_1$-$C_5$ alkyl or $C_3$-$C_6$ cycloalkyl;

or $R_1$, $R_2$ and ring A constitute a fused 5- to 6-membered heterocyclic ring

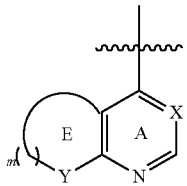

which is substituted or unsubstituted and contains 1-3 N, wherein m=2-3, X is optionally selected from CH or N, and Y is optionally selected from C, N or O;

B is optionally selected from: aryl, heteroaryl, monocyclic or polycyclic alkyl;

$R_3$ is optionally selected from: hydrogen, halogen, trifluoromethyl or $C_1$-$C_3$ alkyl;

$R_4$ is optionally selected from: hydrogen, $C_1$-$C_5$ alkyl, $C_3$-$C_6$ cycloalkyl, $C_1$-$C_3$ alkoxy, substituted or unsubstituted phenyl;

$R_5$ is optionally selected from: hydrogen, —($CH_2$)$_r$—COOR$_{22}$, —($CH_2$)$_r$—NR$_{23}$R$_{24}$, -L- heteroaryl or

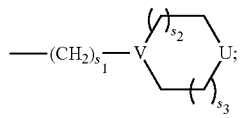

r, $s_1$, $s_2$, and $s_3$ in $R_5$ are each independently selected from 0, 1, 2 or 3;

V is optionally selected from: CH or N;

U is optionally selected from: O, S, CR$_{23}$R$_{24}$ or NR$_{23}$;

$R_{22}$ is optionally selected from: hydrogen or $C_1$-$C_4$ alkyl;

$R_{23}$ and $R_{24}$ are optionally selected from: H, $C_1$-$C_3$ alkyl, $C_3$-$C_6$ cycloalkyl, —NH($C_1$-$C_3$ alkyl), —N($C_1$-$C_3$ alkyl)($C_1$-$C_3$ alkyl) or —C(=O)($C_1$-$C_3$ alkyl);

L is optionally selected from: $C_1$-$C_3$ alkyl, —NR$_{25}$—, —NR$_{25}$CO—, —CONR$_{25}$—, —O—, —CO—, —SO— or —SO$_2$—; $R_{25}$ is selected from: $C_1$-$C_3$ alkyl;

$R_6$ is optionally selected from: hydrogen, halogen, $C_1$-$C_5$ alkyl, $C_2$-$C_6$ alkenyl, $C_3$-$C_6$ cycloalkyl, $C_4$-$C_6$ cycloalkenyl, $C_1$-$C_5$ alkoxy, trifluoromethyl or trifluoromethoxy;

$R_7$ is optionally selected from: hydrogen, $C_1$-$C_5$ alkyl or $C_3$-$C_6$ cycloalkyl;

$R_8$ is hydrogen;

or $R_7$, $R_8$, ring C and ring D constitute a 5- to 7-membered aliphatic heterocyclic ring

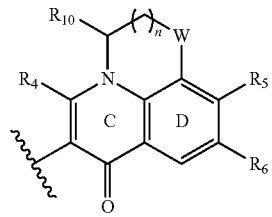

wherein, n=0-2; W is optionally selected from $CH_2$ or O; and $R_{10}$ is optionally selected from H or $CH_3$.

2. The substituted quinolone derivative, or a pharmaceutically acceptable salt or a stereoisomer thereof according to claim 1, wherein when the $R_1$, $R_2$ and ring A constitute a fused 5- to 6-membered substituted heterocyclic ring, the fused 5- to 6-membered substituted heterocyclic ring has one of the following structures:

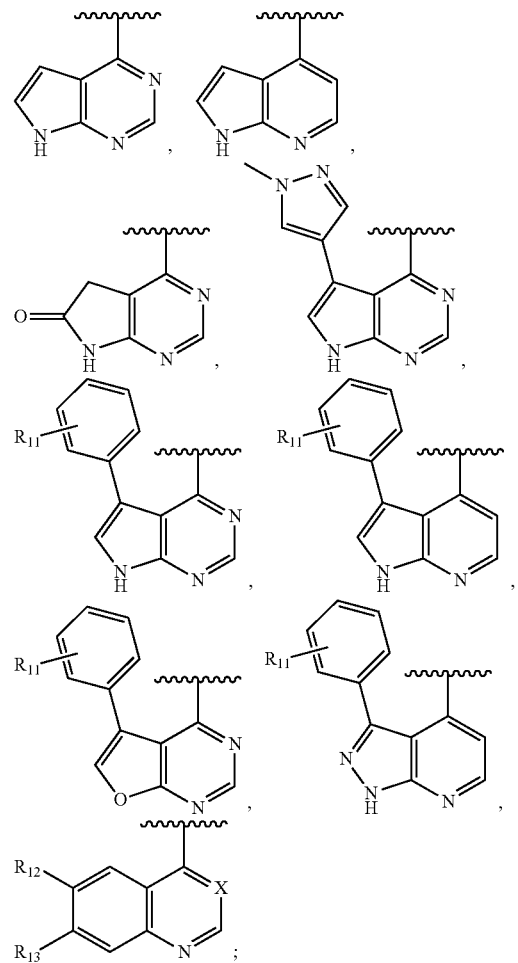

wherein, X is N;

$R_{11}$ is optionally selected from: hydrogen, halogen, methyl, ethyl, propyl, isopropyl, cyclopropyl, methoxy, ethoxy, propoxy or isopropoxy;

$R_{12}$ and $R_{13}$ are the same or different and are optionally selected from: hydrogen, halogen, —(CR$_{15}$R$_{16}$)$_O$R$_{14}$, —O(CR$_{15}$R$_{16}$)$_O$R$_{14}$, —(CR$_{17}$=CR$_{18}$)$_p$R$_{14}$, —O(CR$_{17}$=CR$_{18}$)$_p$R$_{14}$,

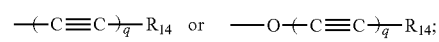

wherein, o, p, and q=0-6, and $R_{10}$, $R_{15}$, $R_{16}$, $R_{17}$, and $R_{18}$ are the same or different and are optionally selected from: —H, —F, —Cl, —Br, —I, —CF$_3$, —OCF$_3$, —OH, —COOH, —COOCH$_3$, —COOC$_2$H$_5$, —COOC$_3$H$_7$, —COOCH(CH$_3$)$_2$, —COOC(CH$_3$)$_3$, —(C=O)—NR$_{19}$R$_{20}$, —SO$_m$—NR$_{19}$R$_{20}$, —CHR$_{19}$R$_{20}$, —OR$_{19}$ or —NR$_{19}$R$_{20}$; m=1-2;

$R_{19}$ and $R_{20}$ are the same or different and are optionally selected from: hydrogen, halogen, or $C_1$-$C_6$ alkyl; or, $R_{19}$ and $R_{20}$ constitute a saturated or an unsaturated 5- to 8-membered heterocyclic group;

or, $R_{12}$ and $R_{13}$ constitute a substituted or an unsubstituted $C_5$-$C_{18}$ aliphatic cycloalkyl which contains 1-4 heteroatoms.

3. The substituted quinolone derivative, or a pharmaceutically acceptable salt or a stereoisomer thereof according to claim 1, wherein the $R_4$ is selected from the following structures: hydrogen, methyl, ethyl, propyl, isopropyl, butyl, isobutyl, pentyl, isopentyl, cyclopropyl, cyclobutyl, cyclopentyl, cyclohexyl, methoxy, ethoxy, propoxy, isopropoxy or

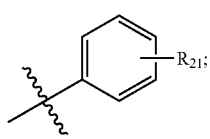

wherein, $R_{21}$ is optionally selected from: hydrogen, halogen, $C_1$-$C_5$ alkyl, $C_3$-$C_6$ cycloalkyl or $C_1$-$C_5$ alkyl;

the $R_5$ is selected from the following structures: hydrogen,

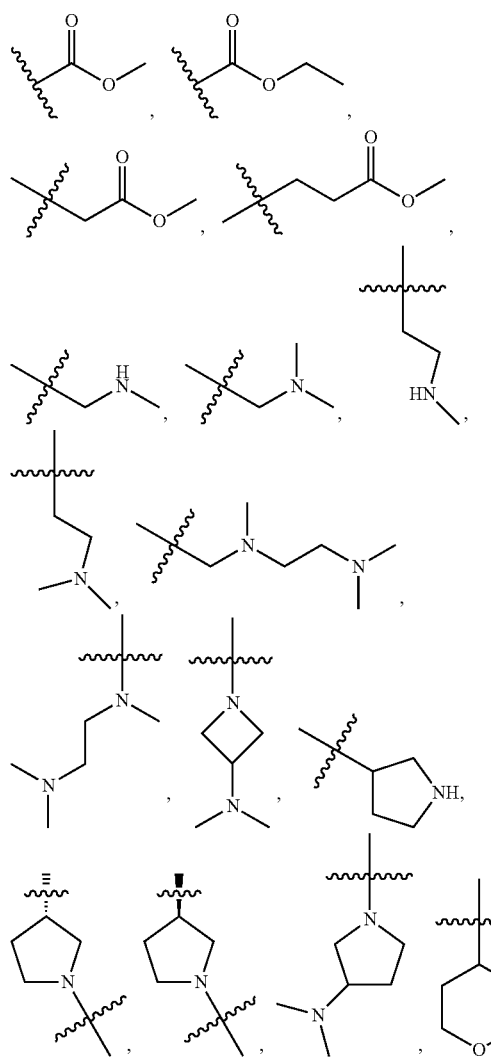

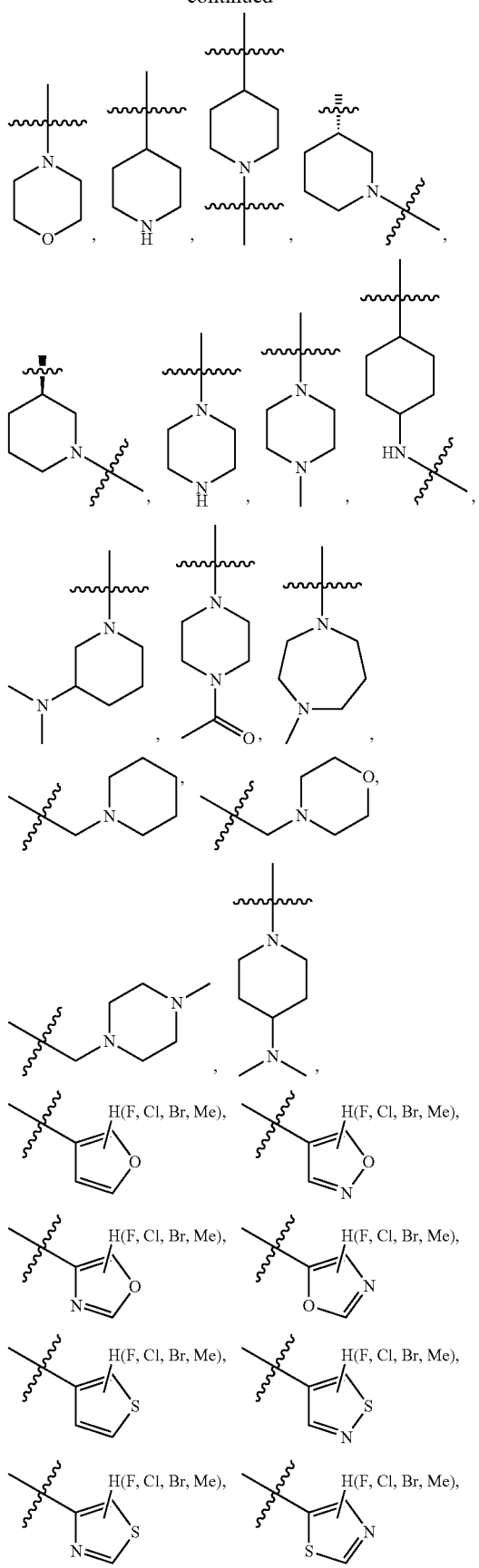

121
-continued

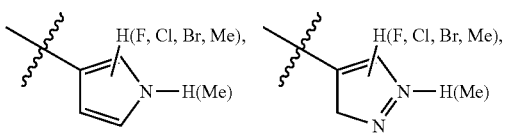

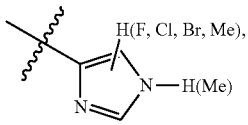

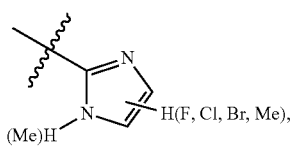

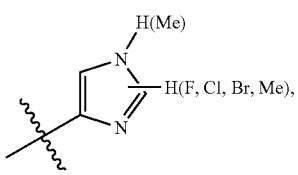

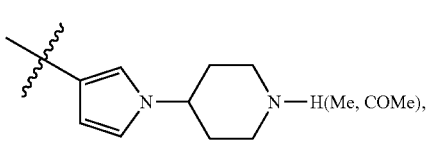

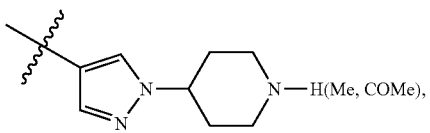

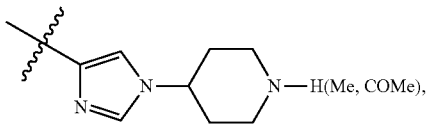

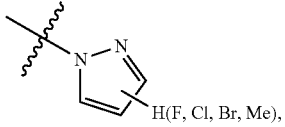

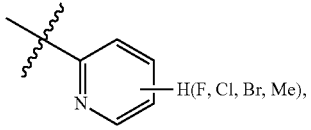

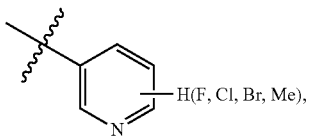

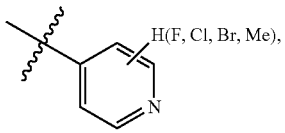

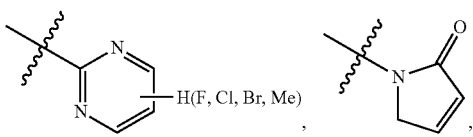

122
-continued

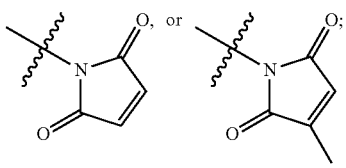

the $R_6$ is selected from the following structures: hydrogen, fluorine, chlorine, bromine, methyl, ethyl, propyl, isopropyl, butyl, isobutyl, tert-butyl, pentyl, isopentyl, propenyl, isopropenyl, butenyl, pentenyl, cyclopropyl, cyclobutyl, cyclopentyl, cyclohexyl, cyclobutenyl, cyclopentenyl, cyclohexenyl, methoxy, ethoxy, propoxy, isopropoxy, trifluoromethyl or trifluoromethoxy;

when the $R_8$ is H, $R_7$ is selected from the following structures: hydrogen, methyl, ethyl, propyl, isopropyl, butyl, cyclopropyl, cyclobutyl, cyclopentyl or cyclohexyl;

and when the $R_7$, $R_8$, ring C and ring D constitute a fused tricycle, the fused tricycle is one of the following structures:

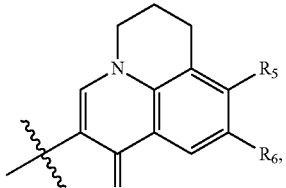

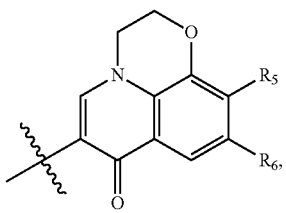

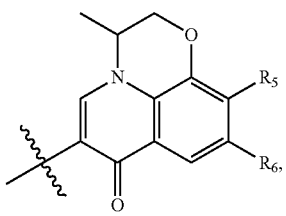

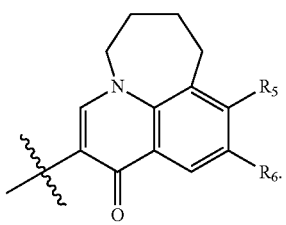

4. The substituted quinolone derivative, or a pharmaceutically acceptable salt or a stereoisomer thereof according to claim 1, having a structure as shown below:

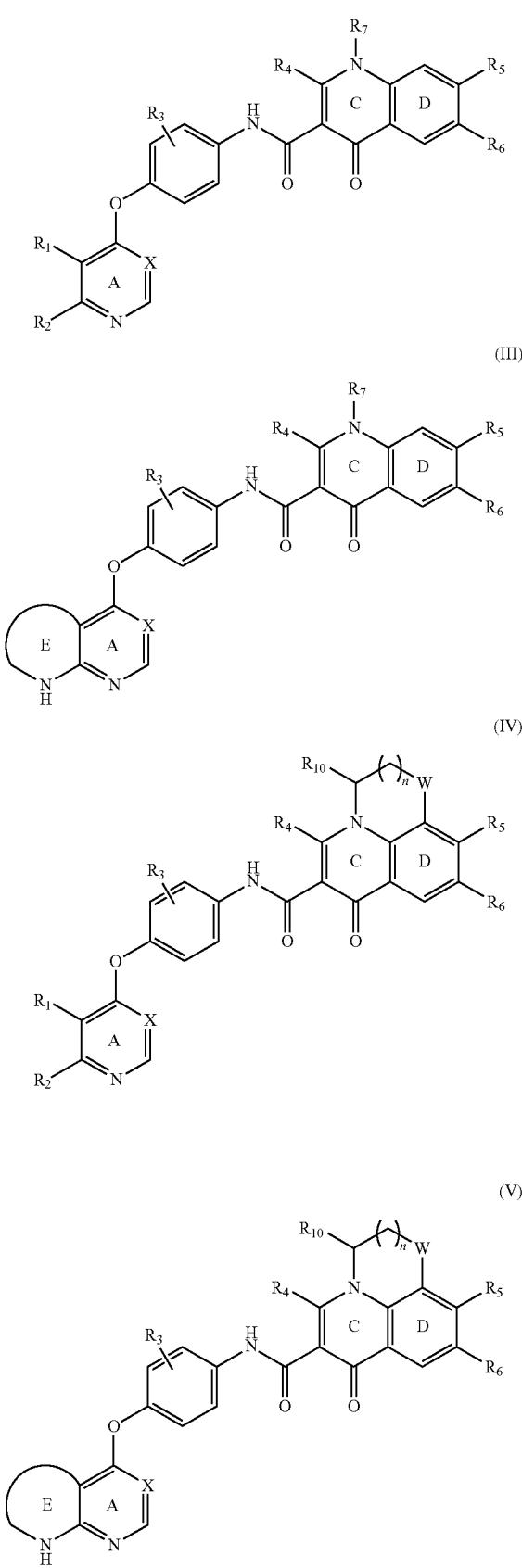
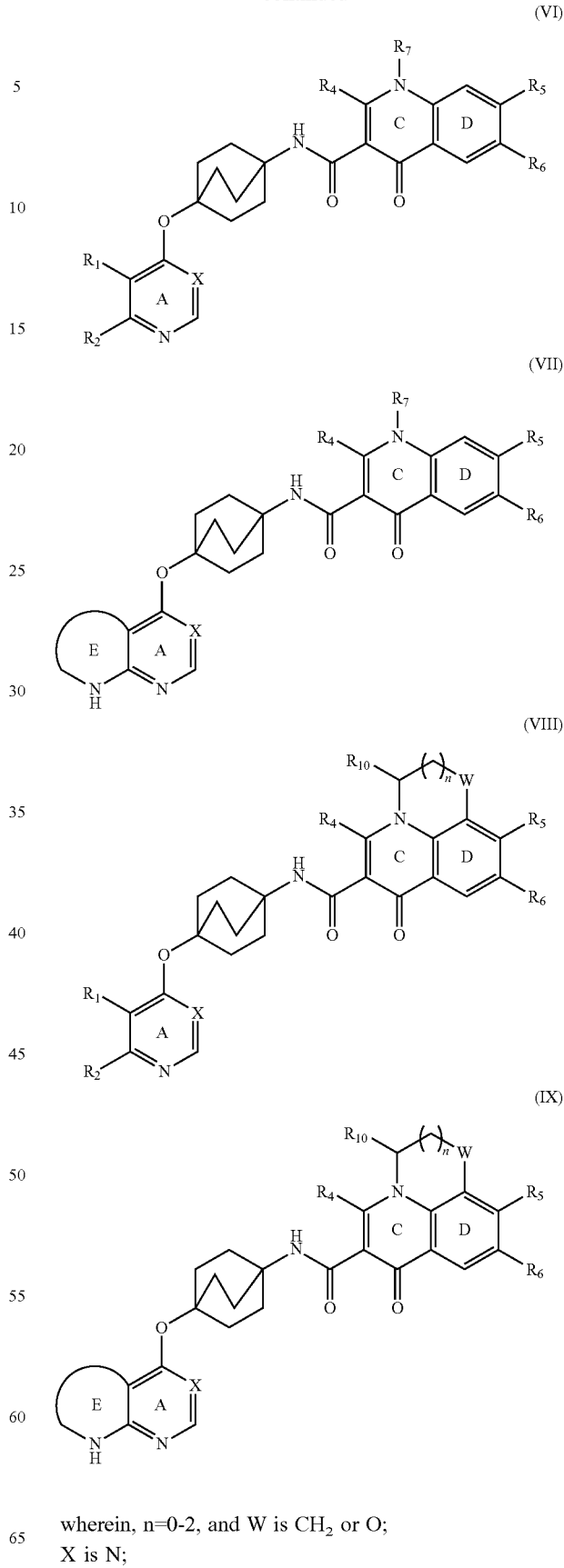
wherein, n=0-2, and W is $CH_2$ or O;
X is N;
$R_1$ is optionally selected from: hydrogen or halogen;

$R_2$ is optionally selected from:

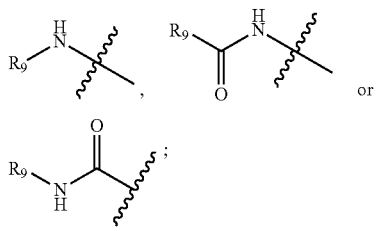

$R_9$ is optionally selected from: hydrogen, $C_1$-$C_5$ alkyl or $C_3$-$C_6$ cycloalkyl;

$R_3$ is optionally selected from: hydrogen, halogen, trifluoromethyl or $C_1$-$C_3$ alkyl;

$R_4$ is optionally selected from: hydrogen, $C_1$-$C_5$ alkyl, $C_3$-$C_6$ cycloalkyl, $C_1$-$C_3$ alkoxy, substituted or unsubstituted phenyl;

$R_5$ is optionally selected from: hydrogen, —($CH_2$)$_r$—$COOR_{22}$, —($CH_2$)$_r$—$NR_{23}R_{24}$, -L-heteroaryl or

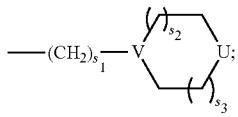

r, $s_1$, $s_2$, and $s_3$ in $R_5$ are each independently selected from 0, 1, 2 or 3;

V is optionally selected from: CH or N;

U is optionally selected from: O, S, $CR_{23}R_{24}$ or $NR_{23}$;

$R_{22}$ is optionally selected from: hydrogen or $C_1$-$C_4$ alkyl;

$R_{23}$ and $R_{24}$ are optionally selected from: H, $C_1$-$C_3$ alkyl, $C_3$-$C_6$ cycloalkyl, —NH($C_1$-$C_3$alkyl), —N($C_1$-$C_3$ alkyl)($C_1$-$C_3$ alkyl) or —C(=O)($C_1$-$C_3$ alkyl);

L is optionally selected from: $C_1$-$C_3$ alkyl, —$NR_{25}$—, —$NR_{25}C_0$—, —$CONR_{25}$—, —O—, —CO—, —SO— or —$SO_2$—; $R_{25}$ is selected from: $C_1$-$C_3$ alkyl;

$R_6$ is optionally selected from: hydrogen, halogen, $C_1$-$C_5$ alkyl, $C_2$-$C_6$ alkenyl, $C_3$-$C_6$ cycloalkyl, $C_4$-$C_6$ cycloalkenyl, $C_1$-$C_5$ alkoxy, trifluoromethyl or trifluoromethoxy;

$R_7$ is optionally selected from: hydrogen, $C_1$-$C_5$ alkyl or $C_3$-$C_6$ cycloalkyl;

or $R_7$, ring C and ring D constitute a fused tricycle

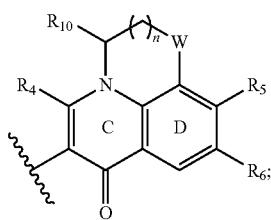

$R_{10}$ is optionally selected from H or $CH_3$;

and the fused tricycle has one of the following structures:

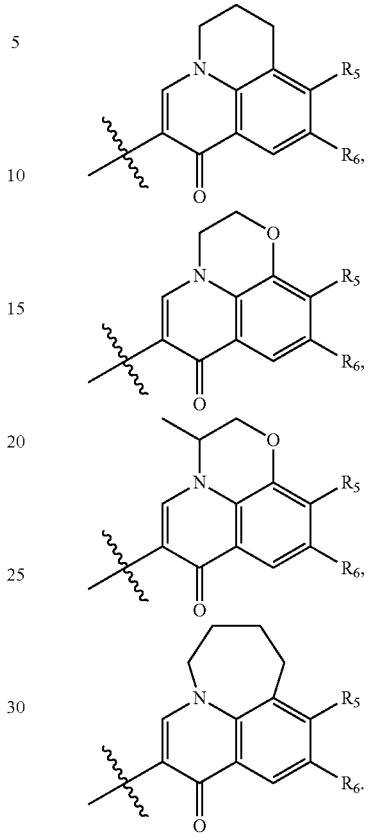

5. The substituted quinolone derivative, or a pharmaceutically acceptable salt or a stereoisomer thereof according to claim 4, wherein $R_4$ is optionally selected from: hydrogen, methyl, ethyl, propyl, isopropyl, butyl, isobutyl, pentyl, isopentyl, cyclopropyl, cyclobutyl, cyclopentyl, cyclohexyl, methoxy, ethoxy, propoxy, isopropoxy or

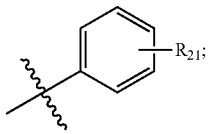

wherein $R_{21}$ is optionally selected from: hydrogen, halogen, $C_1$-$C_5$ alkyl, $C_3$-$C_6$ cycloalkyl or $C_1$-$C_5$ alkyl;

$R_5$ is optionally selected from: hydrogen,

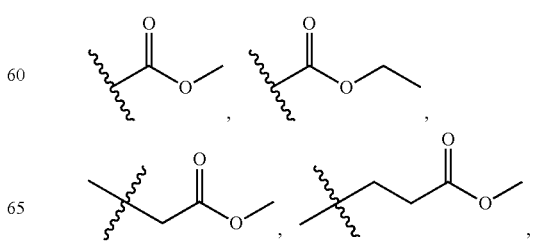

127
-continued
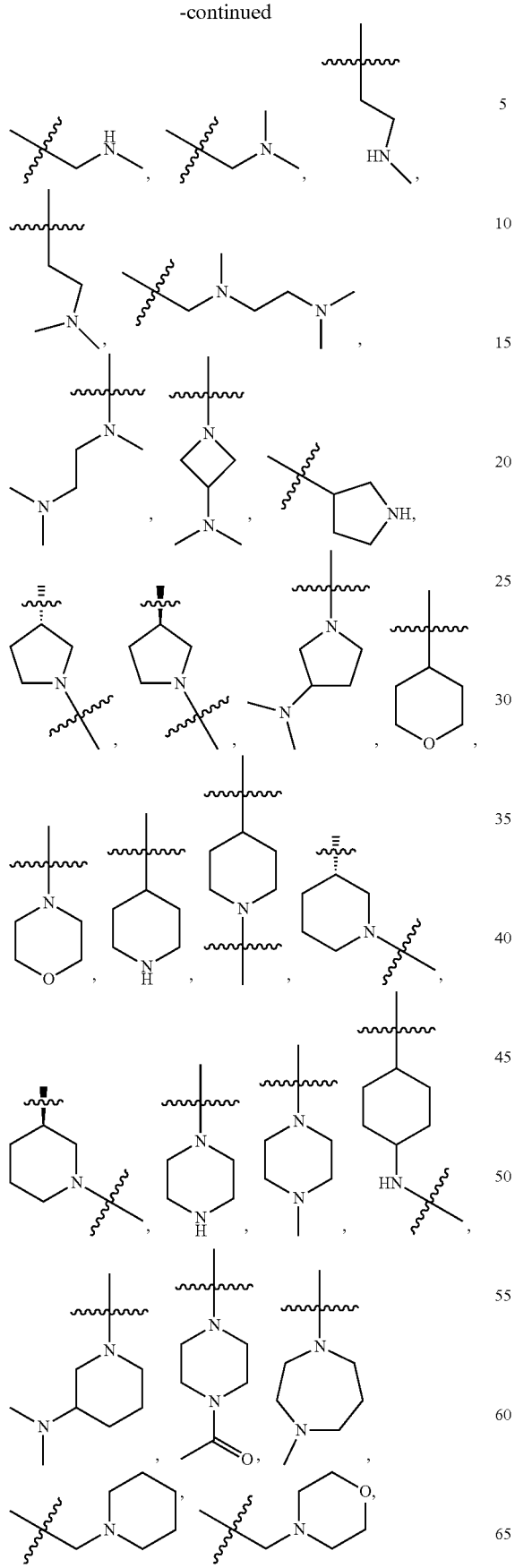
128
-continued
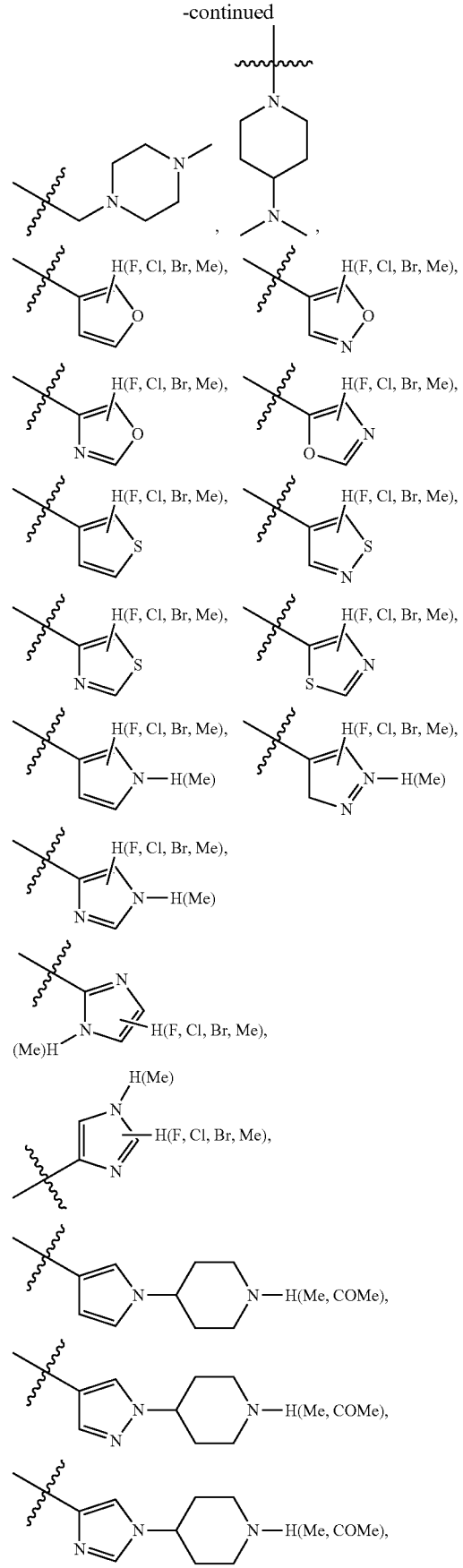

-continued

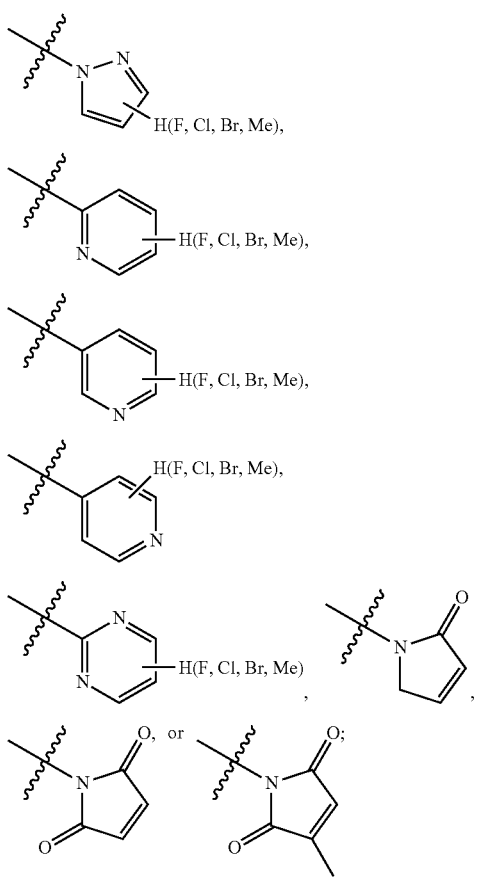

R₆ is optionally selected from: hydrogen, fluorine, chlorine, bromine, methyl, ethyl, propyl, isopropyl, butyl, isobutyl, tert-butyl, pentyl, isopentyl, propenyl, isopropenyl, butenyl, pentenyl, cyclopropyl, cyclobutyl, cyclopentyl, cyclohexyl, cyclobutenyl, cyclopentenyl, cyclohexenyl, methoxy, ethoxy, propoxy, isopropoxy, trifluoromethyl or trifluoromethoxy.

6. The substituted quinolone derivative, or a pharmaceutically acceptable salt or a stereoisomer thereof according to claim 4, wherein ring E and ring A constitute a substituted, fused 5- to 6-membered heterocyclic ring which has a structure as follows:

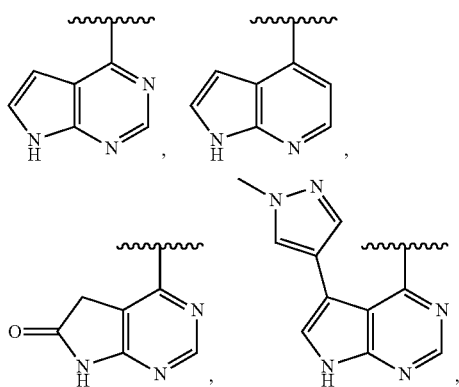

-continued

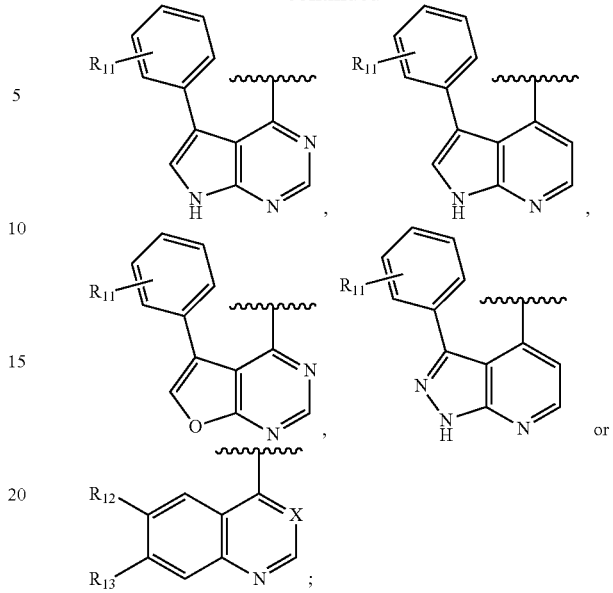

wherein, X is N;
R₁₁ is optionally selected from: hydrogen, halogen, methyl, ethyl, propyl, isopropyl, cyclopropyl, methoxy, ethoxy, propoxy or isopropoxy;
R₁₂ and R₁₃ are the same or different and are optionally selected from: hydrogen, halogen, —(CR₁₅R₁₆)ₒR₁₄, —O(CR₁₅R₁₆)ₒR₁₄, —(CR₁₇=CR₁₈)ₚR₁₄, —O(CR₁₇=CR₁₈)ₚR₁₄, —(C≡C)ｑ—R₁₄ or —O—(C≡C)ｑ—R₁₄;

wherein, o, p, and q=0-6, and R₁₀, R₁₅, R₁₆, R₁₇, and R₁₈ are the same or different and are optionally selected from: —H, —F, —Cl, —Br, —I, —CF₃, —OCF₃, —OH, —COOH, —COOCH₃, —COOC₂H₅, —COOC₃H₇, —COOCH(CH₃)₂, —COOC(CH₃)₃, —(C=O)—NR₁₉R₂₀, —SOₘ—NR₁₉R₂₀, —CHR₁₉R₂₀, —OR₁₉ or —NR₁₉R₂₀;
R₁₉ and R₂₀ are the same or different and are optionally selected from: hydrogen, halogen, or C₁-C₆ alkyl; or, R₁₉ and R₂₀ constitute a saturated or an unsaturated 5- to 8-membered heterocyclic group;
or, R₁₂ and R₁₃ constitute a substituted or an unsubstituted C₅-C₁₈ aliphatic cycloalkyl which contains 1-4 heteroatoms.

7. The substituted quinolone derivative, or a pharmaceutically acceptable salt or a stereoisomer thereof according to claim 1, selected from one of the following compounds:
N-(3-fluoro-4-(5-phenyl-7H-pyrrolo[2,3-d]pyrimidin-4-yloxy)phenyl)-1,2,6-trimethyl-4-oxo-1,4-dihydroquinoline-3-carboxamide;
6-chloro-N-(3-fluoro-4-((3-phenyl-1H-pyrazolo[3,4-b]pyridin-4-yl)oxy)phenyl)-1,2-dimethyl-4-oxo-1,4-dihydroquinoline-3-carboxamide;
N-(4-((7H-pyrrolo[2,3-d]pyrimidin-4-yl)oxy)-3-fluorophenyl)-6-chloro-1,2-dimethyl-4-oxo-1,4-dihydroquinoline-3-carboxamide;
6-chloro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide;

N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide;

7-chloro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide;

5-chloro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide;

N-(3-fluoro-4-(5-phenyl-7H-pyrrolo[2,3-d]pyrimidin-4-yloxy)phenyl)-1,2-dimethyl-4-oxo-7-(trifluoromethyl)-1,4-dihydroquinoline-3-carboxamide;

6-fluoro-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide;

N-(4-((1H-pyrrolo[2,3-b]pyridin-4-yl)oxy)-3-fluorophenyl)-6-chloro-1,2-dimethyl-4-oxo-1,4-dihydroquinoline-3-carboxamide;

N-(3-fluoro-4-((5-phenyl-7H-pyrrolo[2,3-d]pyrimidin-4-yl)oxy)phenyl)-1,2-dimethyl-4-oxo-6-(trifluoromethyl)-1,4-dihydroquinoline-3-carboxamide;

6-chloro-N-(3-fluoro-4-((3-phenyl-1H-pyrrolo[2,3-b]pyridin-4-yl)oxy)phenyl)-1,2-dimethyl-4-oxo-1,4-dihydroquinoline-3-carboxamide;

6-bromo-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide;

N-(3-fluoro-4-((5-phenyl-7H-pyrrolo[2,3-d]pyrimidin-4-yl)oxy)phenyl)-1,2-dimethyl-4-oxo-1,4-dihydrobenzo[g]quinoline-3-carboxamide;

N-(3-fluoro-4-((5-phenyl-7H-pyrrolo[2,3-d]pyrimidin-4-yl)oxy)phenyl)-6-methoxy-1,2-dimethyl-4-oxo-1,4-dihydroquinoline-3-carboxamide;

N-(3-fluoro-4-((5-phenyl-7H-pyrrolo[2,3-d]pyrimidin-4-yl)oxy)phenyl)-2,6-dimethyl-4-oxo-1,4-dihydroquinoline-3-carboxamide;

1-ethyl-N-(3-fluoro-4-(5-phenyl-7H-pyrrolo[2,3-d]pyrimidin-4-yloxy)phenyl)-2,6-dimethyl-4-oxo-1,4-dihydroquinoline-3-carboxamide;

N-(3-fluoro-4-(5-phenyl-7H-pyrrolo[2,3-d]pyrimidin-4-yloxy)phenyl)-2,6-dimethyl-4-oxo-1-propyl-1,4-dihydroquinoline-3-carboxamide;

1-butyl-N-(3-fluoro-4-((5-phenyl-7H-pyrrolo[2,3-d]pyrimidin-4-yl)oxy)phenyl)-2,6-dimethyl-4-oxo-1,4-dihydroquinoline-3-carboxamide;

2-ethyl-N-(3-fluoro-4-(5-phenyl-7H-pyrrolo[2,3-d]pyrimidin-4-yloxy)phenyl)-1,6-dimethyl-4-oxo-1,4-dihydroquinoline-3-carboxamide;

N-(3-fluoro-4-(5-phenyl-7H-pyrrolo[2,3-d]pyrimidin-4-yloxy)phenyl)-1,6-dimethyl-4-oxo-2-phenyl-1,4-dihydroquinoline-3-carboxamide;

9-fluoro-N-(3-fluoro-4-((5-phenyl-7H-pyrrolo[2,3-d]pyrimidin-4-yl)oxy)phenyl)-3-methyl-10-(4-methylpiperazin-1-yl)-7-oxo-3,7-dihydro-2H-[1,4]oxazino[2,3,4-ij]quinoline-6-carboxamide;

1-cyclopropyl-6-fluoro-N-(3-fluoro-4-((5-phenyl-7H-pyrrolo[2,3-d]pyrimidin-4-yl)oxy)phenyl)-4-oxo-7-(piperazin-1-yl)-1,4-dihydroquinoline-3-carboxamide;

6-ethyl-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide;

6-(tert-butyl)-N-(3-fluoro-4-((5-phenyl-7H-pyrrolo[2,3-d]pyrimidin-4-yl)oxy)phenyl)-1,2-dimethyl-4-oxo-1,4-dihydroquinoline-3-carboxamide;

N-(3-fluoro-4-((5-phenyl-7H-pyrrolo[2,3-d]pyrimidin-4-yl)oxy)phenyl)-1,2-dimethyl-4-oxo-6-propyl-1,4-dihydroquinoline-3-carboxamide;

N-(3-fluoro-4-((5-phenyl-7H-pyrrolo[2,3-d]pyrimidin-4-yl)oxy)phenyl)-1,2-dimethyl-4-oxo-6-(trifluoromethoxy)-1,4-dihydroquinoline-3-carboxamide;

6-ethyl-1,2-dimethyl-4-oxo-N-(4-((5-phenyl-7H-pyrrolo[2,3-d]pyrimidin-4-yl)oxy)phenyl)-1,4-dihydroquinoline-3-carboxamide;

6-ethyl-1,2-dimethyl-N-(3-methyl-4-(5-phenyl-7H-pyrrolo[2,3-d]pyrimidin-4-yloxy)phenyl)-4-oxo-1,4-dihydroquinoline-3-carboxamide;

N-(4-(7H-pyrrolo[2,3-d]pyrimidin-4-yloxy)-3-fluorophenyl)-6-ethyl-1,2-dimethyl-4-oxo-1,4-dihydroquinoline-3-carboxamide;

6-ethyl-N-(3-fluoro-4-(3-phenyl-1H-pyrrolo[2,3-b]pyridin-4-yloxy)phenyl)-1,2-dimethyl-4-oxo-1,4-dihydroquinoline-3-carboxamide;

6-ethyl-N-(3-fluoro-4-(5-(4-methoxyphenyl)-7H-pyrrolo[2,3-d]pyrimidin-4-yloxy)phenyl)-1,2-dimethyl-4-oxo-1,4-dihydroquinoline-3-carboxamide;

6-ethyl-N-(3-fluoro-4-(5-phenyl-7H-pyrrolo[2,3-d]pyrimidin-4-yloxy)phenyl)-1-methyl-4-oxo-1,4-dihydroquinoline-3-carboxamide;

N-(3-fluoro-4-((5-phenyl-7H-pyrrolo[2,3-d]pyrimidin-4-yl)oxy)phenyl)-9-methyl-1-oxo-1,5,6,7-tetrahydropyrido[3,2,1-ij]quinoline-2-carboxamide;

N-(3-fluoro-4-(5-phenyl-7H-pyrrolo[2,3-d]pyrimidin-4-yloxy)phenyl)-1,6-dimethyl-4-oxo-1,4-dihydroquinoline-3-carboxamide;

N-(3-fluoro-4-(5-phenyl-7H-pyrrolo[2,3-d]pyrimidin-4-yloxy)phenyl)-1,2-dimethyl-4-oxo-6-(prop-1-en-2-yl)-1,4-dihydroquinoline-3-carboxamide;

6-cyclopropyl-N-(3-fluoro-4-(5-phenyl-7H-pyrrolo[2,3-d]pyrimidin-4-yloxy)phenyl)-1,2-dimethyl-4-oxo-1,4-dihydroquinoline-3-carboxamide;

6-cyclopentenyl-N-(3-fluoro-4-(5-phenyl-7H-pyrrolo[2,3-d]pyrimidin-4-yloxy)phenyl)-1,2-dimethyl-4-oxo-1,4-dihydroquinoline-3-carboxamide;

N-(3-fluoro-4-(5-phenyl-7H-pyrrolo[2,3-d]pyrimidin-4-yloxy)phenyl)-1,2-dimethyl-4-oxo-6-phenyl-1,4-dihydroquinoline-3-carboxamide;

N-(3-fluoro-4-(5-phenyl-7H-pyrrolo[2,3-d]pyrimidin-4-yloxy)phenyl)-1,2-dimethyl-4-oxo-6-(1-piperidin-4-yl)-1H-pyrazol-4-yl)-1,4-dihydroquinoline-3-carboxamide;

N-(3-fluoro-4-(5-phenyl-7H-pyrrolo[2,3-d]pyrimidin-4-yloxy)phenyl)-6-isopropyl-1,2-dimethyl-4-oxo-1,4-dihydroquinoline-3-carboxamide;

6-cyclopentyl-N-(3-fluoro-4-(5-phenyl-7H-pyrrolo[2,3-d]pyrimidin-4-yloxy)phenyl)-1,2-dimethyl-4-oxo-1,4-dihydroquinoline-3-carboxamide;

methyl 3-((3-fluoro-4-(5-phenyl-7H-pyrrolo[2,3-d]pyrimidin-4-yloxy)phenyl)carbamoyl)-1,2-dimethyl-4-oxo-1,4-dihydroquinoline-6-carboxylate;

N-(3-fluoro-4-(7-methyl-5-phenyl-7H-pyrrolo[2,3-d]pyrimidin-4-yloxy)phenyl)-1,2,6-trimethyl-4-oxo-1,4-dihydroquinoline-3-carboxamide;

N-(4-(6,7-dimethoxyquinazolin-4-yloxy)-3-fluorophenyl)-6-ethyl-1,2-dimethyl-4-oxo-1,4-dihydroquinoline-3-carboxamide;

N-(4-((6,7-dimethoxyquinazolin-4-yl)oxy)-3-fluorophenyl)-6-fluoro-1-methyl-7-(4-((5-methyl-2-oxo-1,3-dioxol-4-yl)methyl)piperazin-1-yl)-4-oxo-1,4-dihydro-[1,3]thiazeto[3,2-a]quinoline-3-carboxamide;

N-(4-((6,7-dimethoxyquinazolin-4-yl)oxy)-3-fluorophenyl)-9-fluoro-8-(4-hydroxypiperidin-1-yl)-5-methyl-1-oxo-1,5,6,7-tetrahydropyrido[3,2,1-ij]quinoline-2-carboxamide;

N-(4-(6,7-dimethoxyquinazolin-4-yloxy)-3-fluorophenyl)-6,8-difluoro-1-(2-fluoroethyl)-7-(4-methylpiperazin-1-yl)-4-oxo-1,4-dihydroquinoline-3-carboxamide;

N-(4-(6,7-dimethoxyquinazolin-4-yloxy)-3-fluorophenyl)-6-fluoro-1-(4-fluorophenyl)-4-oxo-7-(piperazin-1-yl)-1,4-dihydroquinoline-3-carboxamide;

5-amino-1-cyclopropyl-N-(4-(6,7-dimethoxyquinazolin-4-yloxy)-3-fluorophenyl)-7-(3,5-dimethylpiperazin-1-yl)-6,8-difluoro-4-oxo-1,4-dihydroquinoline-3-carboxamide;

1-cyclopropyl-N-(4-(6,7-dimethoxyquinazolin-4-yloxy)-3-fluorophenyl)-7-(4-ethylpiperazin-1-yl)-6-fluoro-4-oxo-1,4-dihydroquinoline-3-carboxamide;

7-(3-aminopyrrolidin-1-yl)-1-(2,4-difluorophenyl)-N-(4-(6,7-dimethoxyquinazolin-4-yloxy)-3-fluorophenyl)-6-fluoro-4-oxo-1,4-dihydro-1,8-naphthyridine-3-carboxamide;

N-(4-(6,7-dimethoxyquinazolin-4-yloxy)-3-fluorophenyl)-1-ethyl-6-fluoro-4-oxo-7-(piperazin-1-yl)-1,4-dihydro-1, 8-naphthyridine-3-carboxamide;

1-cyclopropyl-N-(4-(6,7-dimethoxyquinazolin-4-yloxy)-3-fluorophenyl)-6-fluoro-4-oxo-7-(piperazin-1-yl)-1,4-dihydroquinoline-3-carboxamide;

N-(4-(2-chloropyridin-4-yloxy)-3-fluorophenyl)-6-ethyl-1,2-dimethyl-4-oxo-1,4-dihydroquinoline-3-carboxamide;

N-(4-(2-benzylpyridin-4-yloxy)-3-fluorophenyl)-6-ethyl-1,2-dimethyl-4-oxo-1,4-dihydroquinoline-3-carboxamide;

6-ethyl-N-(3-fluoro-4-(3-phenylfuro [2,3-b]pyridin-4-yloxy)phenyl)-1,2-dimethyl-4-oxo-1,4-dihydroquinoline-3-carboxamide;

N-(4-(2-carbamoylpyridin-4-yloxy)-3-fluorophenyl)-6-ethyl-1,2-dimethyl-4-oxo-1,4-dihydroquinoline-3-carboxamide;

N-(4-(2-aminopyridin-4-yloxy)-3-fluorophenyl)-6-ethyl-1,2-dimethyl-4-oxo-1,4-dihydroquinoline-3-carboxamide;

6-ethyl-N-(3-fluoro-4-(5-(1-methyl-1H-pyrazol-4-yl)-7H-pyrrolo [2,3-d]pyrimidin-4-yloxy)phenyl)-1,2-dimethyl-4-oxo-1,4-dihydroquinoline-3-carboxamide;

2,6-diethyl-N-(3-fluoro-4-(5-phenyl-7H-pyrrolo [2,3-d]pyrimidin-4-yloxy)phenyl)-1-methyl-4-oxo-1,4-dihydroquinoline-3-carboxamide;

N-(4-(6,7-dimethoxyquinazolin-4-yloxy)-3-fluorophenyl)-2,6-diethyl-1-methyl-4-oxo-1,4-dihydroquinoline-3-carboxamide;

N-(4-(2-carbamoyl-3-chloropyridin-4-yloxy)-3-fluorophenyl)-6-ethyl-1,2-dimethyl-4-oxo-1,4-dihydroquinoline-3-carboxamide;

N-(4-((2-amino-3-chloropyridin-4-yl)oxy)-3-fluorophenyl)-6-ethyl-1,2-dimethyl-4-oxo-1,4-dihydroquinoline-3-carboxamide;

N-(3-fluoro-4-(5-phenyl-7H-pyrrolo [2,3-d]pyrimidin-4-yloxy)phenyl)-2,6-dimethyl-4-oxo-1-phenyl-1,4-dihydroquinoline-3-carboxamide;

6-ethyl-N-(3-fluoro-4-(6-methoxy-7-(3-morpholinopropoxy)quinazolin-4-yloxy)phenyl)-1,2-dimethyl-4-oxo-1,4-dihydroquinoline-3-carboxamide;

N-(4-(7-(2-(dimethylamino)ethoxy)-6-methoxyquinazolin-4-yloxy)-3-fluorophenyl)-6-ethyl-1,2-dimethyl-4-oxo-1,4-dihydroquinoline-3-carboxamide;

6-ethyl-N-(3-fluoro-4-(6-methoxy-7-(3-(4-methylpiperazin-1-yl)propoxy)quinazolin-4-yloxy)phenyl)-1,2-dimethyl-4-oxo-1,4-dihydroquinoline-3-carboxamide;

6-ethyl-N-(3-fluoro-4-(6-methoxy-7-(2-(pyrrolidin-1-yl)ethoxy)quinazolin-4-yloxy)phenyl)-1,2-dimethyl-4-oxo-1,4-dihydroquinoline-3-carboxamide;

6-ethyl-N-(3-fluoro-4-(6-methoxy-7-(3-methoxypropoxy)quinazolin-4-yloxy)phenyl)-1,2-dimethyl-4-oxo-1,4-dihydroquinoline-3-carboxamide;

N-(4-(7-(3-(dimethylamino)propoxy)-6-methoxyquinazolin-4-yloxy)-3-fluorophenyl)-6-ethyl-1,2-dimethyl-4-oxo-1,4-dihydroquinoline-3-carboxamide; and N-(4-(6,7-dimethoxyquinazolin-4-yloxy)-3-fluorophenyl)-6-ethyl-1,2-dimethyl-7-(4-methylpiperazin-1-yl)-4-oxo-1,4-dihydroquinoline-3-carboxamide.

8. The substituted quinolone derivative, or a pharmaceutically acceptable salt or a stereoisomer thereof according to claim 1, selected from one of the following compounds:

9-fluoro-N-(3-fluoro-4-((5-phenyl-7H-pyrrolo[2,3-d]pyrimidin-4-yl)oxy)phenyl)-8-(4-hydroxypiperidin-1-yl)-5-methyl-1-oxo-1,5,6,7-tetrahydropyrido[3,2,1-ij]quinoline-2-carboxamide;

6-ethyl-N-(2-fluoro-4-(5-phenyl-7H-pyrrolo[2,3-d]pyrimidin-4-yloxy)phenyl)-1,2-dimethyl-4-oxo-1,4-dihydroquinoline-3-carboxamide;

N-(4-((6,7-dimethoxyquinazolin-4-yl)oxy)-3-fluorophenyl)-9-methyl-1-oxo-1,5,6,7-tetrahydropyrido[3,2,1-ij]quinoline-2-carboxamide;

(S)—N-(4-((6,7-dimethoxyquinazolin-4-yl)oxy)-3-fluorophenyl)-9-fluoro-3-methyl-10-(4-methylpiperazin-1-yl)-7-oxo-3,7-dihydro-2H-[1,4]oxazino[2,3,4-ij]quinoline-6-carboxamide; and N-(4-((6,7-dimethoxyquinazolin-4-yl)oxy)-3-fluorophenyl)-9-fluoro-3-methyl-10-(4-methylpiperazin-1-yl)-7-oxo-3,7-dihydro-2H-[1,3,4]oxadiazino[6,5,4-ij]quinoline-6-carboxamide.

9. A pharmaceutical composition for the treatment of a tumor mediated by AXL kinase, comprising the substituted quinolone derivative, or a pharmaceutically acceptable salt or a stereoisomer thereof of 1, or a prodrug molecule thereof, and a pharmaceutically acceptable carrier.

10. A method for treating a tumor mediated by AXL kinase, comprising administering the substituted quinolone derivative, or a pharmaceutically acceptable salt or a stereoisomer thereof according to claim 1, or the prodrug molecule thereof to a mammal alone or in combination with a pharmaceutically acceptable carrier.

11. The method according to claim 10, wherein the tumor is any one of hematological tumor, gastrointestinal stromal tumor, histiocytic lymphoma, non-small cell lung cancer, small cell lung cancer, lung adenocarcinoma, lung squamous cell carcinoma, pancreatic cancer, breast cancer, prostate cancer, hepatoma, skin cancer, epithelial cancer, and nasopharyngeal cancer.

* * * * *